United States Patent
Kere et al.

(10) Patent No.: US 7,355,022 B2
(45) Date of Patent: Apr. 8, 2008

(54) GENE FUNCTIONALLY RELATED TO DYSLEXIA

(75) Inventors: Juha Kere, Stockholm (SE); Mikko Taipale, Heidelberg (DE); Jaana Nopola-Hemmi, Helsinki (FI); Nina Kaminen, Helsinki (FI)

(73) Assignee: Licentia Ltd., Helsinki (FI)

( * ) Notice: Subject to any disclaimer, the term of this patent is extended or adjusted under 35 U.S.C. 154(b) by 0 days.

(21) Appl. No.: 10/681,199

(22) Filed: Oct. 9, 2003

(65) Prior Publication Data

US 2004/0138441 A1 Jul. 15, 2004

Related U.S. Application Data

(63) Continuation-in-part of application No. 10/364,505, filed on Feb. 12, 2003, now abandoned.

(60) Provisional application No. 60/355,782, filed on Feb. 12, 2002.

(51) Int. Cl.
 *C07H 21/04* (2006.01)
 *C12Q 1/68* (2006.01)

(52) U.S. Cl. ............... 536/23.1; 536/24.3; 435/6; 435/91.1; 435/91.2

(58) Field of Classification Search ............... None
See application file for complete search history.

(56) References Cited

U.S. PATENT DOCUMENTS 5,474,796 A * 12/1995 Brennan .................. 427/2.13
2003/0092019 A1* 5/2003 Meyer et al. .................. 435/6

OTHER PUBLICATIONS

Marino et al. (E. J. Human Genetics, vol. 13, pp. 491-499, 2005).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Scerri et al. (J. Med. Genet. vol. 41, pp. 853-857, 2004).*
Wigg et al (Mol. Psychiatry, vol. 9, pp. 1111-1121, 2004).*
Taipale et al. (Genbank Accession No. AF337549, Feb. 2, 2002).*
Applied Biosystems Product Catalog (1993, pp. 135-157, 160-164).*
NIH-MGC (Genbank Accession No. BE972748, Oct. 4, 2000).*
Elena L. Grigorenko, *J. Child Psychol.Psychiat.*, vol. 42, No. 1, (2001), pp. 91-125.
E.L. Grigorenko et al., *Am. J. Hum. Genet.*, vol. 60, (1997), pp. 27-39.
M.M. Nothen et al., *European Child & Adolescent Psychiatry*, vol. 8, Suppl. 3, (1999), pp. 56-59.
Jaana Nopola-Hemmi et al., *J. Med. Genet.*, vol. 37, (2000), pp. 741-775.
Jaanamarja Nopola-Hemmi, *Academic Dissertation*, Helsinki University Biomedical Dissertations No. 16, Department of Pediatric Neurology and Department of Medical Genetics, University of Helsinki, Finland, (Sep. 2002).
M. Taipale et al., *NCBI*, Accession No. AF337549.1, *Homo sapiens* EKN1, (Jan. 17, 2001).
M. Taipale et al., *NCBI*, Accession No. AAL73230, EKN1 (*Homo sapiens*), (Jan. 17, 2001).
N. Kaminen et al., *NCBI*, Accession No. AY178583, *Pan troglodytes* EK1, (Nov. 13, 2002).
N. Kaminen et al., *NCBI*, Accession No. AY178592, *Pan paniscus* EKN1, (Nov. 13, 2002).
N. Kaminen et al., *NCBI*, Accession No. AY178601, *Gorilla gorilla* EKN1, (Nov. 13, 2002).
N. Kaminen et al., *NCBI*, Accession No. AY178610, *Pongo pygmaeus* EKN1, (Nov. 13, 2002).
M. Taipale et al., *EBI*, Swall Accession No. Q8WXU2, EKNI (Human), (Mar. 1, 2002).
M. Taipale et al., *NCBI*, Accession No. AF337549.1, *Homo sapiens*EKN1, (Feb. 2, 2002).

\* cited by examiner

*Primary Examiner*—Jeanine A. Goldberg
(74) *Attorney, Agent, or Firm*—Birch, Stewart, Kolasch & Birch, LLP

(57) ABSTRACT

The present invention describes a novel human gene, DYXC1, which is functionally related to dyslexia. DYXC1 gene encodes a 420-amino acid residue protein. DYXC1 is expressed in several tissues, including the brain, and is localized in the nucleus. In addition, four single nucleotide polymorphisms (SNPs) in DYXC1 mRNA have been characterized in this invention. The invention provides diagnostic methods and materials for analysing allelic variation in DYXC1 gene. This invention also provides polypeptides encoded by DYXC1 gene and antibodies binding to said polypeptides.

7 Claims, 12 Drawing Sheets

```
hDYXC1    1  MPLQVSDYSWQQTKTAVFLSLPLKGVCVRDTDVFCTENYLKVNFPPFLFE
mDYXC1    1  MPVRVSEFSWQQTPATIFLSLPLRGVCVRDADVFCGESYLKVNFPPFLFE
                ^4C->T hDYXC1   51  AFLYAPIDDESSKAKIGNDTIVFTLYKKEAAMWETLSVTGVDKEMMQRIR
mDYXC1   51  LFLYAPIDDGKSKAKIGNDTILFTLYKKEPVLWDSLSVPGVDKEMMQRIR hDYXC1  101  EKSILQAQERAKEATEAKAAAKREDQKYALSVMMKIEEEERKKIEDMKEN
mDYXC1  101  EKSILQAQEKAKEATEAKAVAKREDQRYALGEMMKIEEEERKKLEDLKEN hDYXC1  151  ERIKATKALEAWKEYQRKAEEQKKIQREEKLCQKEKQIKEGRKKIKYKSL
mDYXC1  151  ERKKATSELEAWKECQKKADGQKRVQRKEKPLE-GKQ-AEETKALKPRGL
                                                      ^572G->A hDYXC1  201  TRNLASRNLAPKGRNSENIFTEKLKEDSIPAPRSVGSIKINFTPRVFPTA
mDYXC1  199  PRKAPPTRLPTEGRNWENIFPEKLKEDRVPAPRSAGSIQISFTPRVFPTA hDYXC1  251  LRESQVAEEEEWLHKQAEARRAMNTDIAELCDLKEEEKNPEWLKDKGNKL
mDYXC1  249  LRESQVAEEEEWLHKQAEARRAMSTDIPEFFDLKEEERNPDWLKDKGNKL
                                                  |*********
hDYXC1  301  FATENYLAAINAYNLAIRLNNKMPLLYLNRAACHLKLKNLHKAIEDSSKA
mDYXC1  299  FATENYLAAVDAYNLAIRLNCKIPLLYLNRAACHLKLKNLHKAIEDSSKA
             ****TPR1***************|   |***************TPR2********
hDYXC1  351  LELLMPPVTDNANARMKAHVRRGTAFCQLELYVEGLQDYEAALKIDPSNK
mDYXC1  349  LELLTPPVADNANARMKAHVRRGTAFCQLELYVEGLQDYEAALKIDPANT
             ******|         |**************TPR3***************|
hDYXC1  401  IVQIDAEKIRNMIQGTELKS--
mDYXC1  399  VVQNDAEKIRNIIQGTALKSRD
                   1249G->T^    ^1259C->G
```

Figure 2a.

GENE FUNCTIONALLY RELATED TO DYSLEXIA

CROSS REFERENCE TO RELATED APPLICATIONS

This application claims priority under 35 U.S.C. § 120 to PCT International Application No. PCT/FI03/00110, which has an international filing date of Feb. 12, 2003, which designated the United States, which claims priority under 35 U.S.C. § 119(e) to U.S. Provisional Application No. 60/355,782, filed on Feb. 12, 2002. This application is also a Continuation-in-Part of application Ser. No. 10/364,505, filed on Feb. 12, 2003, now abandoned which claims priority under 35 U.S.C. § 119(e) to U.S. Provisional Application No. 60/355,782, filed on Feb. 12, 2002. The entire contents of all of the above application are hereby incorporated by reference.

The present invention relates to a novel human gene functionally related to dyslexia, especially variant forms (e.g. alleles) thereof that predispose an individual to develop dyslexia. Thus, this invention also relates to the polymorphism of said gene as well as diagnostic methods and materials for analysing allelic variation in said gene. This invention also provides polypeptides encoded by said gene and antibodies binding to said polypeptides. The materials of the invention can be used to study the brain processes such as reading, phonological processing, rapid naming and verbal short term memory.

BACKGROUND OF THE INVENTION

Dyslexia, or specific reading disability, is the most common childhood learning disorder. It is estimated that about 3-10% of people have specific difficulties in reading, despite adequate intelligence, education and social environment. Several different theories have been put forth to account for the diverse symptoms seen in dyslexic subjects. At present, it is thought that dyslexia is primarily a phonological deficit, emphasizing the linguistic basis of this condition (1-3). However, it is possible that dyslexia is not specific to language. Rather, it may result from a deficit in processing fast temporal data, be it visual or auditory. This temporal processing deficit would, consequently, manifest itself primarily as dyslexia (4).

Available evidence suggests that dyslexia is a neurological disorder with a genetic basis. Functional brain imaging studies have illustrated that dyslexia has universal neurobiological correlates (5). There is extensive evidence of genetic factors which contribute to dyslexia. There are significant differences, however, in the heritability of different components of dyslexia (6). Linkage and association studies have pinpointed several loci for dyslexia. In particular, two loci have been promising. DYX1 in chromosome 15q21 was the first locus to be associated with dyslexia (7), and the results have been replicated in three independent studies thereafter (8-10). The presence of a second dyslexia locus, DYX2, in chromosome 6p21 has also been established (11).

We have previously reported a translocation t(2; 15)(q11; q21) which segregates with dyslexia (12). In the present invention, we have cloned the breakpoint and narrowed down the breakpoint interval within a 3229 bp region with Southern hybridization. This region contains a 301 bp AT rich sequence. Considering that AT rich repeats are known to occur at many chromosomal rearrangement sites (13), the 301 bp AT rich sequence is likely to be the exact breakpoint site. Furthermore, we have unexpectedly discovered and characterized a novel gene residing in the breakpoint region, which gene we named DYXC1 and which is causally correlated with dyslexia.

A candidate gene for developmental dyslexia is disclosed in Taipale et al. (Proceedings of the National Academic of Sciences 100:11553-11558, 2003), which is incorporated herein by reference.

SUMMARY OF THE INVENTION

The present invention describes a novel human gene, DYXC1, which is causally correlated with dyslexia. The coding sequence of DYXC1 is 1260 bp in length (SEQ ID NO: 1), and it encodes a predicted protein of 420 amino acids (SEQ ID NO: 3). DYXC1 is expressed in several tissues, most abundantly in brain, lung, kidney and testis. DYXC1 protein resides in cell nuclei, and in brain, it localizes to a subset of cortical neurons and glial cells. DYXC1 protein appears rapidly upregulated and translocated after brain ischemia. The predicted 420 amino-acid protein contains three C-terminal tetratricopeptide repeat (TPR) domains, thought to mediate protein-protein interactions. Besides these domains, it bears no similarity to known proteins. Transfection and immunofluorescence studies indicate that DYXC1 is a nuclear protein.

The coding sequence of DYXC1 was predicted from the genomic sequence of BAC clones RP11-178D12 and CTD-2137J4. The length of DYXC1 mRNA is 1993 bp (SEQ ID NO: 2), and it encodes a predicted protein of 420 amino acids. DYXC1 consists of 10 exons spanning approximately 78 kb of genomic DNA (FIG. 1D). The start codon (AUG) of DYXC1 is located 369 bp from the predicted transcription initiation site in exon 2. Putative promoter of DYXC1 has a TATA box (TATAAAT) at position −31.

In one aspect, the invention features isolated DYXC1 nucleic acid molecules having the sequence of SEQ ID NO:1 or a complement thereof; homologs and variants thereof as well as fragments thereof. In a preferred embodiment the isolated DYXC1 nucleic acid is mammalian. In an even more preferred embodiment the isolated DYXC1 nucleic acid is from a primate, most preferably the DYXC1 nucleic acid is human. The invention features also vectors comprising the disclosed nucleic acid as well as host cells for the expression or amplification of such vectors.

In addition, we have characterized in this invention five single nucleotide polymorphisms (SNPs) in DYXC1 mRNA. One sequence variant (1249G→T) introduces a premature stop codon and is inherited with dyslexia in a three-generation family. The frequency of the polymorphism is significantly (p=0.0278) elevated in dyslexic subjects, compared to control samples. The polymorphism truncates the predicted DYXC1 protein by four amino acids, suggesting that it is a functional SNP. Thus, in another aspect, the invention features nucleic acids comprising at least one single nucleotide polymorphism in any one of the following positions as defined by SEQ ID NO: 1: position 4 (C preferably to T), 572 (G preferably to A), 1249 (G preferably to T), 1259 (C preferably to G); and SEQ ID NO:2: position 205 (C preferably to T).

The invention further provides polypeptides encoded by DYXC1 gene or allelic variants thereof and antibodies binding to said polypeptides. The invention also relates to diagnostic methods, kits and materials for analysing allelic variation in DYXC1 gene and its cellular function.

DESCRIPTION OF THE DRAWINGS

FIGS. 2A, 2B, 2C, 2D and 2E. 2A, Comparison of the protein sequences of human DYXC1 SEQ ID NO: 3 and mouse mdyxc1 SEQ ID NO: 5. The SNPs found in this invention are marked with a circumflex accent, and the three TPR domains are marked with asteriks. 2B, RT-PCR from human multiple tissue cDNA panels I and II (Clontech). Lanes: 1)λ/φX174 size marker, 2) heart, 3) brain, 4) placenta, 5) lung, 6) liver, 7) skeletal muscle, 8) kidney, 9) pancreas, 10) spleen, 11) thymus, 12) prostate, 13) testis, 14) ovary, 15) small intestine, 16) colon, and 17) leukocyte. 2C and 2D, DYXC1 Northern blot from Multiple Tissue Northern (MTN) Blot panels I and II (Clontech). Lanes in FIG. 2C: 1) heart, 2) brain, 3) placenta, 4) lung, 5) liver, 6) skeletal muscle, 7) kidney, 8) pancreas; Lanes in FIG. 2D: 9) spleen, 10) thymus, 11) prostate, 12) testis, 13) ovary, 14) small intestine, 15) colon, and 16) leukocyte. 2E, Cellular localization of DYXC1 protein. Cos-1 cells transfected with DYXC1-V5 fusion construct were stained with monoclonal mouse a-V5 antibody and FITC-conjugated α-mouse-IgG (grey). DAPI stained nuclei are shown in light grey.

DETAILED DESCRIPTION OF THE INVENTION

Figure 1A:
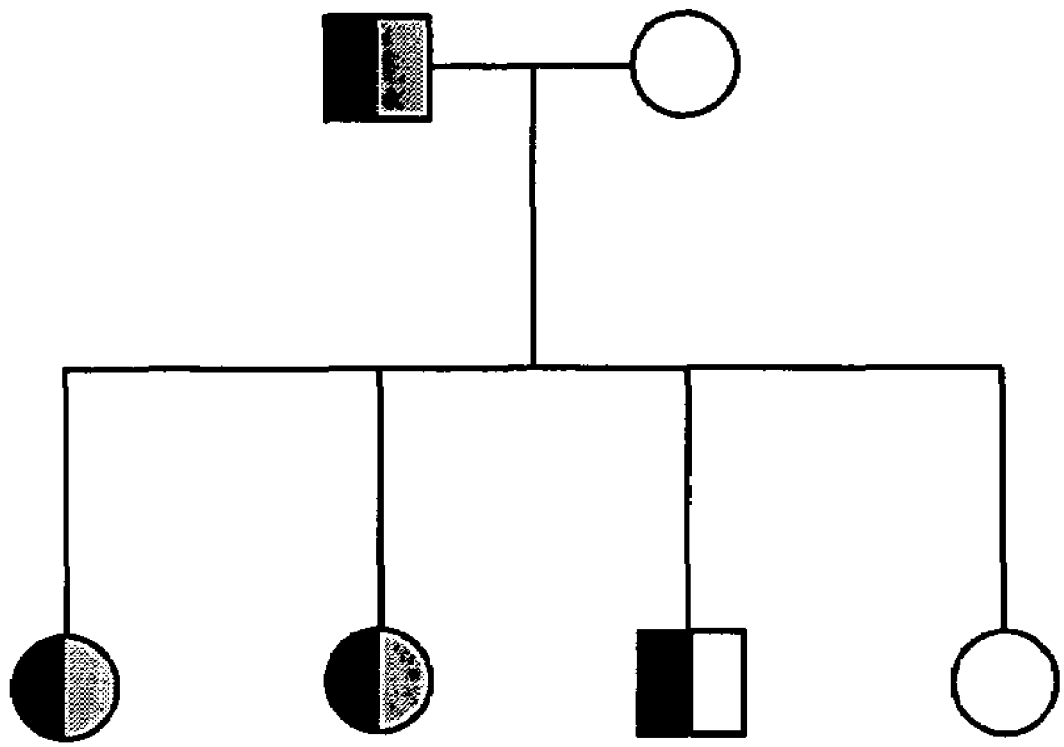
FIGS. 1A, 1B, 1C and 1D. 1A, Pedigree of the studied family. Black fill denotes translocation, grey fill dyslexia. 1B, Fluorescent in situ hybridization with BAC clone 178D12 as a probe, showing hybridisation signals in chromosomes 15, der(15), and der(2). 1C, Southern hybridization with a probe derived from 178D12 shows genomic rearrangement with six restriction enzymes in the studied sample (T) compared to the control sample (C). 1D, Physical map of the breakpoint region, including DYXC1 (black) and an intronic pseudogene (white), drawn to scale. Black triangle illustrates the Southern hybridisation probe position, grey bar denotes the breakpoint interval.

This invention is based on the discovery and characterization of a novel human gene termed DYXC1. The human DYXC1 gene is 1260 bp in length (SEQ ID NO: 1) and it encodes a 420-amino acid residue protein (SEQ ID NO: 3). The cDNA of total DYXC1 mRNA (SEQ ID NO:2) has been deposited in GenBank with accession number AF337549. DYXC1 maps to human chromosome 15q21. The present invention shows that previously reported balanced translocation breakpoint t(2;15)(q11;q21) segregating coincidentally with developmental dyslexia is located in DYXC1 thus indicating that DYXC1 is linked to dyslexia. In addition, it was unexpectedly discovered in the present invention that point mutations, i.e. SNPs, in DYXC1 segregate with the susceptibility to develop dyslexia.

The present invention provides DYXC1 nucleic acids, homologs thereof and fragments thereof. The human DYXC1 cDNA sequence is disclosed in SEQ ID NO: 1. Preferred homologs, such as chimpanzee (SEQ ID NO:13), pygmy chimpanzee (SEQ ID NO:19), gorilla (SEQ ID NO:15), orangutan (SEQ ID NO:17) and mouse dyxc1 (SEQ ID NO: 4), have a sequence at least about 79% homologous with a nucleotide sequence of SEQ ID NO: 1. In a preferred embodiment, the DYXC1 nucleic acid is from a mammal, e.g. a mouse, primate or human. In another preferred embodiment the nucleic acid has the sequence of SEQ ID NO: 1 a complement thereof or a fragment thereof. In one embodiment of the invention the fragment disclosed can be a primer or probe, which is capable to hybridise specifically to the DYXC1 nucleic acids described herein. The preparation and modification of primers and probes capable of binding to a known nucleic acid are well-established techniques in the art (see, for example, Current Protocols in Molecular Biology, eds. Ausubel et al, John Wiley & Sons: 1992). Generally, a primer or a probe is a substantially purified oligonucleotide being 12 to 60 nucleotides long, preferably 16 to 40 nucleotides. A primer or probe need not reflect the exact sequence of a template, i.e. a target nucleic acid, but must be sufficiently complementary to hybridise with the template under stringent conditions.

The invention also involves nucleotide sequence variants capable of encoding DYXC1 polypeptides. Such variants include sequences that differ from the disclosed DYXC1 nucleic acids by one or more nucleotide substitutions, additions or deletions, such as allelic variants. Said nucleotide substitutions may also arise due to the degeneracy of the genetic code. The nucleic acids of the invention can also be described as capable of hybridising under stringent conditions to the nucleic acid sequence of SEQ ID NO: 1 or 2 or a complement thereof. Such stringent DNA hybridisation conditions are well-known in the art, e.g. 6×NaCl/sodium citrate (SSC) at about 45° C. is applied for a hybridisation step, followed by a wash of 2×SSC at 50° C. or, e.g., alternatively hybridization at 42° C. in 5×SSC, 20 mM NaPO4, pH 6.8, 50% formamide; and washing at 42° C. in 0.2×SSC. Those skilled in the art understand that it is desirable to vary these conditions empirically based on the length and the GC nucleotide base content of the sequences to be hybridised, and that formulas for determining such variation exist (See, for example, Sambrook et al, "Molecular Cloning: A Laboratory Manual", Second Edition, pages 9.47-9.51, Cold Spring Harbor, N.Y.: Cold Spring Harbor Laboratory Press (1989)). Nucleic acids of the invention, fragments thereof and variants thereof with sufficient similarity to the non-coding strand of said nucleic acids to hybridise thereto under stringent conditions are useful for identifying, purifying, and isolating nucleic acids encoding other, non-human, mammalian forms of DYXC1. Thus, such polynucleotide fragments and variants are intended as aspects of the invention.

The present invention also provides plasmids and vectors encoding an DYXC1 polypeptide, which constructs can be used in the expression of said DYXC1 polypeptide in or from a host cell. The selecting of a suitable plasmid or vector for a certain use is within the abilities of a skilled artisan. As the host cell may be any prokaryotic or eukaryotic cell, a plasmid or vector encoding an DYXC1 polypeptide can be used to the production of said DYXC1 polypeptide as a recombinant protein via microbial or eukaryotic cellular processes. Typically, said plasmids and vectors comprises a ligated nucleic acid encoding a recombinant protein, said nucleic acid operably linked to at least one transcriptional regulatory sequence (See, for example, Sambrook et al, "Molecular Cloning: A Laboratory Manual", Second Edition, Cold Spring Harbor, N.Y.: Cold Spring Harbor Laboratory Press (1989)).

The present invention further describes the characterization of single nucleotide polymorphisms (SNPs) in human DYXC1 gene. SNPs can be used in mapping the human genome and, when a SNP is linked with a disease or condition, to clarify genetic basis of the disease or condition, in this particular case, at least of dyslexia. In this invention we have characterized five single nucleotide polymorphisms (SNPs) in DYXC1 mRNA (SEQ ID NOS:1 and 2). Accordingly, the present invention provides an DYXC1 nucleic acid comprising a SNP in any one of the following positions in the nucleic acid sequence of SEQ ID NO:1: position 4; 572; 1249 or 1259. Allelic variation at position 4 consists of a single base substitution from C preferably to T. Allelic variation at position 572 consists of a single base substitution from G preferably to A. Allelic variation at position 1249 consists of a single base substitution from G preferably to T. Allelic variation at position 1259 consists of a single base substitution from C preferably to G. The present invention also describes a SNP in DYXC1 mRNA at position-164 outside the coding sequence of DYXC1. This position corresponds to position 205 set forth in SEQ ID NO:2. Allelic variation at position −164 consists of a single base substitution from C preferably to T.

The SNP variant of DYXC1, wherein the single base substitution is at position 1249 (G→T), introduces a premature stop codon and is inherited with dyslexia in a three-generation family. The frequency of the polymorphism is significantly (p=0.0278) elevated in dyslexic subjects, compared to control samples as shown in Examples. The polymorphism truncates the predicted DYXC1 protein by four amino acids, suggesting that it is a functional SNP.

Further, new polymorphic gene regions in DYXC1 nucleic acids can be identified by determining the DYXC1 nucleic acid sequences in population of invidivuals. If new polymorphic region (e.g. SNP) is found, then the link with a specific disease can be determined by studying specific populations of individuals, such as dyslexics. A polymorphic site or region may be located in any part of a gene, e.g., exons, introns and promoter region.

The present invention makes available DYXC1 polypeptides. Such polypeptides can be recombinant proteins produced by, e.g., the host cells described hereinabove, said recombinant proteins being isolated from other cellular proteins. Preferably, said polypeptides have an amino acid which is at least about 78% identical or homologous to human DYXC1 protein of sequence set forth in SEQ ID NO: 3. In a preferred embodiment, an DYXC1 polypeptide of the present invention is mammalian, e.g. murine or human, DYXC1 protein. In addition, the present invention provides splice variants of DYXC1 protein.

An DYXC1 polypeptide of the invention can also be used as an antigen to produce antibodies. Techniques of preparing antisera, poly- or monoclonal antibodies are well-known protocols in the art (see, for example, Antibodies: A laboratory Manual, eds. Harlow and Lane, Cold Spring Harbor Laboratory Press: 1988). Thus, the present invention makes available DYXC1 specific antibodies. Especially, the antibodies of the invention can be labeled with a detectable label and used in the determination of the presence of DYXC1 polypeptides in a sample, e.g. for diagnosis of dyslexia.

The present invention further provides means for prognostic or diagnostic assays for determining if a subject has or is likely to develop dyslexia, which is associated with the variation or dysfunction of DYXC1. Basically, such assays comprise a detection step, wherein the presence or absence of a genetic alteration or defect in DYXC1 is determined in a biological sample from the subject. Said detection step can be performed, e.g., by methods involving sequence analysis, nucleic acid hybridisation, primer extension, restriction enzyme site mapping or antibody binding. These methods are well-known in the art (see, for example, Current Protocols in Molecular Biology, eds. Ausubel et al, John Wiley & Sons:1992).

In particular, the present invention is directed to a method of determining the presence or absence of an DYXC1 SNP of the invention in a biological sample from a human for diagnostics of dyslexia or for assessing the predisposition of an individual to dyslexia. Said method comprises determining the sequence of the nucleic acid of a human at one or more positions 4, 572, 1249 and 1259 in the DYXC1 gene or mRNA as defined in SEQ ID NO:1 and position 205 as defined by SEQ ID NO:2 and determining the status of the human by reference to polymorphism in DYXC1 gene. In a preferred embodiment the sample is contacted with oligonucleotide primers so that the nucleic acid region containing the potential single nucleotide polymorphism is amplified by polymerase chain reaction prior to determining the sequence. The final results can be obtained by using a method selected from, e.g., allele specific nucleic acid amplification, allele specific nucleic acid hybridisation, oligonucleotide ligation assay or restriction fragment length polymorphism (RFLP). These methods are well-known for a skilled person of the art (see, for example, Current Protocols in Molecular Biology, eds. Ausubel et al, John Wiley & Sons: 1992, or Landegren et al, "Reading Bits of Genetic Information: Methods for Single-Nucleotide Polymorphism Analysis", Genome Research 8:769-776).

The invention also features diagnostic or prognostic kits for use in detecting the presence of DYXC1 SNP in a biological sample. The kit provides means for the diagnostics of dyslexia or for assessing the predisposition of an individual to dyslexia mediated by variation or dysfunction of DYXC1. The kit can comprise a labeled compound capable of detecting DYXC1 polypeptide or nucleic acid (e.g. mRNA) in a biological sample. The kit can also comprise nucleic acid primers or probes capable of hybridising specifically to at least of portion of an DYXC1 gene or allelic variant thereof. The kit can be packaged in a suitable container and preferably it contains instructions for using the kit.

It is also realised in the present invention that transgenic non-human animals, such as transgenic mice, which include a heterologous form of an DYXC1 gene, can be designed and produced utilising the disclosure presented herein (see, for example, Manipulating the Mouse Embryo: A laboratory Manual, eds. Hogan et al, Cold Spring Harbor Laboratory Press, 1986). Such transgenic animals can be useful as animal models for studying, e.g., the function of DYXC1 gene and alleles thereof, or for expressing recombinant DYXC1 polypeptides.

A further embodiment of the present invention is a method for identifying a mutant DYXC1 nucleotide sequence in a suspected mutant DYXC1 allele which comprises comparing the nucleotide sequence of the suspected mutant DYXC1 allele with a wild-type DYXC1 nucleotide sequence or a part thereof, wherein a difference between the suspected mutant and the wild-type sequence identifies a mutant DYXC1 nucleotide sequence. In said method the sequence of said suspected mutant DYXC1 allele can be compared with the sequence of one or more wild-type DYXC1 gene sequences selected from the sequences set forth in SEQ ID NO: 1, SEQ ID NO:2, SEQ ID NO:6, SEQ ID NO:7, SEQ ID NO:8, SEQ ID NO:9, SEQ ID NO:10 and wild-type allelic variants thereof. For the screening of new point mutations, deletion mutations and insertion mutations in DYXC1 a plentiful of techniques well-known for a skilled artisan can be utilised, such as methods involving sequence analysis, nucleic acid hybridisation, primer extension, restriction enzyme site mapping and particularly methods described below in Experimental Section and Materials and Methods.

Screening Assays

The subject methods include screens for agents which modulate the activity of DYXC1 gene or protein. The methods are amenable to automated, cost-effective high throughput screening of chemical libraries for lead compounds. Identified reagents find use in the pharmaceutical industries for animal and human trials; for example, the reagents may be derivatized and rescreened in vitro and in vivo assays to optimize activity and minimize toxicity for pharmaceutical development. More specifically, identified reagents may find use in the treatment of dyslexia or brain ischemia.

The invention further provides methods (also referred to herein as "screening assays") for identifying modulators, i.e., candidate or test compounds or agents (e.g., peptides, peptidomimetics, peptoids, small molecules or other drugs) which bind to DYXC1 protein, have a stimulatory or inhibitory effect on, for example, DYXC1 expression or DYXC1 activity, or have a stimulatory or inhibitory effect on, for example, the expression or activity of a DYXC1 substrate. Compounds thus identified can be used to modulate the activity of DYXC1 in a therapeutic protocol, to elaborate the biological function of the DYXC1, or to identify compounds that disrupt normal DYXC1 activity. The preferred DYXC1 used in this embodiment are human, primate or mouse DYXC1 of the present invention.

In one embodiment, the invention provides assays for screening candidate or test compounds which are substrates of a DYXC1 protein or polypeptide or biologically active portion thereof. In another embodiment, the invention provides assays for screening candidate or test compounds which bind to or modulate the activity of a DYXC1 protein or polypeptide or biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. J. Med. Chem. 1994, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) Anticancer Drug Des. 12:145).

In one embodiment, an assay is a cell-based assay in which a cell which undergoes a simulated ischaemia is contacted with a test compound and the ability of the test compound to modulate DYXC1 activity is determined. Determining the ability of the test compound to modulate DYXC1 activity can be accomplished by monitoring, for example, cell death, cell growth, cell attachment, and cell chemotaxis. The cell, for example, can be of mammalian origin, e.g., a neuronal cell or a non-neuronal cell. In preferred embodiment, the ability of the test compound to modulate DYXC1 activity is accomplished by monitoring DYXC1 activation with Western blot, immunohistochemical staining using anti DYXC1 antibodies, or fluorometric assays.

Determining the ability of DYXC1 protein or a biologically active fragment thereof, to bind to or interact with an agent can be accomplished by one of the methods described above for determining direct binding. In a preferred embodiment, determining the ability of DYXC1 protein to bind to or interact with an agent can be accomplished by determining the activity of DYXC1 protein. For example, the activity of DYXC1 can be determined by detecting the induction of a reporter gene (recombinant DYXC1 gene products labelled with detectable marker), or detecting a target-regulated cellular response (i.e., cell attachment, cell adhesion, cell growth, cell death, neurite outgrowth or cell migration).

In yet another embodiment, an assay of the present invention is a cell-free assay in which DYXC1 protein or biologically active portion thereof is contacted with a test compound and the ability of the test compound to bind to DYXC1 protein or biologically active portion thereof is determined.

Assays for the Detection of the Ability of a Test Compound to Modulate Expression of DYXC1

In another embodiment, modulators of DYXC1 expression are identified in a method wherein a cell is contacted with a candidate compound/agent and the expression of DYXC1 mRNA or protein in the cell is determined. The level of expression of DYXC1 mRNA or protein in the presence of the candidate compound is compared to the level of expression of DYXC1 mRNA or protein in the absence of the candidate compound. The candidate compound can then be identified as a modulator of DYXC1 expression based on this comparison. For example, when the expression of DYXC1 mRNA or protein is higher (i.e. statistically significantly higher) in the presence of the candidate compound than in its absence, the candidate compound is identified as a stimulator of DYXC1 mRNA or protein expression. Alternatively, when expression of DYXC1 mRNA or protein is lower (i.e. statistically significantly lower) in the presence of the candidate compound than in its absence, the candidate compound is identified as an inhibitor of DYXC1 mRNA or protein expression. The level of DYXC1 mRNA or protein expression in the cells can be determined by methods described herein for detecting DYXC1 mRNA or protein or by methods which a skilled artisan can readily adapt for use in the present invention.

Combination Assays

In another aspect, the invention pertains to a combination of two or more of the assays described herein. For example, a modulating agent can be identified using a cell-based or a cell free assay, and the ability of the agent to modulate the activity of DYXC1 protein can be confirmed in vivo, e.g., in an animal such as an animal model for brain ischemia.

This invention further pertains to novel agents identified by the above-described screening assays. Accordingly, it is within the scope of this invention to further use an agent identified as described herein in an appropriate animal model. For example, an agent identified as described herein (e.g., a DYXC1 modulating agent, an antisense DYXC1 nucleic acid molecule, a DYXC1-specific antibody, or a DYXC1-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The choice of assay format will be based primarily on the nature and type of sensitivity/resistance protein being assayed. A skilled artisan can readily adapt protein activity assays for use in the present invention with the genes identified herein.

One preferred embodiment of the invention is a screening method, wherein a compound that modulates the expression of DYXC1 is identified, the method comprising:
  (a) incubating a cell that can express DYXC1 gene with a compound under conditions and for a time sufficient required for the cell to express DYXC1 gene, when the compound is not present;
  (b) incubating a control cell under the same conditions and for the same time without the compound;
  (c) measuring expression of DYXC1 gene in the cell in the presence of the compound;
  (d) measuring expression of DYXC1 gene in the control cell; and
  (e) comparing the amount of expression of DYXC1 gene in the presence and absence of the compound, wherein a difference in the level of expression indicates that the compound modulates the expression of DYXC1 gene Another preferred embodiment of the invention is a method of identifying a compound that modulates DYXC1 activity, the method comprising:

(a) incubating a cell that has said activity with a compound under conditions and for a time sufficient required for the cell to express said activity, when the compound is not present;
  (b) incubating a control cell under the same conditions and for the same time without the compound;
  (c) measuring said activity in the cell in the presence of the compound;
  (d) measuring said activity in the control cell; and
  (e) comparing the amount of said acitivity in the presence and absence of the compound, wherein a difference in the level of activity indicates that the compound modulates the activity of said gene Another preferred emdiment of the invention is a method for affinity purification of a substance that binds to the DYXC1, comprising the following steps: a) contacting a source suspected to contain said substance with an immobilized DYXC1 under conditions whereby said substance to be purified is selectively adsorbed onto the immobilized DYXC1; (b) washing the immobilized DYXC1 and its support to remove non-adsorbed material; and (c) eluting said substance from the immobilized DYXC1 to which they are adsorbed with an elution buffer.

Experimental Section

Fine Mapping of the Translocation Breakpoint

Figure 1B:
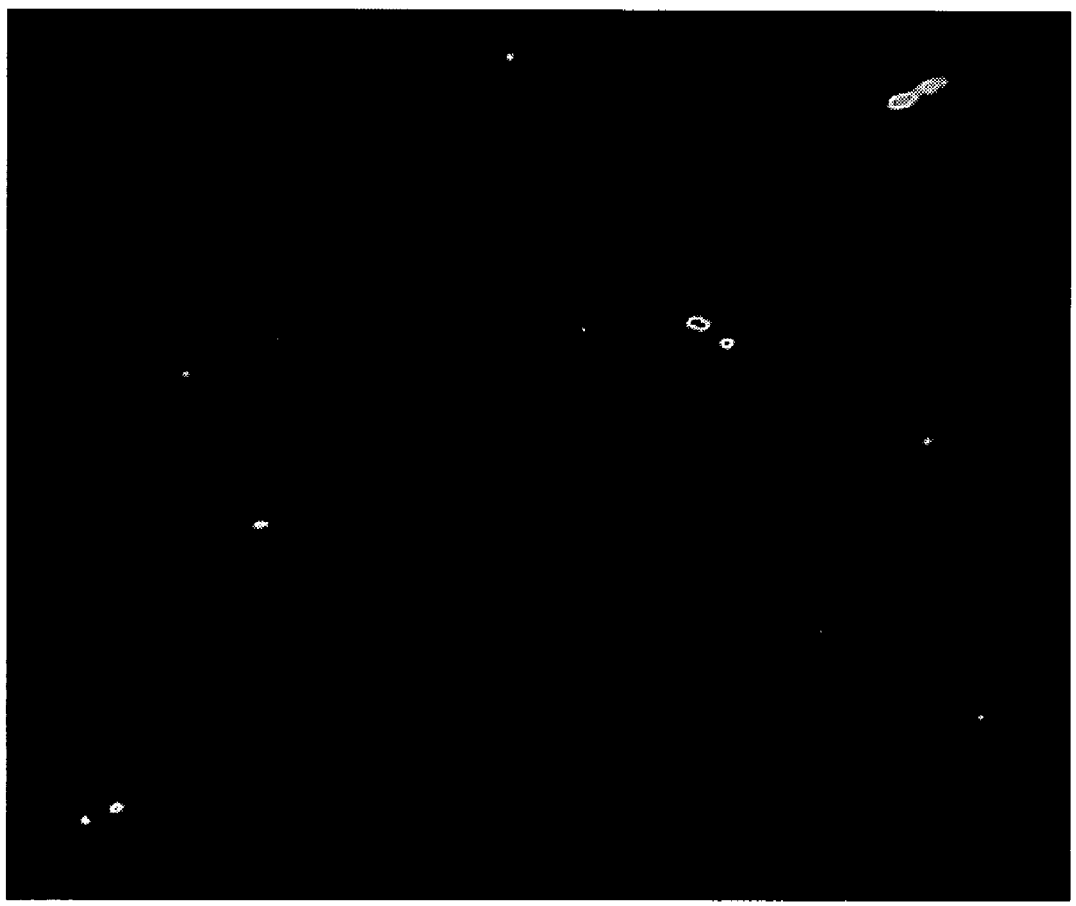
Figure 1C:
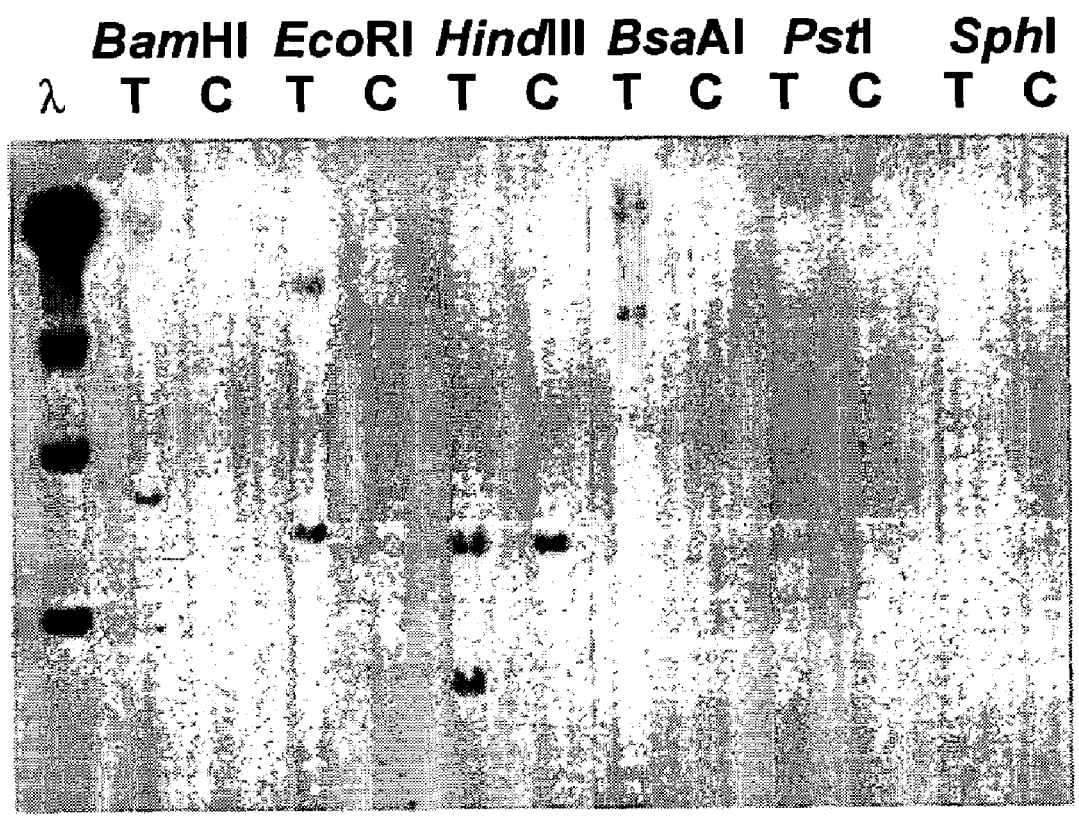
Figure 1D:
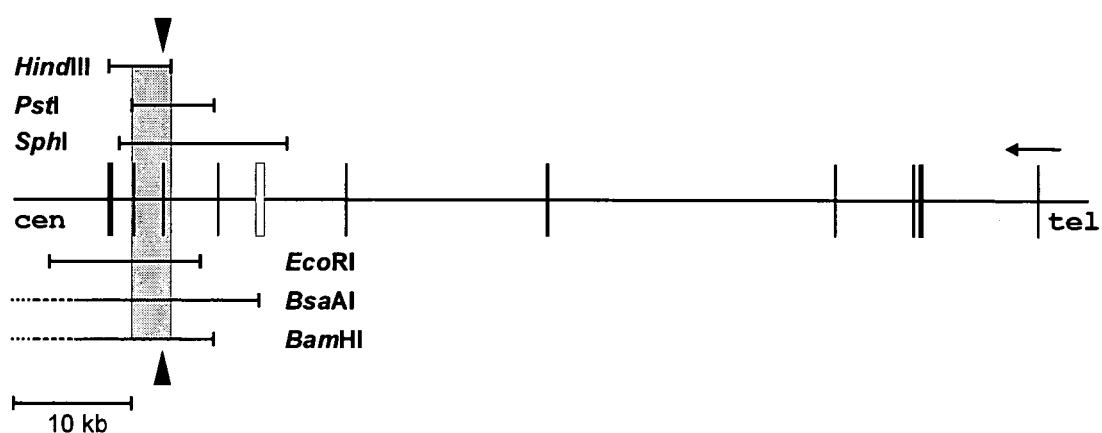

The translocation and the phenotypes of the members of the family studied here (FIG. 1A) have been described previously (12). Fluorescent in situ hybridization (FISH) restricted the location of the translocation breakpoint within the BAC clone RP-11-178D12 (AC013355; FIG. 1B). The clone contained two known genes, cell-cycle restoration protein 8 (CPR8) and complementation class B phosphoinositol glycan (PIG-B), in addition to the genes described herein. To further localize the breakpoint, we used amplified non-repetitive genomic DNA fragments from the BAC clone RPCI-11-178D12 as probes in Southern hybridization. A probe corresponding to nucleotides 102317-102837 of the complete sequence of 178D12 revealed a genomic rearrangement with 6 different restriction enzymes (FIG. 1C). Thus, we could pinpoint the breakpoint to a region of 3229 bp, limited by the restriction sites for PstI and HindIII (FIG. 1D). The breakpoint region includes exons 8 and 9 of a novel gene, DYXC1 (see below).

Characterization of DYXC1

The coding sequence of DYXC1 was predicted in silico from the genomic sequence of BAC clones RP11-178D12 and CTD-2137J4. Exon-intron boundaries were confirmed with RT-PCR. The length of DYXC1 mRNA, obtained by RT-PCR, is 1993 bp, and it encodes a predicted protein of 420 amino acids. DYXC1 consists of 10 exons spanning approximately 78 kb of genomic DNA (FIG. 1D). Three promoter prediction programs (see below) identified a promoter precisely before the 5' end of the RT-PCR obtained mRNA, suggesting that the cloned mRNA is nearly complete. The start codon (AUG) of DYXC1 is located 369 bp from the predicted transcription initiation site in exon 2. Putative promoter of DYXC1 has a TATA box (TATAAAT) at position −31.

Database searches revealed several mouse ESTs homologous to the human DYXC1 mRNA. We could thus construct the mouse mDYXC1 in silico by connecting the overlapping EST clones. The mDYXC1 mRNA (SEQ ID NO: 4) encodes a 421-residue protein (SEQ ID NO: 5) that is 78% identical with the human DYXC1 (FIG. 2A). The human DYXC1 protein does not have any significant homologies to other known proteins. It has, however, three C-terminal tetratricopeptide repeat (TPR) domains, corresponding to amino acids 290-323, 324-357, and 366-399. These TPR domains are thought to mediate protein-protein interactions (14, 15).

Figure 2B:
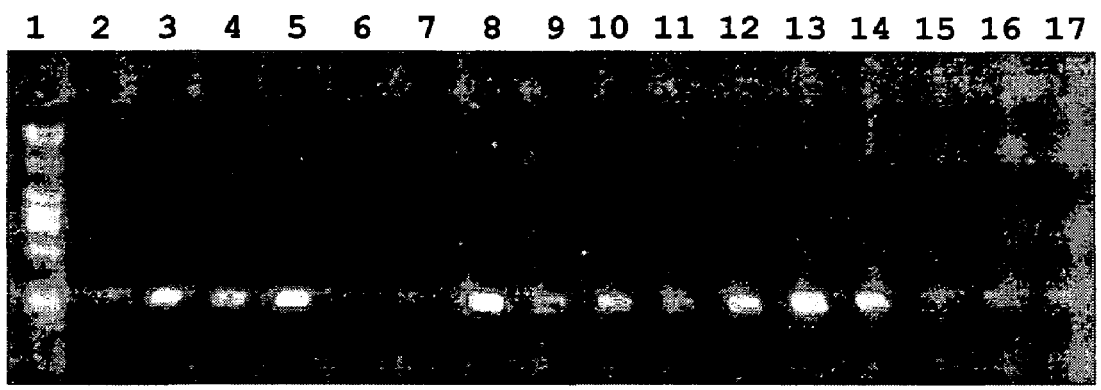
Figure 2C:
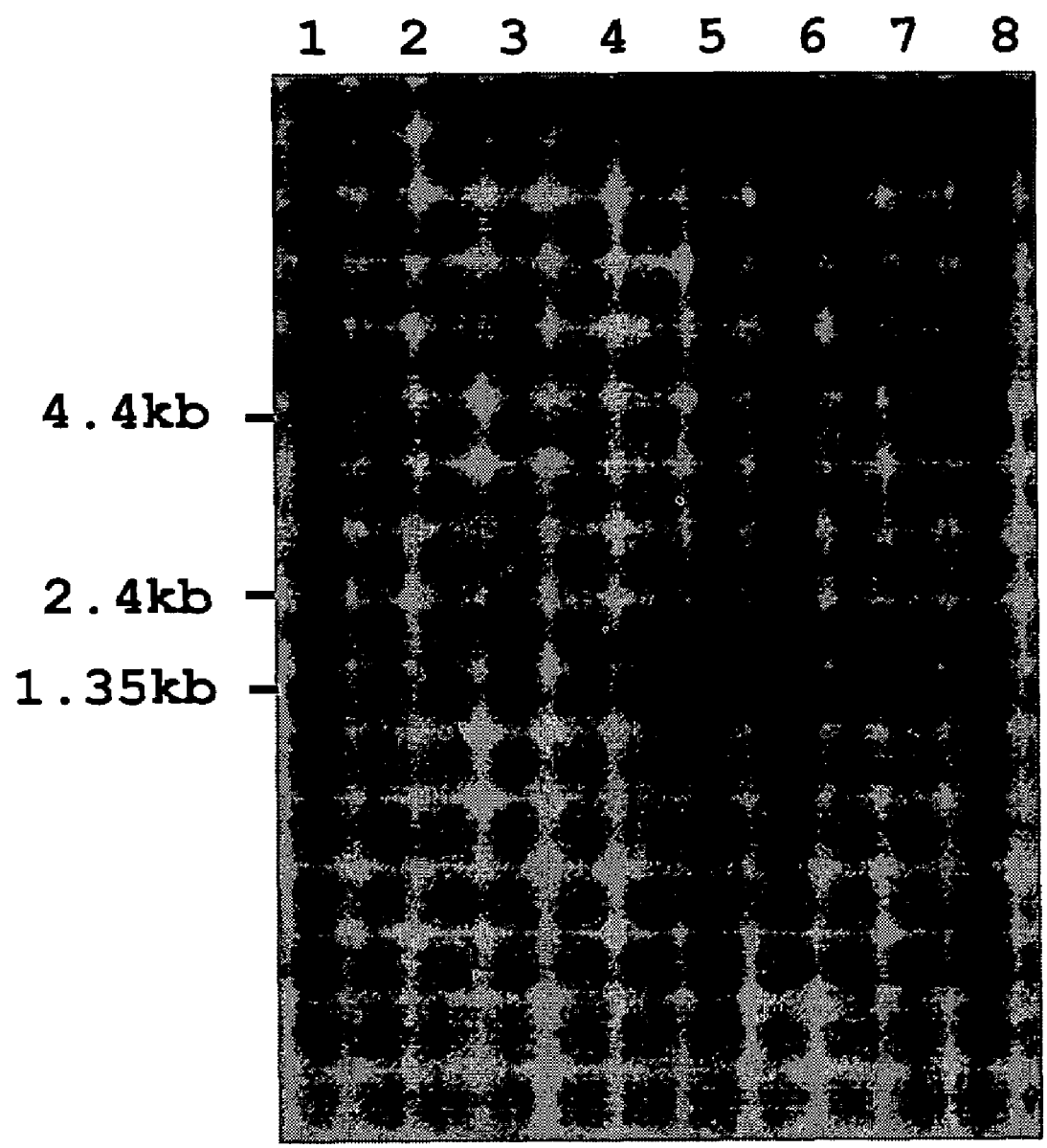
Figure 2D:
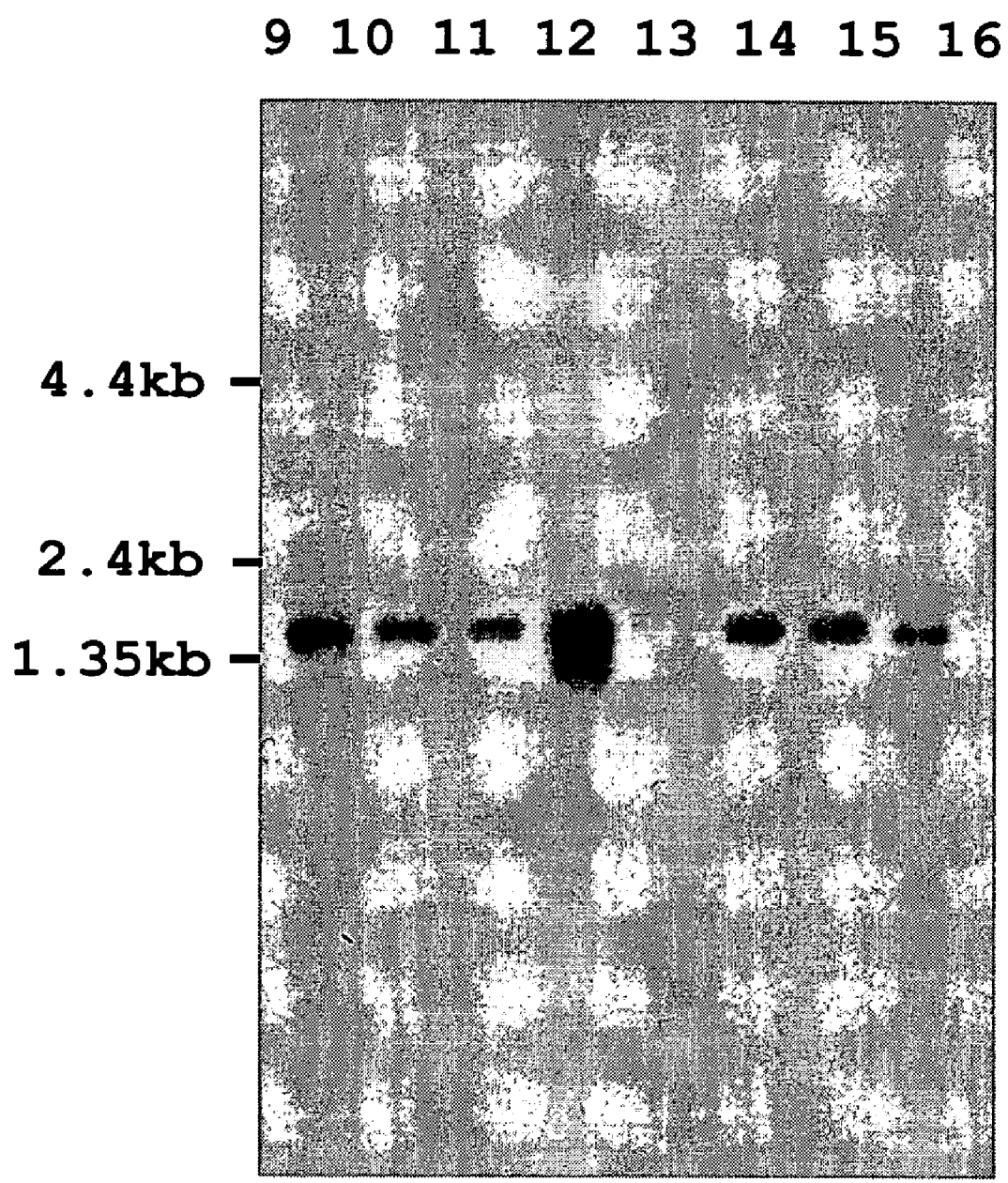

The human DYXC1 mRNA appears to exist in several different splice forms: exons 9 and 2 can be omitted, and there is an alternative acceptor splice site in intron 2. All these arrangements, however, alter the reading frame, leading to truncated protein products. DYXC1 mRNA can be found in several tissues. It is most abundantly expressed in brain, lung, kidney and testis (FIG. 2B). Northern blot of human adult kidney tissue revealed an approximately 2 kb transcript, corresponding to the predicted size of DYXC1 mRNA (FIG. 2C).

Figure 2E:
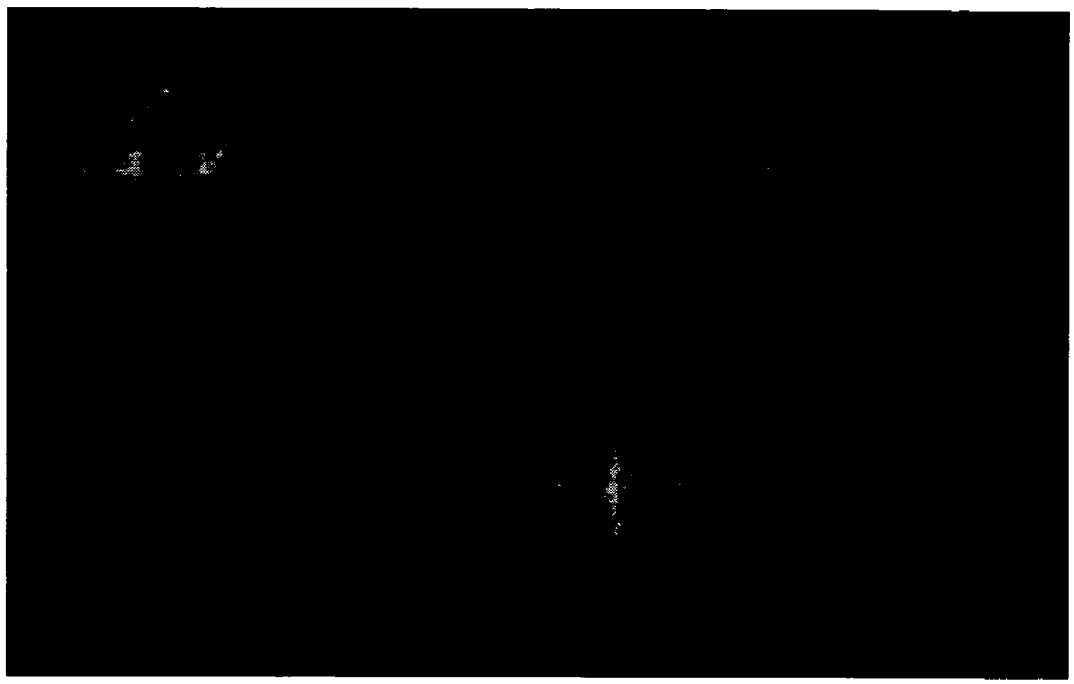

The cellular localization of DYXC1 in transfected monkey kidney COS-1 cells was studied using immunofluorescence. The full-length DYXC1 cDNA was cloned into a mammalian expression vector containing a C-terminal V5 epitope and a polyhistidine tail. DYXC1-V5/His fusion protein showed a staining pattern similar to DAPI staining, suggesting that DYXC1 is a nuclear protein (FIG. 2E).

Association Analysis of DYXC1 SNPs

Figure 3:
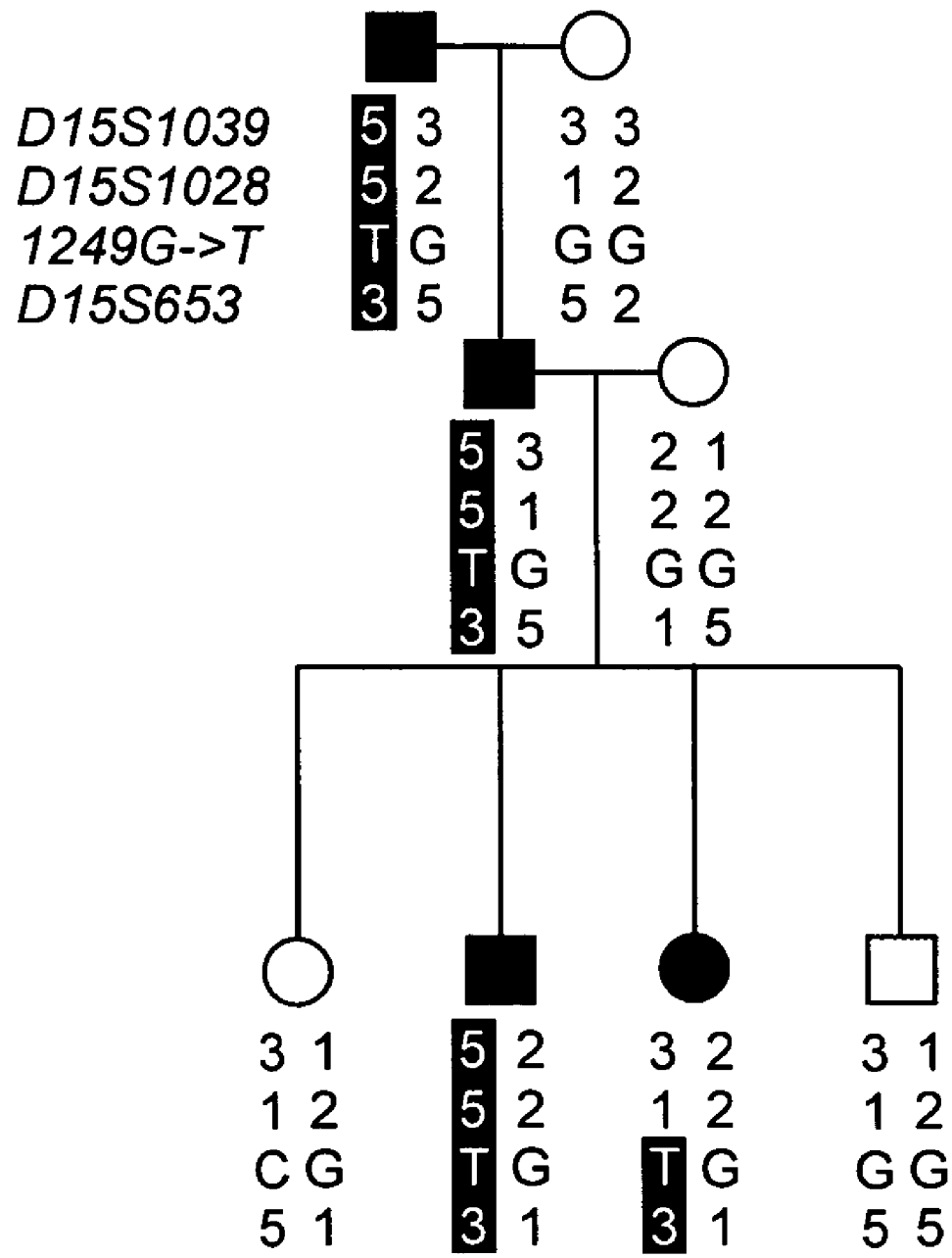
FIG. 3. Pedigree of the family in which two DYXC1 polymorphisms are transmitted with dyslexia. Alleles for four loci are shown below individuals. Black rectangle indicates the haplotype transmitted with dyslexia in this family.

The present invention also describes single nucleotide polymorphism in DYXC1. In order to find polymorphisms in DYXC1, we screened the DYXC1 cDNA from 57 dyslexic individuals from 22 unrelated families with single-stranded conformation polymorphism (SSCP) analysis to characterize sequence variants. As a control, we screened 91 anonymous blood donors from Turku and Kuopio, and 15 non-dyslexic subjects from the 22 dyslexia families. In this way, we found three SNPs. Two of the SNPs (4C→T, 572G→A) were in the coding region, whereas a third one (−164C→T) resided in the 5' untranslated region (Table 1). Both the SNPs in the coding region resulted in amino acid substitutions.

nation showed that this alteration did not segregate with dyslexia in the extended pedigree. Likewise, the frequency of 572G→A did not differ significantly between the two groups. The third SNP, −164C→T was found in 6 dyslexic individuals from three families and in 5 control subjects. In one three-generation family, the T allele segregated with dyslexia (FIG. 3). In the other two families, there was no consistent pattern of inheritance with dyslexia.

To search for additional SNPs, we sequenced the whole coding region of DYXC1 from an individual carrying the T allele in the family presented in FIG. 3. We found a G to T transversion at position 1249 of the DYXC1 mRNA, which results in a substitution of a glutamic acid for an ochre stop codon at amino acid position 417. The appearance of a stop codon leads to the deletion of the C-terminal tetrapeptide Glu-Leu-Lys-Ser (residues 417-420 of SEQ ID NO: 3). In the family of FIG. 3, 1249G→T was transmitted in the same chromosome as −164C→T, thus segregating with dyslexia.

Screening of all 57 dyslexic subjects for 1249G→T showed that the SNP is relatively common with a frequency of 0.123 (14/114 chromosomes). In the control group, the frequency was only 0.055 (10/174 chromosomes in blood donor samples, 1/28 chromosomes in control subjects of dyslexia families). All the control subjects were heterozygous for the SNP, whereas there was one dyslexic subject homozygous for the SNP. In conclusion, the frequency of 1249G→T is significantly (p=0.0278) higher in dyslexic individuals.

In further studies we found three more SNPs. One of the SNPs (271 G→A) was in the coding region and resulted in amino acid substitution, whereas two (−3G→A and −2G→A) resided in the 5' untranslated region (Table 1). SNP −3G→A showed significant association with dyslexia (P=0.006). SNP −3G→A is located in the binding sequence of the transcription factors Elk-1, HSTF, and TFII-1. Elk-1 is a transcriptional activator expressed in rat brain neurons and its activation has been associated with learning in rats. The −3G→A SNP affects also the Kozak sequence near the translation initiation site.

Primate Genes

The nonhuman primates chimpanzee, pygmy chimpanzee, gorilla and orangutan were sequenced for the genomic

TABLE 1

Frequency of single nucleotide polymorphisms in dyslexic subjects and controls.

| SNP | Codon change | Amino acid position | Frequency Dyslexia | n | Control | n | p-value |
|---|---|---|---|---|---|---|---|
| −164C → T* | — | — | 0.0517 | 58 | 0.0286 | 105 | 0.2219 |
| −3G → A** | — | — | 0.083 | 54 | 0.031 | 113 | 0.0020 |
| −2G → A*** | — | — | 0.009 | 54 | 0 | 113 | 0.7150 |
| 4C → T | Pro → Ser | 2 | 0.0172 | 58 | 0 | 105 | 0.1259 |
| 271G → A | Val → Ile | 90 | 0.019 | 54 | 0.053 | 113 | 0.9248 |
| 572G → A | Gly → Glu | 191 | 0.4811 | 53 | 0.5202 | 99 | 0.7792 |
| 1249G → T | Glu → STOP | 417 | 0.1228 | 57 | 0.0545 | 101 | 0.0278 |
| 1259C → G | Ser → Cys | 420 | 0.0789 | 57 | 0.0769 | 104 | 0.9482 |

*corresponds to position 205 set forth in SEQ ID NO: 2
**corresponds to position 366 set forth in SEQ ID NO: 2
***corresponds to position 367 set forth in SEQ ID NO: 2

4C→T, a nonconservative substitution of proline-2 to serine-2, was found from two dyslexic individuals (a father and a son), but not in any of the control subjects. Further examisequences corresponding to human exons and differed for 3, 2, 5 and 6 amino acids (0.7%, 0.5%, 1.2% and 1.4% of residues), respectively (Table 2).

TABLE 2

Comparison of DYXC1 cDNA between human and four nonhuman primates.
Nucleic acid and amino acid changes are shown for each exon
of DYXC1 in comparison to the human sequence; + indicates
the presence of a change in a nonhuman species.

| Exon | Nucleic acid change | Amino acid change | Chimpanzee | Pygmy chimpanzee | Gorilla | Orangutan |
|---|---|---|---|---|---|---|
| 1 | none | | | | | |
| 2 | 6T>C | | + | + | + | + |
| 2 | 47C>T | A16>V | | | + | |
| 2 | 48G>C | | + | | | |
| 2 | 107C>T | T36>M | + | | | |
| 3 | none | | | | | |
| 4 | 284T>C | M95>T | | | | + |
| 4 | 384C>T | | + | + | + | + |
| 5 | 473C>A | A158>E | + | + | + | + |
| 5 | 516A>C | Q172>H | | | | + |
| 5 | 520A>G | K174>E | | | + | |
| 5 | 540A>G | | | | + | |
| 5 | 572G>A | G191>E | + | + | + | + |
| 5 | 583A>T | I195>L | | | + | + |
| 5 | 591T>C | | | | + | |
| 5 | 611T>C | L204>S | | | + | |
| 5 | 624T>C | | | | + | |
| 6 | 639G>A | | | | | + |
| 7 | 789A>G | | | + | | |
| 8 | 909G>A | | + | + | + | + |
| 9 | none | | | | | |
| 10 | none | | | | | |

Remarkably, the DYXC1 protein differs from its pygmy chimpanzee and chimpanzee counterparts at 2-3 amino acids, but from gorilla and orangutan at 5-6 residues. For comparison, the level of coding divergence is higher for DYXC1 than that observed for FOXP2, the product of a gene implicated in a speech and language disorder (26). Thus, as suggested for FOXP2, the DYXC1 gene may reveal important evolutionary differences related to brain functions between the primates.

Expression of DYXC1 Protein in Human Brain

Figure 4:
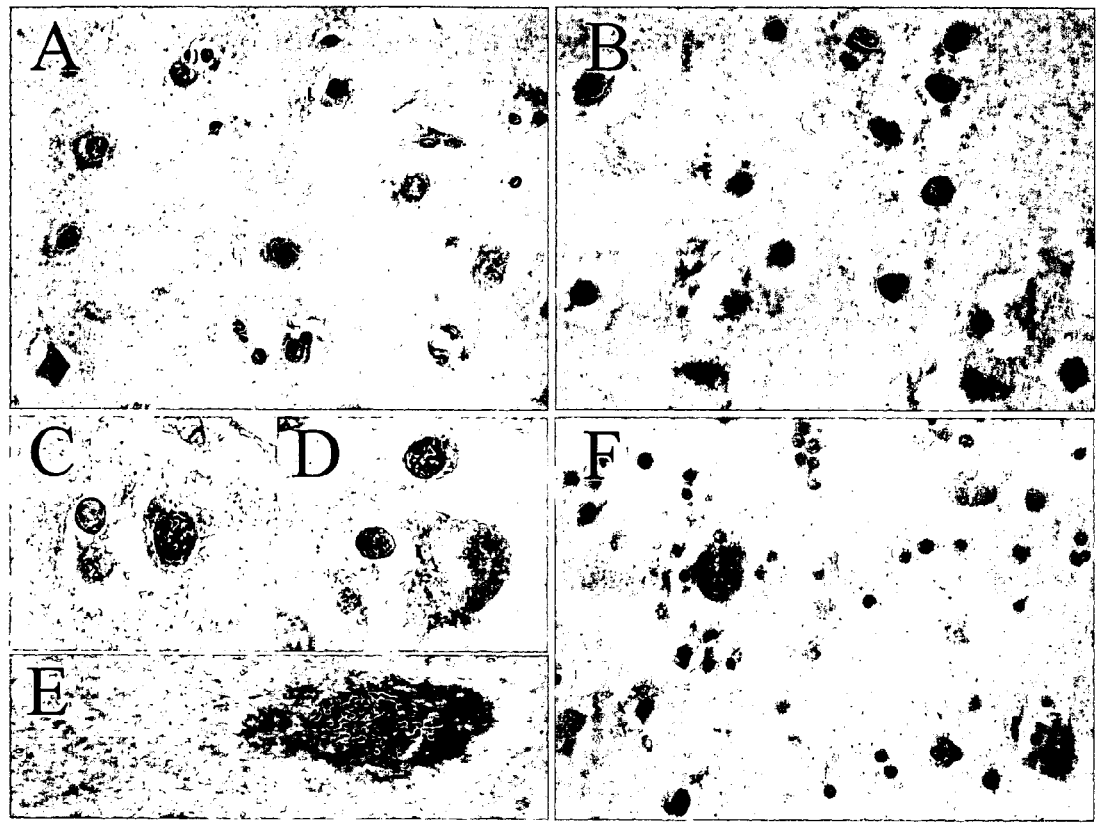
FIG. 4. Immunostaining patterns for DYXC1 observed in normal human brain tissue from an individual died immediately after sudden cardiac arrest. A, Characteristic immunoreactivity in cortical brain tissue demonstrating a variable density of nuclear expression in a minority of neurons. (Original magnification ×30). B, Typical staining result in white matter, where also a fraction of cell nuclei are densely positive in contrast to clearly negative adjacent cell nuclei. (×40). C, Positive neuronal nucleus adjacent to negative glial cell nuclei (×100). D, Negative neuronal cell body adjacent to neighboring small cells representing probably glial cells (×100). E, High magnification illustration of a large pyramidal neuron expressing clearly intranuclear localization of DYXC1 protein (×100). F, Typical view of an adjacent tissue section stained with preimmune (control) serum indicating the lack of non-specific staining in neuronal and glial cell nuclei (×30).

Light microscopy of normal human brain sections revealed a strikingly nuclear expression pattern for DYXC1 immunoreactivity, consistent with the transfection results. Both in cortical neuronal cell populations and white matter glial cells, a minority of cell nuclei expressed DYXC1 immunoreactivity (FIGS. 4A,B,E). Characteristically, even neighbouring, identical appearing cells had different expression (FIGS. 4C,D), which, together with the lack of staining obtained with preimmune serum (FIG. 4F), supports the specificity of the observed immunoreactivity.

Figure 5:
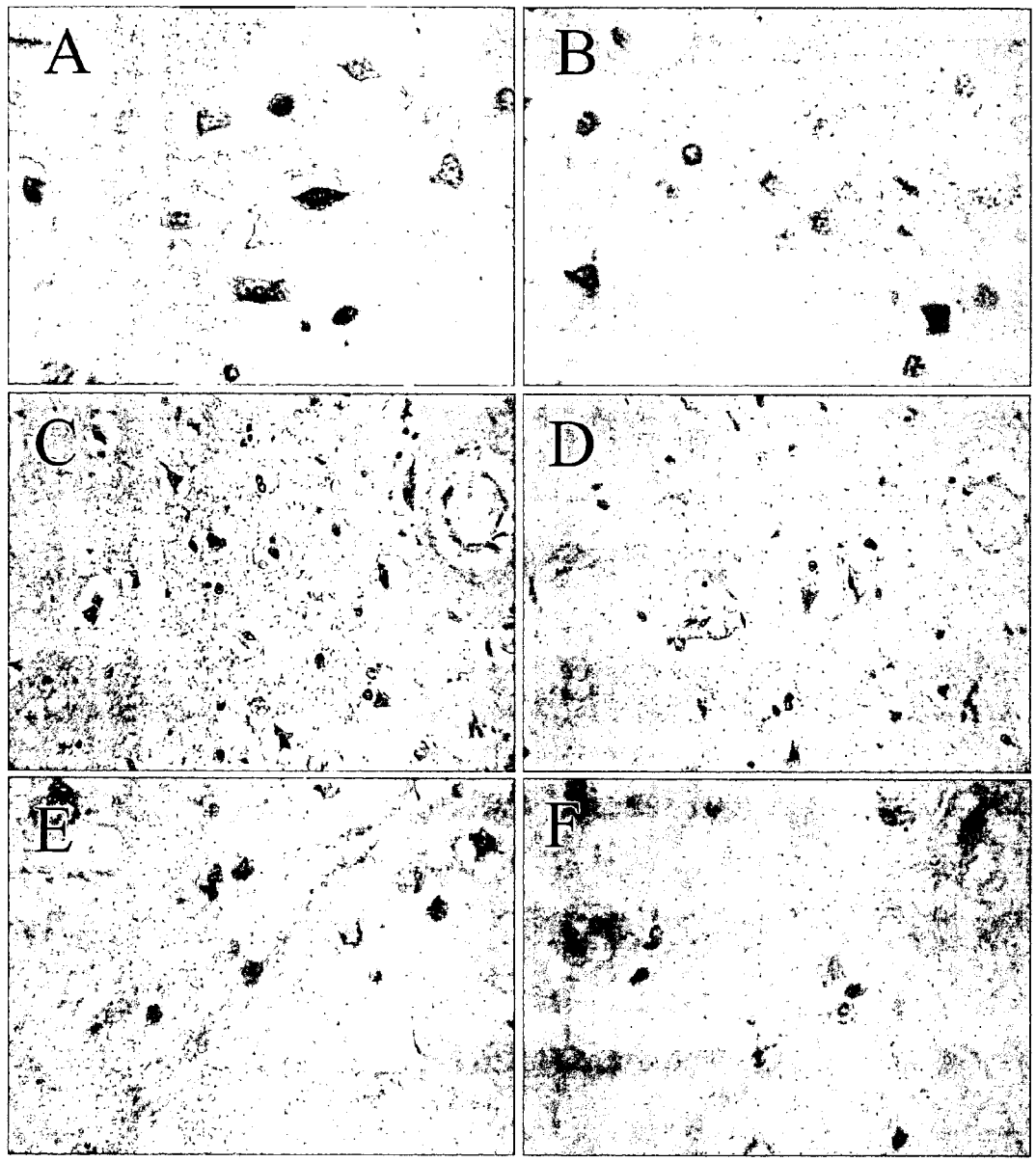
FIG. 5. Immunostaining patterns for DYXC1 observed in human ischemic brain tissue of three victims of acute ischemic stroke. A, Typical immunostaining result in a subject deceased at 23 h after the onset of stroke symptoms. Note the characteristically cytoplasmic staining pattern present in a subset of ischemic neurons. Compare to FIG. 4 from non-ischemic brain tissue, where typically nuclear expression was found. (×40). B, Same neuronal population identified from adjacent section stained with preimmune (control) serum (×40). C, Typical immunostaining pattern in ischemic brain tissue area of another subject deceased 26 h after the onset of stroke symptoms. Note the increased fraction of pyknotic neurons expressing dense, predominantly nuclear, DYXC1 immunoreactivity. (×20). D, Same neuronal population identified from adjacent section stained with preimmune (control) serum (×20). E, Immunoreactivity for DYXC1 observed in a more advanced, vacuolized, stage of tissue ischemia demonstrating faint expression also in neuronal processes. This subject died 60 h after the onset of stroke symptoms. (×40). F, Same tissue area identified from adjacent section stained with preimmune (control) serum (×40).

We studied DYXC1 immunoreactivity also in individuals died soon after the onset of acute ischemic stroke (FIG. 5). In contrast to the typically nuclear expression in the normal brain, also cytoplasmic expression was observed in ischemic brain areas (FIG. 5A). In cortical areas representing early ischemic morphology, the fraction of positive cell nuclei or cytoplasms appeared increased (FIG. 5C) as compared to non-ischemic brain or contralateral hemispheres. In most ischemic sections studied, also structures corresponding to neuronal processes were frequently found to be immunoreactive for DYXC1 (FIG. 5E). Since only a limited number of subjects with short post-ischemic intervals were available, quantitative or statistical analysis of expression was not attempted.

Observations from both normal and ischemic human brains demonstrated that DYXC1 protein is expressed in a fraction of human glial and neuronal cells. Since only a fraction of neighbouring, identical appearing cells expressed DYXC1 immunoreactivity, we suggest that DYXC1 does not represent a structural house-keeping element of brain cells. Instead, it may relate to the functional state of the cells. Examination of DYXC1 expression in ischemic brain tissue suggested that it is involved dynamically in the functional cell state changing in the face of metabolic challenge. Since the topographic expression in the ischemic tissue included cytoplasms and even neuronal processes, DYXC1 may also have extranuclear functions, and may be rapidly translocated from nuclei to cytoplasms when the cell undergoes metabolic stress. These results from human cerebral ischemia warrant more systematic studies on the role of DYXC1 in cell stress and ischemia as well as dyslexia.

Materials and Methods

Ascertainment of Patients and Psychological Assessment

Patients were selected among families of dyslexic children from the Department of Pediatric Neurology at the Hospital for Children and Adolescents, University of Helsinki, Finland and from the Association of Learning Disabled Individuals of Helsinki (HERO), participating in the genetic study of dyslexia. The study was approved by the Ethical Committee of The Children's Castle Hospital and informed consent was obtained from the participants. Pedigrees of two families are shown in FIG. 1A and FIG. 3. The diagnosis and degree of dyslexia was determined by Finnish reading and spelling tests designed for children (16) and adults (17). The intelligence quotient (IQ) was determined by WAIS-R (18) or WISC-R (19). Reading-related neurocognitive skills (phonological awareness, rapid naming and verbal short-term memory) were assessed by neuropsychological tests (20-23).

FISH and Southern Blotting.

RPCI-11 BAC clone 178D12 (Genbank accession number AC013355) was used as a probe in fluorescent in situ hybridization. The protocol for FISH has been previously described (12). 15 μg of total genomic DNA from an individual carrying the translocation and from an unrelated control person was digested with BamHI, EcoRI, HindIII, BsaAI, PstI, or SphI, and run in 0.7% agarose gel. DNA was transferred to Hybond N+membrane (Amersham Pharmacia Biotech) with standard alkaline blotting method. PCR fragments derived from human genomic DNA were TA-cloned into pCR2.1 TOPO-TA vector (Invitrogen, Carlsbad, Calif.), and insert was removed with EcoRI digestion and gel-purified (Qiagen, Venlo, The Netherlands). α32P-labeled insert was used as a probe in Southern hybridization. Hybridization was performed overnight at 65° C. in Church buffer (0.5 M NaHPO$_4$, 1 mM EDTA, 7% SDS, 1% BSA), and the filter was washed in 2×SSC, 0.05% SDS at 65° C. for 1 hour. Filters were autoradiographed with a phospho-imager plate.

Cloning of DYXC1 and Sequence Analysis

Novel genes in the sequence of clone 178D12 were predicted in silico with Genscan (24) and Fgenes software. Predicted genes were confirmed by sequencing RT-PCR products. DYXC1 cDNA has been deposited in GenBank with accession number AF337549. Mouse mDYXC1 was constructed from two overlapping EST sequences (accession numbers BG242087 and AK005832) and verified by comparing it to all available mouse mDYXC1 EST sequences. cDNA sequences of mDYXC1 and hDYXC1 were aligned with ClustalX. The alignment was improved manually, and shaded with BOXSHADE. The secondary structure of the TA rich region was predicted with MFOLD (available at http://bioinfo.math.rpi.edu/~mfold/dna/form1.cgi) with default parameters. The expression of DYXC1 was analyzed by RT-PCR from Clontech's multiple tissue cDNA panels 1 and 2. RT-PCR was performed in 25 μl volume in the following conditions: 94° C. 2' (94° C. 1', 68° C. 2')×30, 1×DyNAzyme buffer with MgCl$_2$ (Finnzymes, Espoo, Finland), 0.2 u DyNAzyme II polymerase (Finnzymes), 15 pmol forward primer GTTGACAGAATGCTGTTCCACGTCG (SEQ ID NO:11), 15 pmol reverse primer CAAGCTGAGGCACGAAGAGCAATGA (SEQ ID NO:12). Promoter region of DYXC1 was predicted with TSSG and TSSW software at Baylor College of Medicine, available at the Baylor College of Medicine website, and neural network promoter prediction (NNPP) software at University of California, Berkeley, available at the University of Califorina, Berkeley website. The genomic sequences of nonhuman primates corresponding to all exons were determined by direct sequencing after PCR amplification with human-specific intronic primers (primer sequences are listed in Table 3).

TABLE 3

Human-specific intronic primers for DYXC1 (SEQ ID NOS: 22-42).

| Primer Name | Primer Sequence | Primer Length | Product Length | Exon | SEQ ID NO: |
|---|---|---|---|---|---|
| EKN1-1F | AACAGACTGCCTGGTGCTCT | 20 | 268 bp | exon 1 | 22 |
| EKN1-1R | CACACCAAAGTTTGAGAACCACT | 23 | | | 23 |
| EKN1-2.1R | AAGATGAGCCTGTTGCTCGT | 20 | 476 bp | exon 2 | 24 |
| EKN1-2.1F | CAAGCAGAGGGTATGGGTCTAC | 22 | | | 25 |
| EKN1-2R | AGAAGCTTCGGACCACACC | 19 | 431 bp | exon 2 | 26 |
| EKN1-3F | CGCGTGCTTAATTTGTGTAA | 20 | 299 bp | exon 3 | 27 |
| EKN1-3R | TCCCCTACACAATATAGGTGCTT | 23 | | | 28 |
| EKN1-4F | AAAGAAATCTCATCCTGGGTCA | 22 | 327 bp | exon 4 | 29 |
| EKN1-4R | GAAAATGCTGAGGAAGTCCAG | 21 | | | 30 |
| EKN1-5F | CAATGGCAAGAGTTTAGAGGTATG | 24 | 456 bp | exon 5 | 31 |
| EKN1-5R | TCAATGTGCCAAAACAGTAACC | 22 | | | 32 |
| EKN1-6F | TGTTTAGGATTTGGGGGTGA | 20 | 395 bp | exon 6 | 33 |
| EKN1-6R | GGAAATTCTAAAACATATTCATGACG | 26 | | | 34 |
| EKN1-7F | CCACTGGAGGAAGATGGAAA | 20 | 244 bp | exon 7 | 35 |
| EKN1-7R | TGTCTTCATACATGATAAAGCTCAT | 25 | | | 36 |
| EKN1-8F | GGTAAGCCATCCTCTTTGTCA | 21 | 337 bp | exon 8 | 37 |
| EKN1-8R | TCAACTGAACAGAAAAGATCATCA | 25 | | | 38 |
| EKN1-9F | CTCCCCAAGTGTTGGGATTA | 20 | 305 bp | exon 9 | 39 |

TABLE 3-continued

Human-specific intronic primers for DYXC1 (SEQ ID NOS: 22-42).

| Primer Name | Primer Sequence | Primer Length | Product Length | Exon | SEQ ID NO: |
|---|---|---|---|---|---|
| EKN1-9R | TGGAGTCCTTAAAAGTCACGA | 21 | | | 40 |
| EKN1-10F | GGTACTTGTTCTGAACCATGCTACTA | 26 | 502 bp | exon 10 | 41 |
| 126403-F | CAAGGGCAAGCTTAATTCAGTAACACA | 27 | | | 42 |

Single-Strand Conformational Polymorphism Analysis (SSCP)

DYXC1 exons were amplified with PCR (primer sequences available from the inventors on request) and digested with suitable enzymes to obtain 100-300 bp fragments. Denaturing gel was run for 16 hours at room temperature with 5 W constant power. Gels were stained with silver according to standard protocols.

SNP Analysis

Polymorphisms −164C→T, 4C→T, and 572G→A introduced novel Tsp45I, MnlI, and MboII restriction sites, respectively. Exon-specific PCR products were digested with the appropriate enzyme and run on a 1.5% agarose gel (−164C→T, 4C→T) or on a polyacrylamide gel (572G→A), followed by silver staining. As 1249G T had no effect on restriction sites, exon 10 was directly sequenced from all subjects. A standard one-tailed Fisher exact test was used to evaluate the statistical significance.

Cellular Localization of DYXC1

Full-length DYXC1 cDNA was cloned into pcDNA3.1/V5-6×His expression vector (Invitrogen). Monkey kidney COS-1 cell line was transfected with 3 μg of the construct, with FuGENE6 (Roche) as a transfection reagent, according to manufacturer's protocols. Cells were stained with mouse anti-V5 antibody (Invitrogen) and FITC-conjugated goat anti-mouse IgG (Sigma-Aldrich). Nuclei were stained with DAPI. The specificity of anti-V5 antibody was tested with standard western blotting methods.

Immunohistochemical Study of Brain

To investigate whether DYXC1 is expressed in mature human brain, brain tissue from six deceased individuals was stained with anti-DYXC1-antiserum raised in rabbits against the peptide CATEAKAAAKREDQK (SEQ ID NO:21) (antibody production purchased from Sigma-Genosys). The patients had died of cardiac arrest or ischemic stroke. In the five individuals with stroke, the post-ischemic time before death varied from 15 to 60 h, and brain samples were obtained at rapid autopsies with post-mortem delays varying from 10 to 40 h. Tissue blocks with cortical and some subcortical tissue were obtained from the core or an area close to the core of the infarction with no specific reference to the topographic location and control samples were dissected from homologous contralateral locations for comparison. Tissues were fixed in formalin and embedded in paraffin, and used for research by permission of the appropriate Ethical Review Board of the Helsinki University Central Hospital. Immunohistochemical methods and use of this post mortem autopsy material for studies on other proteins have been described (25). The dilutions of antiserum used were 1:100-1:200, and all stained sections were compared to adjacent tissue sections incubated with the preimmune serum in identical conditions and dilutions. No antigen retrieval methods were necessary. Light microscopy of tissue sections was performed with Leitz Laborlux D microscope (Leitz, Wetzlar, Germany) equipped with Nikon Coolpix 995 digital camera (Nikon, Japan).

The publications and other materials used herein to illuminate the invention, and in particular, to provide details with respect to its practice, are incorporated herein by reference.

REFERENCES

1. Catts, H. W. (1989) Defining dyslexia as a developmental language disorder. Ann. Dyslexia, 39, 51-64.
2. Grigorenko, E. L. (2001) Developmental dyslexia: An update on genes, brains, and environments. J. Child. Psychol. Psychiatr., 42, 91-125.
3. Lyon, G. R. (1995) Toward a definition of dyslexia. Ann. Dyslexia, 45, 3-27.
4. Habib, M. (2000) The neurological basis of developmental dyslexia: an overview and working hypothesis. Brain, 123 Pt 12, 2373-99.
5. Paulesu, E., Demonet, J. F., Fazio, F., McCrory, E., Chanoine, V., Brunswick, N., Cappa, S. F., Cossu, G., Habib, M., Frith, C. D. et al. (2001) Dyslexia: cultural diversity and biological unity. Science, 291, 2165-7.
6. Wijsman, E. M., Peterson, D., Leutenegger, A. L., Thomson, J. B., Goddard, K. A., Hsu, L., Berninger, V. W. and Raskind, W. H. (2000) Segregation analysis of phenotypic components of learning disabilities. I. Nonword memory and digit span. Am. J. Hum. Genet., 67, 631-46.
7. Smith, S. D., Kimberling, W. J., Pennington, B. F. and Lubs, H. A. (1983) Specific reading disability: identification of an inherited form through linkage analysis. Science, 219, 1345-7.
8. Morris, D. W., Robinson, L., Turic, D., Duke, M., Webb, V., Milham, C., Hopkin, E., Pound, K., Fernando, S., Easton, M. et al. (2000) Family-based association mapping provides evidence for a gene for reading disability on chromosome 15q. Hum. Mol. Genet., 9, 843-8.
9. Grigorenko, E. L., Wood, F. B., Meyer, M. S., Hart, L. A., Speed, W. C., Shuster, A. and Pauls, D. L. (1997) Susceptibility loci for distinct components of developmental dyslexia on chromosomes 6 and 15. Am. J. Hum. Genet., 60, 27-39.
10. Schulte-Körne, G., Grimm, T., Nothen, M. M., Müller-Myhsok, B., Cichon, S., Vogt, I. R., Propping, P. and Remschmidt, H. (1998) Evidence for linkage of spelling disability to chromosome 15. Am. J. Hum. Genet., 63, 279-82.
11. Cardon, L. R., Smith, S. D., Fulker, D. W., Kimberling, W. J., Pennington, B. F. and DeFries, J. C. (1994)

Quantitative trait locus for reading disability on chromosome 6. *Science,* 266, 276-9.
12. Nopola-Hemmi, J., Taipale, M., Haltia, T., Lehesjoki, A. E., Voutilainen, A. and Kere, J. (2000) Two translocations of chromosome 15q associated with dyslexia. *J. Med. Genet.,* 37, 771-5.
13. Edelmann, L., Spiteri, E., Koren, K., Pulijaal, V., Bialer, M. G., Shanske, A., Goldberg, R. and Morrow, B. E. (2001) AT-Rich Palindromes Mediate the Constitutional t(11;22) Translocation. *Am. J. Hum. Genet.,* 68, 1-13.
14. Ramarao, M. K., Bianchetta, M. J., Lanken, J. and Cohen, J. B. (2001) Role of rapsyn tetratricopeptide repeat and coiled-coil domains in self-association and nicotinic acetylcholine receptor clustering. *J. Biol. Chem.,* 276, 7475-7483.
15. Blatch, G. L. and Lassle, M. (1999) The tetratricopeptide repeat: a structural motif mediating protein-protein interactions. *Bioessays,* 21, 932-939.
16. Häyrinen, T., Serenius-Sirve, S. and Korkman, M. (1999) *Lukilasse. Lukemisen, kirjoittamisen ja laskemisen seulontatestisto peruskoulun ala-asteen luokille 1-6.* Reading and writing test designed for and normated in Finnish elementary school. Psykologien kustannus Oy, Helsinki.
17. Leinonen, S., Müller, K., Leppanen, P., Aro, M., Ahonen, T. and Lyytinen, H. (2001) Heterogeneity in adult dyslexic readers: Relating processing skills to the speed and accuracy of oral text reading. *Read. Writ. Interdisc. J.,* 14, 265-296.
18. Wechsler, D. (1992) *Wechsler adult intelligence scale revised* (WAIS-R). Psykologien kustannus Oy and The psychological corporation USA, Helsinki.
19. Wechsler, D. (1984) *Wechsler intelligence scale for children revised* (WISC-R). Psykologien kustannus Oy and The psychological corporation USA, Helsinki.
20. Korkman, M., Kirk, U. and Kemp, S. (1997) *NEPSY Lasten neuropsykologinen tutkimus.* Revised version. Psykologien kustannus Oy, Helsinki.
21. Denckla, M. B. and Rudel, G. R. (1976) Rapid automatized naming (R.A.N.): Dyslexia differentiated from other learning disabilities. *Neuropsychologia,* 14, 471-479.
22. Christensen, A.-L. (1982) *Lurian neuropsykologinen tutkimus. Luria's neuropsychological test.* Psykologien kustannus Oy, Helsinki.
23. Wolf, M. (1986) Rapid alternating stimulus naming in the developmental dyslexias. *Brain Lang.,* 27, 360-379.
24. Burge, C. and Karlin, S. (1997) Prediction of complete gene structures in human genomic DNA. *J. Mol. Biol.,* 268, 78-94.
25. Lindsberg, P. J., Carpén, O., Paetau, A., Karjalainen-Lindsberg, M.-L. & Kaste, M. (1996) *Circulation* 94, 939-945.
26. Enard, W., Przeworski, M., Fisher, S. E., Lai, C. S. L., Wiebe, V., Kitano, T., Monaco, A. P. & Pääbo, S. (2002) *Nature* 418, 869-872.

The invention claimed is:

1. An isolated, purified DYXC1 nucleic acid selected from the group consisting of: SEQ ID NO:1 or the complement of SEQ ID NO:1.

2. A vector comprising the nucleic acid of claim 1.

3. A host cell comprising the vector of claim 2.

4. An isolated nucleic, acid molecule encoding DYXC1 amino acid sequence of SEQ ID NO:3.

5. A kit for use in the diagnostics of dyslexia or in assessing the predisposition of an individual to dyslexia, comprising a container; and in said container:

a nucleic acid comprising the nucleic acid sequence of SEQ ID NO:1 or the complement thereof.

6. The kit according to claim 5 further comprising instructions for using the kit.

7. The kit according to claim 5, wherein said nucleic acid is labeled.

* * * * *

SEQUENCE LISTING

<160> NUMBER OF SEQ ID NOS: 42

<210> SEQ ID NO 1
<211> LENGTH: 1263
<212> TYPE: DNA
<213> ORGANISM: Homo sapiens
<220> FEATURE:
<223> OTHER INFORMATION: coding sequence for human DYXC1 (cDNA)

<400> SEQUENCE: 1

```
atgcctcttc aggttagcga ttacagctgg cagcagacga agactgcggt ctttctgtct      60
ctgcccctca aaggcgtgtg cgtcagagac acggacgtgt tctgcacgga aaactatctg     120
aaggtcaact ttcctccatt tttatttgag gcatttcttt atgctcccat agacgatgag     180
agcagcaaag caaagattgg gaatgacacc attgtcttca ccttgtataa aaaagaagcg     240
gccatgtggg agaccctttc tgtgacgggt gttgacaaag agatgatgca aagaattaga     300
gaaaaatcta ttttacaagc acaagagaga gcaaagaag ctacagaagc aaaagctgca     360
gcaaagcggg aagatcaaaa atacgcacta agtgtcatga tgaagattga agaagaagag     420
aggaaaaaaa tagaagatat gaaagaaaat gaacggataa aagccactaa agcattggaa     480
gcctggaaag aatatcaaag aaaagctgag gagcaaaaaa aaattcagag agaagagaaa     540
ttatgtcaaa aagaaaagca aattaaagaa ggaagaaaaa aaataaaata taagagtctt     600
actagaaatt tggcatctag aaatcttgct ccaaaaggga gaaattcaga aaatatattt     660
actgagaagt taaaggaaga cagtattcct gctcctcgct ctgttggcag tattaaaatc     720
aactttaccc ctcgagtatt cccaacagct cttcgtgaat cacaagtagc agaagaggag     780
```

```
gagtggctac acaaacaagc tgaggcacga agagcaatga atactgacat agctgaactt      840
tgcgatttaa aagaagaaga aaagaaccca gaatggttga aggataaagg aaacaaattg      900
tttgcaacgg aaaactattt ggcagctatc aatgcatata atttagccat aagactaaat      960
aataagatgc cactattgta tttgaaccgg ctgcttgcc  acctaaaact aaaaaactta    1020
cacaaggcta ttgaagattc ttctaaggca ctggaattat tgatgccacc tgttacagac    1080
aatgctaatg caagaatgaa ggcacatgta cgacgtggaa cagcattctg tcaactagaa    1140
ttgtatgtag aaggcctaca ggattatgaa gcggcactta agattgatcc atccaacaaa    1200
attgtacaaa ttgatgctga aagattcgg  aatgtaattc aaggaacaga actaaaatct    1260
taa                                                                   1263

<210> SEQ ID NO 2
<211> LENGTH: 1993
<212> TYPE: DNA
<213> ORGANISM: Homo sapiens
<220> FEATURE:
<221> NAME/KEY: CDS
<222> LOCATION: (369)..(1628)
<220> FEATURE:
<223> OTHER INFORMATION: human DYXC1 mRNA as cDNA

<400> SEQUENCE: 2
tcctctccta ttatgcaaac ccacaccatg gatccagcag actactctgg ccccagcatg       60
ctgctccttg ggatgatggg agaaggggga aacctgtgtt ttctcttggt tttagggtat      120
gggtctactt ctttgaacat tcgctcagat cgtaaggtaa ccccaagaat cggcatcact      180
ctctggtctg ggcgcctgga tagtcacgca tggagtccgc gaggtgctgg cgccggagca      240
cgctgggaac gccgggctcc cggccggcct gacccggaag gctggcgca  tggtaaccc c      300 agcttcccta gcaaccaagc aggcgcaaga agcaaccagc cgcgctatcc gctcccgttg      360 ctaccgga atg cct ctt cag gtt agc gat tac agc tgg cag cag acg aag        410
         Met Pro Leu Gln Val Ser Asp Tyr Ser Trp Gln Gln Thr Lys
           1               5                  10 act gcg gtc ttt ctg tct ctg ccc ctc aaa ggc gtg tgc gtc aga gac        458
Thr Ala Val Phe Leu Ser Leu Pro Leu Lys Gly Val Cys Val Arg Asp
 15                  20                  25                  30 acg gac gtg ttc tgc acg gaa aac tat ctg aag gtc aac ttt cct cca        506
Thr Asp Val Phe Cys Thr Glu Asn Tyr Leu Lys Val Asn Phe Pro Pro
                 35                  40                  45 ttt tta ttt gag gca ttt ctt tat gct ccc ata gac gat gag agc agc        554
Phe Leu Phe Glu Ala Phe Leu Tyr Ala Pro Ile Asp Asp Glu Ser Ser
             50                  55                  60 aaa gca aag att ggg aat gac acc att gtc ttc acc ttg tat aaa aaa        602
Lys Ala Lys Ile Gly Asn Asp Thr Ile Val Phe Thr Leu Tyr Lys Lys
         65                  70                  75 gaa gcg gcc atg tgg gag acc ctt tct gtg acg ggt gtt gac aaa gag        650
Glu Ala Ala Met Trp Glu Thr Leu Ser Val Thr Gly Val Asp Lys Glu
     80                  85                  90 atg atg caa aga att aga gaa aaa tct att tta caa gca caa gag aga        698
Met Met Gln Arg Ile Arg Glu Lys Ser Ile Leu Gln Ala Gln Glu Arg
 95                 100                 105                 110 gca aaa gaa gct aca gaa gca aaa gct gca gca aag cgg gaa gat caa        746
Ala Lys Glu Ala Thr Glu Ala Lys Ala Ala Ala Lys Arg Glu Asp Gln
                115                 120                 125 aaa tac gca cta agt gtc atg atg aag att gaa gaa gaa gag agg aaa        794
Lys Tyr Ala Leu Ser Val Met Met Lys Ile Glu Glu Glu Glu Arg Lys
            130                 135                 140
```

```
aaa ata gaa gat atg aaa gaa aat gaa cgg ata aaa gcc act aaa gca      842
Lys Ile Glu Asp Met Lys Glu Asn Glu Arg Ile Lys Ala Thr Lys Ala
        145                 150                 155 ttg gaa gcc tgg aaa gaa tat caa aga aaa gct gag gag caa aaa aaa      890
Leu Glu Ala Trp Lys Glu Tyr Gln Arg Lys Ala Glu Glu Gln Lys Lys
160                 165                 170 att cag aga gaa gag aaa tta tgt caa aaa gaa aag caa att aaa gaa      938
Ile Gln Arg Glu Glu Lys Leu Cys Gln Lys Glu Lys Gln Ile Lys Glu
175                 180                 185                 190 gga aga aaa aaa ata aaa tat aag agt ctt act aga aat ttg gca tct      986
Gly Arg Lys Lys Ile Lys Tyr Lys Ser Leu Thr Arg Asn Leu Ala Ser
                195                 200                 205 aga aat ctt gct cca aaa ggg aga aat tca gaa aat ata ttt act gag     1034
Arg Asn Leu Ala Pro Lys Gly Arg Asn Ser Glu Asn Ile Phe Thr Glu
            210                 215                 220 aag tta aag gaa gac agt att cct gct cct cgc tct gtt ggc agt att     1082
Lys Leu Lys Glu Asp Ser Ile Pro Ala Pro Arg Ser Val Gly Ser Ile
225                 230                 235 aaa atc aac ttt acc cct cga gta ttc cca aca gct ctt cgt gaa tca     1130
Lys Ile Asn Phe Thr Pro Arg Val Phe Pro Thr Ala Leu Arg Glu Ser
        240                 245                 250 caa gta gca gaa gag gag gag tgg cta cac aaa caa gct gag gca cga     1178
Gln Val Ala Glu Glu Glu Glu Trp Leu His Lys Gln Ala Glu Ala Arg
255                 260                 265                 270 aga gca atg aat act gac ata gct gaa ctt tgc gat tta aaa gaa gaa     1226
Arg Ala Met Asn Thr Asp Ile Ala Glu Leu Cys Asp Leu Lys Glu Glu
                275                 280                 285 gaa aag aac cca gaa tgg ttg aag gat aaa gga aac aaa ttg ttt gca     1274
Glu Lys Asn Pro Glu Trp Leu Lys Asp Lys Gly Asn Lys Leu Phe Ala
            290                 295                 300 acg gaa aac tat ttg gca gct atc aat gca tat aat tta gcc ata aga     1322
Thr Glu Asn Tyr Leu Ala Ala Ile Asn Ala Tyr Asn Leu Ala Ile Arg
                305                 310                 315 cta aat aat aag atg cca cta ttg tat ttg aac cgg gct gct tgc cac     1370
Leu Asn Asn Lys Met Pro Leu Leu Tyr Leu Asn Arg Ala Ala Cys His
        320                 325                 330 cta aaa cta aaa aac tta cac aag gct att gaa gat tct tct aag gca     1418
Leu Lys Leu Lys Asn Leu His Lys Ala Ile Glu Asp Ser Ser Lys Ala
335                 340                 345                 350 ctg gaa tta ttg atg cca cct gtt aca gac aat gct aat gca aga atg     1466
Leu Glu Leu Leu Met Pro Pro Val Thr Asp Asn Ala Asn Ala Arg Met
                355                 360                 365 aag gca cat gta cga cgt gga aca gca ttc tgt caa cta gaa ttg tat     1514
Lys Ala His Val Arg Arg Gly Thr Ala Phe Cys Gln Leu Glu Leu Tyr
            370                 375                 380 gta gaa ggc cta cag gat tat gaa gcg gca ctt aag att gat cca tcc     1562
Val Glu Gly Leu Gln Asp Tyr Glu Ala Ala Leu Lys Ile Asp Pro Ser
                385                 390                 395 aac aaa att gta caa att gat gct gag aag att cgg aat gta att caa     1610
Asn Lys Ile Val Gln Ile Asp Ala Glu Lys Ile Arg Asn Val Ile Gln
        400                 405                 410 gga aca gaa cta aaa tct taatgactat tagaagtaac taagtattgt            1658
Gly Thr Glu Leu Lys Ser
415                 420 tataagtttt ttaaaaacaa ctggaggcat ctttgtacat attatggcca gttgtacaga   1718
atcgctttct gtttagtact ttagttctgt tgagggcaaa atattataaa tctatagaaa   1778
ataaactgtt tgacttgaat catttctgaa taagtaaatc taaataagaa tctattttaa   1838
ttccttattt cttcatatta atacatatgt atactttttt gtgttactga attaagcttg   1898
```

-continued

```
cccttgtaac aaaatatgtt ttggtatagt taccaggaca cttactgatt aatttttaac   1958
aaggtagaat tttaaaataa aagatttata aataa                              1993
```

<210> SEQ ID NO 3
<211> LENGTH: 420
<212> TYPE: PRT
<213> ORGANISM: Homo sapiens
<220> FEATURE:
<223> OTHER INFORMATION: human DYXC1 mRNA as cDNA

<400> SEQUENCE: 3

```
Met Pro Leu Gln Val Ser Asp Tyr Ser Trp Gln Gln Thr Lys Thr Ala
  1               5                  10                  15

Val Phe Leu Ser Leu Pro Leu Lys Gly Val Cys Val Arg Asp Thr Asp
             20                  25                  30

Val Phe Cys Thr Glu Asn Tyr Leu Lys Val Asn Phe Pro Pro Phe Leu
         35                  40                  45

Phe Glu Ala Phe Leu Tyr Ala Pro Ile Asp Asp Glu Ser Ser Lys Ala
     50                  55                  60

Lys Ile Gly Asn Asp Thr Ile Val Phe Thr Leu Tyr Lys Lys Glu Ala
 65                  70                  75                  80

Ala Met Trp Glu Thr Leu Ser Val Thr Gly Val Asp Lys Glu Met Met
                 85                  90                  95

Gln Arg Ile Arg Glu Lys Ser Ile Leu Gln Ala Gln Glu Arg Ala Lys
            100                 105                 110

Glu Ala Thr Glu Ala Lys Ala Ala Lys Arg Glu Asp Gln Lys Tyr
        115                 120                 125

Ala Leu Ser Val Met Met Lys Ile Glu Glu Glu Arg Lys Lys Ile
    130                 135                 140

Glu Asp Met Lys Glu Asn Glu Arg Ile Lys Ala Thr Lys Ala Leu Glu
145                 150                 155                 160

Ala Trp Lys Glu Tyr Gln Arg Lys Ala Glu Glu Gln Lys Lys Ile Gln
                165                 170                 175

Arg Glu Glu Lys Leu Cys Gln Lys Glu Lys Gln Ile Lys Glu Gly Arg
            180                 185                 190

Lys Lys Ile Lys Tyr Lys Ser Leu Thr Arg Asn Leu Ala Ser Arg Asn
        195                 200                 205

Leu Ala Pro Lys Gly Arg Asn Ser Glu Asn Ile Phe Thr Glu Lys Leu
    210                 215                 220

Lys Glu Asp Ser Ile Pro Ala Pro Arg Ser Val Gly Ser Ile Lys Ile
225                 230                 235                 240

Asn Phe Thr Pro Arg Val Phe Pro Thr Ala Leu Arg Glu Ser Gln Val
                245                 250                 255

Ala Glu Glu Glu Trp Leu His Lys Gln Ala Glu Ala Arg Arg Ala
            260                 265                 270

Met Asn Thr Asp Ile Ala Glu Leu Cys Asp Leu Lys Glu Glu Glu Lys
        275                 280                 285

Asn Pro Glu Trp Leu Lys Asp Lys Gly Asn Lys Leu Phe Ala Thr Glu
    290                 295                 300

Asn Tyr Leu Ala Ala Ile Asn Ala Tyr Asn Leu Ala Ile Arg Leu Asn
305                 310                 315                 320

Asn Lys Met Pro Leu Leu Tyr Leu Asn Arg Ala Ala Cys His Leu Lys
                325                 330                 335

Leu Lys Asn Leu His Lys Ala Ile Glu Asp Ser Ser Lys Ala Leu Glu
```

```
                    340                 345                 350
Leu Leu Met Pro Pro Val Thr Asp Asn Ala Asn Ala Arg Met Lys Ala
            355                 360                 365

His Val Arg Arg Gly Thr Ala Phe Cys Gln Leu Glu Leu Tyr Val Glu
        370                 375                 380

Gly Leu Gln Asp Tyr Glu Ala Ala Leu Lys Ile Asp Pro Ser Asn Lys
385                 390                 395                 400

Ile Val Gln Ile Asp Ala Glu Lys Ile Arg Asn Val Ile Gln Gly Thr
                405                 410                 415

Glu Leu Lys Ser
            420

<210> SEQ ID NO 4
<211> LENGTH: 1697
<212> TYPE: DNA
<213> ORGANISM: Mus musculus
<220> FEATURE:
<221> NAME/KEY: CDS
<222> LOCATION: (48)..(1307)
<220> FEATURE:
<223> OTHER INFORMATION: murine DYXC1 mRNA as cDNA

<400> SEQUENCE: 4
cggacgcgtg ggcgacgtaa agtggctgtg cagtccctgg tccgcc atg cca gtg         56
                                                  Met Pro Val
                                                    1 cga gtg agc gaa ttc agc tgg cag cag acg ccg gcc acg atc ttc ctg       104
Arg Val Ser Glu Phe Ser Trp Gln Gln Thr Pro Ala Thr Ile Phe Leu
  5                  10                  15 tcg ctg cct ctg cgg ggc gtc tgc gtg cgc gat gct gac gta ttc tgt       152
Ser Leu Pro Leu Arg Gly Val Cys Val Arg Asp Ala Asp Val Phe Cys
 20                  25                  30                  35 ggg gaa agt tac ctg aag gtt aac ttt cct cca ttt tta ttt gag ctg       200
Gly Glu Ser Tyr Leu Lys Val Asn Phe Pro Pro Phe Leu Phe Glu Leu
                 40                  45                  50 ttt ctc tat gct ccc ata gat gat ggg aag agc aaa gcc aag att gga       248
Phe Leu Tyr Ala Pro Ile Asp Asp Gly Lys Ser Lys Ala Lys Ile Gly
             55                  60                  65 aat gac acg att ctt ttc aca ttg tat aaa aag gag cca gtt ctg tgg       296
Asn Asp Thr Ile Leu Phe Thr Leu Tyr Lys Lys Glu Pro Val Leu Trp
         70                  75                  80 gat agc ctt tct gtg ccg ggt gtt gat aaa gag atg atg cag aga ata       344
Asp Ser Leu Ser Val Pro Gly Val Asp Lys Glu Met Met Gln Arg Ile
     85                  90                  95 aga gaa aaa tct atc ttg caa gca cag gag aaa gca aaa gag gcc aca       392
Arg Glu Lys Ser Ile Leu Gln Ala Gln Glu Lys Ala Lys Glu Ala Thr
100                 105                 110                 115 gaa gca aaa gct gtt gcc aag cga gaa gac cag aga tac gca cta ggc       440
Glu Ala Lys Ala Val Ala Lys Arg Glu Asp Gln Arg Tyr Ala Leu Gly
                120                 125                 130 gag atg atg aag att gaa gaa gag agg aaa aaa ctc gaa gat ctg            488
Glu Met Met Lys Ile Glu Glu Glu Arg Lys Lys Leu Glu Asp Leu
            135                 140                 145 aaa gaa aat gaa cgg aaa aag gca act agc gaa tta gaa gcg tgg aaa       536
Lys Glu Asn Glu Arg Lys Lys Ala Thr Ser Glu Leu Glu Ala Trp Lys
        150                 155                 160 gaa tgt caa aag aaa gct gac gga caa aaa aga gtc cag agg aag gag       584
Glu Cys Gln Lys Lys Ala Asp Gly Gln Lys Arg Val Gln Arg Lys Glu
    165                 170                 175 aaa ccg ctc gag gga aag caa gct gaa gag acc aaa gct cta aaa cct       632
Lys Pro Leu Glu Gly Lys Gln Ala Glu Glu Thr Lys Ala Leu Lys Pro
```

|   |   |   |   |   |   |   |   |   |   |   |   |   |   |   |   |
|---|---|---|---|---|---|---|---|---|---|---|---|---|---|---|---|
| Lys | Pro | Leu | Glu | Gly | Lys | Gln | Ala | Glu | Glu | Thr | Lys | Ala | Leu | Lys | Pro |
| 180 | | | | 185 | | | | | 190 | | | | | 195 | |

```
cgg ggt ttg ccc cgg aag gcc cca ccc act cgc ctc ccc aca aga ggg      680
Arg Gly Leu Pro Arg Lys Ala Pro Pro Thr Arg Leu Pro Thr Arg Gly
            200                 205                 210 agg aat tgg gaa aac ata ttt cct gag aag tta aag gaa gac aga gtc      728
Arg Asn Trp Glu Asn Ile Phe Pro Glu Lys Leu Lys Glu Asp Arg Val
                215                 220                 225 cct gcg cct cgc tcc gct ggc agt att caa atc agc ttt acc cct cga      776
Pro Ala Pro Arg Ser Ala Gly Ser Ile Gln Ile Ser Phe Thr Pro Arg
            230                 235                 240 gtg ttc cca aca gca ctt cgg gaa tcc caa gtc gca gaa gag gag gag      824
Val Phe Pro Thr Ala Leu Arg Glu Ser Gln Val Ala Glu Glu Glu Glu
        245                 250                 255 tgg ctg cat aaa caa gca gaa gca cgg aga gcc atg agc act gac ctt      872
Trp Leu His Lys Gln Ala Glu Ala Arg Arg Ala Met Ser Thr Asp Leu
260                 265                 270                 275 cct gag ttc ttt gac tta aaa gaa gaa gag agg aat cca gac tgg ttg      920
Pro Glu Phe Phe Asp Leu Lys Glu Glu Glu Arg Asn Pro Asp Trp Leu
                280                 285                 290 aaa gac aag gga aac aaa ttg ttt gca aca gaa aac tat ttg gca gcg      968
Lys Asp Lys Gly Asn Lys Leu Phe Ala Thr Glu Asn Tyr Leu Ala Ala
            295                 300                 305 gtt gat gca tat aat tta gcc ata cga ctg aac tgt aag atc cca tta     1016
Val Asp Ala Tyr Asn Leu Ala Ile Arg Leu Asn Cys Lys Ile Pro Leu
        310                 315                 320 ttg tat ttg aat cgg gct gct tgc cac ctc aaa tta aaa aac cta cac     1064
Leu Tyr Leu Asn Arg Ala Ala Cys His Leu Lys Leu Lys Asn Leu His
325                 330                 335 aag gcc atc gag gac tct tct aag gca cta gag tta ttg aca cca cct     1112
Lys Ala Ile Glu Asp Ser Ser Lys Ala Leu Glu Leu Leu Thr Pro Pro
340                 345                 350                 355 gtt gct gac aat gcc aat gca aga atg aag gca cac gtc cga cga ggg     1160
Val Ala Asp Asn Ala Asn Ala Arg Met Lys Ala His Val Arg Arg Gly
                360                 365                 370 aca gcg ttc tgt caa cta gaa ttg tat gtt gaa ggc ttg caa gat tat     1208
Thr Ala Phe Cys Gln Leu Glu Leu Tyr Val Glu Gly Leu Gln Asp Tyr
            375                 380                 385 gaa gct gca ctt aag att gac cca gcc aac aca gtt gta cag aac gat     1256
Glu Ala Ala Leu Lys Ile Asp Pro Ala Asn Thr Val Val Gln Asn Asp
        390                 395                 400 gca gag aag att cgg aat ata att caa ggg acg gca ctg aag tct cgt     1304
Ala Glu Lys Ile Arg Asn Ile Ile Gln Gly Thr Ala Leu Lys Ser Arg
405                 410                 415 gac                                                                  1357
Asp
420 taccgggcta gtgagccttt ggaatggcag tgcctgacga atcatctcca aggggaaaat   1417 ggcctagctc tcactgcctt tgatcccagt accgggaagg cagaggtagg caagtctcta   1477 tgagcttgag gccagccaga gctcgacagc atgcaaaaca caaaagaaag ccagagaaca   1537 ggctgtttga gtcctcaatc ttggcacagg gattggctgg gctctgatgt tgctgttgaa   1597 attgccagga tactactgag gaatctcacg aatagaattt ccacataaaa gattgtgcat   1657 ataaaatatt cttattatat taaatatagt atttcattcc                        1697
```

<210> SEQ ID NO 5
<211> LENGTH: 420
<212> TYPE: PRT

<213> ORGANISM: Mus musculus
<220> FEATURE:
<223> OTHER INFORMATION: murine DYXC1 mRNA as cDNA

<400> SEQUENCE: 5

```
Met Pro Val Arg Val Ser Glu Phe Ser Trp Gln Gln Thr Pro Ala Thr
 1               5                  10                  15

Ile Phe Leu Ser Leu Pro Leu Arg Gly Val Cys Val Arg Asp Ala Asp
            20                  25                  30

Val Phe Cys Gly Glu Ser Tyr Leu Lys Val Asn Phe Pro Pro Phe Leu
        35                  40                  45

Phe Glu Leu Phe Leu Tyr Ala Pro Ile Asp Asp Gly Lys Ser Lys Ala
    50                  55                  60

Lys Ile Gly Asn Asp Thr Ile Leu Phe Thr Leu Tyr Lys Lys Glu Pro
65                  70                  75                  80

Val Leu Trp Asp Ser Leu Ser Val Pro Gly Val Asp Lys Glu Met Met
                85                  90                  95

Gln Arg Ile Arg Glu Lys Ser Ile Leu Gln Ala Gln Glu Lys Ala Lys
            100                 105                 110

Glu Ala Thr Glu Ala Lys Ala Val Ala Lys Arg Glu Asp Gln Arg Tyr
        115                 120                 125

Ala Leu Gly Glu Met Met Lys Ile Glu Glu Glu Arg Lys Lys Leu
    130                 135                 140

Glu Asp Leu Lys Glu Asn Glu Arg Lys Lys Ala Thr Ser Glu Leu Glu
145                 150                 155                 160

Ala Trp Lys Glu Cys Gln Lys Lys Ala Asp Gly Gln Lys Arg Val Gln
                165                 170                 175

Arg Lys Glu Lys Pro Leu Glu Gly Lys Gln Ala Glu Glu Thr Lys Ala
            180                 185                 190

Leu Lys Pro Arg Gly Leu Pro Arg Lys Ala Pro Pro Thr Arg Leu Pro
        195                 200                 205

Thr Arg Gly Arg Asn Trp Glu Asn Ile Phe Pro Glu Lys Leu Lys Glu
    210                 215                 220

Asp Arg Val Pro Ala Pro Arg Ser Ala Gly Ser Ile Gln Ile Ser Phe
225                 230                 235                 240

Thr Pro Arg Val Phe Pro Thr Ala Leu Arg Glu Ser Gln Val Ala Glu
                245                 250                 255

Glu Glu Glu Trp Leu His Lys Gln Ala Glu Ala Arg Arg Ala Met Ser
            260                 265                 270

Thr Asp Leu Pro Glu Phe Phe Asp Leu Lys Glu Glu Glu Arg Asn Pro
        275                 280                 285

Asp Trp Leu Lys Asp Lys Gly Asn Lys Leu Phe Ala Thr Glu Asn Tyr
    290                 295                 300

Leu Ala Ala Val Asp Ala Tyr Asn Leu Ala Ile Arg Leu Asn Cys Lys
305                 310                 315                 320

Ile Pro Leu Leu Tyr Leu Asn Arg Ala Ala Cys His Leu Lys Leu Lys
                325                 330                 335

Asn Leu His Lys Ala Ile Glu Asp Ser Ser Lys Ala Leu Glu Leu Leu
            340                 345                 350

Thr Pro Pro Val Ala Asp Asn Ala Asn Ala Arg Met Lys Ala His Val
        355                 360                 365

Arg Arg Gly Thr Ala Phe Cys Gln Leu Glu Leu Tyr Val Glu Gly Leu
    370                 375                 380

Gln Asp Tyr Glu Ala Ala Leu Lys Ile Asp Pro Ala Asn Thr Val Val
```

```
                385                 390                 395                 400
        Gln Asn Asp Ala Glu Lys Ile Arg Asn Ile Ile Gln Gly Thr Ala Leu
                        405                 410                 415

Lys Ser Arg Asp
                420

<210> SEQ ID NO 6
<211> LENGTH: 50000
<212> TYPE: DNA
<213> ORGANISM: Homo sapiens
<220> FEATURE:
<223> OTHER INFORMATION: human DYXC1 chromosomal gene region,
      nucleotides 1-50000

<400> SEQUENCE: 6
aagcttttgc tttccttgat catgtactgt tgagaaagca atatttggaa acattgttgc      60
atttttaaca ttatctttaa gaattaaaag gcacatacct ttgatgccat aattctggtt     120
ctaggagcta cttgtaaatc tctctaaagg catttataca tggatttta ttgcagcaac      180 agcagaggct tggaaacaac ttaaacattg atcaatatgg aggggactag tttaatgaat     240
catggtgtag tcacactgta gaatactact cagctattac aaaataaaga agttctaaat     300
agagtgatat ggaatgatct ccaagtaaga aagcaaggta cactgtgtgt actgtgtgta     360 cttttgtctca tttgtgtcct ccccgccaaa aaaataataa taatatactt taatatatct    420
agattatctt tggaaaggta ggccagaaac tagtaatagt ggtggcctct gagacaggga    480
accagttact aaagatttta gagtgagaga gagagacttg cttttcact gaaagaataa    540 taaatatggg agcagggatg aatggctatt tctggctcaa actatgggaa agacttttt    600 gaaacagata atgataataa aagtattgct cttgtctaac gaaaatagaa aacattaaca    660
ggtaaatata atagatatta ctatgagata taaagtaact tcacttacaa gtgggaaata    720
ttacctgaat ttttttttt ttaggtggtg atagtggact ggatgggtta ggaggaccag    780
gtgtacaact aggaagccca gataagaaaa agcgcaaggc aaatacacag gtaaactgac    840
attttcttta ataaaagttt ttcttttgcta gtatggtcag gctgatgagg taaatttgaa    900
cttggtcata agttttgttt tctattcaag tgattgtact tttaatcatt cattgtactt    960
tcaatcaatc attccagtga tggtactttc tttttttttt tttttttttt tttttttttt   1020
tttttttttt ttaggtggat tcttgctctg ttgccagact ggagtgagtg cagtggggtg   1080
atctcagctc actgcaacct ccacctccca ggttgaagcg attctcctgc ctcagcctcc   1140
caagtagctg gaattacagg cacgcgccac catgcccagc taattttgt attttagta     1200 gagacgggct ttcaccatgt tgatcaggat ggtctcaatc tcttgacctc gtgatccacc   1260
cgcctcggcc tcccaaagtg ctaggattac aggtgtgagc caccacgcct cgctgtattt    1320
ttttttgttt aagtctgtaa ctagtggcta ttgtcagact ataggcatag actagatact   1380
gcaaaaagga agtgtgggca aattaaaatg cttgttctta ggctgggcat ggtggctcat   1440
gcctataatc ccagcccttt gggaggccaa ggtgggtgga ttacttgagg ccaggagttc   1500
gagaccagac tggccaacat ggggaaagcc cttctctact aaaaatataa aaattagccg   1560
ggtgtggtgg cacactcctg taatcccagc tattgcggag gctgaggcat gagaattgct   1620
tgaacctgga aggtagaggt tgcaatgagc tgagatcacg ccactgcact ccagccttgg   1680
tgacagcgtg agactctgtc tcaaaaaaaa attaaaatta aaatgcttgt tctttaaatct  1740 aatttaaagg ttttaaagg gcatgaatgc ctgcagttct attaaaagat ttcaaaatat   1800
```

```
atagtaacaa ttttaacctg aaataattgt tcaactataa tagtgattta gtattatgtg    1860
catatcacga agcaatcatg atggaggcct ttttttgtta taacttgtgg ttgtaacaag    1920
caattatata tacaggctct cactgtttta ttctttataa atttgaagca ctctttctat    1980
gataaaggct actagtaagt atgtgtgtac agattactga tcttttttatc attttgacca   2040 ccatctgtta aacttgcagt gtgactaaaa ctggcagttt attttttcag tctgaggccc    2100
agaacttaat gttttggaaa tattttaatt gtatctccct gaagttaagc taggggaaaa    2160
acttagattc tgattgttgt tatttaactt tatgactgtt tggtgtatga gaggtatttt    2220
aggttagact gctttagtat ttaagtgaaa gtttctagag ttataggtaa gcatattaaa    2280
tgaaaattag gataatgaag cttcttttga aagttaacta cttttggttt ttgaagttac    2340
aatggatttg agctcagaaa atcatacttt attttcttt ggaaatgaaa taaaactaaa     2400 tattttatc agcaagtata attaaatata aacattagtc aaaattgaaa ggtcaagtga     2460
agataataaa tgtttgttaa cactgcaaga gaaatttgac taatactagg ttcacaggta    2520
ttaaggtaac aggacaattt taataatgta tttgatcgaa aacatgtatt ttactttaca    2580
ttctcatttc agggaccttc tttccctcca ttgtctgagt atgctccacc accgaatcca    2640
aactctgacc atctagtggc tgctaatcca tttgatgaca actataatac tatttcctat    2700
aaaccactac cttcgtcaaa tccatatctt ggccctggtt atcctggctt tggaggctat    2760
agtacattca gaatgccacc tcacgttccc ccaagaatgt cttccccata ctgtggtcct    2820
tactcactca ggaaccagcc acacccattt cctcagaatc ctctgggcat gggttttaat    2880
cgacctcatg cttttaactt tgggccacat gataattcaa gtttcggtaa tccatcttat    2940
aataatgcac taagtcagaa tgtcaacatg cctaatcaac attttagaca aaatcctgct    3000
gaaaatttca gtcaaattcc tccacagaat gctagccaag tttctaaccc cgatttggca    3060
tctaattttg ttcctggaaa taattcaaat tttacttctc cgttagaatc taatcattct    3120
tttattcctc ccccaaacac ttttggtcaa gcaaaagcac cacccccaaa acaagacttt    3180
actcaaggag caaccaaaaa cactaatcaa aattcctctg ctcatccacc tcacttgaat    3240
atggatgaca cagtgaatca gagtaatatt gaattaaaaa atgttaatcg aaacaatgca    3300
gtaaatcagg agaacagccg ttcaagtagc actgaagcca caaacaataa ccctgcaaat    3360
gggacgcaga ataagccacg acaaccaaga ggtgcagcag atgcctgcac cacagaaaaa    3420
agcaataaat cctctcttca cccaaaccgt catggccatt cgtcttctga cccagtgtat    3480
ccttgtggaa tttgtacaaa cgaggtgaac gatgatcagg atgccatctt atgtgaggcc    3540
tcttgtcaga aatggtttca tcggatctgt actggaatga ctgaaacagc ttatggcctc    3600
ttaactgcag aagcatctgc agtatggggc tgtgatacct gtatggctga caaagatgtc    3660
cagttaatgc gtactagaga aacttttggt ccatctgcag tgggcagtga tgcttaatca    3720
aaggcattaa ctaaagtggg tttatttttcc tgtgcattgc agaagttcat tgacacagga    3780
ttttaatgtt ttacattatt tttttaaatg catacacaaa acattattt acttagtttt     3840 tattaatcac ttcatcacta gagcaaattt tttattgtct ttgcttgctg tcttaaatga    3900
gaataatgta tatggggggtg ctttagaaac ataaataaat gttagttgtt gttatttatc   3960
acaaacataa aagcctcttg aaacttcaaa ataatatata acaaatgtag gcaagtttta    4020
acttttaaaa gttagaatca ttgaaaaacg tgtatttcag tgctgaactt tggttgtacc    4080
atattaaaga tttagttcaa aaagtttatc aaggatccac ttaacacgtc ttcacaaacat   4140 aatatatgta actgtaacat gggggaaagc atacattttt atggattaaa aaaataatag    4200
```

```
tatgcacaca gattcctcct ccactagggt ctttggaatc aatgaatttc atatttcaag    4260
tgagttttca ggatatctgt ttgtacagat acgagacaga tcttagcata tagtaaattc    4320
tcagtaagta ttgttgatta acttgtggat ggtaccacat gaaattgcta atattagatc    4380
agttgaaaat tgactgcaat tagtaaagtt ggtataacgt acgttcccag ttgtgctatt    4440
tagaattatg atagtattat gctcctactt ttctttgata ttgagttgtc ttgttattgt    4500
ttattgtttt ccagagaaat actatagtat ccacagaaga attgtgaata cttttttata    4560
attttgaact gggacatatt gcagatgagg aaggtagaaa catccatttg gccttagagg    4620
gctctgctag taaaagaact actcagtggt ggtttgaaaa atcttgttct ggggatctga    4680
atttcaaaaa tgaaccctag gggagatcaa aatccatttt aaacaaagat caattaagag    4740
ccaaagtgaa atctaacttg caaacaacaa tttgaagcct tgcagcagac ttaaggaatt    4800
cccgctctga ctggggaaaa gtataaaaat ggacctgaga gtaccctctt gagggatgat    4860
caagaatgga gacagttgga gttgtgctca ttaagattca aaacagcaga aatccatttt    4920
tggagcagat tataacctgt ggccaaaaaa aaaaaatgtg tgctgtttga cagctaatgg    4980
caatttatac aatcattgga ggctggtaaa gctccctaat atgttgccac cattatcatt    5040
gcaaccaaaa aaattctgaa gattgtgtgg tgatctacga aagagataaa taattactgt    5100
tatttaaacc caagtgaaac aatgacggca gcagcatatt atcaagaaat ttaaattatg    5160
catgaaaatg tgatttaaaa acaatgtcct ttgggtaaca cacaagaacc tacactttca    5220
cagacaagga ctcgacctca catgtcacaa gctactaaag caaagttaag tgacttgggc    5280
tatgaaattt tgtcatgtcc attttagtca ctggaccttt attccatgga ctactgtcta    5340
tcatttggag cttttctaa gaaacaatgc attccccaat cgagatgaag taactggaag    5400
atgttaacaa tttatacagc ctaacaaatg atgaatttta taaaagttag acctttaata    5460
ttctgttgga agaaaactat tcatgctcct gatgcatatt ttgattgaat aaaacttatt    5520
tttttaaata cattgttta attttgacct acaaaaacag caatttcata tggtacaagg    5580
taatacaagg ttttctccat ttacccttga ctagttagag gtgagtacaa atatttttca    5640
gtagttgtaa atatttatc tttacaattt taggaaacaa aatgatataa actatacttc    5700
taggtactcc tttgtgtgaa aactttacca gttgaagcag gttaaaatgc agtattttgg    5760
gctgacaggc atttgatggt gttcagtagt gtacttgaag atctcatttt acttggattt    5820
tttattatac atatttctct aaatgtttaa ggacctagtt atgttgctcc tgaaagttta    5880
atgagtgctg atttttaata aatgatgcac tgtatgctgt atgcctagtt gtagcatcag    5940
atcatgattt attattaccc tgaatagagc tagatgatag atattttgag tagaactttc    6000
cagtgttctc aggagttaac actttacatg gtagtacttg agttgtgatc attactaaaa    6060
tcaattatgc agtttcttaa acccttatc tctttaagtt tcagtagtta gctgttttg    6120 tgaaaatgaa ataacttctc ccaagctagt ctaaaggtat gtgttatgca atataattca    6180
ttttctattt ccacatagtt gttttttaaaa acctacaaac aggtgaattt ttattccaggt    6240 gtttaggtct tcaaagcacc ttacttaaat aagaatctgt aaatattcaa aagaaaaact    6300
cacggttcat tctgatagtg aatcatagcc aaactgtaat catagctgat gaatagcgtt    6360
catgtgtttg aattaatttt cctgctagtt ctacatttgt ctctacataa tgctaagtca    6420
aaagttatat agatgctttt ggatggaata agtgatgaac tgtaagaata gccagatgat    6480
aatttgtctg aagaaggcta ttatacaaac tgaaatggct tcttaggata aatgataagc    6540
```

```
tgccttcaac tttaaaaata tgcagtgatg gaaaaaaaca caggtggaat tgtaccttt    6600 ttggtataat cccttcctt cactgaaagt cctcatctta cacacacaca cacacacaca    6660 cacccccac agttctcca acatccttga gttttgctta aattcaacct ggctaactat    6720
gagcatctag gtttactcac caaagctagg ttattgacag aaaggtgggt ttttttgt     6780 tttttgtt ttgtttgtt ttgttttgt tttgccag tcttgctctg ttgcccaggc         6840
tggagtgcag tgatgagatc tcggctcact gcaacgtctg ccttcctggt tcaagtgatt   6900
ctcctgcctc agcctcctga gtagctggga ttacagtcgc ccaccatcac acctggctaa   6960
tttttgtatt tttagtagag acgggttcac catgttggcc aggctggtgt caaactcctg   7020
acctcaagtg atctgcccgc ctcagcctcc caaagtgctg ggattacagg tgtaagccac   7080
cacgcctggc cagacagaaa attttaaaaa gcatcagttc ctttctcaga acttgacttg   7140
ctcatgcact agagaatttg tggtccacat gcttctaggt gttactcgat tcactaatac   7200
tgaaacagct cagcttgtga agataaatt gttcttcaga cagagtgctt agaattagat    7260
ttgtgatcag tgttttcctt ttgtgtgaaa tactttagag tactgctata attgttattc   7320
aaattagaag gttatataca taaaactaaa gattttcttg tactagtgct tattcttcat   7380
aaacacagtg taaagaaatc tactttttg gtggtttgtt ttagactccc aactctgcct    7440
agtggcagaa aaacctctta atagtgtggg tcatcataaa atctgccaac tttaatccaa   7500
ataagtatca agagtcttca ttcaatattc tttcaaactt gtttgtctcg aacaaattag   7560
agttttagca cttattgttc aatgtactat agtaattgta tttaatagta agaaaatata   7620
taagcaatga ttttttaaaa gggagttctc aagagttttg gatttctttc tgccgtgtat   7680
agaggtttct tatgcatgga catttgtgct gtttttatatc tttttcaatt aaaaaaaaat  7740
ttaaaggcat caggctccct aagttcattt gtaaatagtg gcttggaact ctacacaata   7800
gggaagctcc taaaggctca tttagaccat aatctagtta atagtatcat gctgaactct   7860
cagttttctt taggaaaacca atcaatcagt gtaggaggga gaaagaagca gaggtcttgt  7920
ctttttcctg atgtgattag gaggttaagt tctttggtgt gggtttcttt gcatttgccc   7980
ccttaccatg ctaaactctg gtgaaatgta taagcagcct tggcttttcc tctcctgggt   8040
gctctgtgct tcaacatttt atatctttcc tcccatcaga aatcctgtgt ctttgtgtgg   8100
cagtagtagt tggctagact ttaagagaaa agcatttct actaaggtat gaatgaagat    8160
agtgggaaaa gtgtcattaa atttcttttt taaaaagta tgtttattaa gaatgaatct    8220
ttaatatcta acatttcaga caatatgacc gcatttcaga taccatggga agcagtacat   8280
ttagtgaatt agctggtact gtctgagggt acttccagtt tccttaggc tgttgtgact    8340 tttcacagct tcctctcctc taattctgaa cttagagatt ttcttctcat ttctaatttt   8400
tagtagctta ttgttccatc cagtagagca ttataaaagt cacatctgca tcttccaact   8460
tatggtacag tgatgggaat ttggaagcac ccctggagca aagaggctag ggatagcatt   8520
aacatctccc aagacaagtg gtataggga atgaaggaa agactgtggc catgtatatg     8580
ccaggcgtta atacatcaga gctgcctgta tttaatttaa aacttttgat gaaactcagt   8640
ggataagcat ctttgtcata ttttgtcaat aatacattac ttgcaattat attaaaactt   8700
attctaaata cctgtacctt tcttgttctg tagatgtgta gatgatgttg cttgtttgtc   8760
aaaatattat cttttataaa agaaagtcct gcttcttatc atgatgtatg tgacttaaat   8820
gattgtttca tattaaaact atttcttcct tatgtactgt ttacatatac ctcttttgg    8880 gatattagtt cagtactttt atacaaatct gagtgtgttc cacattggtg acatgtattt   8940
```

```
ttgcagtaac ttttttgtttt gttcttagaa catgtctaaa gtaacacatg cactagtgct    9000
gtggtctgtg gcaaaattac tgtaattcaa attggaaaaa aaatgtttc cagactttgt      9060
ccaacattta ttcctatggc aaaggaaatt actatgtaat actaattatt tcttatgctg    9120
gtatgtttta agctactcta tgaagtatgt gaaacatcaa tatttatgga ttaatagatg    9180
gcctgatgtc tttcaaatgg gagaggagta aattttagtg ttaccaactc atgcacttg      9240
taatacaata aatcttaaaa ttttttatttt ccacttacag gtatacttta ctaaataatt   9300
accttaaatg gcagtgcata ttaggatttt ttagcacata ctactaaaat tatatagtaa    9360
cttttaactt gtgctgatat ttcccaacca aaaaagacat cattcacttc atcataacca    9420
aaataagtag tactgtaata tttatcttca tttatttaga catgattaag ataccgtaag    9480
actcctctaa tttacctgga attttttagcc attgattcaa ggacttgaat gctgtttact  9540
tggtactacc taatgaaagg atttggtaat aaaggttata atcacgattt taaagaaaaa    9600
tgtttcatct tgaaggcaaa ttttttaagct ttttatttag aggtgtttac ttaagaatag   9660
taatttaaaa gcattcttat tttgtcatta agacaagtac ccaaaagaat tgtaataagt    9720
aatacttggc caatgcaaat ttgtacattt gaaatcatac acttgaaaga aaaaaatgaa    9780
ggcttgtgag tgcttaaact gcatatcttt ttaaaaattc aaattttaga catatcagtt   9840
taaattatcc ttaataaggt tttactatgt cagtgatgta tattacaaaa tgtctaccta   9900
tgttatgtta atgatatctc tatactgcat catattcggc atggttatgg tatattttgt   9960
acttttgatt gtggactatt gataggattg atatagcaat aaatctgatt cagacttaat   10020
atttttaaaa acgctagata ccatactgta tcataatcct attatatttg acttgaatgc   10080
ccaaaatttt catagttcta tattttatgt taaaaattta gtattacatg ttagggattt   10140
atttttgtct gctatttttca catacattct tttagaactg agtctgtttc tatttagatc   10200
atagacgtct aaagaagtat tattaattca tgaactgctt tgtggaaaaa tttaaataaa   10260
gtatgaaatg actagattac cccaaattgt ttattttttt ttttggttaa tgaccaggtt   10320
acaattctca gacaaatgaa attggcttga taactgattg aatatagtag ataatggaaa   10380
gtttgactct ttaagggctt ccaagtgtta aatacattct caattctgaa ttacttcata   10440
gtaactactt aaataatggt aagccaattc tcctttttct ttttgagata tttaacacaa   10500
tttgcgtctt ctgatcccat tcccttcttc cccaaaaacc atgctagaat ttaaaattgg   10560
aagagtttaa tttgtcatct acattttagt tttttttattc tatagataag taagaagaca   10620
agtagacgtt ctgctgtcaa gacagtccat gttattgttg gccattcttt tcagggataa   10680
tgcttaatgt tatttgtgcg ttgtataagg aatgttgttt atcagtatat agacctacca   10740
ttagtagaaa tgatgtatgg caggcttttct tgaataatat gtattgtaag tttgtttcct   10800
atagtgttat tatggttcag attcttttaa ataaagctag ttttttaaaga gaaaaataac   10860
ttttttaaagc gtttgacttt catcaggaca agtaggtgtg agaatcttgg ctttgggtgg   10920
gagatgtcca gtataacatc aagcagggaa tagcctacaa tttatcagtg taattttata   10980
ctaaggagag aaccagtatt tttagtcagg ccttgctgta tacatatttt ttctgtgaag   11040
tctattcaga aaactgagtc ctggatttcc ttaagaaatt gtgagcatga catatttact   11100
ttgatttttaa cagtttgtga cttcagttct gttagtaaaa attatttgga gaagagtttt   11160
acaacttcag cagcttaatg accccctgggg cagagacacc actgtagcaa atattaagaa   11220
caaacttgtg gctgggtgca gtgactcacg cctgtaattc cagctactcg ggaggctgcg   11280
```

```
gcacgggaat cacttgaatc caggaagcag aggttgcagt gacagtgagc tgagattgtg    11340
ccgctgcact ccagcctggg cgacggagcg agactcacga gactctgtct caaaaaaaaa    11400
aaaaaaaaag aaaagaaaaa aagaacaaac tttcttgaat gataagacct ctagtttcct    11460
tgaaacaatc atcagttgcc ttgagtctgt tacataaaaa gaggctgaat aaaataatgt    11520
gtcaactgat gaaagcttga cattataggt aagaagtgat aagatgaaat ctcaagataa    11580
aatttgaatg cgtgacattt caaatttaat aggaaaaaat aaaatatgt gtatctcgct    11640 gaaggagaga gaagatatat atagagagaa ttcttatcaa ataacattga tgctctaagt    11700
tactccctct gttttaaaca tatagcagtg ataaatatga aaagataaaa ttgaactcaa    11760
aaccatgcta aatccaagga caagtaatat tgtacagaaa gaaagcatga gccatggtga    11820
agcagtagcc tgcctgactc tgagttctca agcagaaact tgcagtagga aattctaatc    11880
tgacaaggta atgaggtcta aacatcttaa aacatgagat gcaataacag tgctaaaagg    11940
gaaatatata gctttagatt attttaagt ccaaagtatg atgagctaag ttgatctcaa    12000
gagactaaga aaacaacaac aacaaaaaac ttgaaagtag aaggaaggaa ataataagaa    12060
ataaaatagg aaaacactag aaggaataag aagaccataa ataggttatt taaacaataa    12120
agatgaggcc cagagcggtg gctcatgcct gtaattccac actttgggag gccaaggtgg    12180
gaggatcact taagcccagg agttcaagat caacctgggc aacataagga gactctgtct    12240
acaaaaaatt ttttttaatta gctaagtgtg gtggtgcaca cctgtggtct cagctgctca    12300
ggaggctgag gtgggagtat tgcttgagcc caggagttga ggctatagtg ggccttgata    12360
tgccgctgca cttcagtctg agcaagagaa caagaccttg tctaaaaaaa aaaaaaaaac    12420
tgagcctctg acaagactga tttttttttt tttttttttt tttttttttt ttgagatgga    12480
aacttgttct atcacccagg ctagagtgca gtggcacgat cttggctcgc tgcaatctcc    12540
acctcccagg gtcaagcaat tctcgtgcct cagcctcctg agtagccggg attacaggcg    12600
catgccacca tacctagcta attttttgtat ttttagtaaa gacggggttt caccatgttg    12660
gctaggctgg tcttgaactc ctgacctcaa gtgatccgcc tgcctcagcc tcccaaagtg    12720
ctgagattac aggcatgagc cactgtgccc ggccaaaact gatttttttt tttttttaa    12780 tggtaggcag aaatatcagg aatgaaaatg gaggcaagca tagcactgct ttaagccggt    12840
gctgagctgg gatttctctc cgctgctgta ccacttgtga aaggaagcta aaaactgaaa    12900
cctaccttca actgatacct ggggctctaa tttataggaa gatgcagggc taaggggggta    12960 gaaatacgca gttttaaaa tgtacagagt tggtaactgg tttacaatat gaagaaagaa    13020
ttgaagcagt gaattagcat gtaacacctc gctgaattgg ggtccctaag acacaagttg    13080
gaggcaaccc aaaattgcta gaaagaaaag gatgaaccca gaggaaagaa agataaatga    13140
agggaacaaa aaagacactg cgaatcaaaa tttctgaaca catgagatct gaagacagga    13200
aaaccagcaa atcaataccct tttgaaattt cagtccactc aagatgaaaa taatggaata    13260
aactgaaact ttaaataagt ttgcttagga ctttgaaaag taagctaaac aataaaatag    13320
aaatgatgaa acccaaataa gtagacatta atccattcaa tatttactg tcttaatatg    13380 ttcaggcgct cttctggatg ctagaactat agcagtaaat caaacagaca aaatcacta    13440 ttcatgaggt ttttattcta atgatacaga cagtaaaagg gtaagtgcaa ttaagaaatg    13500 aagggggctag gtgcagtggc tcacacctgt aataggaaaa taataggaaa ataataggaa    13560
aaagaaaaat actaatcaaa gaaatatagc aggccgggtg cggtggctca cgcctgtaat    13620
cccagcactt tgggaggcca aggtggacgg atcacctgag gtcaagggtt tgagagcagc    13680
```

```
ctgaccaaca tagtgaaacc ccgtctctac taaaaataca aaaattagcc gggggtggtg   13740
gcatgcacct gtaatcctaa ctactcggga ggctgaggca ggagaatcgc ttgaacctgg   13800
gatgcggagg ttgcagtgag ccgagatctt gctactgcac tccagcctgg caacagagc   13860 aagactccat ctcaaaaaaa aaaaaaaaaa agatagaaaa aagtatacca gaaaaatact   13920
aatcaaagaa atatagcagg ctgggcacct tgttcacatg agccagcagc agcagcagta   13980
gtggcatagt ggcagcatgg tgggggcaca cccatccgct gcagcaggat gtagcaggtg   14040
ctggggtgcc tgcctttgtg caggcattca ccacagtggc gaaggagtac agcttccagg   14100
ggcccctgct ggtgactatg tgtgcggttg gctggtggta gtgttagaat ggggtgcagg   14160
caggcgcaat ctgtatgtgt tctctgtgca ccacaggcag gggtggtcac tcaagtcggg   14220
ggaggttccg ctggtctctg tgcctagttt cattcccatg gcagtgttgg tgcaagggca   14280
tgccagcaaa gcaatgtggg gggttgctgt gggccaggca aaacagcgtg tagggaggga   14340
gtgggtggcc tggtgtgtgg ctgtgggggc tgtcctgctg tagttctctt gatggtcagg   14400
catggtccac cagcacagaa actatgatgt gagcccccag gacacccaag gctgtttgac   14460
aggcaggctc aatcaggcct gggcccagg aggggccagc agaccaacgg atgctcatgt   14520
cagaccggcc tgtctgatgg gcaagaccac gtaacagagt tcaggtccaa cacttcctct   14580
agggctaaag tctcctatgg gagcatgttg agcctagaga gatgggttat cctggccatg   14640
cttcgctaca gatgctccca caccaaaccc tctgggctcc tcttcagcag acgtgctgcc   14700
cctaccagtt ctctgagcag ctatccctgc caactcaagg gtccttggtg gtcaggggt    14760 ctcctgccag gattccagag gcacgcagtg agagtgggtt gctccttacc agttcaactt   14820
acctgttccc tcagagtttc tgagggccag gaatgagtcc tggtgcatag tagccccatg   14880
cagggctccc agcttcctcc tgcttcagcc tagcttctgt gtcttcccct tgttcattct   14940
ggtgccttcc ctctgaagat ctgttaggag tataacagtc atctcagtcc ctcagtggca   15000
gctgttccat ctggttgcat ctagttggcc accttgcccc cattttcacc caagaaaaca   15060
ttttataaat atttttaaaa ccccaccaaa atgataaaat aatcatggac atgtatgatt   15120
gcaaaagagc ctcaacatat ataaagcaga agatacaatc acagagaatt atagggagaa   15180
ataagcagca attgcttaag attttaaaac aaatttcttt cagaaaatga tagtccaagc   15240
atcaaatttt ttaaaattat ttttaatata tattttgtc cacttaggct gctataacag    15300
aatactattg actaggtagt atgcagacta tgttgtctga ccaaaagata atgaaaaaaa   15360
actatgtatg tttagaaaat gaaagtaaac tcttgacctc atgttccgcc tgcctcggat   15420
tgagaccatc ctggcaaaca tggtgaaacc ccgtctctac taaaaatata aaagttagcc   15480
aggtgtggtg gcaggcacct gtagtcccag ctactcggga ggctgaggca ggagaatcac   15540
ttgaatctag gaggcagacg ttgcagtgag ccaagatcat gccactgtac tccagcctgg   15600
tgacagagcg agattccatc aaaaaaaaaa aaaaaaaaa aaaggtaaa ctctttagta     15660 cttaattcat cagaaggaaa gttatgtaac atttatacct taaagacaac ttaaatacta   15720
cacatcaaaa ccacagggt aggtttagga tatagaaaac tgcaagaac ctcatttcca     15780 ctctaaccat gagaaaaagc tggataatcc acaaaaccat gacttttct aaaaccatca    15840 tagagctaat tttaaaggca atcaagtaat ctgaatagca aagagaaaca agattctcca   15900
aggagagaaa gcacattaac gatttcacat ttagcaaagt ggaagagaaa ggtggccatc   15960
atatcaatgg gaaagaagaa atcaactaaa ttgttttaaa ggccatatat gggttagtgt   16020
```

```
gtcagtttgt cataggtggg ggcctcagac accaagtgag tttgcactcc cttgtaggcc    16080
ttcactggat gctcaagaaa atgactgggg gcaggagaga agactgaaga aatcccctc     16140 acccaccacc cacagcagtg gttcaaatgt tcatgtgatt agtagattct tggcgacagg    16200
cataaagtgc aattttctaa ccccttctct cctacaaatc aaaagtctta aaacattggg    16260
gaggatcatc aaactctttt gtccctggac acaggcaaag aattattgtt tttaggggag    16320
ggccagaaga aaagcttgtt tgcttcttgg taacagatag gaaactatcc caataccaga    16380
acaaaggcaa agatccattg ctgctggaat ggtaagggag gaagggtaaa ggaaaaaact    16440 cttttgccact gtaggaagga cagggaattt cttgggcaaa ggaggcttca ttgatatcaa    16500
gcagattatg agaggaagtc ctggaagggg gtaggaaact gtgtccctag accaatcaca    16560
aagataaggc agagctggtg gccatgagag gaaggaaaag aataatgagg aagtcccact    16620
actgagacac aggtcctgtg cctctcccct aagcacaaga ccttagtagc acacctgtag    16680
aggaatctga agtttgtgtt gcactaaaga cagctctacc aacaacaaaa cccaaaccca    16740
gctcagccaa ggcaaacaaa agctgagaat ttgttgcaag cagacctgtg ctaccagaaa    16800
gattaaagga tgttcttcac gtcgtatgtt ctcataagtg ggagctaagc tatgaggatg    16860
tgaagccata ataatgacac atggactttg gggactcggg gaaagggtgg taaggggggtc    16920 aaggataaaa gactacaaat tgggttcagt gtatgctgct cgggtgatgg gcgcaccaaa    16980
atctcgcaaa tcaccactga agaacttact catgtaacca aataccacct gttccccaaa    17040
aacctatgga aataaaacac acacacacac acgaaaagaa ataaataatt cttcttttga    17100
gaagtctgaa aaaaggatg ttcttcaggc agaaggatta tattgcagag aaacttgtat     17160
ccacaccaaa aaatgaatag tgttggaagt agtaaaaatg aaggtaaata taaaagatat    17220
ttcttcttgt ttgtaattgc tttgacccac atattatata tatgtctca tatatagaga     17280 gagagactgt ctatatatat atagtctatt gatttctgaa aacattgcca agataattca    17340
atggagaaag ggtacacttt ttaaacacat gatacgagac aattggacaa ccatatgtga    17400
aaaaatgagc ctggacctat acttggtatc atataaaaat ttaactcaaa atgaaacaca    17460
gatctacatt taagacctaa aaccataaca tttctagaag aaaatcaaaa agctttgtgt    17520
gttaggttag aaaactattt cttagttaag actcaaacaa atattttaaa tgttgttaaa    17580
ctgagcttta tcacaaaact tctattattt aaaagacatt gtgaaggatg aaaagacaaa    17640
catacaataa aataaaataa ttgaaaagca catatctcat aaaggattct tgtatccaga    17700
atacataaca cacatgtagc agacatatca ccgaagagtg aaacaaataa gcacatgaaa    17760
agatgcttaa catcactggt caccagacaa atgcaaatta aaactgtagt gaggtacaaa    17820
tagacaacta ctagatttaa taaaatgttt taaaagccca caaaactact gatacccagt    17880
cctggtgaat atgcagagta atggaaactt ttatacattg ctggtagaaa tgtaaaattt    17940 gtactttga agtagtttag tagtttctta taacattagt aaacttaaac ctatcatatg      18000
gcccagcaat tatatttta agtatttact cctgaatgtt tatagcagtt ttattcataa     18060
ttaccaaaaa ctggaaacaa ccaaaatgtc taccaactat agaatggaca aacgactctt    18120
tgtacatgta tatcatataa tacttagtaa aaaaaaagaa tgcatgaaac acaacagcac    18180
agacggatct ccaaagcatt gagctaaata agaagaaaac gaaagggttc atactacatg    18240
atttccttat ataacattct gaaaagaca aacaataag aaaagaattc agttcagtgg      18300
ttgccaggga tcgggctgg gaggatgtaa ctgagtagcc taggttcaaa atgcattttg      18360
agactttttt ttcttccttt tcttcctttt agccttgaaa cataccttaa tactctttgt    18420
```

```
ttccctgcct tcccaccaga cactcttgtg cactggtagt ttatctaatt atgtgcccag    18480
aagttgcagg ggctaatctt gagataaacc aggcatggaa acccaggtgt gaaattctag    18540
agattacctc agagcagtta gtcaacagcc tcaccattgt tgagatgatg ccagcctgca    18600
ctccaagtgg accatgactc aggataacca gtggaacaag acacacagac ctcgtaccca    18660
gcaccattcc tgcatgcctt ccattccaag ttcccctctt taaacccctg tccacggcct    18720
aaagtttgaa atagtctgtt aagagcacga gtctggacat tccccatctg ctagcgtttg    18780
aataaaagct gtttcccttt ggtcacacct catttctcat actttgactt ctaacagtga    18840
gcagttgaac ttgagtcagt tacaggagga ggaaattgac tgcaaagaaa tacgagaaaa    18900
ctttggtgag atggaaatat tttatatctt ggttgtggtt gaggttacat agctgtttat    18960
attgatcaaa actctagaac aatatatctc aaacgagtgg attttactgc atgtaaatta    19020
tacctcagta aacctaactt taaaattcta agatacagct ctcgcaatat ttggaaggcc    19080
aatttgcagt cttaaatgaa cctataaaaa ccaaggagct tttaaaaaaa tgaattatga    19140
tttaactcaa gagtttgaag aataacaagt agaagaatgg aaacaaatgt aagagcaaaa    19200
gttaatgaaa tgaaaaatgg gagaagatca acaaaaataa aggttatttt tactagtctt    19260
tcaaaaaact aataaacatg taataagaga gatgggacag aaagagatta tacaaacaag    19320
caatattagg aataaaaaca tgattatctt agataaagta gaaaatgcta taagtagctt    19380
tatgtcaatg gaggctaaga ctagttgcag gaagaataag aaataggata ttggtgtgat    19440
tgcagattat ctgtctccca caaaacacta atcaattaca aagaagaaaa ttatgacttt    19500
acagtgaaga aacttggcag acaccaatat gacaggtgat gaccaatgtt accagtggtg    19560
ggaacagtca accgcatatg tccgtactat ggctgatact cttacaaggg catagtttca    19620
tttccatgat attcctgcca tgaatgcatg acctgagtgt gatcataagg aaacatccag    19680
ctcaaggatc actctacaaa aggtaaggcc tgtactcttt caaagactaa ggagcttttt    19740
gagattggag aaaactgaag agacttgata actgtattag tccattttca cgctgctgat    19800
aaagacatac ccgagactgg gaagaaaaag agttttaatt ggacttacag ttccacaggt    19860
ttaactctgt gcacaaacta gtcagtccac tgaaaaggat aacagacagg tgagtttgtg    19920
tcctttgatt gcttaggatc tgttgctaat ttgctgaact gaagctgcaa gagccttgtg    19980
tttttgagca tctagtggga aaagtcttta cctctggttg tgtgagtttg agatatattc    20040
ctacctcagc gggggtggag ggggagggta taagtaaaat aaattagaag actcttaaa    20100 gagtaccgtt atgattgttt tggagcaatg tcaccactct ctcctcaggg attttaggca    20160
atgtctggag acattttggg ctgttacaat ttgggggtgc ttttggcatc taatgggtag    20220
agatttggtg tgctgccaca cagctcacaa tgctcaggac cgccctgcat gacaaaacaa    20280
ttatctggct taaaatgaca atcgttttag agaaactgaa aagcacttat ataaatctaa    20340
tattctcaac atttcctcaa cataaattga atgtctaatg ctttaaatgt gatagcctgc    20400
ttaaaaaaaa aaagtccttc tcacagaagc tgctagctca aaagcacttt aaaaaaaagc    20460
acttagaaaa aaaaaaaaaa acaagaaatc aagttcatgc aattaaacta gactgataat    20520
ttgggtttaa aaaataactg tatcaggccg tgtgtagtgg ctcatgcctg tactctcagc    20580
actttgggga ctgagttggg tgggtctctt gaggccagga gttcaagacc agcctggcca    20640
gcatggtgac accccgtctc tactaaaaaa aaaaacaaa aaaacaaaaa aacattagct    20700
gggtgtggtg gcacatgcct ttaattccag ctactactgg ggaggctgaa gcacgagaaa    20760
```

```
tgcttgaacc tgggagacag agtttgcagt gagccaagat tgcaccactg cagtccagcc   20820
tgagagacag agtgagactg tttccaggaa aaaaaaaaaa aaaaaaaaaa acaccaaaaa   20880
agtcgtatat ttttctgatt atatcagtgt gaagaaaaaa tacaagtata caagttttat   20940 tcttttttaaa aatatggatt gtttacataa aggtaatttt gttttttgttc ctttttttc   21000 aggttcagga atacatgtgc aggtttgctg tataggtaaa ttgcgtgtca tggagatttg   21060
gtatacagat tattttatca ctcaggtaat aagcatagcg ccgggtgggt agtttgttga   21120
tcctcacctt ccttccgccc ttcactctta agcaggccct agtgtctctt gtttccttca   21180
ttgtgtctat atgcacttaa tgtttagctc ccacttgtaa gtgagaacat gcagtatttg   21240
gttttctgtt cctgtgttag ttcacttaga ataatggcct tcagctccat ccatgttgct   21300
gcaaaaaaca tgatcttgtt cttttttatg gctgcgtagt aatccatggt gtatatgtac   21360
tacattttct ttatccagtt caccattcgt gagcatctag gttgattcca tgtctttgct   21420
gttgtgaata gtgctgtgat ggacatatgt gtgcatgtgt cattatggta gaattattta   21480
tattcctttg ggtatataca caataatggt attgctgggt tgaatggtga ttctgctttg   21540
tgttctttga gaaatcacca aactgctttc cacagtggct gaaataagtt acattcccac   21600
caacagtgta taagtgttcc cttttctctg caaccttgcc agcatctatt attttttgac   21660
tttttaataa tagccattct tactggtgtg agatgttatc tcattgtggg tttgatttgc   21720
atttcgaaga gaattgctac tttgaatttc tgacatttct tatacagatt taatctgata   21780
agctaatatt attcctacgt aatatttagg atgaggaaca gtgaataatt ttgtttaagt   21840
ggattggttt ataattctga caaacttttt tttgttattt gttttgttttg gtttgttttc   21900 ttcttagaga caggtctcgc tctgttgccc aggctggagc acagtggtgc tatcatagct   21960
caccgtaacc tcaaactcct gggtataagt gatcatccta tctcagcctc ctgagcagct   22020
aggactacag gtccatgcca ccatgtctgg ctaatttatt tgttttgtaa agatgggggt   22080
ctcactttga tgcccatgct ggtctcaaac tcctggcctc aagcaattat ctggccttac   22140
cctcccaaag tgctggaatt gcaggcatga gccactgctc ctggcctctg acaaagtttt   22200
taatatcaac agtacattag gggcctccag acctgggccc ccagcacagc ttcccaggcc   22260
ctgcctgatc acttcaatcc gttgcagctc tgcattctc tgaggaggaa atcccagaga   22320
ccatccacag gctgtctgcc attgccactg cagtggtacc cacctttgct gccctctggc   22380
tggggaagga acaaagagcc taattgcttt gctggcagct cccatatgtg gaggagccca   22440
gtctctcttt cctataatcc ctcaacccac tgcttttcac caggtagggc ccccagcttg   22500
ggcctgtagc acagcctgca gtaggtttgt gttttttctag ggtggagctt ctgcaggcaa   22560
ctgacagccc ctctgttact gtagcagtat ctgcccttcc tgccatcagg ctggggaagg   22620
aaaaaatagc ctgagtgctt tactcacacc tccagcacgc catagccgcc ctgcagagaa   22680
gaagtcagac tcttccccat gggccctcca tccccctgct attcaccaag cagggatccc   22740
agacttgagc ccacagtgca gcctcctcac cttgggctga ttgttctgat tggcagtggc   22800
cctgcgtttc tctggggcag agacccaaga gacgagtgaa aggccctcta ccattgccac   22860
tgccaaggtt cctgcccctg ctgcccccaa gctggggagg aacaaaaag cctgagcttg   22920 ccacaaagct gtgttgtgca ggcctggagt gccaagccga gatctgtggc cagcactcaa   22980
gtggaagagg agcccacatt cagagagcac tgacagggag catggctgcg tatgtgagga   23040
aatgaaagag gagccacgtg gctaagagct accggcccta tggttagcgc catctactgg   23100
atcacagctc aaacttcaac atcaaaaata cttctgttag tagaccctgt gaaaccaagg   23160
```

```
acaaaaatcc agccccaaat aaacaccctg cacaaagcct cagccctctg aaaacatcca    23220
gaaacaaatc caactggcta tattgaaatt acaccacagt taaggaacat cagcacacag    23280
atgagaaaga accagtacaa gaactcaggc aactctaaaa gccatagcgt ttgcttacct    23340
ccaaatgact gcgctagctc cccagcaata gttcttaacc agaatgaaat ggctgaaatg    23400
acagacatag aattcagaat ctggatggca atgaagatca ttgagattca gtagagagct    23460
gaaatccatt ccaaggaatc taagaaatcc agtaaaatga ttcaagagat gaaagatgaa    23520
atagccatat agggaaccaa actgagctga tagagctgaa aaactcacta caagaatctt    23580
ataatacaat cagaagtatt aacagtataa taaaccaagc tgaagaaaca atctcagagc    23640
ttgacaatca gttcttcaaa ttattcaatc agacaaaaat aaggaatttt tttgaataag    23700
caaaacctct gagtaatatg ggattatgta agagaccaa atcaatgacc cattgacatc     23760
cctgaaagag aagaagagag agaaagcagc ttggaaaaca tatttgggaa tattaaccat    23820
gaaaatttcc ccaaccttac tagaaaggtt gacattcaaa ttcaggaaat ttagagaagc    23880
cctgcaaggt actattcaag gctatcaccc tgaagacaca tagtcattag attcttcaag    23940
gtcaacatga aagaaaaaat gttaaaggca gctagagaga aggggcaagt caccaacaaa    24000
gggaacccca tcaggctaac aatggacctt tcaacagaaa tcctacaagc cagaaaaact    24060
tggggctaat agtcagcatc cttaaagaaa agaaattcca accaagaatt tcatatccag    24120
ccaaatgaag cttcataagt gaaggagaaa taaaatcctt ttcagacaag caaatgctaa    24180
gggaattcat taccaccaga cttgccttac gagaggtttt taagggagtg ctaaacaggg    24240
aaatgaaaga ccattactga ccaccacaaa aagacactca agcatattga ccattgaaac    24300
taaagcaaat atgcaatcaa gtcttcaagt ctacataaca accacctaac aatacaatga    24360
tgtgatcaaa tcagcacaca tcaatactaa cttttgaatgt aaagggggcta aaaatcccac    24420 ttaaagggca tggagtggca agctggataa agaagcaaga cccagtggta tgctatcatc    24480
aagagaccca tctcacatgc aaggacaccc acaggctcaa agtaaaggga tgaagaaga    24540 tctctcaagt aaacagaaaa caaaagagta ggagctgcaa ttcttatttc agacaaaaca    24600
gactttaaat gaagaatgat caaaaaggac aaagaaggca ttacacagtg ataaagagct    24660
cagttcaaca agaagattta actagactaa atatatatta accgaacact ggagcactag    24720
attcataaga caacttctta cagacttaca aagagactta gataaccaca caataatagt    24780
gaaagacttc aatgcccact gacagtattg gacagatcac tgaggcagaa taactgacaa    24840
agatatttgg gatctaaact tgacacttga ccaaatagac ctaacagaca tctacagaac    24900 acttcacccca caaaagcag aatatacatt cttctcatct gcacatggca tacactctga    24960
aattgaccac atgctgagcc atgaagcaat tctcaactaa ataaaaaaaa atcataccaa    25020
ccacattctc agaccaccat gcaataaaaa tagaaatttt tatttctatt atttatttc    25080 tattattatt tatttaccaa gaagatctct caaaaccaca caattaaatg gaaattaaat    25140
aatctgctct ggaatgactt ttgggtaaac aataaaaatta aggcagaaac taagaaatta    25200
tttgaaatga atgaaaatga agatacaaaa taccagaatc tctaggacat agctaaagca    25260
atgttaagag gaaagtttag gctgggcgca gtggctcaca cctgtgatcc cagcagcact    25320
ttgggaggcc aaggcaggcg aatcacaatg tcaagagatt gagaccatcc tggccaacaa    25380
cgtgaaactc cgtctctact aaaaatacaa aaattagctg ggcgtggtgg caagtgcctg    25440
tagtcccaac tactagggag gctgaggcag gagaatcact tgaacccggg aggcggagct    25500
```

```
tgcagtgagc cgagatcatg ccactgcact ccagcctggt gacaattaaa tggaacctca    25560
cctgctcggg aggctgaggt tggagaatgg catgaaccca ggagacagag gttgcagtga    25620
gccaagatcg cgccactgca ctccagcctg ggtgacagag caagactccg tctcaaaaaa    25680
aaaaaaaaaa aaaaaaatt aaataagtga gaaagatctc aaattaacaa cctaacttta    25740
cacctagaga aactagaaga aaaacacaaa gccagcccca acgctggcag aagaaaagaa    25800
ataatcaaaa gcagagctga actgaacaaa atggagatga gaaaagccat acaaaagatc    25860
aacaaaacca aaagctgctt ttccgaaaga ataagattga tagactgtta gctaaactaa    25920
taaaaaaaga gagaagatcc aaataaacgc aatcagaaat gacaaagagg acatgaacac    25980 caacccata gaaatacaaa aaccatcaga aactattatg aacatctcta tgcacacaag    26040
ctagaaaacc tacagcaaat gggtaaattc caggaaacat acaacctcca aagattaaac    26100 cagaagaaa ttgaaacccc aaaaagatca ataatgagtt ctgaaactga atcagtaatg    26160
aaaatcctac ccgaccctgg accacatgga ttcacaactg cattctacga aatgtataaa    26220
gcagagctgg taccaatcct actgaaacta ttccaaaaaa ttgaggagga gggtatcctt    26280
cctaactcat tctatgaggc cagcatcatt gtgatacaaa aacctggcag agacacaaca    26340 aaaggagaa ctttaggtca atatctctgg taaagatagg tgcaaaaatc ttctacaaaa    26400
tactaacaaa ccaagtccag tagcatatca aaaagcgaat ccaccacaac caagtaggct    26460
ttttccctgg gatgcaaggt tggttcaaca caggtaaatt aataaatgtg atttatcaca    26520
taaacagaac taaaaacaaa actaaatgac catctcaata aagaagaaaa ggcattcagt    26580
aaaactcaac acactttcat gttaaaaacc ctcaacaaac caggcgttga agatacattc    26640
ctcaaaataa taagagccat ctatgacaaa cccacagtca acatcatatt gaatgggcaa    26700
aagctgtaag tattcccctt gagaactgga acaagacaag gatgcctgct cttatcactc    26760
ctattcagta cagtactgga gctcctagat agagcaatca ggcaagagaa agaaataaaa    26820
gacatcaaaa taagaagaga ggaagctaaa ctatctctct tcacagaaaa tatgattcta    26880
tacctagaaa accctacagt ctctgcccaa aatctcctaa tctgataaac aacctcaaag    26940
tctcccagat ctgataaaca acttcagcaa agtttcagga taaaaaaat cgatgtacaa    27000 aattcaggag catttctaca caccaataat gtcccagctg agagccaaat taaaaaaaaa    27060
aatctcattc acaataacca caaaagaat aaaacaccta ggaatacatg tattagtccg    27120
ttttcatgct gctgataaag acatacctga gactgggcaa tttgcaaaag aaagaggttt    27180
aattggactt agagttccat gtggctgggg aaagctcaca atcacggtag aaagcaagga    27240
ggagcaagtc acatcttacg tggatggtgg caggcaaaga gaggagcact tgtgcatgga    27300
aactcctgtt tttataatca tcagatctcg tgagacttac tctctctcat gagaacagca    27360
tggaaaatac ctgcccccat gattcaatta cctccctcca ggtccctctc acaacacgtg    27420
ggaattcaag atgagatttg ggtggggaca cagccaaacc atatcaatac atctaaccag    27480
ggaagtgaaa gatttctata atgagaatta caaacagtg ctgaaagaaa tcagagacaa    27540
aacaaacaaa cggaaaaaca tcccatgctc atggacagga agaatcaata ttgttaaaat    27600
ggtcatactg ctcaaagcaa tttacagatt cgatgctgtt cctatcaaac tcctcacatt    27660
ttccacagaa ttagaaaaaa actatttaa gattcatttg gaaccaaaaa agagcctgta    27720
tagccaaagc aatcctaagc aaaagaaca aagccagaga catcacacta cctgacttca    27780
aactatacta caaggcttcc gtaacaaaaa caggatggtg ctagtacaga aacagacata    27840
taaagcaatg gaacaagtta gaggacccac agataaagtc acgcatctgc aaccatatga    27900
```

```
tcttcagcaa agctgatgct aacaagcagt gggaaaagaa ctcactagtc aaaaaatggt    27960
gctaggataa ctggctagcc atatacagaa tgttgaaact ggaaccctat gtttcaccat    28020
gtacaaaaat gaactcaaca tggattaaag actgaagtgt aaaacctaaa agtataaaaa    28080
ccctagaaga aaacctagga aatactcttc tgggcatcag acctgacaaa gacttcatga    28140
tgagaattcc aaaagcaatt gcaacaaaag caaagactga caatagggac ctaattaaac    28200
taaagagctt ctacacagca aaagaaacta tcaacagagt taacaggcaa cctagagaat    28260
ggaagaaaat ctttgcaaac tatgcatctg acaaaagtct aatattcagc atctataaag    28320
aacttagatc aacaagcaaa atcaaatga ccccattaaa aaaatggcaa aggacatgaa    28380
cagatacttc tcaaaagaag acatacacac caataagcat atgaataaat gctcaatatc    28440
actaatgatt agagaaatgc aaatcaaaac cacaatgaga taaccatctc acactagtca    28500
gaatggctac taataaaaag tcaaaaaata acagatgctg gtgaggttgt ggagaaaagc    28560
aaatgcttat acactgttgg tgggaatgta aattagttca gccactgtgg aaagcagtct    28620
ggagatttct taaggaactt aaaatagagc taccatttga cccagcaatc ccattactgg    28680
gtatatactc agaggaatat aaatcattct gccaagatca taaagacaca tgcataaaga    28740
cacatgcatg catatgttca ttgcagtact attcacaata gcaaagacat ggaatcaacc    28800
taaatgccca tcaatggtag actggataaa gaaaaagtgg tccatatata ccatggaaca    28860
ttatgcagcc ataaaaaagg acaagatcgt gtcctttgta gcaacatggg tggggttgga    28920
agtcattatc ctaagcgagt taacataggt acagaaaacc aaataccaca tgttctcact    28980
gataagtggg agccaaacat tcactttaag attctgaact atattcaatt aagtcataaa    29040
taatctttga atgctttgat aatttctttt tttttttttt ttttgagatg gagtctcgct    29100
ctgtcgccca ggctggagtg cagtggcaca atctcggctc actgcaagct ccgcctcgcg    29160
ggttcacacc attctcctgc ctcagcctcc cgagtagctg ggactacagg cacccgccac    29220
cacacctggc caattttttt gtatttttag tagagatggg atttcaccgt gttagccagg    29280
atggtctcga tctcctgacc tcgtgatccg cctgcctcgg cctcccaaag tgctaggatt    29340
acaggtgtga gccatcgtgc ccggcctgct tgataatttt ctaagtaata tagaatcccc    29400
agaccaatct cagttgttat ttcgtacaca tgcttttgga ttttattttt ataagttata    29460
gagtggttct ttgagtctta ctaatgagcg tgttaatttt ttccacttca atgtgtgaaa    29520
gggatgtgtg tggacatatg aggttgcatt atgtgaactt atgagctttt ctgggctact    29580
aaatgcttct tatatgtaac aaatagttct caattgccac ttcttagtag tttccatgaa    29640
gtaaaagtag cttctttgat tacagttcta aataatacaa gtggtagaga ttattgcagg    29700
tgcagtgtga cagagaagta tgaagagaac actattattt aaagcaaagt gtttggtgta    29760
gaatgttaaa gaagatagta aaggatgaaa cttggatggt gaggaaaatt aaagtcatgc    29820
aaacagtgaa ctttatttgc cttggtttat cataactaca gataatgagc ctgaaaagaa    29880
gcaataaaat ttattacaac tgttagtaag ttttgcccaa tttttatgag ttttacgagt    29940
agaaatttaa gataaagtaa aaatgtaaag tttttaactg cctaaagttt aggttaatac    30000
aaaattataa tttatttttt cccttatgtt aaaatgataa attggtttca gagccttcag    30060
tctgttgtta accacaggca ggttattttt ttaccttcaa tttaatctac tcagataatg    30120
aaactttatt tttttgagac agggtcttgc tctgtcaccc aggctggagt gcagtggtgc    30180
caacatggat cattgcagcc ttccattcct gtactcaagc aatcctccca cctaagctcc    30240
```

```
ctgagtagct gggactacag gtgtgagcca ccacgcctga gtaattttt ttttttttta    30300 gagacattat ctcactatgt tgctcaggct ggtttcaaac tactgagctc aagcgtcaag    30360
tgctctgccc acctcagttt cccaaagtgc tagggttata ggtgtgagcc actgtgccca    30420
gcctgcaatt ttatatctca caagaaaagt tttctgattt tgtcatggcc ttgattacag    30480
tacttaaaaa caaaaacaaa aacaaagta ctcatgctga aaaagctgaa gttccttaca     30540
attgtgttat cttttaggat ttttttcacc ctatatttt cttttctcta gtgtcaactc     30600
ctgtgccaac cttgatttat aggtagtcaa gttaaaataa ttcattgttc tcagatttct    30660 atgattttt cttaatcaag tgacaaattc tgctatgata actttttgat tatgcttttc     30720
caagatcgaa ccctaaatta tattttcaaa aattcaagat gtcttttaga cctaactgtt    30780
tttgagtttt cccaagaggc ccctaaaaat catgaagatt tattcttttt tttttttttt    30840
ttgtgagata gagcctcact ccattgccag gctagagtgc aatggcgtga tcttgccact    30900
agatttattc tttactcaaa aaggaatggt aaaataatt gaaattgcct gatatatttc      30960
atatttctga agtagcagaa cattattgta agaactgcat gggaaaagct gtcaaattta    31020
aagttcaacc atttctagtt caatttttag gtaaatagta ccaatataaa catgtttcag    31080
agattatgca cttagcataa ttttttcaatg tcttcactat ccatagtatg ttctttcctt   31140
tgaggaaaat attgaccaaa tcctttttaa acagttatat attgtatacc agtagagagt    31200
ttttctcttc tccattttca tttagcatca ggcattcagt attatcatcg gcaggttatt    31260
tctgcttttc tctcatgctc acctgaagcc tttgctataa gctgtaggtt agaaagggtc    31320
ttggctgggc gcagtggctc acagcacttt gggaggccaa gatgagagga tcgcttgagg    31380
ccaggagttc aagaccagcc tggtcaacag agcgagatcc catctctcag aaagaaaaaa    31440 aagaaagaa agaagaaaaa aagaaagaaa caaaggaagg aaggaaggaa aagaaagaag    31500
gaaggaagga aaagaaagaa agaaggaagg aaagaaagga aggaaggaaa agaaagaaag    31560
aaggaaagaa agagagagag agagagagaa tgaaagaaag agagaaagaa agaaagaaaa    31620
gaaaggaaaa gaaaaaaaga aagaaagatt gcctcaatct aaggaggaaa cacttagggc    31680
attgcagaag actatagaat tgatatcctc agctattgat acgtcaagaa attaagacag    31740
aggcagtgaa aagtgatgg atctgagaga tatttaggac tctgaggttg attggatttg     31800
tggcacctat ctgatatgat ttggatgttg tcccctccaa atctcatgtt gaaatggaat    31860
cctcagtgtt gaaattaggg cctgctggga ggtgtttgga tcatggggga ggatcccttg    31920
tgaatagctt agcaccgtcc ctttggtgat gagcgaattc ttgctctgag ttcacccaag    31980
atctggttgt ttaaaagtct gtggcacctc ctcctgtctc tcttgctccc actctcacta    32040
tgggacatgc tagcttttctg ttgccttcca ccatgattgt aagctttctg aggcctcacc   32100
agaagcagat ggcaacacta cgcttcttgt aaagcctgca gaaccattag ccaattaaac    32160
atgttttctt tataaattat ccatttgtat ttatagcatg caaaaatgac cgaacacact    32220
atcataggta taattatcaa attcaaaagc attcagttcg tgaatattaa agcttcagt     32280 tttgttctca ctcagataga aaaaccatt tcatgtctgt caggatgtga atcagaaaaa     32340
tgactgtggc tgggcatggt ggctcgtgct tgtaattcca acacattggg aggctgaagt    32400
gggaagattg cttaaagcca agagttcaaa accagcctgg gaaaaatata aagaccctgt    32460
ctctacagaa aagttaaaaa aaaaaatgct tctggtaaag tccaagaaga aaacgataga    32520
tctgctcaaa tgtctgaata aagtattgat aaatatgaggg ctttacacaa aatcataatt   32580
aatcctttca atacccctaca tatagatatt attgcttgca ttttacagat aaggaaactg   32640
```

-continued

```
aggcttgggg ggagaacctt actcagggtc atacagctaa taaaagtaga attggctgag    32700
tgtagtggtg cacgcctgaa attccagcac tttgggaggc tgaggtggga gggaggcttc    32760
tgcccaggtt gcagtgagct atgatgacag tgccactgga ttcctgcctg ggtgacagag    32820
tgggaccctg tcactaaaaa aaaaaataac gataattaaa aaaaaaaaaa agaaaagtag    32880
actaggcata ctaacccaat ttgtccagtt acaaacactt gattagagga ccaattttg     32940 atgctaagga attaaaaaaa aaaaaaagga ttttaccctg gaaagatgtt aacattccca    33000
acattcctga ccttagatcc tgagccccct ggtttaaagg ccgcctctct gaaccacttc    33060
cagttgcact ttctccaagt gtaaggaagc tgttcacctg caacctgctc acccttctac    33120
atcatggttt ggctacctcg aatccctgcc aacagcccc aggctacttc ccggagtctt     33180
ttctctggct agtccttctg agggtggcct gtgagtcttg agtgtacatc tctatgtcca    33240
atgacaggct gttagctctg ctatgttcct gcatgaaacc ccaaggagac tgagaattcc    33300
aaatgtaaat ttggccttcc aggtcattat gaatgcatat tcagactatg taaggaaata    33360
gagtttattt tattaaatac tttcttagct taatttataa ctaccgtgta acatttgatt    33420
cacatgtata agggaggagc ccacccctca tattgtctta tgccctaggc tgcgtcttgc    33480
tcctgtacac ggatgacctt ctgctggaac atgccatggc agttgggtgt gcgaagggga    33540
cggatgccct gcttcagcac ctggagaact gtgtgtataa ggtgtccaag aagaaagctc    33600
agatctgcag acagcaggta cactacctgg gattcgctat tcggaaaggg gagcgcagcc    33660
tggggtcaga aagaaagcgg gtcatctgca gcctacagga acctaaaacc agaaggcaag    33720
taagggaatt cctgggagct gtgggttttt gcagattatg gattccaaac tttgctgtac    33780
tggtcaagtc tttgtatgga gttacaaagg ggggcgaccg ggagtctttt gaatggggac    33840
ctctacaaca gcaagccttt cgtgagttaa aggaaaacct tatgtcggcc ccagtcctag    33900
gactaccaga tttgacaaag cccttttacac tgtatgtgtc agaaagagat aaaatggcag    33960
ttggagtttt aacccagact gtggggccct ggccaaggcc agtagcctat ctctcaaaac    34020
aactagatgg ggtttctaaa ggctgggccc catgtctaag ggccctggca gcaacagccc    34080
tgttagcaca agaaggagat aaactaaccc ttgggcaaaa cctgaatata aaggcccccc    34140
gtgctgtggt aactttgatg aataccaaag gacagcatca gctaacaaac gctagattaa    34200
ccaagtacca aagctggctg tgtgaaaatt cccacataac cactgaagtc tgtaacaccc    34260
taaatcccac caccctgctc ccagtatgag agcccagtcg agcataactg tgtagaagtg    34320
ttggactcag tttgttctag cagacctgac tttcaggacc agccatgggc atcagtagac    34380
tgggagttat acgtggatgg gagcagcttc atcaacccac aaggagaaag acatgcagga    34440
tatgtggtgg taactttgga tgctatcatt gaagccaaac tgttgccaca gggacgtcag    34500
cccagaaggc tgagctcact gctttaactt gggctctaga actcagtgaa ggtaagactg    34560
taaacatcga cactgactct cgatatgcct ttctaaccct ccaagtgcgt ggagcattat    34620
ataaggaaaa gggccggtta aactctgggg gaaaggacat aaaatatcaa caagaaattc    34680
tacaattatt agaggcagtg tggaaacctc agagagtggc agtcatgcac tgcaggggac    34740
accagcgaac ctccacttca gtggccttag gaaactcccg agctgactca gaagctcaaa    34800
aagcagcatc taccccttac tgggcatcgg tagcagcctc cttactccct caaacacctg    34860
acctggtacc tacctattct aaggaagaaa aagaatgttt caacacagaa gggggcaagt    34920
aataaaagaa ggatggatca gactgccaga tgggagggaa gctgtgccgc agttgctggg    34980
```

```
agccacaatc atactggcca tgcatgaaac cactcatcta ggtcaagagt cacttgaaaa    35040
gttgttaggc cggtacttct acacttgcca gcccttgcca aagcagtagc acaacggtgc    35100
gttacttgca gacagcagaa cgcaaggcaa ggccccactg ttctgcccgg cctataagct    35160
tacggagtag ctccttttga ggatcttcag gtggaattca cagaaatgcc aaaatgtaga    35220
ggtaacaagt atttgctggt tcttgtgtgt acttactctg ggtgggcgga gtcttcccca    35280
acacgaaccg aaaaggccta cgaagtaacc cttgtgcttc tccgagacct tattcctagg    35340
tttggactgc ccttatgaat cagctcagat aacgggccgg cgtttgtggc tgacttggta    35400
cggaagacag caaaggcatt aggaatcact tggaagctgc gtgccgccta ctgacctcag    35460
agtttcggaa aggtggagcg aattaatcgg actatcaaaa atggtttagg gaaagcacgt    35520
caggaaacag gattaaaatg gatacaggcc cttcctatgg tattgtttaa aattagatgc    35580
accccttcta agaaaacagg atactcccct tatgaaatac tgtatcatag gcctcctact    35640
atactacggg gacttccagg cactccccga gagttaggtg acattgagtt acagcgacag    35700
ctacaggctt tgggaaaaat tacacagaca atctcgactt gggtaaatga gaggtgtcct    35760
gtcagcttgt tctccccagt tcatccttcc tttccagttg atcgtgtgtg gatcaaggac    35820
tggaacgtag ccccctttgcg gccatggtgg aaaggacctc agaccgtcat cctgaccacc    35880
cccacggctg taaaggtaga aggaatccca gcctggatcc accacagcca tgtgaaactg    35940
gcagccgctg aaacctggga ggcaaaaccg agcccggaca cccctgcga agtgactctg    36000 aggaggccga caaaccctgc tccagtcaca cccggaagct gactggtcta cgcacggccg    36060
aagcatgagg agaatcatcg tgggactcat tttccttata atttggactt gtatagtaaa    36120
aacttccact gattttcccc gcatggagga ctgctctcag tgtatacatc aggttactga    36180
ggtaaggcaa caagttaaaa caatctttct gttctatagt tactgtgaat gcctaggaac    36240
tttaaaagga acatgtttat atactgacac tcagtacaag gtatgtagcc taggaaacga    36300
ccggccagct gtgtgttatg acccctctga gcttatccaa cacgaaactg aaaaggccta    36360
cgaagtaacc cgtgtgcttc cctgagacct tattcctagg tttggactgc ccttacgaat    36420
tggcttagat aatgggccgg cgtttgtggc tgacggtttt tgaaataaga ttaagggctg    36480
aagactagtg gggacgcgta aatgatacaa gtaaagtaat agccagaaca gaagagaaag    36540
gggtgcccaa acacataatc ttgaaatttg atgcctgtgc tgtcattagt ggcagtaaat    36600
taggaagggg atgtggctct tttgggaaaa aggcgatatg actgaaaata agtacatttg    36660
tcatgaatta ggactgtgtg gaaatgaatg tgaacactgg tcttgtgtca tttaggccac    36720
ttggataaaa aaatgaaaag gatccagtcc acttcagaaa ggaaaaagtg gcccttcctg    36780
tactaaggga caatgtaacc ccttagagct agcaacaacc aatcccttg atccttgctg    36840 gaaaagaggg gagcatgtga ccttaggaat cgatggggca ggactggatc cttgagtaaa    36900
tatcttagtt cgaggagaag tttacaaacg ctctgctcag ccagtgtttc aaactttcta    36960
agatgaacta aatgtgccag taccagaaat tccaggaaaa acaagaaatt tgttttttgca    37020 attagccaag catgtagccc agtctctcag tgtcacttca tgttatgtat gtggaggaac    37080
tgtgatggga gatcaatggc catgggaagc ccaagaatta gtacctacag acccagttcc    37140
caatgaattc ccagctcaaa agagtcacct tgataatttc tggaccctga gcctcaatt    37200 attggacaat attgcatagc tagagaagga aaataattca ctcaccccttt aggacaactt    37260 agttgtctgg gacagaaact gtataatggt accacaaaaa cagtcacttg gtggagttca    37320
aatcacacag aaaggaatcc atttagtaaa ttcccaaggt tgcaaaccat gtggacccac    37380
```

```
ctggagtccc actaggactg dacagccccc actggattat actggctatg tgggcataga    37440
gcttacgcta aattacctgg ccagtgggca ggtagttgta ttactggcac tattaaacca    37500
tctttcttcc tactgtccat aaagacaggc gaactcctgg gcttccctgt ctatgcttcc    37560
catgaaaaaa gaagcatagc tataggaaat tggaaagata atgaatggcc cccagagaga   37620
atcatacaat attatggacc tgctacttgg ggacgagatg gttcatgggg atactagacc    37680
cccatttaca tgctcaacca aatcatatgg ttacaagctg tcttagaaat aatcactaat    37740
atgggctggg cgcggtggct cacacctgta atcccagcac tttgggaggc caacgcaggt    37800
ggatcacgag gtcaggagat tgagaccatc ctggctaaca tggtgaaacc ccgtctctac    37860
taacaataca aaaaattagc cagggtggt ggcgggtgcc tgtggttcca gctacttggg      37920
aggctgaggc aggagaatgg cgtgaacctg ggaggcagag cttgcagcga gccgagattg    37980
tgccactgca ctccagcctg ggcgacagag tgagactcca tctcaaaaaa aaaaaaaaaa    38040
agaaaagaaa gaaagaatca ctaataaaac cgacagagcc ttgactattc tggcctgtca    38100
agagactcag atgagaaatg ctatctatca aaatagattg gctcttgact acttgctagc    38160
agctgaagga ggggtctgtg ggaaattaa ccttactaat tgctgtctac acgtagatga     38220
tcaagggcaa gtagttgaag acatagtcag agatatgata aaactgtcac atgtgcccat    38280
gcaagtgtgg catggatttg atcctggggc catgtttgga aaatggttcc cagtgttagg    38340
aggatttaaa actcttataa taggagttat attagtaata ggaacctgct tactgctccc    38400
ttgtttgcta cctgtacttc ttcaaatgat aaaaagcttc atcgctacct tagttcacca    38460
aaatgcttca gaacaactgt actatatgaa tcactatcga tctgtcttgc aagaatacat    38520
gggtagtgag gatgaaagtg agaactccca ctaattgact gaggttctca agtggggga    38580
ataagggagg agaccacccc tcatattgtc ttatgcccaa tttctgcctc caagaaaga    38640
agtaaaaatt aaaaggcaga aatggaatcc acaggcagat agcccagcat cacgccctgg    38700
gcctggtagt taagaatcaa cccctgacct aactgctcgt gttatctata gatttcagac    38760
attgtatgga aaaacattgt gaaaatccct gtcctgtttt attccgttct gatgaccggt    38820
gcatgcagct cccagtcacg tacccactgc ttgcttaatt gatcacgacc ctctcacgcg    38880
gaccccgtta gagttgtaag cccttaaaag ggacaggaat tgctcactcg gggagctcgg    38940
tttttggaaa cgtgagtctg ctgatgcttc cagctgaata aagccctttc cttccacaac    39000
tcggtgtcgt ctgaggggtt cttgtctgtg gttcgtcccg ctacacgtac agggtaatgg    39060
tttaatattt catgaataat attaattgta tttcaaaatt aatgtggtta aatatactga    39120
tatactttaa tacatttttt caacagttta atgttttggc atagataata aatacaaata    39180
ggaatttgca tttatctaat gacaaaatgt taacatttta aactctactc agttataaac    39240
taaactcaat tttaaaatgt ttaaaaaatg tgtggatgac acaaaaacaa accttcatgt    39300
ttgtttatat tctcccctta ttaatcctct ttaaggatta attaagccta caaaattcta    39360
ctttaataat agttgttctc cttaagagtc cctaaaact ttttttttta attaaataac      39420
taggccaggt gtggtggctc acacctgtaa tcccagcact ttgggaggct gaggtgggta    39480
gatcccctga ggtcaggcat tcaagaccag cctggccaac atggtgaaac cccgtctcta    39540
ctaaaaatac aaaaaaatta gccaggcatg gtggcgcatg cctgtactcc cagttactag    39600
ggaagctgag gcaggagaat cacttgaacc caggaggtgg aggtttcagt gagccaggat    39660
cacaccactg cactccagtc tgggcaatgg agcgagactc cgttttgaaa aaaaaaaat    39720
```

```
gaaataagtg gtattgtgcc aaaacaagtc taataggaaa aacaatcaag ctcatacccct    39780 ataaatatat atctaagata ttaggaccca aaagaaaagg aaaattatgc agggtcactt    39840
cacattctac atgacctcta cctagatatt ctcatttaat tttaaatcac attatcattt    39900
ccgaaagccc aaatttaaaa tagtaaaata actaatgcat ttaacaccta gtgcctagag    39960
tttggtctgt aaagctattc tccactaaat agaactaaaa gttcttggag aatttcaatt    40020
cctagagaaa aaaaagaaa agaaaaacct ttaaggtgga cctaagtgat cttgctacta    40080
gaatgaggga tttttttaaa tgccttttaa agttccaaag tggtgttaag aaaacataga    40140
aagcaacctt ttccaatggc aaaatttcga atttttgcaca tcaaaagtaa ataaaattat    40200
aggtaattaa ttttaggtta cgaatagtaa atcatactta atttttgctc cataatgtat    40260
gcttacactc tctaagaacc tcaggatatg aaataaggaa ataagtatgc ttgtgtacta    40320
tagagattgt tttgaaattt ttactttaaa cttgtaatat ttttttacaaa caaaataatt    40380 tatgggattta catacataaa ctattaataa taaaggaat aagtataaat ctatcactga    40440
aaattacaga gagaggaaaa aaataacctg gtgatatggt ttggctgtgt caccacccaa    40500
atctcatctt gaattgtagt tcccataatc ccaacgtggg gacccagtgg gtgataaccg    40560
aatcatgggg gcagttacct ccatgctgct cttgtggtag tgggtgagtt ctcatgagat    40620
ctgatgattt tataaggggc ttccccctac tttgctctgc acttctcctt gctgcggtca    40680
tgtgaagaag gacgtgtttg cttttccttc caccaagatt gtaagattcc tgaggcctcc    40740
ccagccttgc agaattgtga gtcaattaaa cctctttcct ttataaccca gtcttgggta    40800
tgtctttatt agcagcgtga gaacagacta atacacctgt cagtctcctt catgctttct    40860
gattgcacgc tttaatgcaa tgaccagaat caaacagaaa cgaccttggg tgttttctct    40920 ggatttttcct gggcaaccag ccagtgggac ctggaccttc tggctcacag ttggagggc    40980 tacacctgaa ctcagctttt catgggatgg acagtttctt ccaacacaag ttccaacaac    41040
tttctgtttg acccaaggtc tccagatact ggataatggg cttttttcaaa aaataccctat    41100 cgggccgggc gcagtggctc acgtctgtaa tcccagcact ttgggaggcc gagggggcg    41160 catcacgagg tcaggagatt aagaccatcc tggctaacac agtgaaaccc cgtctctact    41220
aaaaatacaa aaaattagcc gggcatggtg gcgggcgcct gtagtcccag ctactgggga    41280
ggctgaggca gaagaatggc gtgaacccgg gaggtggagc ttgcagtgag ctgagatcgt    41340
gccactgcac tccagcctgg gcgacagagt gagagtctgt ctcagacaaa caaacaaaca    41400
aataaatgcc tgtaaacaga ctgcctggtg ctctagtagt ttccttactg acaaaattct    41460
ttttgtgtgt gccctataaa taggagagca acaagaggat gggattcctc tcctattatg    41520
caaacccaca ccatggatcc agcagactac tctggcccca gcatgctgct ccttgggatg    41580
atgggagaag ggggaaacct gtgttttctc ttggttttgt aagtttcccc tttcccccagt    41640 aaaactcatc ccttaatcta gtggttctca aactttggtg tgtatcaaaa ttatctggta    41700
ggctggataa aacacagatt gctgtgcccc acttccagaa cttctggttc aatagatcta    41760
gaaggagact gggaatttgc atttctaaca ggtccccaga tgatggtaat attgctggtg    41820
gtggtgggga ggaccacatt ctgagaacct ctgtatttaa ttttatttgt atttatttat    41880
tttatttatt gttttaattt aattttttgag tccctgttac tcaggctaga gtgcagtggc    41940
ataatcatag tccactgtaa cctgaactcc tggcctcaag tgacactccc aaagtgctga    42000
gattacaggc gtgagacaca atgtgcatcc cgggccttcg ttttaattca tacagtgtga    42060
ctatgtggta atcagttctg ttggttacca aaaaggctcc cacttgtatg aacttcacat    42120
```

```
aagagttaac cactctcctt tctagtgcct atctttacag acgaccctg acttatgatg    42180 gtttctcttt gatttcctaa ctttacagtg atgcaaaagc tatatgcatt cagtagaaac    42240
catgctgtga gtaccatac aaccattctg tttttcattt ttaatacagt attcaataaa    42300
ttacagggta tattagacac tttattacac cttattatgt tagatgactt tgcccaactg    42360
taggctaatg taagtgttct gagcatgttt aaggtagggt agcctaagct atggtgtttg    42420
gtaggttagg tgttttacat gtattttga cataggatat tttcaactta tgatgggttt    42480
atcaggaggt aaccacattg taagtagaga agtgtttgta tagttttacc acatacctag    42540
gaatccttat ctagtggatt cagtttccgt tgttcaaaag ttttataaag gccaggcatg    42600
gtagctcatg cctgtaatcc cagcactttg ggagatggaa gtgaacggat cacctgaggt    42660
cagaagttcg agaccagcct ggccaacatg gtgaaacccc acctctaata aaatacaaa    42720 aaattagcca ggcttggtgg tgggtgcctg taatcccagc tactcaggag gctgagacag    42780
gagaatcgct tgaacctggg aggcagagat tgcagtgagc caagatgccc cattgcactc    42840
cagcctgggt gacaagagtg aaactccatc aaaaaagaa aaagaaaaa taaaaagta    42900 aaagttgtat aaaatagcat tatttcttga ggatattatt tgacttgctt ttttcactca    42960
tccatccaat gtatagctat cattcactca ttttttattgt tgtataatat tctgttttgt    43020
gtatatacct gttgaaagac atttggctta ttttcaggtt tttttctatg aagttgctat    43080
gaacacctat aaatgtttcc tagtgtatag gaccaagact ttttctaggg cagtaattct    43140
cagatggggg aaattttgct attcccaccc acccctgaaa cccagaagac atttggcaat    43200
gtctggagac acttttatta ttagaactca ggagtgttac tagaattaag agggtggatg    43260
ctgctaaaca tcttaaaatg cacagagcag cctaaattat acaaaatgat ccagcctata    43320
atgttaatag tgtggaggct gaaaaaccct gttgtaggac agtggttcac aaagcatcag    43380
catcacctag gaacttgcta gaaatctcta agatagatac ataggagtgg aattgctggt    43440
tataaaataa gcaggtattc acattaataa gattatgcca atttgcccat tttattgtgg    43500
ggttgtgttt cttttttctct atatatttg tttatatgtt ctctttgttt attattgaga    43560
aagagggcaa aaagcagccc ctgatattca gaagctgacc tggcactcac agcttggcca    43620
taatattatt ctgttgaaca ttaacaattt aaatctcata gaataccaag ctgagacaaa    43680
agtactctga gatcacaata aaatgagaca aggccacttc atagcattat ctaagcatag    43740
gcaaaaacaa ggtctttgtg tcacccataa gataacagac ccccctttc tggataaaat    43800 gtacaacagc tacttttttt attattatac tctaagttct aaggtacatg tgcacaacgt    43860
gcaggtttgt tacataggta tacatgtgcc atgttggttt gctgcaccca tcaacttgtc    43920
acttacatta ggtatttctc ctaacgctat ccctccccca gcccccccac ctctcaacag    43980
gccccagtgt gtaatgttcc cctccctgtg tccatgtgtt ctcatttttc aactcccact    44040
tacgagtgag aacacgtggt gtttggtttt ctgcccttgt gctattttgc tgagagtgat    44100
ggtttccaga ttcatccatg tccctgcaaa ggacgtgaac tcctccttt ttatggctgc    44160 atagtattcc atggtgtata tgtgccacat tttctttatc cagtctatta ttgatggaca    44220
tttgggttgg ttccaagtct ttgctattgt gaatagtgcc tcagtaaaca tacgtgtgca    44280
tgtgtcttta tagtagcatg atttataatc ttttatatat acccagtaat gggattgctg    44340
ggtcaaatgg tatttctagt tctagatcct tcaggaatct tcacactgtc ttccataatg    44400
gttgaactaa tttacactcc caccaaaagt gtaaaagtgt tcctatttct ccacatcctc    44460
```

-continued

```
tccagcatct attgtttctt gacgttttaa tgatcaccat tctgactggt gtgagatggt    44520
atctcactgt ggttttgatt tgcatttctt tgatgaccag tgatgacaag cattttttca    44580
tatgtctgtt ggatgcataa atgtcttctt ttgagaagtg tctgttcata tcctttgctc    44640
acttttgat ggggttgttt ttttcttgta aatttgttta agttctttgt agattctgga     44700
tattagccct ttgtcagatg gatagattgc aaaaattttc tcccattctg taggttgcct    44760
gttcactctg atgatagttt cttttgctgt gcagaagctc tttagtttaa ttagatccca    44820
tttgtcaatt ttggcttttg ttgccattgc ttttggtgct ttagtcatga agttttttgcc   44880
catgcctatg tcctaaatgg tattgcctaa gttttcttct agggttttta tggttttagg    44940
tcttacattt aagtctttaa tccatcttga gttaattttt gtataaggtg taaggaaggg    45000
atccagtttc agctttctac atatggctag acagttttcc cagcacattt attaaatagg    45060
gaatcatttc cccattgctt gtttttatca ggtttgtgaa agatcagatg gttgtagatg    45120
tatagtgtta tttctgaggc ctctgttctg ttccattggt ctatatatct cttttggtac    45180
cagtgccatg ctgttttggt tactgtagcc ttgtagtata gtttgaagtc aggtagtgta    45240
atgcctccag ctttgatctt tttgtttagg attgtcttgg ctatgcgggt tcttttttgg   45300
ttccatatga accttaaagt agttttttcc aattctgtga agaaagtcat tggtagcttg    45360
ttggggatag cattgaatct ataaattacc ttgggcagta ggaccatttt cgcaatattg    45420
attttttccta tccatgagca tggaatggtc ttccattttgt ttgtgtcctc ttttatttca  45480
ctgagcagtg ttttgtagtt ctccttgaag aggtccttca catcccttgt aagttggatt    45540
cctaggtatt ttattctctt tgtagcaatt gtgaatggga gttcactcat gatttggttc    45600
tctgtctgtt aatggtgtat aggaacgctt gtgattttttg cacattgatt ttgtatcctg   45660
agactttgct gaagttgctt atcagcttaa ggagattttg ggctgaggct atgcggtttt    45720
ctaaatagac aatcatgtcg tctgcaaaca gagacaattt gacttcctct cttcctactt    45780
gaataccta tattgctttc tcttgcctga ttgccctggc cagaacttcc attactatat     45840
tgaattggag tggtgagaga gggcatcctt gtcttgtgcc ggttttcaaa gggaatgctt    45900
ccagttttg cccattcagt ttgatattgg ctgtgggttc ctcataaata gctcttatta     45960
ttttgagata cgttccaaca atacctagtt tattgagagt ttttagcatg aaaggctatc    46020
gaattttgtc aaaagccttt tctgcatcta ttcagatgat catgtggttt ttgtctttgg    46080
ttctgtttat gtgatggatt atgtttattg atttgcgtat attgaaccag ccttacatcc    46140
cagggatgga gccgacttga tcgtggtgga taagctttct gaggtgctgc tggattcggt    46200
ttgccagtat tttattgagg atttttgcat cgatgttcct tagggatatt ggcctaaaat    46260
tatctttttt tgttgtgttt ctgccaggct ttggtatcag gatgatgctg gctcataaaa    46320
tgagttgggg aggattccct cttttccgat tgattggaat agtttcagaa ggaatggtac    46380
cagctcctcc ttgtacctcc agtagaattc ggctctgaat ccgtctggtc ctggactttt    46440
tttggttggt aggttattaa ttattgcttc aattgcagag cctgttattg gtctgttcag    46500
agattcaaat tcttcctggt ttagttttgg gagggtgtat gtgtcgagga atttatgcat    46560
ttcttctaga ttttctagtt tatttgcgta gaggtgttta tagtattctc tgatggtagt    46620
ttgtatttct gtggtatcgg tggtgatatc ccgtttatca ttttttattg cgtctatttg   46680
attcttttct cttttcttct ttattagtct tgctacaggt ctatcaattt tgttgatctt    46740
ttcaaaaaac cagctgctgg attcactgat tttttttgaat ggttttttgt gtctctatct   46800
ccttcagttc ttttctgatc ttagttattt cttgccttct gctagctttt gaatgtgttt    46860
```

```
gctcttgctt ctctagttct tttaattgtg atgttagggt gtcgatttta gatctttcct   46920
gctttctttt gtgggcattt agtgctataa atttccctct acacactgct ttaaatgtgc   46980
cccagagatt ctggtacgtt gtgtctttgt tcttactggt ttcaaataac atctttattt   47040
ctgccttcat ttcgatattt acccagtaat tcaagagcaa cagctacttt tttttaccag   47100
tcatcacgta gggaagaaaa aatatcttct ccttctaccc ttctaagttc ttgactgggg   47160
cctttgtaag aaagagaga ttaacaatac aaaaaacata caaatttatt caatataagt   47220
ttacataaca tgggaacctt cttaaggaca tgaagaatgg aagaaatgat taaacctgag   47280 cattttatg ctaggtttga tagagaatga aaagtcatag gaaaacctaa taacacaaag    47340
gatatgagct gcaattcctt cagcttaaaa taattaattt ttaaatattt aaattttaaa   47400
aatttaatta aagtgtcata atttggggta gcatgtcctg aactccatca atagaattac   47460
ccttgctttc tgaaaacact catactatgg gggaaccaaa cctccttctc ctaaattcta   47520
aaactgtctt actgagacac cccatgatgt gtgttctctc ttgctcagtg agcaatgaat   47580
tcatcttgtt caaccacaaa tgtccctgtg tctctggctg aagggcatat ttcagagatc   47640
ttaatagtct ttattatgcc ttttggtgag caccacttct tttttttttt tcttttgaga   47700
cagagtcttg ctcttgttgc ctaggctgga gtgcagtggc atgatctcgg ctcaatgcaa   47760
cttccgcctc ccaggttcaa gcgattctcc tgcctcagcc tcctgagtag ctgggattac   47820
aggcacacac caccacctct ggctaatttt tgtatttta atagagatgg ggtttcacca    47880
tgttggccag gctggtctca aactcttaac ctcaagtgat ccacctgcct cggcctccca   47940
aagtgctggg attacaggcg tgagccaccc cgcccagccc agtgagcaac acttcttaat   48000
tttagttcgt tttaatttt ttgcctccct aatgagtgct ttttatgtta tatttaagaa    48060
atcctggccc ggcgtggtgg cttacacctg taatcccggc actttgggag gccgaggtgg   48120
gttgatcacg aggtcaggag atcgagacca tcctggctaa cacggtgaaa ccccgtctct   48180
actaaaaatg caaaaaatca gccggatgcg gtggcgggca cctgtagtcc cagctactag   48240
ggaggctgag gcaggagaat ggcgtgaacc caggaggcgg agcttgcagt gagccgagat   48300
agcgccactg cactccagcc tgggcgaaag agcgagactc cgcctcaaaa aaaaaaaaa    48360 aaagaaagaa agaaatcctg ccaggcacag tggctcacgc ctgtaatccc agcactttgg   48420
gaggccgagg tgggcggatc atgaggtcag gagatcgaga ccatcttggc caatacggtg   48480 aaacccgtc cctactaaaa atacaaaaat tagctgggct tcgtggtgca tgcccatagt    48540
gccagctact caggaggctg aggcaggaga atcgcttgaa ccccggaggt ggaggttgca   48600
gtgagccgag atcgcgccac tgcactccag cctggtgaga gagtgagact ccgtctgaaa   48660
aaacaacaac aaaaaaatcc tttcttactc caatatcata caggtatttt ttttttttaag  48720 tttccatttt tttttttttt tttttttgag actcagtttc actcttgttg ctcaggctgg   48780
agtgcaatgg cacgctctca gctcatggca acctctgcct cctgggttca gcaattctc    48840 ctgcctcagc ctcccgagta gctgggatta cagacatgtg ccaccatgcc tggctaattt   48900
tgtattttta gtagaaacga gctttctcta tgttcgtcag gctggtcttg aactcccaac   48960
ctcaggtgat ccgcccacct cggccttcca aagtggtggg attacaggca tgagccacca   49020
cgcccggcca acttgacaag tttttaaggt ataattcatt cagagtctaa aagtttagta   49080
ggatcatggt agtcaggaga ataatttcac tgcagaggtg tgtatgtgtt tagcaaagtg   49140
attgctaaca gattttcctg aaatccccga cagcacaaag tatcctttac attattatct   49200
```

```
ttcatgcata taaaatctca catatttctg tatagtggga gaacctggac tttaacattt    49260
tatatgaaag aaatgcataa accctgtctt tagaagataa tgtaagattt ggaaacaata    49320
tggtaaaagt aggaatagaa caaaaggggg aaaatgacaa agaaattttt ttaaaaaag     49380 tccatgggat tcgtgggttt ctcagcttaa agggacaagg gaaagcaagt ctaggatgac    49440
tcccagtatt caaagttacc agaagcttga gatgatgaac tgctaaggta gtgagtgtgc    49500 cctatttttgg ggaaaagatg gttttctctt caagtctgtt gctccttatc tttcctcaat   49560
gaatttctaa ggagcattga aatttgtgtg aagaaaggc ttccaaaagt aaataagttt     49620
aaaatccagg gttttgtatt atactttcag atttccacaa aggcccagtt tctctgtttt    49680
ttttttaaag ttaaaaaaaa gttgaaaatc aaagccccca agtgggaagt aatttgtgtg    49740
tatctaaata ttgtatacat tcactgtttt atcccagcaa tttataaact gggtgtgcag    49800
aaagcagcct ggagcaaaaa cattgtaatg ggagttaaga gatcaggatt ttaatgatgg    49860
tctgctacta atctatacga aaatggtttg tgtataggtt tcagattcct taaatatgta    49920
gaataagact acataatctt caagcttctc tgcagcactt aagttcagat tctacttaag    49980
cacttacgga atgtgtcagt                                                 50000
```

<210> SEQ ID NO 7
<211> LENGTH: 50000
<212> TYPE: DNA
<213> ORGANISM: Homo sapiens
<220> FEATURE:
<223> OTHER INFORMATION: human DYXC1 chromosomal gene region,
      nucleotides 50001-100000

<400> SEQUENCE: 7

```
gtaattccaa tttaccctat tccagatttg tagcaaagca tttgtcagat gaatcatagg      60
gtggtttctc ttcagttttc aaactttgga gcaaaaccta tataggtgct tttggcggcc    120
ttacagttaa taggatttgc aggatacaat agttttagac aagctcctgg tatgtgttgt    180
gaacaaacgt tttctgaaga ggaatttgga gcaaagcaac tatttcaggg aacagtttgc    240
aaactgggga gttgaagcct taggtgtaaa acaaaggtgc attccagaga acaaagggag    300
ggtttgggtt ttacagcaaa agtttctgcc caggttccca gtcaggttcg tttatacaaa    360
tgaacgattg aaccgcactt agttctgatt ggttgataca gctgagccct gattggttga    420
ggcaggtgag ccctataaga cccaacactc aacagaggtg tgggtttggg gagaacgcag    480
agtccatgtg tgacctctag taggtaaatg accacgtgtc tctattttaa atttagaccc    540
agttagccgc tctggatgtt gacggattgg ctctttcagg ttcacatttg ttcacagtct    600
gtatgaccaa gaaatttgca aaacagaaca actagcgcta actcttaata gcctcagtca    660
gaataaacag acaagacact gcaccaaggg cgtatgggca ttgcacctgc tcctcatggg    720
ctgctttccc gagccttatg cccacagccc tccttagcat tatcgcatta tgaggctgga    780
agtgcttttt ttttttcttt ttttcttttt ttttcttttt tttttttga  dacggagttt     840 cgctcttgtt tccaggctg gagtgcaatg gcgcgattt ggctcactgc gacccctgcc      900
tcccgggttc aagcgattct gctgcctcag cctcagcctc cagagtagct gagattacag    960
gcatgcacca ccacgcccgg ctaatttttgt attttttagta gaggcggggt ttctccatgt  1020
tggtcaggct ggtctcgaac tcccaacctc aggtgatccg cccgcctcgg cctcccaaag   1080
ttctgggatt acaggcgtga gctagcgcgc ccgaccccaca gagtgctttt tttttttttt  1140
ttttttctca agcagagggt atgggtctac ttctttgaac attcgctcag atcgtaaggt    1200
```

```
aaccccaaga atcggcatca ctctctggtc tgggcgcctg gatagtcacg catggagtcc    1260
gcgaggtgct ggcgccggag cacgctggga acgccgggct cccggccggc ctgacccgga    1320
agggctggcg catggtaacc ccagcttccc tagcaaccaa gcaggcgcaa gaagcaacca    1380
gccgcgctat ccgctcccgt tgctaccgga atgcctcttc aggttagcga ttacagctgg    1440
cagcagacga agactgcggt ctttctgtct ctgcccctca aaggcgtgtg cgtcagagac    1500
acggacgtgt tctgcacgga aaactatctg aaggtaagaa tgcaagtctt gcctgccggt    1560 ctccggggt gtggtccgaa gcttctgcaa gagcgcagct gggcacgagc aacaggctca    1620
tctttgccga taaacgtcct aaattttaa tcctattaaa aaaatgaatc ccatacaggt    1680
aacacaccat ctgtagacag ataatcagat cagagactac ttttatccag ggcttcctca    1740
tatgccttgc taatctttca ctacctggca taaatttagt gggccttttta gaaagttatt    1800 ttacctttt cacgtgtttc ttaatacgcg tgcttaattt gtgtaactaa cttagtttct    1860
gttttcaccc ttctgcatag gtcaacttc ctccatttt atttgaggca tttcttatg    1920 ctcccataga cgatgagagc agcaaagcaa agattgggaa tgacaccatt gtcttcacct    1980
tgtataaaaa agaagcggcc atgtgggaga cccttctgt gacgggtggt aagttcttta    2040
ttaaaagatg ttcatctggt tgtaccttttt cggtttcaga cctttaaaa aatttatt    2100 tgaagcacct atattgtgta ggggaagata gattttttt ttttaagagt cttgctctgt    2160
cgcccaggct ggagtgcagt gacatgatct cggcttactg caacctctgc ccccggggtt    2220
caagggattc tcctacctca gcctctcaag tagctgggat tataggtgtc cgccaccacg    2280
cccggctaaa ttttttttgta tttttggtag agcgttttgc catgttggcc aggctggtct    2340
cacactcctg accggtcatt aagtgatcca cccgccttga cctcccaaag tgctgggatt    2400
acgggtgcga gccaccacac ccggccagat agactttcct tttactctcc aaggttcaat    2460
agctgggtct ataaaataaa ctaacaacag aaggattgac agaagaaaat gtatagaaat    2520
ttatgaattt ttaatattag tgcttgaggg catcacaggg aaaaaagtga ataccccca    2580 agcggtgaga tttgagagtt tagggactgt cttaataggg gaaggggag gggatgtagg    2640 ccgcttagaa caggaaatga ttttaggaa agatgaatgg atccttagaa gaatagatag    2700
gaaatgtgat agcttttaac aaaatttgtc agagtgtggt gttgacttgt agttccttt    2760 tctgggagaa tagtcaatat tccctggtta atgaaactcc aggggaagag atttatgaca    2820
cttgggttcc tttggaaaat ctgttttag gcagataaga ggagttctgg caaaacctct    2880
ccctgcattt gctgctttca agtgccttta actcaaaatg atcgctatat gaaagcagca    2940
tattttgggg tggcatatcc tgaactcatt caattgctgt tttagaaaaa aaaaaaggct    3000
tatgagccta atttaagtga tacagtgctt cagcagccat ttaaataaac ctaaaggctg    3060
aattagtcaa agttagagca cattaagcag aagatgtggg ctcatgtctt aagggtaagc    3120
cctcctgata tatagccttt attgagtact taactttgcg ttaggtgtta acatgcctgt    3180
aattccatga aacaacctgt cacttaggta ttattaccct tttttacag gggaggctac    3240 tgacatatgg aaagtttgag taattggcaa atcacacag ctagtgactg gcagcctgga    3300
actggagcct tagcagtttc actctagagc agatgttccc aaccctggct acatatttga    3360
atcagctatg gaattttaaa ataatactct aatccagtga atcagtttc tgggaatagg    3420 actcaggtgt tggaagtttt gaaaagcttt ccaggaatta taatgtgcag ccaaagttga    3480
aatccccagt tgttgtttgt ttgtttggaa agacagagtc tcgctcagtc acccaggctg    3540
gagtgcagtg atgcgatctc ggctcactgc aacctccgcc tccctaggtt taagtgattc    3600
```

```
ttcagcctca gcctcccaag tagctgggac tacaggcacg tgccaccacg tccagctaat    3660
ttttgtattt tttagtagag acaaggtttc actatatgtt ggccaggctg gtctcaaact    3720
cctgacctca agtgatccac ccacctcggc ctcccgaagt gccgggatta cagccatgag    3780
ccaccgcgac cggcctgaca tccccagttt taaagctagt tctctgtagt cttattaagc    3840
tagttgtcag tgctttgtac taataccaag atcagcttcc atagtcagta attgtcctct    3900
actgctttag ccctgttttc ctccttcctt ctttagttgt catgttttct aatactttat    3960
gtttactgcc tggaatttat ttttttttaat tttgagtttt ttaagagata gaatctcacc    4020
ctatcaccaa cgctggagtg cggttggtgt taccatagct cattgtaacc tcaaactcct    4080
aggttccagc aattctcctg cctcgacctc ctgagtagca gggactacag gtgtgcacca    4140
aaacacctag gtaattgttt ttattttgt agagacaggg tctcactatg ttgccgatag    4200
gtcttgaact cctaggctca agtgatcctc ccactttggc ctcccaaatg ctgggatttc    4260
aggcgtgagc cactgcaccc agactactgc ctggaatttc ttttaagcct ttggcattaa    4320
gccttgaata tggactcttg agggtagaaa gagttgcaac cattctttct atcaaggctt    4380
tcttggtatc ttgtagtgga atttaatttt taatttccaa gaccaaggta gaatttattt    4440
ttctaagatc gggtattcag ctcagagaat actggttaag gtaggttaac atagccagtt    4500
tacttaattt tttttttttt tttttttttt ttttagtga gccccagact acctaaagag    4560
ttttaaagaa tcaggttcct gttttttgac ctcttacttc ctctgtgact cagtaagtct    4620
atgttggggc ctgaggatgt cataacacac ccagtctgtt ttgacttctt acctaaaatt    4680
gaatatacat ttattttgac tcttgtaaat taacttttc tgtaaaggac cagatagtat    4740
tttagacttc acaggccata tggtctctgt catatctatt cagctctgcc attgtagcac    4800
aaaagtagcc acaggtgatt catatttatg gacaatgaaa tttgaatttc atctaatttt    4860
taaatgccac aaaatgttat tttgatttt ttcatccatt taaaaatgtg aaaattattc    4920
aaggcttgtg ggctgagggg aaacaggtgg caggtcggat ttggcccatg ggtcatagtt    4980
tgccaacctc tgatttagac aaatcaaaac agtcttaaaa ctgacttaag ctcagcgcag    5040
tggctcatgc ttgtaatccc atcactttgg gaggccgagg caggtgaatc acctgaggtc    5100
aggagtttga ccagcctg gccaacatgg tgaaaccctg tctctactaa aaatacaaaa    5160
cttcgtcagg cgtggtagtg gatgcctgta gtcccagcta cttgggaggc tgatgcagga    5220
gaatcgcttg aacccgggtg gtggaggttg cagcgagctg agatctcacc actgcactcc    5280
agcctgcgca acagagcgag actccatctc aaaaaaaata aaaaataaaa aaccactaat    5340
ttatatcaca atgaacattg attctacttc agaaaccagg tttgagattc ctttagaaat    5400
caaactcagt ttgccgggcg cgctggctca cgcctgtaat cccagcactt tggtaggccg    5460
aggcgggctg atcatctgag gttgggagtc cgagaccagc ctaaccaaca tggagaaacc    5520
ccgtctctac taaaaataca aaattagccg ggcatggtgg cgcatacctg caatcccagc    5580
tactcaggag gctgaggcag gagaatcact ttaacccggg aggcggaggt tgcggtgagc    5640
cgagattgtg ccattgcact tcagcctggg caacaagagc gaaactcagt ctcaaaaaaa    5700
aaaaaaaaca agaaagaaat caaactcagt tttgccaggt tacagtggct catgcctaaa    5760
gtaatctcag cacctttagga ggccaaggtg ggaggatcat tgagcccag gaattcaaga    5820 ccagcctggg caacataggg agacttcacc tctattaaaa aaaaaaaatt agccgggcat    5880
agtggcatgt gccttatagt cccagctact tgggaggctg aggttggagg atcacttgag    5940
```

```
cccaagaggt ggaggctgca gtaagccatg ctcataatgc tgcactccaa cctgggtgac   6000
agtatgtgat cctctctcaa aaaaagaaa tcaaactcaa ttttacttgc aattcagtgg    6060
gattatttat ttaaccattt ttttttcaca taaaatattg tggaactcca gtttatacac   6120
gtagactgtc tacctcatta ttcagactct aattttctc attttttctg gaaattcctt    6180
cttgatacac tctttatttc tattagacat ggagtatttc atttgggaag ttaatgttct   6240
tccagttatt tctgccgctg aagctgactt agctgtctac cttcctgttt ttaaacagca   6300
ggagagatga aagaggctt cagacctaac ttcagtacta gttcttagcc aagatcttag    6360
atgaataaaa ttacacactt ttacttacct ctaactgata tttaacattc tcttcaattg   6420
tgaagatagg caacaaataa tagtagtatc ttagtctgtt tgggtactat aacaaaatac   6480
catcaactga gaagcttata aacaacagaa ctttatttct cacactcctg taggctggga   6540
agtccagatc aaggtcctgg caggtttggt atgcggtgag ggctcacttt cctgtagatg   6600
gcaccgtact gtgtcctcac atggtggaag gggcaagtct gctttctggg gccttctgta   6660
taaggacact acctcccaaa aggcctcacc tacaaataat atcacattaa gggttgggat   6720
tttaacataa gagttttagg gagacataaa cattcagacc atagcaagta gtatcaacaa   6780 aaacaaagt atgtttatat cagagatacc tcttttatac tctactttga aattacaata    6840
ttagacttgt tgctatatat taatgcatta ataaagaagc acataatcgt gtatcacaat   6900
ttggccggcc gcagtggctc acgcctgtaa tcccagcact ttcggaggcc aaggcaggcg   6960
gatcacaagg tcaggagatc aagaccatcc tggccaacat ggtgaaaccc cgtctgtact   7020
aaaaatataa aaattaggtg ggcgtggtga tgcccacccg tagtcccggc tacttgggag   7080
gctgaggcag gagaattgct tgaacccagg aggcggggt tgcagtgagc tgagatcgga    7140
ccacagcact ccagcctggc aacagagcaa gactccggct caaaaaaaaa aagtatatca   7200
caattttatt tcttaatgtt ttataagtgt tttgatataa ctgagtttct ttgtagacct   7260
gtatatttta tttcatacat tttaaaacat tgtgaaagga tttataagga ttcactactc   7320
tgccaaggtg tctgctgcac aaaaaaggtt aagaacccat gcctgggta tgattcatcc    7380 ctctacccac cccttatcta ctctccccta ctttgtcttc ccctcaagtt ttctcctctc   7440
cccttctgtt tttttttttc tgcttaaagg ctagatcttt tccttaggc tctgatcctt    7500 cccttttgtaa gataatttac ccattgatcg tagtcttcag tttgtgaaac tttgggccac   7560
atcaaatata aagataactg tgagatcttg cgtggtggct catgcctgta attccagcac   7620
tttgggaggc caaggtagga gcatcgcttg agcccaggag ttcaagacca gcctgggcaa   7680
tatagtgaga cctcgtctct acataaaatt taaaaattag ccagatgtgt tggcacacac   7740
ctgtagtccc agctactcag gaagctgagg taggaggatt gcttgagccc aggaggttaa   7800
ggttacatta agctgtgatt gcttaactgc actccagcag cctgggtgac agagagagac   7860
ctagtctcag gaaaacaaac aaacaagctg tggatgtaa ggttttatat atatttatat    7920
atattatata aaatattata tataaatata tataaaacct taccattat attattatat    7980 actattataa tataatatta tatattatat tatatactat tatataataa tagtatataa   8040
tattattata taatoaatata atattatcta taatatataa tatatatttt atatttttata 8100 tattatataa atgatgattt attgtgatca ggttttataag caaatagccc tagtttctta   8160
acagagaagg aagaggataa atgtgtcctt gcaccttcat cctcaccctc tccctctcat   8220
tacctgcctc ttgtgtccct ccccatccc ttcttcttcc tctccacccc cttcattctc    8280
tagtcattca ttattattac agttagttgc ttacctttta acattagctt cttggccagt   8340
```

```
ttaatattga aaaatatttt ccatgttcct tgtgaagttg ggtacaaaga aatctcatcc    8400
tgggtcagtt tatttaagta gttttctcat aagtaaagca aatttgtcat aattctaatt    8460
tagcaatatt ctgtacattt tagttgacaa agagatgatg caagaatta gagaaaaatc    8520 tattttacaa gcacaagaga gagcaaaaga agctacagaa gcaaaagctg cagcaaagcg    8580
ggaagatcaa aaatacgcac taagtgtcat gatgaaggta agttgcagaa tgacaggcaa    8640
gtcctctaaa gagataatag tagactatgt gaggatagtg agttccagct gctggacttc    8700
ctcagcattt tcttcatact ttgtttagag gacttactat gttatataga ctgtctgcta    8760
tttatatgtg tgtttttttt tttcttgaga ccgagtctca ctctgtcgcc caggctggag    8820
tgcagtgcgg tgatctgggc tcactgcaag ctccacttcc cgggttcatg ccattctcct    8880
gcctcagcct cctgagtagc tgggactaca ggcacctgcc accatgccag ctaattttt    8940 ttgtgttttt agtagagaca gggtttcacc gtgttagccg gatggtctc gatctcctga    9000 cctcgtgatc tgcccgtctc ggcctcccaa agtgctggga ttagaggcgt gagccaccgt    9060
gcccggccca tgtttgttct tgaaatctga atgaaagtca aaggtgtaaa agttggacag    9120
ttgtttcagg gagagggttc tatttctagg ggagtaaaaa taaagtttca atggtgcaag    9180
tgttttactt cttttttaaat cttggaataa cagatatgat tttaaaacag aagcatattt    9240
aaaacattat tgtcaaattt ttttaactgt taagggtttt aagtgaaagt tttaatcagc    9300
aatatatttt ttgagaaaca attcacattc catataattt acccatttaa agtgtacaat    9360
ttaatagttt ttagtacatt cagagttgtg taaccattac tacagtcaat tttagaacat    9420
tttcatcacc ccccaaaaag caccaatacc cctaagcagc cactccccat ttcccctaac    9480
acttagtcct aggcaactgc ttatctattt tctgtctcaa tagatatacc tattttgagt    9540 aattttaca aaaaaattct tatctcaggc caagcgcagt ggctcatgcc tgtaatccca    9600
gcacttttgg gaggccgagg cgggcggatc atgaggtcag tagttcaaca ccagcctggc    9660
caacacagtg aaaccctgtc tctactaaaa atacaaaaat cagccgcgcg tggtggtggg    9720
cacctgtaat cccagctact cggtaggctg aggcaggaaa atcgcttgaa cccaggaggt    9780
ggaggttgca gtgagcggag attgcgccac tgcactccag cctgggcgac agagtgagac    9840
gccgtctcaa aaaaaaaaa aaacttctt atctcgaatt cccatttga catgttgcag    9900 tgactaagga atctataata cgcattattt aagattttg tggacccatg actgttttt    9960 ggattttcat aactagcatt gttttctatt atcaacagtt tatgattcca aagatttgtc   10020 cactttttt atcacttcca cttaactttt tttttttttt ttttgaaat ggtgtctggc   10080 tctgttgccc aggctggagt gcagtggtga atctcagct cactgcaacc tctgccactc   10140
gggttcaaga gattctcatg cctcagtctc ctgagtagct gggactacag atgtgcacca   10200
ccacgcctgg ctaattttt atatttttag tagagacagg gcttcaccat attggccagg   10260
ttggtgtcga gctcctgacc tcaagtgatt cacccgcctt ggcctcccaa agtgttggga   10320
ttacaggcat gagtcaccgc actgagccat atactttgtc ttttacttaa taattgaact   10380
ggtcagctgg tcaaagattc ctgcctttag catacttaat tccatctttt ctttattgta   10440
tgatcacagc tgttggcctt ttgatttat cattttcatg aatttaaaaa aattaatata   10500
gaatttgtgg caatagatat tcactgaaat aataaaacag ttaataatg gcacacttac   10560 tgctgtattg gtatgtcaaa acagaacagt tgaccagcag gaagcaccac tatgttgtac   10620
cttgaaggtt tgttttttgt tttttttttt tgagatggag tcttgcttag tcgcccaggc   10680
```

```
tggagtgcag cggcgcaatc tcagctcact gcaagctctg catcctgggt tcacaccatt    10740
cttctgcctc agcctcccga ataggtggga ctacaggtgc ctgccactac gcctggctaa    10800 ttttttttgta tttttagtag agacaggggt tcactgtgtt agccaggatg gtctcgctct    10860
cctaacctcg tgatctgccc gtcttggctt cccgaagtgc tgggattaca ggtgtgagct    10920
gccgcaccca gctgaagttt tcaatttact aatgtatgaa agcttgactt tggtattggg    10980
aaaggtgatt tagaggaatt aatatataaa atatgaagat acgggttata ttaagaggac    11040
agaacctaca aaagccagta tcctgttcca caaattgtct gttttctctc ttccctcagt    11100
agtgttgaga gttgggagta tgttttgttt catccttatt atagccatta tcaagtaaat    11160
tggtgctcaa acatttgaat aaattaatat gaatgcatta ctctagtact atgtacccgt    11220
agcaaacgtc tactttggtg aattagctga agctattttc actctgtgca atcctagaca    11280
ctgttaagaa aagaactttg acgatccagt aagagcaaat agtaacaaaa ggcaacatat    11340
tgttagctta agttagcata aattaatta aacttgaag gacatctacc aaaaataagt    11400 ggttttttaag tagtaacctt ttaaaaaata attagtgggg ctgtgtcaat tcgctatact    11460
gtgtgtacag gtattattct gcttgggcta ccctaacaaa atgttgttta acagaaattt    11520 atttttctcat agatcaaggt ctggtagggt ctctttctgg ttagactctc tgttttggg    11580 gccttcttgc tgcgctctta cgcagcaaaa aaaaaaaag aaaagaaaa agattggtat    11640 ttcatcctga gagtatggtc aaggaatcca aagcagtatt gtttgtgctg aatcctggaa    11700
aatgaatcac aattaggttc ctggtagaaa gagagggaaa acctcattgc agaagtgctt    11760
ttaaagcccc tgctgtgtca tatttgctaa tgtaccatta gccaaatcaa gtcacatagc    11820
caagtccaga tttaaagatt ggaaaaatag actatacttc ttggaaagag aggtataatg    11880
ggaaaatgac attacaattt ggataggtat atgaaaataa ggcacacaaa ggaacattta    11940
ttggtcagaa ataatatcct aatgtgtcca gaatttattc cctctggtgg gttcttggtc    12000
tcactgactt caagaatgaa gccgcatacc tcatggtgtg ttacagctct taatggtggc    12060
gcgtccggag ttgttttgttc ctctcggtag gttcgtggtc ttgctgagtt caggaattaa    12120
gctgcagacc ctcacggtga ctgttacagc tcttaaaggt ggcgcggacc cgaagagtga    12180
gcagcagcaa gatttattat gaagagtgaa agaacaaagc ttccacagca tggaagggga    12240
cccgagccag ttgccgctgc tggctggggt ggccagcttt tattcccttta tttgtccccg    12300 tctatgtcct gcggattggt ccatttttaca gagtgctgat tggtccattt tacagagtgc    12360
tgattggtgc gtttacaatt gttaagctaa acacagagca ctgattggtg cattttttcca    12420 gaatgctgat tggcgcgttt acaatccttt agctagacac agagcactga ttggtgcatt    12480
tttgcagagt gctgattggt atgtttacaa tcctttagct agacacagag cgctgattgg    12540 tgcatttttta cagagtgctg attggtgcgt ttacaatcct ttagctagac aggaaaagtt    12600
ctccaagtcc ccacttgacc caggaagtcc agctggcttc acctctcact aagatttttga    12660 aaaatttctc aaaggttata gagaactctc ttaagggatt ttccacaaaa gtgtaaaatt    12720
agttgagttt gtcttttaga aagctcgttc tggctaatga gtttgaagag gttgcaggga    12780
ggaggcagag tttttgttaa gatggagaaa ttttgagcat acgtatgttg aggaaggaag    12840
ccagtaaaga gggaaaggtt aataatacaa tgaagagaga agattgatga tggagcagtt    12900
ttctggtgat atggggatat tttatcattt ttgctaatta aaaataaact ttttttttt    12960 tttgagacag ggtctgttgc ccaggctgga atgcaaaatg gcgcaattac agctcactac    13020
attgacctcg caggttcgag agatcctccc acctcagctt cccaagtagc taggactata    13080
```

```
ggtgtatgcc accatgccct gctaatttttt ttgtagttttt tgtagagatg gggtctaact   13140
atgttgccca gcaggaacaa agaatagata tctaaggatc tggaaaattc ttaagcacac   13200
agataattaa aggaattttt actttgcttg gtaaagaagc agggtcatct gggcatggtg   13260
gctcatgcct gtaatcccag cactttggaa ggccgaggca ggtggatcac ctgaagtcag   13320
gagttcaaga tcagcctggt caatatggtg aaaacctgtc tctactaaaa atacaaaaat   13380
tagctgggcg tggtggcagg cacctgtaat cttagctact ctggaggttg aggcaggaga   13440
atggctggaa cccaggaagc ggaggttgca gtgagctgag atcatgccat tgcactcccg   13500
cctgggtaac aaagagtgaa acttcatctc aaaaaaaaa aaaaccaac caaccaacca   13560 accaaacaaa cagaaaaacg aggcagggtc atcaacagaa agggagagat tgaggtggag   13620
gtatagggat atgaggtgat tagtggaagc ttggaatact gatgccagag tcttccaaaa   13680
tgtgcttttt tttcctcttc gctaatcttg gctgctactg cctccttttt ttttttttt   13740 tttttgagat ggagtctcgc tctgttgtcc aggctggagt gcagtggcgc agtcttggct   13800
cactgcaagc tctgcctcct gggttcatgc cattctcctg cctaagtttc ccgagtagct   13860
gcgactacag gtgcccgcca ccacgcccat ctaatttttt gtatttttg gtagagatgg   13920 ggtttcaccg tgttagccag gatggtctcg atctcctgac ctcgtgattt gcctgcctca   13980
gcctcccaaa gtgctgggat tacaggcgtg agccactgcg cttggccgcc tacttttcct   14040
gtcttcttca ctattttgtt ctgtacatta cccacttcta tcttgaattt tttttttatc   14100
atttcttgtt tttgttttgt tttccgcttc aatggaactc tttttccaa ctgatctttt   14160 aaactggata ggtcaaattt gaagtgcatt tttctgctgt ggtttcttaa agttgaaacc   14220
cagaaacctt aatctttgaa agaggtttgc ctgatcatgc agataaggta tgagttgcta   14280
gttgtctatt taatgccata ggacctcaaa atgatcctta tcagtgaata cacatgccct   14340
gtttatcatg gcatgtata actaatgtac aaaaagacca caatgaactg ctttgccatt   14400
ttattctatt ttatgataat aactttcatg attctggcat ttaaaaaatc ctcccatctt   14460
tcttttttct ttcatctcat tcctcttcag tgtatgtcag actttctcag cagcctgtct   14520
tccactttta catgttttgt atttttctcca taaacccgtt cttagagctc tgtacttttg   14580
gtatctcctg ttctgatgtc tttggccagt gtttattcat ttatgtgtta ttggacactt   14640
gggttgcttc caccctttgg ctagtgtgaa taatgctgct gtgaacatga tgtgatggtt   14700
aatactgact gtcaactgat tggattgaag gatgcaaagt attgatcctg ggtgtgtctg   14760
cgagggtgtt gccaaaggaa attaacattt gagtcagtgg gctgggaaag gcagacccac   14820
ccttaatctg ggtggtcacc attgaattgg ctgccagcat ggctagtata taaagcaggc   14880
agaaaaatat gaaaagacga gactggccta gcctcccagc ccacatcttt tgctcgtgct   14940 gggtgttttcc tgccctcgaa catgggactt caagttcttc agttttggaa cttgactgg   15000 ttctccttgc ttcacagctt gcagcaggcc tattgtgata ccttgtgatt gtgtgagtta   15060
atacttaata aactcccctt tatatatatc tatctatact attagttatg tctctctaaa   15120
gaaccctgac taatatacac gagtataaaa atatcccttt gaaatcttgc tttcaattgt   15180
tttgggcttg tatctagaag tggatatagc agatcatatg gtaatggtaa ttctgttttt   15240
tttttttttt ttcctgagac ggagtctcac tctgttgccc aggctggagt gcagtggtgc   15300
gatctcggct cactgcaagc tccgcctccc aggttcaagc cattctcctg cctcagcctc   15360
cccagtagct gggactacag gtgctcacca ccacgcctgg ctaattttt ttgtattttt   15420
```

```
agtagagaca gggtttcacc atgttagcca ggatgatctc gatctcctga cctcgtgatt   15480
cacctgtctc agcctcccaa agtgctggga ttacaggcat gagccaccgc gcccggccta   15540
tttttaattt tttgaggaat tgccatactg tattccatgg catttggacc attttatgtt   15600
ttcatcacag tgtgcaagga ttccggtttc tcccattctc actaacactt gttattttgg   15660
tttttttgaga gtagccatcc taatgggtgt gaagtggtat ctcattgtgg ttttgatgtg   15720
ctcttcagtg ccatttaat ttgaactata tctctgaaac ccactcattc ccttttttcc    15780
taaatctttg agatattggt aagtataaca tttattcttg cttgctcttt tcctctcttc   15840
tcccattatt tggcctatgc tttctcttaa aaaaaaaaaa aaaaaaaaa aaaaaaaaa     15900
aaaaaagctt tattggctgg gtgtgatggc tcatgcctgt aatcccagca ctttgggagg   15960
ctgagcaggt ggactgcttg aggtcaggaa tccgagacca gcctggccca tctctactaa   16020
aaatacaaaa aattagccgt gtgtggtggt gtgcacttgt aatcccagct actccggagg   16080
ctgaggcagg agaatcactt gaacccagaa gacagaggtt gcagtgggcc aagattgtgc   16140
cactgtattc cagcctgggc gacagagtga gactccattt caaaaacaaa aacaaacccc   16200
agctttattg agatataatt tatataccat aaagttcatt cttttaaagt gtagaattca   16260
ttgtttctta gtatgtatac aagttattca gccatcacca ctatgtaatt ctggaacatt   16320
tcataaccat aaaagagac ctattggcca ggcatggtgg ctcacacctg taatcccagc    16380
actttgggag gctgaggggg gcggatcaca aggtcaagag tttgagacca gcctggccaa   16440
tatggtgaat tcccatcact attaaaaata caaaaattag ccaggtgtgg tggtgtgcat   16500
ctgtagtccc agctactcgg aaggctgagg caggagaatt gcttgaacct gggaggcaga   16560
ggttgcattg agccgagatt gagccactgc actacagcct aagcgacaga gcaaaactct   16620
gtctcaaaat aaataaataa ataaataaat aaagagccct attttcatta gcagtcactc   16680
cctactttc cctccaccat agccctggga ggagacagaa tctactgtct gtttctatag    16740
atttgtttac tctagacatt tcacatacag tgtgtggtct ttggatgtga tgcccatcag   16800
tcttttatggg aggctttctt tcacttagca aaatgtatat agggcttata catattgtag   16860
catgtataag ttttttcattc cttttatgg atgaataata tggcatagta tggatggcac    16920
cacattttgt ttatccattc atcagttggt gaaaatttag gttctcttca ccttttggct   16980
attacaaata gtactactat gaccattcat gtacttctag tatttaagta tctgtttttt   17040
gttttgtttt gttttgtttt tgagatggaa tcttgctctg ttgcccaggc tggagtgcaa   17100
tggcatgatc tcagctcact gcaacctctc cttcctgggt tcaagtgatt ctcctgcctc   17160
agcctcctga gtagctggga ttacaggcaa gcaccaccat gcccagctcg tttttttgtat  17220
tttttggtag agacggggtt ttgccatgtt agccaggctg gtctctaact cttgacctca   17280
ggtgatccac ccacctcggc ctcccaaagt gctgagattg catgcatgag ccaccacgcc   17340
tggccttgag tgtctgtttt taattctttc atgtatatac ttaggaatag aattgctggg   17400
tcatttgtaa ttctgtttag ctttttgggg aatcatcaaa tagttttcca caatggctat   17460
actattttc attcccacca acaatgtatg atgattctaa ttttttttaca tctttgccaa    17520
cacttctgtt gttgccagat ggaaagtctt gactatgagt tgtcccagtt cttggcacat   17580
taaacaaaga attgaacaaa atgcacaaac aaagcaataa aagaacaaaa caacgaaagt   17640
gcaggtttac tgaagcaaaa gtacactcca cagagtgtaa gcgggctcaa gcaagcagct   17700
caagagcccc gattgcaatg ttcttttcagg tttgtactaa actaaagaa tttggtagca    17760
ttcctgggta ccgtttagag gcttcccatt ggttgcaccc tacacaaatg aaggcttggc   17820
```

-continued

```
ccattactaa tcagaggctg aagtgaagtc ttggcccata actaattagc aatagggag    17880 agagggggtt ttgtagaggg aggggcctct ggcccttggc atggagaggt ggggttttc    17940 ttttggccca attccaataa gccagctgct agttggcctc aggctccctg ttccagaccc    18000
tgttctgcct catttccccc tgagagactt gatcccaata aatctttatg ggaggcagag    18060
gaactgatgg tctgtcttct gtaattgctt cgtgcggatt agggcagagt ccctacatat    18120
tggggaccac agaactcttg ccctgctctg tctagtggag agaggtgac ttcttgaagg     18180 ctagggctgg catcgtcacc tggaactggc tagaagccct gctgcatgat catttgaagc    18240
ttaatgttct ctaggtgaga agaaataaat ctggttacat gattaaacaa aaatggtcca    18300
aaaatcaatg taagtacaag tattaataat gtgctggcta ggggaaggag ccatgaaacc    18360
cagcttagta tccttgacca ggggccccat gacttggaca actgttgtca tattttagag    18420
gcctggtcag ctaattttgg ggcagcatcc cttactaatc ctgattggtt gatatgaaaa    18480
cagtgctttc cctctaggaa aagatataag ccacttttt cagcagttag gagatccagt     18540
ccctgtatta gtccattctc acactgctaa tgaagacata cccaagatcg ggtaattat     18600 aaaggaaaga gttttcattg agtcacagtt ccacatggct aaggaggcct caggaaacta    18660
ccaatcatgg cagaagacac ctcttaacag ggtggcagga gagagaatga gcaccagcag    18720
gagaaatgcc ataaaacctt ataaaaccat tagatcttgt gagactcact cattatcatg    18780
agaacatcat gggggaaact gcccccatga ttcatttacc tccacctggt cccacccttg    18840
acacgtgggg attattacaa tccaaggtga gatttgggtg gggatacaga gcccaacctt    18900
atcagtcctc ttctgttttg taaagtgact gccaaagagt ctacctgatt ttgtaaggca    18960
tactttgggc agtgtcttcc aagccgtctg aaagctcctt ggacaagcgt tggtaatagg    19020
atagagaagt tggaagccca ctatttcctg tttctacgcc tgcagttatt cgtaaccta     19080 cctgaaaggg tatgagttgg gtggcttgtt tgtgcctgat ggttgcagtt aaaggtataa    19140
tgagagactg gttattggga gctatattga tctcgggggc taagtaaaca agtgtgcagt    19200
gcaaacaatt ggttccagtc catttggcta gtaaacgtaa gtaggaacta gtcccacaca    19260
ggaaaaaggc tgcttgtttt tcaagacaaa aattgttctc tatgatgaac atgtaggtta    19320
gcttgttgtt ttccttttcc caagtggtta aggtccctgc tacagtggcc ctggttaaag    19380
gctggagggg gccttgggta tcgggggatc ccaccccag tatttcaacg taggttcttt     19440 ctgtttttcca taagtgttgg ccagctgaga aataaagaga acagtataa agagaggaat    19500 tttacagctg ggccatcggg ggtgacatca catatcggta ggactgtgat gcctgcttga    19560
gcctcaaacc agcaagtttt tattaagggt ttcaaaaagg gggtgtaaga acagggagta    19620
gatacaaaga tcatatgctt caaagggcaa caagcagaac tactaataag ggtgtaacaa    19680
agatcacata cttctgaggg aacaggacaa agggcaaaag cagaactact gacaagggtc    19740
caacaaagat cacaaggcaa agggcaaaag cagaactact gataagggtc tatgttcagc    19800
agtgcacata ttatcttgat aaacatctta acaacagaa cacaggattc aagagtagag     19860
aactggtctg accacaaatt tacgagggtg gagttttcc cccacccag taagcctgag      19920 ggttctgcag gagaccaggg cgtatctcag tccttatctc aactgcacaa gacagacatt    19980
cccagagccc agagcggcca tttatagacc tccgcctagg aacacattcc tttcccaggg    20040
tattaatatt aatattcctt gctaggaaaa gaatttagcg atatgtctcc tacttgcatg    20100
tccatttata ggctctctgc aagaagaaaa atgtgactct ttttgcctga ccccacagac    20160
```

```
agtcagacct tatggttgtc ttcccttgtt ccttaaaaat tgctattatt ccgttcttt     20220
tcaaggtgca ctgatttcat attgttgaaa cacacatgtt ttacaatcag tttgtacagt    20280
taacacaatt atcacagtgg tcctgaggtg acatacatcc tcagcttacg aagataacag    20340
gattaagaga ttaaagtaaa gacaggcata aattataaaa gtattatttg ggaactgata    20400
aatgtccata ttaaaatgaa atctcccaat ttatgttcct ctgctgcggc tccagccagt    20460
ccctccattc ggggtccctg acttcccgca acacttggga agtactctga gttgcccaag    20520
tggttttgtt ctctcagttt aggtggttat gcttagtgtc taccagccaa cacccagagc    20580
tatttttgta ctgggggact aaaaggcaac tagatgtctc aggattagta tagccttccc    20640
aggggaaaat gtgcatacag ctagtgggcc taccctgaca gtacttagac tgcatatcct    20700
ttaaagtagc cttaactaag ggtggttttc atgaaaacca tacaagtttt ctaaatgatg    20760
cagtctgggt aactgcatag cttacatgat cagataagag gttaatctct aggggtggt    20820
tgcattgaag atatttcaag gtactcaggg cttgaccaaa attttggctt ctttaatac    20880
aaagtggtgc ctggaatttt agttctgtgt gcatcgatat tgggcccta atgggttttt    20940
gaggggatgc aactccagaa aggttgattt gataggactg gagaaggttt actgcttgtc    21000
ttgtcattgt aacctttgtc atttccgtaa ttttgaagtc aaatatgtca tgcaggttca    21060
ttaaattgaa gggagttctt ctcttatagt tggagatttg ggtggggata ttttctcaag    21120
ggcccaagat tgggctggga ttgggatagc agtgtgtttg acttcagctt aattggatgt    21180
tgttttggt tgggataatg actgggtcct ttaagctgta tgttgactgg cactgccatt    21240
ctagcccttc caggcctccc agtataccat gctagcaggt tgacctgttt gttgacatgg    21300
tccagaacgt tgtctgcatc actgaccatt agcacccagg cagtgcttaa attgtagcag    21360
tgcccctatt ttaaccataa aatctcttct gaacaagggg actgggcagc ttggtactat    21420
tagaaacccc tgctggaaaa tttgtttttc aaattggcag gttaaaggag gggtgaaatg    21480
cctgacttta tttttttcctt catttcctat aacagtcatt gtcctagtgg agggctttcc    21540
tgcataagca gtaagtacag agtaacttgc ccctgaatca aaaagaaact gaatttgtgt    21600
acccgttgtg tccagagtta ctcagggatc ctcagtagta atgatgatgt tcctggacag    21660
gggcagtgag gaaggccctg ggcccccttca gtcttcatct agctcctgct tttgcactgc    21720
tagagtctta actgactgag ctcctccgtg ggagctgggg cagtcagtcc tccagtgctg    21780
gggttacagg cacctgccat gatgcccagg taatttttta atttttttt tttttcagta    21840
gagacaggtt ttcaccatgt tggccagatg gatctcaaat tcctgacctt aaatgatcca    21900
cctgcctcag cctcctgaag tgctgggatt tataggtgtg agctgccaca cccagctagg    21960
agtgacagct tctaagctct ttacatgtca aagcctaaac tgatgttcct atgttaattt    22020
tttacctata tagataaaaa acatgcacat atatgtgtat atatgtatat atatatatac    22080
acacacacac gcatacatac atacatactt acatatattt ttaaatattt ttaaaattta    22140
tttttcagtg gttgttctgt gttcctttaa ctgatcacaa tctacttcag gttaatactg    22200
actcagttcc agtaaaatat agcaacttgt tctaatataa ctccatttc tactcctccc    22260
tttggtctat tagtgccatt caggtatgtg tatatgcata tatatttgtt gtaatcccaa    22320
caatatgtgt tatgattta cattaaaaat cattatttct taaaaatct taggtttta    22380
aataaataaa gagtagaaag caaaaatata tatattgtct ttttaaaaag tttattttct    22440
aattgtggta aaatataact aacatacaac ttaccatctt taagtataca gttccatggc    22500
attaagtata ttgacaacca tcactactaa ccatctccag aactctttc ttttttat    22560
```

```
ttttttttga gttggagttt cattctgttg cccaggctgg agtacagtgg cgtgatctca   22620
gctcactgca acctctgcct cctgggttca agtgattctc ctgcctcagc ctcctgagta   22680
gctgggatta caggcgtatg ccaccacgcc cggctaattt tttgtatttt tagtagagac   22740
ggggtttcac catgttggcc aggctggtct ttaactcctg acctcaggtg atccacccgc   22800
cttggcctcc caaagttcgg ggattacagg cgtgagccac catgcctggc cctccagaac   22860
tcatttcgtc ttgcacaatt aaaactctgt acccattaaa caataactct ctattctcta   22920
tcctcccagc ccttgacagc caccattcta cttttttctat gaatttgact attttatgta   22980
aaaaaaaatg acttatttta cttcatgtaa gtggaattat acaatatttg tccttttgtg   23040
actgttttat atttttttagc atactttgtc ttcaaggttc atccttgttt tagcttgtgt   23100
cagaatttcc tttctttta aggctgaatc atgttctatt aaaacgtata gaacacattt   23160
aaaaaaatct gtttgtattg tcttttacgc ttacccacat atttaccatt tctcatactc   23220
ttcattcttt cttgtaggta tgaattagtt aatatctggt atcattttcc tttcctttct   23280
cttttaagag ataaggtctc actctattgt acaggttgga gtgcagtggt acattcatag   23340
ctcactgtaa cttcaaactc ctggtctcaa gcagtcttcc tgccccagcc tcctgagtag   23400
ctgggactac acgcacatgc caccatgcct atctagtaaa gatggggata ctctgtgtta   23460
ctcaggatgg tcttgaactc ctggcttcaa gcgatcctcc tggcttggca tcccaaatca   23520
cacctgggat tgcaggtgcg agccacctcc ccatgccctg ccctttttta aaaagtgta   23580
tcttatagag caggtctatt agcaacatac tccctcagtt ttcatttgtc ttggaaggta   23640
ttttgctttc acttgtgaag aatagttttg ctaaatatag aatttgtggt ttatagttct   23700
gttttttct gtcggtactt tgaacatgtc atttcattgt cttctatcca ttgtttcatg   23760
agagccttaa aaggtgatag ggtcaccatg catccgtagc tctctcattt acataatctt   23820
tccattaaat ttctgactgc ttaagcactt atcctaacca ggatctcaac ctcagaccaa   23880
ctgcaaagtt ttcctctttta ttcccaacca agcctagcac ttttatccac caaagctaca   23940
ggttttcact gccctacccg gaaatgagcc caccctttt agcaacaaac tgctaggttc   24000
ttttggtag tttcatgttg gtatgggttg agcatttatg atcaaaaaat acaaaatctg   24060
aaatgctcca aaatctgtaa cttttgagca ccaacacaat gctcaaagga agtgttcact   24120
ggagcatttt ggatttcaga ttttttggagt aaggatgctc agccagtgtg tattctgcaa   24180
gtattccaaa atctgaaaaa aatccaaaat ctgaaacact tctagttcca agcatttgg   24240
acaagggata ttcagccagt aaaattgcca ggctcatcat cctagctggg aggggttttt   24300
aggagcaacc tcaggccaaa gggcacagct tcttacctttt catacttaga actttagcag   24360
cttttctaga ctaaagactt ttctctttgt agtcttcttt tggttaattt ccagtcccct   24420
gaaatggttg tttttgataa ttttatccag ttttatcctt aatatttgtg gaggggaatt   24480
gccaacctct tcatgttgcc acaaaatctg catgttgtct ttgcagatga attttatatt   24540
tacttatcaa gtttcctaag aagtcctctt ggtattttga ttgaatttac attgactttg   24600
taaatttgca gcgcatcaac atacttataa tattgagatt tccctccagg aacatggcat   24660
ttatctccat ttatttggat atactttaca tctctcagca aaattattta acacacatat   24720
atgacttgct tatatatttt ttgtttgttt gttttgtgtt tgagacgaag tctgtctctg   24780
tatcccaggc tggcgtgcag tggcgcgatc ttggctcact gcaacctcca cttcccaggt   24840
tcaagtgatt ctccttcctc agcctccaga gtagctggga ttacggcgtg cgccactgca   24900
```

```
cctggctaac ttttttgtatt tttagtagag acgaggtttc accatgttgg ccaggctggt   24960
cttgaactcc caacctcagg taatccgccc acctcaacct cccaaagtgc taggattaca   25020
ggcatgagcc accgcccctg gccttatgac ttgcttatat tttgctaagc ttattcattt   25080
atgttttttct ggtgattgct gatgaaatta acgtttccat tgtagtttct aattatttat   25140
tgccagtttg taggaaagta agtttgtttt tataagtttg tataagttga tcttttttttt   25200
tcttttgaga tggagcctca cgctgtcgcc caggctggag tgcagtggca taatcttggc   25260
tcactgcaac ctccgtcttc tgggttcacg cgattcttct gcctcagcct cctgagtagc   25320
tgggactaca ggcatgcacc accacgcctg gctaattttt atatttttag tagagacaag   25380
gtttcaacat gttggccagg ctgatcttga actccttacc tcatgatctg cccacctcgg   25440
cctcccaaag tgttgagatt ataggcgtga gccatcgcgc ccagctagtt gattttatat   25500
gtgactgcct tgctgaactt acttttggtt tgtcagttta ttattttggt tattttaagt   25560
agtgtactat tatttgcaaa tgatgcaatt ctatctcctt gtaatctata tttgtatttc   25620
ttattttttaa aagtttatca tttaggttct gacctctagg aaaatagtaa aacattaggt   25680
atacttgcct tagtgatttt gctggaaata tttctaatat ttcttttatt ttttattttt   25740
attttttttga gacggagtct tgctctgtga cccaggctgg agtgtagtgg cgtgatctag   25800
gctcactgca acctccacct cccaggttca agagattctc ctgcctcagc ttcccgagta   25860
gctgggacta cagttgtgtg ccaccacgcc cagctaattt ttttattttt tgtagagata   25920
ggggttttgc catgttggcc aggctggtct cgaactcctg acctcaggtg atccacctcc   25980
ctcggcctcc caaagtgctg ggattacagg tgtgagccac tgcgcccggc tatttctaat   26040
atttcgtcat gaagtataac atagtcttgg tccttctatc cagcttataa attttttattt   26100
cttattttta ttcccaatat caactgacat tttggcatac actgacatca taatgctttt   26160
ctctattgat ttcctaatac cttaagtaag aaagaccctta tttgatcaag gtgtattata   26220
attttaatat tttcctaggt taagttaccc ctatttgatt aaggtgtatt ataattttaa   26280
tattttccta ggttaagtta cccctatttg attaaggtgt attataattt taatatttt   26340
ctaggttaag tttgcatata tatatatata cacacacaca tatatataca cacatatata   26400
tacacacata tatatacaca catatataca cacatatata tacacatata tatacacata   26460
tatatacaca tatatacaca tatatataca cacatatata tatatataca cacacacata   26520
tatatatata tatatatata tttttttttt ttaggttttt tttttgtttg tttttgaggtg   26580
gcctctcact ctgttaccca ggctggaatg cagtggcgca gtctcggctc actgcaacct   26640
ctgcctcttg ggtttaagcg attctcatgc ctcagcctcc cgaatagctg ggattacagg   26700
tgtgcgctac cacacctagc taattttttgt attttttagta gagatgggtt atcaccattt   26760
tggccaggct ggtctctaac tcctgacttc aagtaatttg cctgactcgg cttcccaaag   26820
tgtttgggttt acaggcgtga gcctccatgc cgggctgagt tgctaatgt tttatttaca   26880
atttttgcat gtaattcaca agtgggattg gcttataaag aacaatgcct tgttgaccag   26940
acattcattc tagattaaaa gaattataca tttcctcttc ttcaaaaatt tagtgtagga   27000
actattcatt attctcgtat tagttttatt tgctgtctgc attaaactaa taacctgtag   27060
taaatggcat cctttttttga acagtacaaa cacctaaaac ccaatttgtt tattttattt   27120
tttttgagaa gtctcactgt gtcacccagg ctagagtgca gtgggcgat cttggctcac   27180
tgtaacctct gcctccgaga ttcaagtgat tctcctgcct cagcctccca agtagctggg   27240
attacaggtg tatgctacca cacccaccta atttttgtat tattagtata gatggggttt   27300
```

```
caccatgttg gccaggttgt tcttgaactc ctgacctcaa gtgatcaacc tgcctgggcc    27360
tcccaaagtg ctgggatttc aggcatgagc cactgccccc gggcctccag tcctttatgt    27420
acgatgatta ttattttagc cttctgagtt tttctgttac tgcatattcc tccgtgtgtc    27480
ttccctgtat tagatgattt ttctttgaaa gaccttcaag gattgtttaa tatttgtcgg    27540
tgtctgtgtt aaattgtgtg tttcctatat tagatgattt ttatttaaaa tatctttaag    27600
agctgggcac ggtggctcac gcctgtaatc cctgcacttt gggaggttga ggcgggtgga    27660
tcatttgaag tcaggagttt gacaccagcc tggccaacat gatgaaaccc tgtctctact    27720
aaaaatacaa aaattagacg ggcatggtgg tacacacctg taatcccagc tactcaggag    27780
gctgaggcag gataattgct tgaacccgag aggcggaggt tgcagtgagc gaagatcgtg    27840
ctactgcact ccagcctggg tgacacagca agactccatc tcaaaataag taagtaaata    27900
aataacaaaa tatctttaag aattgttggc tgggcgtggt ggctcacgcc tgtaatccca    27960
gcactttggg aggccgaggc gggcagatca cgaggtcagg agatcgagac catcctggct    28020
aacacagtga aaccccatct ctactaaaaa tacaaaaaat tagccgggcg tggtagtggg    28080
tgcctgtagt cccagctact cgggaggctg aggcaggaga atggcatgaa cccgggaggt    28140
ggagcttgca gtgacccgag atcgtgccgc tgcactccag cctgggcgac agagtgagac    28200
tccatctgag aaaaaaaaaa aaaagtttta acatttgtcc atctctttat gacatcataa    28260
aaaatatata tttggtccct gcctcttgtt attagcatag agctcctaaa acccatgtaa    28320
ttttctgagt gatggggtgc taggttcatc ttttgttaaa ttatttggat tttgacccag    28380
gttcctgaca cagagctcct aatcccttgg aatttcctat gtaataggaa aatcttttgt    28440
tctaatgagg caactcttga tgggctcttg ggtggtggct ggccaccaga aagaccaagc    28500
tatgactagt tgtctggaac ttgcagcacc cctccccatc attttgatag gggctggaga    28560
ctgacttaat aatcaatcat gctgggtcca ctggcttacg cctgtaattc cagcactttg    28620
ggaggccgag gtgggaggat cgcttgagcc caggagctca agaccagcct gggcaacata    28680
gatagtgaga ccctgactct aaaaacaaca acaacaaaat tagccattcg tggtgctgcg    28740
ggcctgtggt cccaactact tgagaggctg aggtgagagg atcacatgag cctaggaagt    28800
ggaagctaca gtgagctaag gttgtgccac tgcactctcc agcctgagtg acagaacaag    28860
accttgtctc aaaaaaaaaa aaaaaaaaaa aatccgccag gcatagtagc tcatgtctgt    28920
aaatcccagc actttgggag gctgaggtgg gtagatcact tgagcccagg agttcaagac    28980
cagcctgggc agcaagggaa aaccccatct ttacaaaaaa ataacataaa aaattagtca    29040
ggcttggtgg catgtgcctg tgtcccagct acctagaagg ctgaactgga ggatcgttgg    29100
agcccaggag gttgaggctg cagtgagcca tgattgcgcc attgcactcc agcctgggtg    29160
acagagcaag accctgtcta aaaaaaaaaa aaaacccag tcatgcctgc tagataaaac    29220
ctccataaaa ttcctgtaac tatgaggttt ggagaacttc tgggttgctg aacacttgga    29280
gggagaaggc atggaaactc tgtgctcctt ccccggtatc tttccctaga catctctttc    29340
atttgcctct tcctgatttg catctttta ttaaaaatgg gtaaatatgg ctgggcgcgg    29400
tggctcacgc ctgtaatccc agcactttgg gaggcctagg cgggtggatc acctgaggtc    29460
aggagttcaa gatcagcctg gccaacatgg tgaaaccctg tctctactaa aaatacaaaa    29520
attagccagg cgtggtggta tgtgcctgta gacccagcta ctcaggaggc tgaggcagga    29580
caatcacttg aacctgggag gcggaggttg cagtgagccg agatcgtgcc actgcactcc    29640
```

```
agcctgggca acggagtgag actccgtctc agaaaaaaaa aaaaagggt aaatataagc    29700
gaggtattta tctgattcct gtgagccatt gaagcaaatg gtcaaacctg aggaggggt    29760
tgtagaaacc cccaacttat agctgattgg ttagaaatat gggagtcctg gacttatgat    29820
tggcatctgt gtggagactg tcttatggaa ttgagcccctt aacctgtggg atctaatgct   29880
aactccgggt agataatgac agaactgaat tagaggacac atagctgatg ttagagaatt    29940
ggtaagcata ggccgggcgc agtggctcac gcctgtaatc ccagcacttt gggaggtcaa    30000
ggtgggcgga tcacgaggtc aggagatcga ccatcctg gctaacacag tgaaaccccg      30060
tctctactaa aaatataaaa aaaaataaa ttagccaggt gtggtggcag acacctgtag     30120
ttccagctac tcgggaggct gaggcaggag aatggcatga acccaggagg cggagcttgc    30180
agtgagccga gattgcgcca ctgcactcca gcctgggcga cagagtgaga ctccgtctca    30240
aaaaaaaaaa aaaaaaaaa aaaagaatt ggtaagcata ggagaaaccc acaagtttcg      30300
tgatggaagt gacctatgga gtgttgtgag agtatataag aggcataaac agtttgtttt    30360
ttctctgtac actctgtttt tcttttcctt tctttctttc tttttttttt gagaggagcc    30420
tcgctcttgt cccccaggtt tgagtgcaat ggctttatct cggctcactg caacctccac    30480
ctcccaggtt caaatgattc tcctccctct gcctcccaag tagctgggat taagggcctg    30540
ccaccaagcc cggctaaatt ttgtattttt tagtagagac agggtttcac catgttggcc    30600
aggctggtct cgaactcctg acctcagatg atccacctgc ctcagcctcc caaagtgctg    30660
ggatttcagg cgtgagccac cgcgcccggt cactgtacac tctgtttttc tttggtacat    30720
gtagtctctt ttctctttat cataagcttt gtgttatttt cttcttcatg ttttttctctt   30780
cattgtagtt ccttctgtta cctactctgt gaagcctttc ttggtttctc ctcttcatca    30840
ctactctctg aagagctgga ctatttctgt ctctaatata gcttattata aattatcatt    30900
atacctatag ttccctttaac tacatcttgg ctataatacc agaactttcc tgttattttt    30960
tgttgtaaga acagtctcat ttttggtaat taagacttag tcttatgcat tttaaaaact    31020
tcatgtaaaa ttcattcttc ttgcagggag tatgatgggt gagggtgtct gactctccac    31080
atattctccc tttttcatgt gttggggcag agagtgaaaa aaggcagaca tataattagg    31140
ctgggtgaag tcgtctttta ggttgtggct tcctctctaa catggagtgt tcatcatgcc    31200
ttattgtgag gcatttaaat tttgtttcat tgccatgtgt agattcttcc tggttcaatc    31260
tgttggcagc ttactggcaa ctctctgaac taagaatata tagtaataat tagcatattt    31320
tgtgcttaat ttaagcctga ggtaaaattg ggactacagg aaatttttcat tcagtgtccc   31380
gtgaaattta tttaaagtc agcatctcac aggaaaataa tcagtcttct agaagagagt     31440
attatgtcat gtagatatta cagagcacct ttcagtgcac aggtttcata ctcgtaatgt    31500
taaatctcta ttttaaagta atacaacatt tagggacctt catcctagca tatccatagt    31560
ctagaaccac ttcagatgtc ctatttaaat gtaaattaat ttaaatgtac attaatgaaa    31620
cttaaataac attaaaaatt cagttcctga gtctcagtag ccacatttga agtacttaat    31680
tagccacctg tggctagtgg ctactatatt ggatagcaca gacattttga tcattgaagt    31740
aagtgcttct ctagtggata gaggtaagaa attttttctta ccataggaaa gtcagataca   31800
tggagtcaat catgtacacc aactaggtac tctgtttcac aaggttttttt tcttgccca    31860
tgtgagggaa gtttgaaagg cagaaaagtt gccacacacc tgtacaagat actgcttttca   31920
aattcatctg atatttagct ctttgaaagt gtcagacaac tactagtgca aacataggtt    31980
ttgcagcagg attaagactt caaatatttc cacccagcag agacagaccg tcttgttcat    32040
```

| | | | | | |
|---|---|---|---|---|---|
| ccttcctatt | tccttttcta | ctgttccctc | ttccttcagt | ccttaggact | gaagggttgg | 32100 |
| cacaacttcg | gttgacaggg | taagacttgg | gataagttga | aaagcaaatg | tttgaatata | 32160 |
| tgtgttggga | tgtgtgtgtg | tgtgtgtgtg | tgtgtagatt | ttgagagaag | tggcttaact | 32220 |
| cctagaataa | taaatttcta | ttatttttc | taccaagccc | ttaggtatca | tctaattgaa | 32280 |
| tgcctgccca | cattttacat | ataagtaaac | tgaggttgga | gaaagtgatt | gcctaagacc | 32340 |
| atacagctaa | tggtagatct | gggactaaaa | tctttgttcc | atgactccaa | caccaatggt | 32400 |
| ttttctcctg | aatcatttac | ctttcccatt | ttaattcata | attcactact | acctattgtt | 32460 |
| acaaatacaa | tggcaagagt | ttagaggtat | gaataactaa | ttattgtaat | gaatttctca | 32520 |
| tttaaataaa | tgttgctttt | atgtatttta | aagaatttgg | taattgcaat | tgttatagat | 32580 |
| tgaagaagaa | gagaggaaaa | aaatagaaga | tatgaaagaa | aatgaacgga | taaaagccac | 32640 |
| taaagcattg | gaagcctgga | aagaatatca | aagaaaagct | gaggagcaaa | aaaaaattca | 32700 |
| gagagaagag | aaattatgtc | aaaaagaaaa | gcaaattaaa | gaagaaagaa | aaaaaataaa | 32760 |
| atataagagt | cttactagaa | atttggcatc | tagaaatctt | gctccaaaag | gtaaaatgat | 32820 |
| taagaatttc | ttgagtagtg | agtcctgttg | gtgaagtata | tatgacgctt | ttctttttt | 32880 |
| gtaaatctat | tcacagcatt | aggttactgt | tttggcacat | tgagaataag | caattcagta | 32940 |
| caaagactaa | agtaaagaca | tttcttcttt | cggggataat | gaagttttct | aataaaatga | 33000 |
| gcaaggattc | gttcaaggat | tcgaaaagaa | gagtgtcttc | tttgcttgtg | tgctttcttt | 33060 |
| tgaaatttac | aaagatgttg | ttaaataagt | gcttaactca | ggcccaaaaa | gacttggagt | 33120 |
| ggactagcaa | tgtcagaagc | attcatttat | tccattagag | ataagaaact | aggaatttca | 33180 |
| ttaaaagacc | ttttcctcac | atcacttagg | aaaatgagta | ctataagcag | acttactcta | 33240 |
| cagcaaataa | agattgcttc | tagcttttaa | tcttggtgta | ttcaaaaaca | gataaattaa | 33300 |
| tataattttt | tttttgaga | caaggtctgg | ccctatcgcc | caggctggag | tgcaatggtg | 33360 |
| tgatctgagc | tcactgcagc | ctctgcctcc | ccagctcaag | ccatcctgcc | ttagcctccc | 33420 |
| aagtagctgg | gactacaggc | atgtgcctca | atgtccagct | aatgcttttt | tgtatttttt | 33480 |
| gtagagacga | ggttttgcca | tgttgcccag | gctggtcttg | aactcgtgag | ctcaagcaat | 33540 |
| ctgcctgcct | tggcctccca | aagtgctgag | attgtgtgca | tgagccacca | tgtccagctg | 33600 |
| atacaaatat | aattcagttt | ttgtatgtgt | gtgttttaa | aattattatt | tcagtagttt | 33660 |
| tggggaaaca | ggtggtgttt | ggttacatgt | ataagttctt | tagtggtgat | ttctgagatt | 33720 |
| ttggtggacc | catcaaccaa | gcagtgtaca | ctgcacccaa | tgtgtagtct | tttatccctc | 33780 |
| accccctgcac | ccttcccccc | tagtcccag | gcccatatca | ttcttatgcc | ttggcatcct | 33840 |
| catagctcag | ctcccattta | tgagtgagaa | catgggccag | gagcagtggc | tcatgcctgt | 33900 |
| aatcctaaca | ctttgggagg | acaaggcggg | cagatcatct | gaggtgggga | gttcgagacc | 33960 |
| agtctgacca | atatggagaa | accccatctt | tactaaaatt | acaaaattaa | ccaggtgtgg | 34020 |
| tggcacatat | ctgtaatccc | agctactcag | gaggccgagg | caggagaatc | gcttgaacct | 34080 |
| gggaggcgga | ggttatggtg | aaccgagatc | gtgccattgc | attccagcct | gggcaacaag | 34140 |
| agcaaaactc | tgtctcaaaa | aaaaaaaaa | aaaagtgag | aacatatggt | atttggtttt | 34200 |
| ccatttctga | gttacttcat | gtagcataat | cgtctccaac | tccatccagg | ttgccgagaa | 34260 |
| tgccattatt | ttattccttt | ttatggctga | gtagcattcc | atgattgtat | gtgtgtctgt | 34320 |
| gtgtgtgtgt | gtgtgtgtgt | gtgtgtatat | atacaccata | ttttctttat | cttctcatta | 34380 |

```
gttgataggc atttaggcta gttctatatt tttgcaattg caattgtgct gctataaaca    34440
tgagtgtgca agtgtctaat gacttctttt tctctagata gatacccagt aggggggattg    34500 ctggatcaaa tggcggttct acttttcgtt ctttaaggca tctatctcca cactgtcttc    34560
catagtagtt gtactagttt acattcccac cagcagtgta aaagtgtccc ttttcaccac    34620
atctacacca acatctgtta ttttttcatt tttaaattat ggtcattctt aacaggagta    34680
aggtggtatc gcattgtggt tttgatttgc atttccctaa taattagcgg tgttgagcat    34740
tttttcatgt ttgttggaca tttgtttgtt tgtttattta ttttgagatg gaatttcgct    34800
cttgttgccc aggctggagt gcaatggcac gatctcggct caccacaacc tctgcctccc    34860
aggttcaagc gattctcctg cttcagcctc ccgagtagct aggattacag gcatgtacca    34920
ccatgcctgg ctaatttaga gatggggttt ctccatgttg gtcaggctgg tctcgaactc    34980
ttgacctcag gtgatccgcc tgcctcagcc tcgaaaagtg atgggattac aggcatgagc    35040
caccacacct ggcgggacat ttgtatatct tcttttgaga attgtctatt catgtcctta    35100
gcccactttt tgatgggatt gtttgttttg ttcttgctga tttgtttgag ttccctgtac    35160
attgtggata ttagtccttc gtcagatgca tagtttgtga agattttctt ccattctgtg    35220
ggttgtctgt ttactgtgct gattatttct tttgctgtgc agaagctttt tagtttaatt    35280
aagtcccatc tatttatctt tgttttgttt tcatttgctt ttggattctt ggccatcaag    35340
tctttgccta agccagtgtt agaagggggtt ttccagtgtt atcttctaga atttttatga    35400
tttcaggtct tagacttaag tctttgatcc atcttgagtt aatttttgtg ttaggggaga    35460
gatgaggatc cagtttcata cccctacatg tggtttgcca attatcccag caccatttgt    35520
tgaataggtt gtccttttcc cactttatgg ttttgtttgc tttgtcaaag attggttggc    35580
tgtatttgac tttatgtctg ggttctctat tctgttccat tggcctatgt gcctgttttt    35640
ataccagtac tatactgttt tggtaactgt ggccttgtag tatagtttga agtcaggtaa    35700
tatgatcccc tcagatttgt tcttttttgct tagtcttgct ttggctatat gggctctttt    35760
tttgttctat atgaatttta ggattgtttt ttctagttct gtgaagaatg atgatgatat    35820
tttgatggga attgcactga atttgtagat tgcttttggc agtatggtca ttttcaaaat    35880
actgattcta cccatctgtg agcatgggat gtatttccat ttgtttgtgt catctatgat    35940
ttctttcagc agtgttttgt agttttcctt gtgagatctt tcacctcttt agttaggtat    36000
attcctaagt attttggttt tttgttttgt tttttgggtt tttttgcagc tgttgtaaaa    36060
gaggttgagt tcttgatgtg attctcagcc tggtccttgt tggtgtatag tagtgctact    36120
gatttgtgtg cattgatttt gtattctgaa actttacttg aattcatata tcagatctag    36180 gagcttttttg gatgaatctt taggattttc taggtatacg atcatatcat tggccaacaa    36240
tgacaacttg acttcctcct tactgattta gatgctcttt ctttctttct cttgtctgat    36300
cgctctggct aggacttcca gtactctgtt aaatagtgtt ggtgaaagtg gacatccttg    36360
tcttgttcca gttctcaggg gaaacacttt caacttttca ctgttttatta taatattggc    36420 catgggtttg tcaaagatgg cttttattac cttaaggtat gtcccttctg tgcccatttt    36480
gctgagggtt ttagtcataa agggatgctg gattttgtca aatgctttgt gtgtgtgtgt    36540
gtgtgtgtgt gtgtgtgtgt gtgtgtgaga cagagtctca ctgtgttcct taggctggag    36600
tgcagtggca tgatcttggc tcactgcaac ctctgcctcc caaattcaag cagttctcct    36660
gcctcaacct cccagtatc tgggattaca ggtgtgcacc accacaccta gctaactttt    36720
tgtatttttt agtagagaca gggtttcgcc atgttggcca ggctggcctc aaaactcctg    36780
```

```
acctcaaatg atccgtctgc ctcggcttcc cgaagtgctg ggattacagg catgagccac   36840
cacactcggc ctcaaatgct ttttctgcat ttattgagat gattgtatga ttttgtttt    36900
gacttctgtt tatgtggtgt attatattta ttgattttt gtgtgtgtat gttaaaccag   36960
ccctgcatcc ctggtatgaa acccacttaa ttatggtgta ttacctttt gatatgctgt   37020
tgcatttggt tagctagtat ttggttgagg agtgttacat ctgtgttcat cagggatatt   37080
gttctgtagt tttcttttt tttttttgt tatgtccttt cctggttttg gtattagggt   37140
agtactggcg ttgtagaatg atttagggag gatttcctcc ttatcttttg aaatagtttt   37200
aataggattg gtaccagttc tcttagaatg tctgttagaa ttcagctgtt gggctgggca   37260
catggctcat acctgtaatc ccagcctttg agaggccaag gcaggcaatc tcctgaggtc   37320
aggagttcaa gaccagcctg cccaacgtgg tgaaacctca tctaactaaa aatacaaaaa   37380
ttagcagggt gtggtggcat gtgcctgtaa tcccatctac tcgggaagct gaggcaggag   37440
aatcgcttaa acccggagat ggaggttgca atgagccgag atctcaccac tgcattccag   37500
cctgggggca agagaacaag accctgtctt aaaaaaaaaa aaccagctgt gaatccatct   37560
ggtcctggac ttttttagt tggccatttt taaattactg tttcaatctc cctacctgct   37620
attggtcttt tcagagtttc tatttcttcc tggcttaatc tgggaggatt gtttaattcc   37680
ttctaggttg aggaatttat ccatctcctg taggttttct agtttgtgtg cacaaaggta   37740
ttcatagtag ctttgaatga tcttttgtat ccctgtggta tttgttgtaa tttctctcat   37800
ttcatttcta atcgagctta tttggatctt attcttttct gggttaatct tactaatggt   37860
ctatcagttt tgtttgtctt ttcaaagaac cagcattttg tttaattttt cttttgtatt   37920
ttttcttc agtttcattt agttctgctc tgatctttgt tatttctttt cttgtgctgg   37980
gtttgggttt gatgtgttct tttttctcta gtttcttgat gtgtgagcct agattgtctg   38040
tttatgctct ttcagacttt ttgatgtagg cgtttagtgc tatgaacttt cctcttagca   38100
ctgcttttgc tgtatcccag aggttttgac tggttgtgtc actattatcg ttcagttcaa   38160
agaattttaa aatttccgtc ttgatttcat tgttgaccca aagatcattc aggggcaggt   38220
tacgtaattt ccatatattt gtatagtttt gagtgttcct tttgaagtca atatccagtt   38280
ttattccact gtggtcttag agagtatttg atataatttt gattttctta aatttactga   38340
gatgggctgg gcgtggtggc tcacacctgt aatctcagta ctttgggagg cctaggtggg   38400
tggatcacga ggtcaggaga tcgagaccat tctggtctct aaccagagac cagaatctgg   38460
tggctaacac ggtgaaaccc catctctact aaaagtacaa aaaattagcc aggcgtggtg   38520
gggggcacct gtagtcccag ctactcggga ggctgaggca ggagaatggc atgaacccag   38580
gaggcggagt ttgcagtgag ccgagactgc accactgcac tccagcctgg gcaacagtgc   38640
aagactctgt ctcaaaaaaa aaaaattatt gagatggctg gcgcagtgg ctcatgcctg    38700
taatcctagc actttgggag gccagggaag gtggatcacc tgaggtcagg agtttgagac   38760
cagcctggcc aacatggtga aaccttgtct ttactaaaaa tacaaaaatt aggctggtgt   38820
ggtggcgggg gcctgtaatc ccagctgctt gggaggctga ggcagaagaa tcacttgagc   38880
ccaagaggtg gaggttgcgg tgagtcgaga tcacgccact gcactccagc ctgggtgaca   38940
aagcgaggct ctgtctcaaa aaaaaaaaa aattattgag acttgttttg tgttctatca   39000
tttggtttat cttggaatga atgttccatg tgctgatgaa aagaatgcat attctgcagt   39060
tgttgggtag aatattctgt aaatatctat taagtccatt tgttctagga tatagtttaa   39120
```

```
atccattatt tctttgttga ctttctgtct tgattacctg tctagtgctg tcagtagagt    39180
actgaagtcc tccactatta ttgtggtgct atctcatttc ttaggtctaa taataactgt    39240
tttataaatt tgagaattcc ggccgggcgc ggtggctcat gcctgtaatc tcagcacttt    39300
gggaggccga ggcgggtgga tcacgggtgg tcaggagttt gagaccagcc tgaccaacat    39360
ggtgaaaccc cgtctctact aaaaacacaa aaattagccg gcgtgctgg cacgcacctg     39420
taatcccagc tactcaggag gctgaggcag gagaattgca tgaatctgga ggtggaggtt    39480
gcagtgagcc gagactgcac cacggcactc cagcctgggc gacagagtga gactctgtct    39540
caaaaaaaaa aataaataaa taagtaaata aataaataaa taaatttgag agttctagtg    39600
ttaggtgcat aaatatttag gattgtgata ttttcctgtt ggactaattc ttttatcatt    39660
atataatgtc ctttttatc ttttttaact gttgttgctt taaagtctgc tttgttttgt    39720
ataagaatag ctattcctgg ctaggcgcag tggctcacgc ctgtaatccc agcactttgg    39780
gaggccgagg cggcagatt acgaggtcag gagtttgaga ccagccaggc caacatggtg    39840
aaactctgtc tctactaaaa atacaaaaat tagccaggcg tggtggcgcg tgcctgtagt    39900
cccagctact tggaaagcta aggcaggaga atcgcttgac cccaggaggc agaggttgca    39960
gtgagccaag attgcaccac tacactccag cctgggcaac agaaggagac tctgtctcaa    40020
aaaaaaaag aaagaaagaa agaaagaaaa aagaatagct actcctgctg actttggtgt    40080
tcatttgcat ggaatatctt tttccaccct gtttatgagt ccttatatgt taggcaagtc    40140
tgttaaaaga cttacttggt tggttgattt ttatccattt gacattctgt atcttttaag    40200
tggagcattt aggccattta cattcaatat cagtattgag atgtgaggta ctgttctatt    40260
catcatgcta gttgttgctg taccttattt tttttcattg tgttattgtt ttatagatcc    40320
tatgagattt atgttttaag gaggttctat tttggtatat tttgaggttt tgtttcaata    40380
tttagaactc cttttagcat ttattgtagt gctggcatgg tagtgacaaa ttcagcatttt   40440
gtttgtttga aaaagacttt atctcgcctc tggttatgaa gcttagtttc actggataca    40500
aaactcttag cggataatta ttttgtttaa ggaggctaaa gataggaccc ccatcccttc    40560
tggcttgcag ggcttctgct aagaaatctg ctgttaatct gataggttct cctttataga    40620
ttacctggtg cttttgcctc acagctcttt tttttttttt ttttgagaca gagtcttgct    40680
ctgtcaccca ggctagagtg cagtagcgtg atctcggctc actgcaacct ccaactcccg    40740
ggttcaagca attctcctgc ctcagcctcc tgagtagctg ggattacagg cacctgccac    40800
cacgcctggc tgattttgt attttagta gagatggtgt ttcaccatct ggttggcca     40860
ggctggtctc gaactcctga cctcgtgatc cacccgcctt ggcctcccaa agtgctgaga    40920
ttacagatgt gggccactgt gcctgacctt gcctcacagc tcttaagatt ctttctttca    40980
tctttacttt agacaatgtg atgactatgt gcctaggcaa tgatcttttt gcaatgaatt    41040
ccccgggtgt tctttgagct tcttgtattt ggatgtctag atctctagca agaccatgga    41100
agttttttctt gattattccc tcaagtatgt tttccaaact tttagatttc ccttcttcct    41160
caggagcacc aattattctt atgtttgctt gtttacataa tctcagattt cttggaggct    41220
ttgttcatt tttaaaattc tttttttctt tgtctttgtt ggattgggtt cgtttgaaag    41280
ccttgtcttt gatctctgaa gttatttctt ctacttgttc aaatctattg ttgaaacttt    41340
ccagtgtatt ttgcatttct ttaagtgtgt ctttcatttc cagaagtttt gattatttt    41400
tctttataat atctatttct ctggagactt ttccattcat atcctccttt ttttaaaaat    41460
ttctttaagt tgattttcac cttcctctag tgccttcttg aggagcttaa taatcaacct    41520
```

```
tctgaattat ttatctggca attcacagat ttcttcttag tttggatcca ttgctggaga    41580
gctagtatga tcttttgggg gtgttacaga accttgtatt gtcatattac tagaattact    41640
tttctggttc cttctcattt gagtagactg tttcagtggt aagatctgga actcaagggc    41700
tactgttcag attcttctgt cccatgggtg ttcccttgat gtggtgccct cccctgcca     41760
ctagggatgg ggcttcctga gagccagact gcagtgattg ttattgccct tctatttcta    41820
gccacccagt tgggcccag gctggtgctg gggaatgtct gcaaagagcc ctgtgatgtg     41880
atccacaggt ctcccagccg tggataccag cacctgttct ggtggtggca ggtgagtgaa    41940
gtggattctg ttggagtctt ttgttgtaat tttgtttagt gcacttcaag tactggttat    42000
gtaagcagtg aagttgtcac gtggacagat tcaggacctc tggctagaca gggtgttgca    42060
ggaagtggaa ttagctgttg ttttctcctt ctttggagca gggttgttct gttatgagtt    42120
gctatggtgg cttgagttcg ttgggctcca gccaggaggt ggcactttca agagggcacc    42180
agctgcagta tagaagagag atataatctt gatgttggcc gggacaagta ctcgggtttc    42240
tcaggtgatg ggcagggcca tagagcaggt agagaaaacc ttgccccatc aggtgggggc    42300
aaggttagtt gggtctgggc tcaggctccc cttgggtggg gcttgctgtg ccacagtgg    42360
gggtggaggg gattctcagg ccaatggaat tatgttccca ggggcattat ggctgcctct    42420
gctgtgctat acaggtcacc agggaggtgg gggaaagctg gcagtgacag gcctcaccta    42480
gctcccaggc agccaccaag gccagtctca ctctggccat gccacccaa ccgcactgcg     42540
tttatatcca ggcagttggt gagcagggct gagatcttgc cccagactat aagccttgcc    42600
actgagaaag caagagggct gttaggcctc accagtccct gcctgcccac actattggct    42660
gtggcttctg cactcgcatc tgtacttccc atttgccccc tctgccacca atttctgctt    42720
aggaaaattc ctgctcagtc aaaattatta caaagttcag ctacaagctt ccttcaccct    42780
gtggtcctgc cccaattcca ctggctgcct tcccgtctcc aaggacctct gtgagatcac    42840
gccaggaatg gcttccttgg actccagctg gggatggaag tacctatagg gctcttcctg    42900
ctgcttcttc tactttcata ttttgctcag ctacctaaat ctatttcagc tcagggtaaa    42960
gttaaatcct tcccctgtga tctggatttt caggttcccc agtggggatg tatgttcaga    43020
gactgacctt ttcttccctc acactttggg aactcacggt ttttcagctg tttcatggca    43080
tttgcagcag cgaaccactt ctttcaaagg gtctgtgaat tctttcagtt ttcctacagt    43140
gtttcttgcg gtgttcctga agtgattctt ggagtaaaag ttcgcattgt gagtctccag    43200
atgctgttct gtccatccag gtggcagctg catgttaatc ctgtctccga tctgccattt    43260
tccctcctat ctcccaatga atataattct atactgaaag ctacgagttt ggttttatct    43320
aattttagaa tattaaactt tgttttggat gcattttccg ccggatgcag tggctcacgc    43380
ctgtaatccc agaactttga gaggctgagg cgggcagatc acctgaagtc gggtgttcaa    43440
gactagcctg accaacatgg agaaaccctg tctctactaa aaatacaaaa ctagccggac    43500
gtggtggtgg gtgcctgtaa tcccagctac tcggaggca ctgaggcagg agaatcgctt      43560
gaacccaggg aggtggaggt tgcagtgaag cgagatcttg ccattgcact ccagcctggg    43620
caacaagagt gaaactccat ctcaaaaaaa aaaaaagaa atatttagta ttttccttac      43680
ataagtcatt attgaattcc tataaattta acattttagt gtaaaatcac atatataata    43740
ataataatta acatttatta ggtgactact atgtgccagg ggattttatt gcttgggtca    43800
ctcagtcttc acaacacttc agtctaagtg ctgctattct tattttagag gaaatagatg    43860
```

```
ttcagaaaaa aaaaataact atgaataagt aaacttgtgg gatttgaacc cagatctggt    43920
ctgcatctga aacctgtgct atttccacca ggtcatatgt ctttacaact ttaacagtga    43980
ggcttggcat attgaaaagt catttagagc ctgggcatgg tggctaacgc ctataatccc    44040
agtactttgg gaggccgagg tgggcagatc acctgaggtt aggagttcca gaccaccctg    44100
ggcaacatgg cgaaaccctg tctctactaa aaatgcaaaa attagccagg tgtggtggca    44160
tgcgcctgta gtcccagtta ctcaggaggc tgaggcagga gaatcacttg aacccaggag    44220
gaagaggctg cagtgagcca agatcgcgcc actgcattcc agtgtgggtg acagagtgag    44280
accctgtctc aaaacaacaa aaacaaaaaa aagtcattta gattgaatat atatatatat    44340
atatatatat attcaatttg ctaatatttt ataagcagtt gtcacattta tcttcatatt    44400
gaggttcagt tatattttc tttcctcata ctgttcttgt ctagattgta taccaaattg    44460
taccagacct atatactata gagcgttttt ctttttctac tatttgaaac aatatagtta    44520
gataagagaa atacctgttg ttttaaggct tagtaaaact tcccctaaaa ctgtctaggt    44580
ctggagtttt tttatggagg ttttttttaaa aaaaaaaaa gattcagttt ctataatagt    44640
tattgattat tgaaattttc caaagtcaat tttggtagtt tgtcttctaa attgtgcatt    44700
ttatctattc aaattcattt tcataaagtt tttatttact tatctgtact ttatctataa    44760
ttatataatt tattaatttc taatattgtt cttttttttg agacaggatc tcaccctgtc    44820
acccaggatg aagtataatg gatctagctt gatgcttaat aaagtaatct atcctttgtt    44880
tctggttgtt ttaaaattct ttccttggt atattatggg ttcattagta taagttcaat    44940
tttatattta tttatctcat aatatcataa cttggagcat actgtcactc agagaacttt    45000
gtcattcatc aattctggga atttcaaaac tattgtcttc aaatattacc ttcttggctg    45060
gtaatttacc ttcttggctc atgcctgtaa tctcagcact ttgggaggct gagttgggcg    45120
aattacttga gaccaggagt tcgagacttg cctggctaac atggtgaaac ccatctcta    45180 ctaaaaatac aaaaattagc tggctgtggt ggcacatagc tgtaatccca gctacttggg    45240
atactgaggc atgggaattg cttgaacccg ggaggcagag gctgcagtga gccaagatcg    45300
tgccactgca ctctagcctg ggtaacagag tgagactctg tctcaaaaac aaaaacaaaa    45360
acaaacaaat attacattat tgtattctct tgttttcaat atatattttc aaattacaca    45420
gatgtttttc tttttttttg agacagagtc ttgctctgtt gtccatgctg gagtgcagtg    45480
gcacgatctc agctcactgc aacctccacc tcctgggttc aagcaattcc cctgcctcag    45540
cctccttagt agctgggact acagatgtgc accaccacac caagctaatt tttgtatttt    45600
tagaagacac ggggtttcac catattggcc acgctgatct tgaattcctg acctcaagcg    45660
atctacctgt cttggcctcc caaaatcctg ggattacagg cgtgagccac catacctggc    45720
caactttctt gtattctctt tatcttcctc agctattttc tgtataatat cctcagatct    45780
atcttctagt ttataaattt tcttcaacca tgactaattt tatgttatac ttgtccaaga    45840 tgttttaat ttcagtgaca atattttca ttttgaaagt tctgtttttt ggccaggcgc    45900
tgtggctcat gcctgtaatc ccagcacttt gggggccga ggtgggtgga tcacgaggtc    45960
aggagatgga gaccatcctg gctaacccgg tgaaacccg tctctactaa agtacaaaa    46020 aattagctgg acgtggtggt gggtgcctgt agtcccagct actcaggagg ctgaggcagg    46080
agaatggcgt gaacccggga ggcagagctt gcagtgagcc gagatcgcgc cactacactc    46140
cagcctaggc gacagagcaa gatgctgtct caaaaaaaaa aaaaaaaaaa agaactgttt    46200
ttttttcaca cctctctgtt ctttgtcact agcttcttag ttttcattat tgatgttagc    46260
```

```
ctgtctttac tggctttaag taagtatgtt taaaatgatc aatctctttc agattgttgt    46320
gctatttcaa agtcttgggg agccagtcgt cttatttgtt gtgtctgctg attgttcctc    46380
atactggatt gtttcctctt gtgaattgtg cttttttgcc tgaccactaa tcttctgcaa    46440
aaacttctta gtgtgtatgt atgaggaaat atcatatatt cttatttgca aaagacttgt    46500
tgatgaggaa tacctggagc ttccatttct tacaagagac attttttcca agcttcactt    46560
tctaagatta gtgagcagag atcgtataag catccttttc actaagagtg atgcccactg    46620
ggcacggtgg ctcatgcctg taatcccagc actttgggag gccaaggtgg gtggctcacg    46680
agatcaggag ttcgagacca gcctggccaa catgatgaaa cccgtgtcta ctaaaaatac    46740
aaaaaaatta gctgggcatg gtggtgcacg tctgtaattc cagctactca ggaggctgag    46800
gcaggagaat cgcttgaacc cgggaggtcc taccttcta tgattctagt ttcatttcca     46860
cctccccacc tctgtaccta tatcagcatt aaatttccag tctccagcca ttgatattaa    46920
tctatttgca tctaaaatct ttccaaacag ctttgtgtca gcttttgaga tgaccctggc    46980
tttaagttcg atgatgaagc atttcctta cttacttttg aaactgaact atatattgaa     47040
ccttttgttt atttattttt tatcaagaat ttgtatgtgt tcataacatt ttaccttttc    47100
ataaaattgc atgtaaaact ttgtagtaaa agttttaacc tgtgttgtta caaacagcaa    47160
atttcttttt tatgttttgc aatttgcaaa tggaaaatag aagagtttgt aaattagata    47220
tatgagtttg gaaattatat atcttatttt tactgtaact agtggtcact gtaatatttt    47280
ttataaacac ataagagttt gtttttctgt agcaatatag ttttttttag ttatcctcat    47340
gggataatag tgatgatttc ctgcatgttc tatatcgtat taatcattag tattattagt    47400
aatctgaagt aaaatgaagt atgcttgatt tttacttct attctatttt ccttcttttt     47460
ttccttttcc tttttttttt ttttttttt ttttagtga cacatgctct gttgtccagg       47520
ctggagtgca gtggcgtgat cttggctcac tgcagcctct gcctcccagg ttgaagcgat    47580
tctcctgcct cagcttccca aatagctggg attacaggtg cctgccacca ccctgactac    47640 atttttgta attttagtag agatgaggtt tcaccatgtt ggccaagctg gtctccaact      47700
cctgacctca gtgatccac ccgcctcagc atcccgaagt gctaggatta caggtgtgag     47760
ccgctgcgcc cagacctatt ttccttcttt tgtattacta tttaaaaata ttatttacag    47820
gctgggtgtg gtggcttaca cctgtaatct cagcactttg agaggccaag atgggaggat    47880
tgcttgagcc caggagttca agagcagcct gggcaacaaa acaagacccc atctctacaa    47940
aaaagcatac aaacaaaaaa ttagccatgt atggtggtgg gcacctgtag tgcctgctct    48000
tgaaaggctg agatgggagg attttttgag ccaagggg ttt caaagctgca gtgtgctgtg    48060
attgcatcac tgcactccag cctcggtgac ggtaataacc ctgtctcaaa aaaaaaaaa    48120 gatattattc acaaaatttt tagtgtgttc tccactgctt tagaaaaccc attctttttc    48180
attttgctct caaattcccc actcctggtt tcttaatgtt atttctctgt gttctggaac    48240
atttatttga gtaatgtatt cacaaaagat gactaggtag tgttggctga gttcttacat    48300
acctagaaat gtcttttgcc attatgagtg agcaacagtt aacttggata taaaattatt    48360
gggatcttgt attaggtagg ttcaagccga gcattgtaaa ataaagcccc aaatgtacag    48420
atcaaataaa gataaaaatt tagttctctt taatgtaata cttgttatg caacagtgct      48480 caacgactgt gttctacaag gccatcctgg ctgatgggat caccctctgtt atcacattat   48540 ttggctttca tctttgagtc taagagcgct ccttcccccc ttgccccagt cctttgaaat    48600
```

```
gtctagtcaa gacccttttcc tagttttcgt ttgtttgttt gttggagacg gagtctcact    48660
ctgttgccca ggctggagtg tatggcacga tctcggctaa ctgcaacctc cacctcccag    48720
gttcaagcaa gtctcctgtc ttagcctccc aagtagctgg gattataggt atgtgccaca    48780
ggcctggcta attttatat ttttagtaga cagggtttt catcatgttg gccaggctgg     48840
tcttgaactc ctgacctcag gtgattggcc cgccttggcc tcccaaagtg ctgtgattac    48900
agacatgagc cactgcgccc gtccttgcca gttctcatta gttctctttg atggctaaaa    48960
cctcttacac tattataaga aagcatatag gagataaagt atgtaggaga tactgctata    49020
gagtttaagg agatagagat ggtattggca gtggtggttt tgcctatgtg cccttctcta    49080
gagttgatgt agagttgcct agagtatcct cccttagagt tgatgtgaat taaacactgt    49140
ggttttacaa agagaacccc agaaaagtag ctgaggccat tgataaagag caggtaggtc    49200
attagctgct atattatcat tgctaaattt tgcattcttt tcttgcagaa aatatatttg    49260
atttatttgt ttaggatttg ggggtgagct ttgatgtgta attactttat cagttgattg    49320
ttaactagaa aatgagaaat aagtgacttg tttgctacca ttgttttttga agggagaaat   49380
tcagaaaata tatttactga gaagttaaag gaagacagta ttcctgctcc tcgctctgtt    49440
ggcagtatta aaatcaactt taccccctcga gtattcccaa cagctcttcg tgaatcacaa   49500
gtagcagaag aggaggaggt atatatactt actctagtta caattaccac aaatgaaaat    49560
actttattt tatttcatct attgaaatta gtactggttc tgaatttctt aagtatttat     49620
tacactaaag aaataacgtc atgaatatgt tttagaattt ccttatgaga aaatatattt    49680
tgcagatgtt tttggctcca gaatagtgat aagagaatac cgacttaata tatgtacagt   49740
aggccgggcg cagtggctca tgcctgcaat cccagcactt tgggagcccg agatgggtgg    49800
atcacttgag gtcaggagtt caagaccaac ctgactaaca tggggaaact ccatctgtac    49860
taaaaataca aaaattagcc tggcgtggtg gcgagcacct gtgatcgcag ctactagcgg    49920
ggctggggca ggagaattgc ttgaacttgg gatgtggagg ttgcagtgag ccgagattgc    49980
accattgtac tccagcctgg                                                50000
```

<210> SEQ ID NO 8
<211> LENGTH: 50000
<212> TYPE: DNA
<213> ORGANISM: Homo sapiens
<220> FEATURE:
<223> OTHER INFORMATION: human DYXC1 chromosomal gene region,
      nucleotides 100001-150000

<400> SEQUENCE: 8

```
gcaacagagt gagactttga atcaaaaaaa aaaaaaaaa aaagcggtct ttttgttgtt     60
gttgtttgtt ttagagatgg agttttttgct cttgttgccc aggctggagt gcagtgggca   120
caatctcagt tcactgcaac ctcctcctcc caggttcaaa caattctcct gcctcagcct   180
ccctagtagc tgggattaca ggcatgcgcc agcatgtctg gctaatttt tatattttta    240
gtagagatgg ggtttcacca tgttggtcag gctggtctca aactcctgac ctcaggcgat   300
ccaccctgct cggcctccca atgtgctggg attataggca tgagccaccg tacccagcca   360
agaactgcat ttttttactg cgaggctgaa ttgatgcatc tttgatttga aaaattgtag    420
aaataagaag atccttaaga cataatgaca agccgggcgt ggtggctcac gcctgtaatt    480
ctagcacttt gggaggccga ggtgggtgga tcacctgagg tcaggagttt gagaccagcc    540
tggccaacat ggtgaaaccc catcgctatt aaaaatacaa aaattagtcc agtgtggtgg    600
```

```
caggcacctg taatcccagc tactcgggag gctgaggcag gagaatcact tgaacccggg    660
ggtcagaggt tgcaatgagc caagattgca ccatttcact ccagcctggg tgaaagagtg    720
aaactctgtc tcaaaaaaaa aaataaaaaa taaaagacat aatgacaata taaataatta    780
tttcatatta ttaaacaagg tattttctat atttgtaaca tttctataat tatacagtta    840
taataataat aataattatt attattttgt gggatggagt ctcgctctgt ccctaggct    900 ggagtgcagt ggcgcagtct ccgctcactg caagctccac ctcctgggtt catgccattc    960
tcttgcctca gcctcccgag tagctgggac tacaggtgcc caccgccacg cccagctaat   1020
tttgtgtagt ttttaataga gatggggttt caccatatta gccaggatgg tctcaatctc   1080
ctgaacttgt gatccaccca cctcggcctc ccaaagtgct gggattacag gtgtgagcca   1140
ctgcgcccgg cccatagaat tatttttgaa ttgtgtttat acacacacac acacacacac   1200
acacacacac acacacacac cctttttttt ttttttttg agttgggggt cttgctctgc   1260
tgcccaggct ggagtacagt gggacaatca tggctcactg tagccttgaa ctcttgggct   1320
caagtgacct tctgcatatt tttcagtaca gaaaaatgaa aatataaaag aattttagat   1380
caatatcctg gatgaacatc gatgcaaaaa tcctcaataa aatgctggca accgaatgc    1440 agcagcacat caaaaagctt atccaccatg atcaaatggg cttcatccct gggatgcaag   1500
gctggttcaa catacgcaaa tcagtaaacg taatccagca tataaacaga accaaagata   1560 aaaccgcat gattatctca ccagatgcag aaaaggcctt tgacaaaatt caacagcact   1620
tcatgctaaa aactctcagt aagctagata ttgatgggaa gtatctcaaa ataataagag   1680
ctatttatga caaacccaca gccaatatca tactgaatgg gcaaaaactg gaagcattct   1740
ctttgaaaac tggcacaaga cagggatgcc ctctctcacc actcctattc aacacagcat   1800
agtgttggaa gttctggcca gggcagtcag gcaggagaaa gaaataaagg ggctcccctc   1860
tcccctctcc cctctcccct ctccctctg ccctctcccc tctccctct gccctctccc   1920 ctctcccctc tgccctctcc cctctcccct ctccctctc tctttccacg gtctccctct   1980
gttgctgagg ctggactgta ctgccgtgat ctcggctcgc tgccacctcc ctgcctcagg   2040
ctcctgtcat tctcctgcct cggcctgccg actgcttggg attgcaggca cgcaccgcca   2100
tgcctgactg gttttttgtat ttttggtgga gatggggttt tgctctgttg cccggctgg   2160 tctccagctc ctgacctcca gctcctgatc tgcccgcctc ggcctcccga ggtgctggga   2220
ttgcagatgg agtcttgctc actcaatgct caatgttgcc cagactggag tgcagtggca   2280
tgatctcggc tcgctacaac ctccacctcc cagccgcctg ccttggcctc ccaaagtgct   2340
aagattacag cctctgcctg ccgccaccc catctaggaa gtgaggaaca tttctgcctg   2400
gccgcccatc gtctgggatg tgaggagtgc ctctgcccag ccgcccagtc tgggatgtga   2460
ggagcacctc tgcccgaccg ccaccccatc tgggaagtgg ggagcgcctc tgcccggctg   2520
ccccgtctgg gaagtgagga gcgcctctgc ccggccgccc atcatctggg atgtgaggag   2580
cgcctctgcc tggccacccc gtctgggaag tgaggagtgc ctctgcgcag ccgccccatc   2640
tgggaagtga ggagcacctc tgcccgtcag ctgccccatc tgggaagtga ggagcgcctc   2700
tgcccggctg ccccgtctgg gaagtggaga gcgcctctgc cagctgcccc gtctgggaa   2760 gtggggagcg cctctgcccg ccgcccatc atctgggatg tgaggagcgc ctctgcctgg   2820
ccgccacccc gtctgggaag tggggagcac ctctgcccag ccggccgtc tgggatgtga   2880 ggagcacctc tgcccggcca ccccatcagg gatgtgagga gcgcctctgc ccggccgccc   2940
catctgggat gtgaggagcg cctctgcctg gccaccaccc tgtctgggat gtgaggagtg   3000
```

```
tctctgcccg gctgccccgt ctaggaagtg aggagcgcct ctgcccggcc accccgtctg    3060
ggatgtgagg agcgcctctg cccggccgcc accccatctg ggaagcaggg tgcgcctctg    3120
ctcggccgcc ctgtctggaa ggtgaggagc gcctctgcct ggctgccctt catctgggat    3180
gtgaggagcg cctctgcccg gccacccggt ctgggaagtg aggagcacct ctgcctggcc    3240 acccgtcta ggatgtgagg agcacctctg cccgaccgcc accccatctg ggaagtgggg    3300
agcgcctctg cccggccgcc ccgtctggga agtgaggagc gcctctgccc ggccgcccat    3360
catctgggat gtgaggagtg cctctgcctg gccaccccgt ctgggaagtg aggagtgcct    3420
ctgcccagct gcccccccccc ccgtctggg atgtgaggag cgcctctgcc cggccgcccc    3480
gtctaggagg tgaggagcgc ctctgcccag ctgccacccc ttctgggaag tggggagcgc    3540
ctctgcccgg ccaccccgtc tgggaggtga ggagcgcctc tgcccggctg ccgcatctgg    3600
gaagtgagga gcgcctctgc ctggctgccc tgtctgggat gtgaggagcg cctctgcccg    3660
gccgccaccc catctgggaa gcggggagtg cctctgcccg gccacccgt ctgggaggtg    3720 aggagcgcct ctgcccggcc accccgtctg ggatgtgagg agcgcctctg cccggccgcc    3780
ccgtctggga ggtgaggagc gcctctgctc ggccgccccg tctgggaggt gaggagcacc    3840
tctgcctggc tgccgcatct gggaagtgag gagcgcctct gcccggctgc ccgtctggg    3900 atgtgaggag cgcctctgcc cggccgccac cccatctggg aagcggggag cgcctctgcc    3960
cggccacccc gtctgggaag tggggagcgc ctcttcccgg ccgccccgtc tgggaggtga    4020
ggagtgcctc tgcctggtgc ccttcgtttg ggaggtgagg agcgcctctg cctggccacc    4080
ccgtctggga ggtgaggagt gcctctgcct ggccgcccca tctgggaggc gaggagcgcc    4140
tctgcctggc cgccccatct gggaggtgta cccaacagct ccgaagagac agcgaccatc    4200
gagaacgggc catgatgacg atggcggttt tgtggaaaag aaaatgggga aatttgggga    4260
aaagaaagag agatcagatt gttactgtgt ctgtgtagaa agaagtagac ataggagact    4320 ccatttttgtt ctgtactaag aaaaattctt ctgcatggga tgctgttaat ctataaccttt    4380 acccccaacc ccgtgcactc tgaaacatgt gctgtgtcaa ctcagggtta aatggattaa    4440
gggcggtgca agatgtgctt tgttaaacag acgcttgaag gcagcatgct cgttaagagt    4500
catcaccact ccctaatctc aagtacccag ggacacaaac actgtggaag gctgcaggga    4560
cctctgccta ggaaaaccag agacctttgt tcatgtgttt atctgctgtc cttctctcca    4620
ctattatcct atgaccctgc acatcccccc tctctgagaa acacccaaga atgatcaata    4680
aatactaaaa aaaaaaaaaa aaaaaaggg tattcaatta ggaaagagg aagtcaaatt    4740 gtccctgttt gcagatgaca tgattgtata tttagaaaac cccatcgtct cagcccaaaa    4800
tctccttaag ctgataagca acttcagcaa agtctcagga tacaaaatca atgtgcagaa    4860
atcacaagca ttcttataca ccaataacag acaaacagag agccgaatca tgagtgaact    4920
cccattcaca attgcttcaa agagaaaaaa atacgtagga atccaactta caaggtatgt    4980
gaaggacctc ttcaaggaga actacaaacc actgctcaac aaaataaaag aggacacaaa    5040
caaatggaag aacattccaa gctcatggat agaaagaatc aatatcgtaa aaatggccgt    5100
gctgcccaag gtaatttata gattcaatgc catccccatc aagctaccag tgactttccc    5160
caaagaattg gaaacaaaac tactttaaag ttcatatgga accaaaaaag aacccacatt    5220
gccaagacaa tcctaagcca aaagaacaaa gctggaggca tcatgccacc tgacttcaaa    5280
ctacactaca aggctacagt aaccaaaaca gcatggtact gatactgaaa cagagatata    5340
```

```
gaccaatgga acagaacaga gccctcagaa ataataccac acatctacaa ccatctgatc   5400
tttgacaaac ctgacaaaaa caagaaatgg ggaaaggatt ccctatttaa taaatggtac   5460
tgggaaaact ggctagccat atgtagaaag ctgaaactgg atcccttcct tacaccttat   5520
acaaaaatta attcaagatg gatgaaagac ttaaatgtta gacctaaaac cataaaaacc   5580
ctagaagaaa acctagacaa taccattcag gacataggca tgggcaagga cttcatgtct   5640
aaaacaccaa agcaatggc aacaaaagcc aaaattgaca aatgggatct aattaaacta   5700
aagagcctct gcacagcaaa agaaactacc atcagagtga acaggcaacc tacagaatgg   5760
gagaaaattt ttgcaatcta ctcatctgac gaagggctaa tatccagaat ctacaaagaa   5820
ctcaaacaaa cttacaagaa aaaaacaacc ccatcgaaac atgggtgaag gatatgaaca   5880
gacacttctc aaaagaagac atttatgcag ccaacagata catgaaaaaa tgctcatcat   5940
cactggccat cagagaaatg caaatcaaaa ccacaatgag ataccatctc acaccagcta   6000
gaatggcgat cattaaaaag tcaggaaaca acaggtgctg gagaggatgt ggagaaatag   6060
gaatactttt acactgttgg tgggactgta aactagttca accattgtgg aagacagtgt   6120
ggcgattcct caaggatcta gacctagaaa taccatttga cccagccatc ccattactgg   6180
gtatataccc aaagattatc aatcatgctg ctataaagac acatgcacat gtatgtttat   6240
tgcagcacta ttcacaatag caaagacttg gaaccaaccc aaatgtccat caatgataga   6300
ctggattaag aaaatgtggc agtaatgtgt gccatccagg gctagagcaa gtgcggcccc   6360
acggcctgca cggccctgag ccatgctgag gagctgcgcc aggcgcctcc gcacgctggg   6420
ggccctttgc cagccgccac cggtaggcag gcgcctgccg ggtagtgagc cgcaacccgc   6480
gctgaggtca ttttcttctg aggaagtcat tcttaaggac tattctgtcc caacccccag   6540
ctggaacaag gacctaagac tgctcttgga ccagtttatg aagaaatgtg aagacggctc   6600
ctggaaacgt ttgccttcat ataaacgtac acctactgaa aggattcaag actttaaaac   6660
ccattttctt gacccaaagc ttatgaaaga agaacaagtg tcacaggccc agctcttcac   6720
cagaagcttt gatgatggcc tgggctttga atacgtgatg ttctacaatg acgttgagaa   6780
aaggatggtt tgcttatttc aaggagtccc ttacctagaa ggaccacctg gattgattca   6840
tggaggtgcc attgcaacca tgattgatgc tactgttggt atgtgtgcaa tgatggctgg   6900
gggaatcgtc atgactgcca atctcaacat cagttgtaaa agacctatcc ctctttgttc   6960
tgttgttagg ataaatagcc aacttgataa agttgaagga agaaattttt tgtttccag   7020 taatgttcag agtgttgatg agaagaccct atattcagag gcgacaagct tacttataaa   7080
gctgaatcct gctaaaagtc tgacataaag agctgctggt gaactccatc tcattctctc   7140
ccctccagaa gaagcagttg tcccccgaat actctgctcc ctcactgctg aatccctgta   7200
gggagaagcc tgccaagagt gaccttccga aacagccttc tgaatacaag gaggattcag   7260
tttccatctt cccaactttt taacacagaa acacttcctg cgagcatttc gacaactctc   7320
agtcagggcg ctgtggctca cgcctataat cccagcactt taggaggcca aggcgggtgg   7380
attgcctgag ctcaggagtt caagatcagt ctggacaaca cgatgaaacc ccgtctctac   7440
taaaataaaa aaaattagcc gggcatggtg gcgtgtgcct gtagtcccag ctactcagga   7500
ggctgaggca ggagaattgc ttgaacccgg gaagcggagg ttgcagtgag ccaagatcat   7560
gccacatcac tccagccttg gcaacagaac gagaacccat ctcaaaacaa aacaaaacaa   7620
aaaaaactct gtctccttag gatgtgttac ctgctccact gcggactgga gaaataaatg   7680
tgtattgaaa cttttcctgc aaacttgaaa atgctagaaa accaagcatg aagaataaat   7740
```

```
acatggcagg gaagacacag acatgtgcat atgcatatac attataagtt agtaagttag   7800
aaagctagct ttgttgtatc tgaacacatg aatcttttg gtcagagtag aagcacagc     7860
caaattctat aggaatgaat acctcaaatc tgttgtctgg gattctagag attaaaccac   7920
tgtgccattt aaaaagaaa aagaaaatg tggcacatag acaccatgga atactatgca     7980
gccataaaaa aggatgagtt catgtccttt gtagggacat ggatgaagct ggaaaccatc   8040
attctcagca aactattgca aggacaaaaa accaaacacc acatgttctc actcataggt   8100
gggaattgaa caatgagaac acttggacac aggaagggga acatcacaca ccggggcctg   8160
ttgtggggtg gtgggagggg ggagggatag cattaggaga tacacctaat gtaaatgacg   8220
agttaatggg tgcagcacac caacatggca catgtataca tatgtaacaa acctgcatgt   8280
tttgcacatg taccctagaa cttaaagtat agtaaaaaaa agaaaaatg aaaatattat     8340
aacccagaaa gataaaataa taatcacatg ggctgggcat ggtggctcac gcctgtaatc   8400
ccagcacttt gggaggccga ggtgggcaga tcacaaggtc gggagttcga gaccagcctg   8460
gccaatatgg tgaaaccccg tctctactaa aaatacaaaa actggccggg catggtggca   8520
cacgcctgta atcctagctg ttcaggaggc tgaggcagga gaattgcttg aacccagaag   8580
gcggaggttg cggtgagctg agatcatgca actgcactcc agcctggggg acagagtgcg   8640
actgtctcag aaaaaaaaa attaataata tcatatgaac tcccagaaag caagaaattt     8700
ggctagaaat tttatctatt gtatttccac cagctattga ggtttaaaaa aaagtttaag   8760
gacgggcacg gtggctcaag cctgtaaccc cagcactttg ggaggccaag gtgggtgaat   8820
cacaaggtca ggagtttgag accagcctgg cccatatggt gaaacccat ctctactaaa     8880
aatacaaaaa attagctggg catggtggcg tgtgcctgta gtcccagcta tttgggaggc   8940
tgaggcagaa gaatcgcttg aacccaggag gcagagggta cagtgaaccg agattgtgct   9000
actgtactcc agcctgggca gctgagtgag actctgtctc aaaagaaaa aaagtttaat     9060
aatgtataaa tatggccagg tgcagtggcc caacgcctgt aatcccagca ctttgggagg   9120
ccgaggtggg cagatcacaa ggtcaggaga tcgagaccag ggtgaaacct cgtctctact   9180
aaaaatacaa aaattagct gggtgtggtg gtgggtgcct gtagtcccag ctacttggga    9240
ggctgaggca ggagaatggt gtgaacctgg gaggcagagc ttgcagtgag ccagatcgc     9300
accactgcac tccagcctga gtgacagagc aagactccgt ctcaaaaata tatatatata   9360
aatattgcaa gattaaaatc accatcattg gccaggcgtg gtggctcacg cctataatcc   9420
cagcactttg ggattccgag gtgggtggat cacgaggtca tgtgttcaat accagcctgg   9480
ccaaaatagt gaaaccctgt ctctactaaa aatacaaaaa ttagccaggc atggtggcac   9540
acgcctgtaa tcccacctac tcgggaggct gaggcaggag aatcacttga acctgggagg   9600
tggaggttac agtgagctga gattgctcca cttgcactcc agcctgggtg acagagcaag   9660
ataaaaaaaa aaaattacca ccatcaagta gtacgttaat ctgctctggc tgctataaac   9720
aaaataccat agactgggtg gcttaaacaa taaacagtca tttcttatag ttctggaggc   9780
tgggaaatcc aagatcaggg tgccagcatg attcttggta ggggtgctca tcataacttg   9840
cggacacca ctttctcact gtgtccacat gggggagctc tgatctcttt ctcttcttaa     9900
aaggataaac tcgttttggg agctctcctc tcatgaccta aacctcatta cctctcagag   9960
gccccactac caaataccga ttcacattga tggttatggc ttcagtatat caatttggag  10020
gagaggtgga gaagacacaa acactcagtg catagcaaat aatatttcaa tccactggag  10080
```

```
gaagatggaa aatctaaaag gaaatgttaa ttaaaaaaag accttttat tcttcataag    10140 acttctttct cattctagtg gctacacaaa caagctgagg cacgaagagc aatgaatact    10200
gacatagctg aactttgcga tttaaaagaa gaagaaaaga acccagaatg gttgaaggat    10260
aaaggaaagt aagttgtttg aactctgatc atgagcttta tcatgtatga agacattagc    10320
agttatcata ggacgagtat ggtggctcat gcctgtaatc ccagccctt gggaggccga     10380 ggtgggatga taacttgaag ccagaagttt gagaccaacc tgggcaacaa agcgagattt    10440
tgtctctaca aaaaacaaa caaaataaaa cattagcctg gtgtggtggt gagcacctgt     10500
agtcccagct actcagaagg ctgcggcggg aggatccccc aagcccagga gttcatggct    10560
gcagtgagct atgattgtgc cactgcactc cagtctgggc aacaagagtg agaccctgtc    10620
tttgaacaaa caaagtagtt atcacattct ctagatattt tgtctgtttg tgtgttgttg    10680
gagaaagata atgcaaataa gcaataagg tagacagggc atccatattt taaaagtcag    10740
ataacaaggc aatgaggctc taattttatt tttttattta aatgtcataa aaatgaaaaa    10800
aattacatct tttggaatgc ttattaaaat tccttttaaa atccgtttta catttgacat    10860
aagtcctttc tgatgtctcc cataaaaacg ggcttttgc aaagctacag ctgtttgat     10920 tattcttatc cattttttt cttttttttt tttgtgagat agtgtctcat tttatcaccc     10980 aggctgagt gtagtggtgc aatctcagct cactgcaacc tctacccgcc aggttcaagc    11040
agttcttctg cctcagcctc tcaagtagct gggattacag gcatccaccg ccacacctgg    11100
cgaatttttt ttgtatttt agtagagacg gggtttcacc atgttggtca agctggtctt     11160
gaactcctga cctctagtga ttcatccacc tcagtctccc aaagtgctgg gattacaggc    11220
atgagccctg gtgtgggacc tattcaaatc catttctaaa gattaccatc ttactgcctt    11280
ccaggtcagt gatgtaaaca caaaaaagat taccatatta tcccagaaat tatcttatat    11340
ctgggcagtc attttattca tttgtatatg gattttttt tttttttga gacaaagtct      11400 cgctcttggt ccccaggctg gcgtgtgatg gcacaatctt ggctcaatgc aaactccacc    11460
tcccaggttc aagcgattct cctgcctcag cctcctcagt agctgggatt acaggcgcct    11520
gccaccacgc ccaactaatt tttgtttcac catgttggcc aggctggtct caaactcctg    11580
acctcaggtg atccgcgcac cttgacctcc caaagtgctg ggattacggg tgtgagccac    11640
tgcacccggc cgtgaatatt ttaacatact gatcaaaaac agtgaattct ggcatattct    11700
gagtggcaat ttgtgttcat attttgaggc ggctatagat attatttatt gtatttcatc    11760
atatacactt ctgtgtttat tttcctatta cttattactt ctataacaaa ctaccaccaa    11820
gtggcttaaa acaacacaaa tttattatct tatagttctg taattcagaa gtccaaaatg    11880
agtttcactg ggccaaaatt aggtgtcaac tgccttcctt ttgaaggctc taggagaaaa    11940
gctgttttct taaatttccg gcttctaagc tgtttgcatt ccttgaattg tggctcccca    12000
gccactgatt gcgttattct gacctctgct tccgtgatct ccttttctga ctctcctgcc    12060
tccttctacc ttttataagg cctcttgtgt ttatgtaagt cccacctaca tcatccaggg    12120
tactctctcc atcaaactct ttaacttatt cacatgtgca aagtccttt tgccgtgtta     12180 ggtaacgttc ataggttctg ggattagaat atggacatct ttttttgggg ggcggggggc    12240 attatcgtc taccacaata tctatatttt tcctttcttt ctacttttc ttggtctttt      12300 ctcttgtctg ttacaacacc agggattgtt ttgtggcgtt tagctggagt tggcaatttt    12360
tctgaaggtt agaagcctgg aactgacagg ttggttcttc taactcccaa gagtaaaacc    12420
atatataatc tttcctcctc tttctcttct tcctttcttc cttcctattc atttattcag    12480
```

```
ccattaaata agcaattatt gattgcttgc tatttgccag actataggca cttaacaaca    12540
gaaatcagga ggagagagac gtacacaaat atttaaaaca ctgtgtggga agtacaataa    12600
catggataag aacaaggtaa tagagccagg tgcggtggct cacgcctgta atcccagcac    12660
tttgggaggc tgaggcgggc ggatcacctg aggttgggag ttcaccagac tgaacagcaa    12720
ggagaaaccc tgtctttact aaaagtacaa aattagctgg gtgtggtggc gcatacctgt    12780
aatcccagct actcgggagg ctgaggcagg agaattgctt gaacctggga ggtggaggtt    12840
gcggtgaatc gagatcgtgc cactgcactc cagcctgggc gacagagtga gactccatct    12900
caagataaaa agaaaatttc tggccaggca cagtggctca cgcctgtaat cccagcactt    12960
tgagaggcca agatgggtag atacttgagt tcaggatttt gagacaagcc tggccaatat    13020
ggtgaaaccc aatttctact aaaaatgtaa aaattggctg ggcacggtgg ctcactccta    13080
taatcccagc actctgggag gccaaggtgg gtggattacc tgaggccagg agtttgagac    13140
cagcctggcc atcatggtga aaccctgtct ctactaaaaa tacaaaaact agtcaggcat    13200
tgtggcgcac acctgtaatc ccagctaatc tgagtctcag aggcatgaga atcacttaaa    13260
cctgggaggt agaggttgca gtgagctgag atggcaccac tgaactccat tctgggcaat    13320
ttagcaagac tgctcaaaaa aataataata attaaaaaaa taataataat gggcaaagaa    13380
cttaaatagg catttctcca agaagagaga caaatggcta gtaaatataa aaagatgttt    13440
aacatcacta accatttggg aaatgtctta tcaaaaccac tatgagatgc cacttcacac    13500
ccattaggat ggctactcag aaaaaaaaca gaaaataaca agtgttagtg aggatgtgga    13560
gaaattagaa tcctgtgcac tgttggtaga ggtgttgaat gatccagctg ctatggaaaa    13620
cactattgtg gttcccaaaa aagtaaaaat agggccgggc gcaatggctc acgcctgtaa    13680
tcccagcgct ttgggaggcc gaagcgggca gatcacctga gatcgggagt tcgagaccag    13740
tctgaccaac atggagaaac cccatctcta gtaaaaatac aaaattagcc aggcgtggtg    13800
gtacatgcct gtaatcccag ctactcagga ggctgacgca ggagaatcgt tgaacctgg    13860
gaggcagagg ttgcggtgag ccaagatcgc accattgcac tccagcctgg gcaacaagag    13920
tgaaactctg tctcaaaaaa caaacaaaca aaaaaagca aagactttgc attttgaaga    13980
aatcctttaa tcgtgtacat ctctttattt gaagagaatt ttggaacatt taaactgaaa    14040
gagtatatcc attgcaagta accaaaaaac ccaatttttt tatattgaaa ggaatttatt    14100
gtcttatata actaaacagc taaggtgtt ttctatttca agtaaagctt gatccagcag    14160
cttaactgta tcatgaaggg ctcggtttct ttctgccttt ttattccttt catatttcca    14220
tagtatcagc tttattctaa tgccagctct tcccacggtc ttaaaaacgg tcagcaacaa    14280
tgtgggctat gtgacttctt cacttatatc cagcagggg agaaatttgc ccaacttttc    14340
attcttcaac tttgaaacca acccacaggc ttcatcctaa gtagaacaat ataggtcaca    14400
ctagcccatc cctgagtcaa ttactggagc aaaaataatg caaatatgcc ctactggctt    14460
aaattactaa tgtctaccct tggaggtggg agtgaggtcc attccattca aatgacaggc    14520
tggtatatgt gaaaagagat ggattcagtg caggcaacgt ttaccctaaa gagaatgcaa    14580
aaagaggtaa gccatcctct ttgtcaaata caattagata ttatttctgt gtttctgttt    14640
caatgttaaa ttgttttttct tctctgtttt tgtctcatta gcaaattgtt tgcaacggaa    14700
aactatttgg cagctatcaa tgcatataat ttagccataa gactaaataa taagatgcca    14760
ctattgtatt tgaaccgggc tgcttgccac ctaaaactaa aaaacttaca caaggctatt    14820
```

```
gaagattctt ctaaggtatg gatatctatg tatgatatat ggtgctttaa atatatccit    14880
ctattaattg gtttaaatga tgatctttt  ctgttcagtt gaaataattg agatgcaaag    14940
attttaaaga ttgtctttct tattgaatct tttttttttt aactgatttt ttactaatgg    15000
acaaggaact ggtgttttt  tgtgacttct atgaatagtt agttagatta aaaatcagct    15060
gttactggcc gggcgcagtg ggtctcgcta tattgcacag gcaggtctcg aactcctggg    15120
ctcaagctat cctcccgcct ctgcctccct gagagctggg attacagaca tgagccaccg    15180
cgcccggcac ccagcccaga tatctctaca atcattttct catttgcagg gtaacttagt    15240
atattctact ttccattact aatatttact gtgtatgtct tgaacttcta cagcttttc     15300
ttttttccat gtcaagataa cttgttttaa gggcatatca tgtgcaaaat ctcttaggta    15360
gcttcttgag attgaggata tggaggacac aaccaagtct tcatcacttt gatatcatac    15420
tacttttatg atccagtttt tctttgactc tcacaatgca aacaaatatt tgttgaatga    15480
atgaataagc tgaatcaccc aatctgaata caaaagccca caaatgctat ttaataattc    15540
ctactggtaa aaataaagct gtggagatgt gaaatgataa gctgaataat aaccttggag    15600
gggtatgaat cccatatagg aacaactgaa aaattcctta agttgttcaa catatctctt    15660
ctggaaaacc tgataataat tatttgtttt atatatatat ataatatata ttatatataa    15720
gaatatatat aatatatata atattatata tattatatat aatatataaa atatattata    15780
tatattatat atattatata tattttatat aatataatat atataattat atataatata    15840
tataatatat ataataatata tgtaatatat ataatatata ttataatata tataaatatat   15900
aatatatgta atatatataa tatatattat atatataaaa caaatatata tatttgtttt    15960
ataaaaacaa ttatatatat ttatatataa aaaacaaata attatatata tatttgtttt    16020
atatatataa tatatttata tttgctaaat tcctgtacca gctaagctaa aaatttaggt    16080
gagtgcttga ggccattttt tttttttttt ttttgagacg aggtcttgct ctgttgccca    16140
ggctggagta caggggcaca atttcggctc actgcaagct ccgcctcccc ggttcacgcc    16200
attctcctgc ctcagcgtcc ggagtagctg ggactgaagg cgcccgccat catacccggc    16260
taatttttg  tattttagt  agagacgggg tttcaccgtg ttagccagga tggtctcgat    16320
ctcctgactt cgtaatccgc ccgcctgggc ctccgcccgc ctgggcctcc caaagtgctg    16380
ggattacagg catgagccac cacacccggc cgaggccttt tgtgtgtgtg tgtgtttgtg    16440
tgagacaaag tctcactctg tcaccaggct ggagtgcagt ggtgcgttct tggcttattg    16500
caacccctgc ctcccggatt caagtgattc tcctgcctca gcctcctgag tagctgggat    16560
tacaggtgcc cgctaccaca tctggctagt ttaagtattt ttagtagaga cagggttttg    16620
ccatgttggc caggctggcc tcaagctcct gactttgggt gatctgccca cctcagcctc    16680
cgaaagtgct ggaattacag gcgtgagcca ccaggcccac ccgaggctta ttttaaaatt    16740
agaatttta  ccatgttttt gcttgtttgt ttttgttttt tgtttttttt gagacggatt    16800
ctcgctctgt cacccaggct ggagttcagt ggcgcgatct cggctctctg caagctctgc    16860
ctccctggtt caagcaattc tccgcctcag gcctcccaag tagctaggac tacaggtgtg    16920
caccaccaca gccagataat ttttgtattt tttttagta  gagacggggt ttcgccatgt    16980
tggccaggct ggtctcaaaa tcctgacttc aggtgatcca cctacctcgg cctcccaag    17040
tgttgggatt acaggcgtga gccaccatgc ccagcctttt gcttgtttaa attaagaaac    17100
tataactttc ttgtaataat tatatatatt ttgtaaggca ctggaattat tgatgccacc    17160
tgttacagac aatgctaatg caagaatgaa ggcacatgta cgacgtggaa cagcattctg    17220
```

```
tcaactagaa ttgtatgtag aaggtaagga attgatagaa atggtttaag tcccaagtta    17280
tactctgaaa aaaatgtcat tggaattatt taagatcgtg acttttaagg actccatttt    17340
taaatatttt tagcatttaa tttattctta gtaatgtctg cagtatatct gacaatacat    17400
gatttctaaa ttatatttaa aaaattcatt gtagaagaga attaaaataa gtgtaaacaa    17460
caagtttcag tctagaaaaa tgctatatta gctgggtgca gatgctcatg cctgtaatcc    17520
cagcactttg ggaggcagag gcgggtggat cacctgaggt cgggagttcg agaccagcct    17580
gaccaacatg gagaaaccct ctactaaaaa cacaaaatta gcttggcgta gtggcacatg    17640
cctgtaatcc cagctacttg ggaggctaag gcaggagaat cccttgaacc cgggaggcgg    17700
agattgtggt gagccgagat catgtcattg cactccagcc tgggcaacaa cagcgaaact    17760
ccttctcaaa aaaaaaaaaa atgctatatt accagacaac tcttcataga aacgtgtgat    17820
aaatgctggg tgtggtgctt cacgcctata atcccaggaa ctggggaggc tgaggtggaa    17880
ggatggcttg aggccaggag tttgagacca gcttgggcaa catagtgaga ccctgtctct    17940
taaaaaaaaa aaatacatga taggctgggt gtggtggctt atgcctgtaa tctcagcact    18000
ttgggaggcc gaagcaggtg gatcacaagg tcaggagatc aagaccatcc gggctaacac    18060
ggtgaaaccc cgtctctact aaaaatacaa aaacaaaatt agccaggtgt ggtggcgggc    18120
gcctgtagtc ccagctactc aggagactga ggccagagaa tggcgtgaac ccggaaggca    18180
gagcttgcag tgagccaaga tcacgccact gcgctacagc ctgggtgaca gagcaagact    18240
ctgtctccaa aaaaaaaaaa aaaagataaa aatatataaa tgatttgaga tatcatggat    18300
atttatctca gagagcttct tcggtcatcc ctgtatgtat gtatgtattt gtgtgtgtgt    18360
gtgtgtgtgt gtgtgtgtgt atacacacac ctaagctcgg aaataactga tccaccatag    18420
tgcatgcaca ttgcttatat ttgttagatt gtattaagtt ctgtaattta gctctatgta    18480
tacagaaaat atagcattta ttttatttta ttttagatag atttagggcc cgggcacggt    18540
ggctcacacc tgtaatccca gcactttggg aggccaaggt gggtggatca tgaggtcagg    18600
agatcgaggc cctactggct aacacggtga accccatct ctactaaaaa tacaaaaaat    18660
tagccaggtg tggtggcagg tgcctgtagt cccagctact caggaggctg aggcagaaga    18720
atggtgtgaa cccaggaggc agagcttgca gtgagccgag atcatgccac tgcactcccg    18780
cctgggcaac agaaggagac tctgtctcaa aaaaaaaga tgggaatcta atttaaaact    18840
tggtacttgt tctgaaccat gctactagtg attatttta ttttaaacaa ctattgtcta    18900
gataaaagaa gtgctaataa aatatttatt gtattaatca tcattgctat ataaacacag    18960
gcctacagga ttatgaagcg gcacttaaga ttgatccatc caacaaaatt gtacaaattg    19020
atgctgagaa gattcggaat gtaattcaag gaacagaact aaaatcttaa tgactattag    19080
aagtaactaa gtattgttat aagtttttta aaaacaactg gaggcatctt tgtacatatt    19140
atggccagtt gtacagaatc gctttctgtt tagtacttta gttctgttga gggcaaaata    19200
ttataaatct atagaaaata aactgtttga cttgaatcat ttctgaataa gtaaatctaa    19260
ataagaatct atttaattc cttatttctt catattaata catatgtata ctttttgtg    19320 ttactgaatt aagcttgccc ttgtaacaaa atatgttttg gtatagttac caggacactt    19380
actgattaat ttttaacaag gtagaatttt aaaataaaag atttataaat aacttttgtt    19440
tgtattaata taccatttaa ttgactgaat ggttgacttt ggtataataa atattgacag    19500
gttgtccgtt agtttccaac tgcacagaac cttattttt tgtttaatac ttctctaatg    19560
```

```
cttgttgttc aagattagac cagttcagcc tagtataaaa caactgttta gaaaaccttta   19620 tattcaactt catttatagg ctgtgcacct gaaaactgat catatttcat aacactatct   19680
ggtgaagata aattttttgag tgaaatagtt ttctagtacc tccaagtaga caagggggag  19740
aaaagacagc aaagtgtaag atattaacct ggaatattat ggtattggta ttggactgca   19800
ccatcatttg tgttgtatca ctgggattat gcaagtgtta agcacaatag cacagcttcc   19860
cttttgcttg tagttactgt aattctctaa ttaaatttta aaggtttttt ttttttttg    19920 agacggagga agtctcccctt tgttgcccag gctggagtgc aatggcgcga tcttggctca  19980
ctgcaagctc tgcctcctgg gttcaggcca ttctcctgcc ttagcctccc gagtagatgg   20040
gactacaggc gcctgccacc acgcctgact aattttttgc attttagta gagatggggt    20100 ttcaccatgt tagccaggat ggtctcaatc tcctgatttc gtgatccacc caccttggcc   20160
tcccaaagtg ctggattaca ggtgtgagcc accgcgccca gcctttttt tttttttct     20220 tgagacacag tttcactctt gttgcccaga ctggagagca gtggcctgat catagctcgc   20280
tgcatcctcc acctcccagg tttaagggat tctcctgcct caggcctcct gagtagctga   20340
gattacaggc accaccacgc ctgattaatt ttttgtattt ttagtaaaga cagggtttca   20400
tcatgttggc caggttggtc tcgaactgct gacctcaggt gatccacccg cctcggcctc   20460
ccaaagtgca gggattacag gcatgagcca ccgcgcccgg ccttatttat ttattttga    20520 gatgtagtct ggctctgtaa cccaggcttt agtgcagtgg tgcaatctcg gctcactgca   20580
acctccgtct cctgggttca agcaattctc ctgcctcagc cttccaagta gctgggatta   20640
caggtgcgtg ccaccacatc tggctaattt ttgtattttt agtagagacg gggttttacc   20700
atgttggcca ggctggtctc gaactcctga cctcaagtgg tctgcctgcc tcagcctccc   20760
aaagtgctgg gattataggc aagaccccccc gcgcctggcc taacaaattt agtttaaagg  20820
tctaattggc ctttatcagt gactcatgaa tcaagcagca tctttatataa agatttagaa  20880 gagacactgc tagaggtggc agaataaaat ggcctttgca aaattatgat taagacagtg   20940
aaagaggctg ggcgcagtgg ctcaagcctg taatcccagc actttgggag gctgaggcag   21000
gcagatcaca aggtcaggag atcgagacta tcctggctaa catggtgaaa ccccccctctc  21060 cactaaaaat acaaaaattt agccaggcgt ggtggcaggc gcctgtagtc ccacctactc   21120
gggaggctga ggcaggagaa tggcgagaac tcggaggcg gaggttgcag tgagccgaga    21180
ttgtgccact gtactccaac ctgggtgaaa gagcaagact ccatctcaaa aaaaaaaaa    21240 aaaaaaaaa aaaagaaaa aaaagacagt gagagagatt taacttaact gaatttatct     21300
tgcttttaac ctccaagctg tccttgttca ttcctgggtg taggctgaac taactttaaa   21360
aaacttagtg tatagtttaa acaaagacag tgacagtcct ttcccaaagc cgacctcctt   21420
cttgcctggg gacggaattg cctttgtagg actaacatta gccacaagat taaaaattat   21480
agtttatgct gggcatggtg gctcatgccc ataatcccag cactttggga cactgaggca   21540
ggtgggtcac ttgaggtcag gagttagaga gcagcctggc caacatggtg aaaccctgtg   21600
tctactaaaa atacaaaaat tagccgggca tggtggcagg tgcttgtaat ccctagctac   21660
ttgggaggct gaggcaggag aatcacttaa aactgggagg tgaaggttgc agtgagcgga   21720
gattgggcca ttgcactacg gcctgggtga caggagtgaa actccatctc caaaaaatt   21780 acggtttaga agtcatactg ctggaggcca ggcgcggtgg ctcatgcctg caatcccagc   21840
actttgggag gccgaggcgg gtggatcacc tgaggtcggg agttcgagac cagcctgacc   21900
aacatggaga caccctgtct gtactaaaaa tacaaaatta gctggacctg gtggcgcttt  21960
```

```
cctgtaatcc cagctactcg ggatgctgag gcaggagaat cccttgaacc cgggaggcgg    22020
aggttgcggt gagctgaggt ggcgccattg cactccagcc tggacaagaa gagcgaaact    22080
ccatctcaaa aaaaaaaaga agtcatactg ctggaggcta caaaattctg accctcccta    22140
aactgctcct aagatcagtg tttacaatat tttgcagacc ctgcacttaa tgaatcagct    22200
ggcaccaccc agatcaataa actgactcat ctaatcttgt ggcccccca accaggaact    22260 aacttagcac aagaaaacag ctccaatctt taatttcatc tctaaccaat gagccactcc    22320
tggctcacca gcttcacctc acccaccaag ttgtctttaa aaactctgct ccctggctgg    22380
gcgcggtggc tcacgcctgt aatcccagca ctttgggagg cttaggcgag tggatcacga    22440
ggccaggagt tcaagaacag cctggccaag atggtgaaac cccgtctcta ctaaaaaaac    22500
aaaaaaatca gccgggtgtg gtggcgggca cctgtaatcc cagccactcg ggaggctgag    22560
gcagagaatt gcttgaaccc aggaggcgga ggttgcagtg agctgagatc gggccactgc    22620
actccagcct gggcgacaga gcgagactgt ctcaaaacaa acaaacaaac aaaaaaaaac    22680
aaaaaaactc tggtcttctg cacagctggt tctgtgtgaa ttactctttc tctgttgcaa    22740
tttccgtgtc ttaataaatt ggctctgtct aggcagcagg cagagtaaac ccctttgggg    22800
gttacaaaaa caattggtat ttatagggta gctgaagcag gaacaagaaa cagcataata    22860
caaaaagtgg gttggttgat gtaacttcag atcactttcc ttgcaagagt taaaacagtg    22920
aggacttccc tatcctgcca gctaaaaggg gcctgtttgg gtatttggct atcttctctc    22980
tcatgattta tcagaagatc agataaacaa ctaaattttg ggccaggctc agtggctcat    23040
gcctgtaatt ccagcacttt gggaggctga gatgggcgga tcacctgagg tcaggggttc    23100
gagaccagcc tggccaatcc cagctccact aaaaatacaa aaattagccg acatggtgg    23160 caagcacctg taatcccagc tactcaggag tctgaggcag gacaatgact gagacagtga    23220
aagagagcta acctaacaga ctccatcttg gttctaacct ttaagctgtc cttgttcctt    23280
cctgtgcata ggctgaacta actttgggag gaacttagtt tatagattat agttggaaac    23340
aaagatgtta acaaccttc tccaaaacct tttccttcct gcctggggat tagactgcct    23400
ttgtaggact aagaaattag ccacaagatt agaaattatg gtttaggagt catgccgttg    23460
gaagttacaa gattctgacc ctcactaaac tgctcctaag atcagtgctt gagatatttt    23520
gcagaccctg cacttgctgg atcagctggc accacctagc tcaataaact ggctcatccc    23580
atcttgtgac ttccacccag gaactgactc agtgtaagag acagcttca attcctattg    23640 atttcatcta cctaaccaat cagcactcct ggctcactgg cttcccccca cccaccaagt    23700
tgtccttaaa aactctgatt cccaaatgct tgggcagtct gatttgatta gtaataaaac    23760
gctggtctcc tgcatagctg gctctgtgtg aattactctg tctctgttgc agttcccctg    23820
tcttgataaa ttggctctgt ctaggcagca ggcaaggtca acccattggg cagttacact    23880
agcgcaagag gttcagtcca atcagtggc cttccataca ttttatttaa cacatcccag    23940
aaagaggttg tgaattacat caagcaaaag ggttctgtcc tacaccaggt ttgggatgat    24000
ttttattttc cacacgttag ctctttgctg acagaggtca aaatattagt cctaatacag    24060
agatattgtc taatagttta gtgttatata aacctattct gtcttggttc cctagtgtag    24120
aagaaaatca gagttgaaca gtaaagtgaa aaaaaaatg cttttactca gtaacttata    24180
ataaggaaaa agagacctca gcatggaacg aggcttagtt cttttcattc ctgtgaggcc    24240
tgagaataaa aaatgaaaaa gaactaggct cagttccaaa tatggcatgg acaagtaggg    24300
```

```
gtttatagcc aaggagtagg ttgggtaatg aaggtggtca gtggatggaa aattaccaag    24360
agaaaacatt aggggttaga ggaattctgg ttaaattgac ctaacaggat tcttgctgaa    24420
gacaggccag gttgatcagt tatcaccggg gggatggtag ggaatgagga atctggtcaa    24480
atatcaaggg tgatcagata ttgatggtgg ggattctggc taaaggaact tggcaggatt    24540
cttgccatga ctgggctctt aagagcaaag tatgtggctg agcgtgatgg ctcacgcctg    24600
taatcccagc actttgggag gccgaggtgg gcggatcaac tgaggtcagg agttcaagat    24660
cagcctgacc aacatggaga acccccatct ctactaacaa tacaaaatta gccaggtgtg    24720
gtggcacatg cctgtaatcc cagctactca ggaggctgag gcaggagaat tgcttgaacc    24780
tgggaggtga cggttgtggt gagccgagaa tgcgccattg cactccagca gcctgggcaa    24840
caagagcaaa actccatctc aaaaaaaaaa gcaaggtaca gccgggcacg gggtctcacg    24900
cctgtattcc cagcactttg ggaggctgag gcaggtggat gatgaggtca ggagttggag    24960
accagcctga ccaacatggt gaaaccctgt ctctactaaa aatacaaaac ttagctgggc    25020
atggtggcgc atgcctgtaa tcccaggtac tcaggaagct gaggcaggag aatcgcttga    25080
acctgggaga cagaggttgc agtgagctga gatcgtgcca ctgcactcta gcctggataa    25140
agagcaaggt gcaaggatgg ggcctagtca aaaaagtggt tcacaggagc ctatctagag    25200
tttggtcaag gagagacctc ttaatcacta gcaagccaac tgctttccaa caaatttcat    25260
ccatgtggga aataagggca aaggattttg cacatgccat ctagggaaaa agtaggtgcc    25320
ttacttcatt ttccactgct gtatcagaat accacagact aggtaattta taaaggacag    25380
agatttattt ggttcatggt tctgcatgct gggcagtcaa gattaaggga ctacatgcat    25440
ctggtgaaga ccttcttgct atatgataac atggcagaat gtatcacata gtaagacagc    25500
atgcaagaag aaaggaaagg aaaaggggggc tgaactcccc tcttttataa ctaaacccag    25560
tcctgcaata actaactcac ttctgtatta acaactttaa tttattcaag agtatggtgt    25620
ccccatgacc taatagtctc ttttgtgtgt gtgacagagt cttgctttgt cacccaggct    25680
agagtgcagt agtgtgatgt aggcttactg caacctccac ctcctgggtt caagtgattc    25740
tcctgcctca gcctcccaag tagctgagat tacaggcatg cgccaccatg cccggctaat    25800
tttggtattt ttagtagaga tggcttttca ccatgttgcc caggctggtc tcaaaactcc    25860
cgacctctgg cgatttgccc accttggcct cccaaaatgc tgggattaca ggtgtgagac    25920
actgtgcctg gcctattttt gtattttta atagagacag catttcacca tattggccag    25980
cctggtctcg cactccttat cttaagtgat ccaccggcct tagcctccca aagtgctgag    26040
attgcaggtg tgagccaccg cgctggcttt actttagctt ttttagtcca tattaaggac    26100
taacatgact ctcagttat cttcagctat atttacatct gattgctgta ggtcagcagt    26160
tctcaaaatg tgttctaatc agaatacaaa tactctggtc agcatggtgg ctcacaccca    26220
taatcccaac actttgggag gtggtgggtt atgcctataa tcccagcact ggggaggagg    26280
tgggaggata acttgagccc aggagtccaa gactaaccta agcaacatag cgagaccccc    26340
atctctacaa aaaatagaaa aaagttagc caggcatggt ggtgcatgac tgtagtccta    26400
gctacttggg aggctgaggt tggaaaatcg cttgagccgg ggaagtcgag gttgaggtta    26460
cagtgagctg tgcttgtgtc attgcgctcc agcctgggtg acagagggag accctgactc    26520
aaaaagaata caaatatgc tatattatat catatcttaa aaaaaaaaaa acttttggct    26580
ctacatctag ctattgcccc atttatctgt tcagtgtgca gcaaaactac ttaaaattag    26640
ttttgagttt ttctgttctt tcttattcca ataaagtttt cctctctacc gcttcttctt    26700
```

```
gtagagagga atacatttat ttatttattt atttatttat ttttgagacg gagttttgct   26760
tgtcacccag gctggagtgc aatgtcgtga tcttggctca ttgcaaactc tgcctcctgg   26820
gttcaagcga ttctcctgcc tcagcctccc gagtagctgg gattacaggc ttccaccatc   26880
acacctggct aattttttgta ttttttagtag agatggagtt tcaccatgtt ggccaggttg   26940
gtctcaaacg cctgacctca ggcgatctgc ccacctcagc ctcccaaagt tctgggatta   27000
caggtgtgag ccttcgagcc tggccttgtt gaaataattc tgtttgaagt catccatgac   27060
ctctgatttg cctaatcaaa ggtcagttct caattcatat gctatatctc caagataat   27120 ttcacactgc tgggtcattc cctctccttg aaacaagctg gcttccagg cctcacagtc   27180 ttctaatttc ctctttcttc agtagtcact ccttcttggt ctcatttgtt tcttcttgtt   27240
ctttgccttg acctctaaat ggtggttttc cctaaagcat agtcctcagg tctgttttct   27300
acctacactt tgtagtctta tctggtttaa tcattttaaa taacatgttc caagtgataa   27360
tcttcaattt gggctactcc cttgaattca agttgtatat tcagttgcct tacatcaact   27420
tgactttcct cagatgttct cttaacctcc tttagagggt gtggtcagac atctccttat   27480 cagaaaccttt ccctttccac ctacctaaag taactccttg ctgaagtact cactttcctc   27540
ctaactctat tttatgtttt ttcccgtaac acttatcact tggcatgttc tatacatcta   27600
gccatatata tttacatagt tacctatgta tgttatcatg ttatttatgc atatattcat   27660 gtgtatttt atttgtaaat atataaaaat atgtatttat acatgctttt tggtctgttt   27720
tctcctgctg ggattcatta gaatctaaac tccattagga ctagcttcta gtgcctagta   27780
tagtcctggg acctttatta ttattattat tattattatt attattatta ttattattat   27840
acattttttt gagacggagt ttccctcttg ttgcccaggc tggagtgcaa tggtgtgata   27900
tcggctcacc gcaacctccg cctctggggt tcaagagatt cttctgcctc agactcccaa   27960
gtagctggga ttacaggcat gcgccaccat gccagctaat ttttttttgta ttttttagtgg   28020 agatggggtt tctccatatt ggtcaggctg gtcttgaact cctgacctta ggtgatctgc   28080
ctgcctcagc ctcccgaagt actgggatta caggcgtgag ccaccatgcc agccagtcc   28140 tgggacttta ataggcactg aatgactgtg tatataatga aattccagat gatatgcttg   28200
attttcagct acttatcctg ataatttttat tattttttag atgaagtctc cctctgtcac   28260
tcaggttgga gtgcagtggc atgatctcag ctcactgcaa cctccacctc ccaggttaaa   28320
gagattcttg tgcctcagcc tctggagtag ctgggattac aggcatgcac caccatgcct   28380
ggctaagcat tttgtatttt tagtagagat gtggtctcac catgttgccc aggcttgcct   28440
tgaactcctg gcttcctgta atcggaccac ctcggcctct caaaagtgct gggattttaa   28500
gtgtgagcca ctgtgcctgg agtatcctga gaattttttt ttttttttttt ttgagatagt   28560 ctcactctgt tgcccaggct gcagtgcagt ggtgtgatct tggctcactg caacctctgc   28620
ctcctgggtt caagcgattc tcctgccgca gcctcctaag tagctgggac tataggcaca   28680
caccaccacg cctggctaat ttttgtatt tttagtagag acggggtttt gtcatgttgg   28740
ctaggctggt ctcgacctgc tgacctcaag tgatctgccc gtctcggcct cccaaaatgc   28800
tgggattaca ggtgtaagcc accgtgcccg gccaatcctg agaatttagc aacaacaaaa   28860
atgaccgaac agtgcaccac tgccataggt aggaattta ggttagtatc tagattctac   28920
atataaaaag gtaaattcac ttgccatgaa ttgggcacct gcagtgaagg gggaaaatgg   28980
tttgtatggt ttatactgca agaacaggct aataaactaa aatgttattg cataattcac   29040
```

```
ttggacatct tgtgcagtgc cccactattt gatgttttga ggaagtgaaa aaaattaatt   29100
tttcttcttg cttgtgccat tactaaatat cagttttggg ggggtatttg gaagaagttg   29160
atgagtctgc agagtttgag ctgtttcctt acatcaagca aattttatga ttagaagatt   29220
caacttttat aatccccctta tgactcacaa atttattctt tctaattgat ggtaatatcc   29280
tgaactgaaa ccaacagggg aaaataacaa tgattttttt tttttccaga aagatactca   29340
gacccaatta tcaacatatg gtttaaacag atggcagctg aaataaatct gtgtgtagta   29400
gaatcaaaga ttttaaagaa ttgtgtagcc tgtcacctgc cactgctcac actgtgttga   29460
agatatataa aattaattgc atttataaaa ataccaca ttgtctcaca tctttgtact   29520
tttatccata tagtttcctc tccctagaat agccttcttt tgatttagct ttatcttctc   29580
caggacactt ctcctgatct ctctggtctc aatttgagca attctgtgtc tgtctgaaag   29640
gcctgtgcat actgcctact ttacattaca aaattatca catattaatt tgctaatctc   29700
attctcccaa aatactttt tttattcttt ttttttgaga cagagttttg ctcttgttgc   29760
ccaggttgga gtgcaatggc gtgatcttgg ctcactgcaa cctccacctc ccaggttcaa   29820
gtgattctcc tgcctcagcc tcccaaagta gctgggatta caggcacccg ccgccatgcc   29880
cagctaattt ttttgtatct tagttgagat ggggtttcac cattttggcc aggccggtcg   29940
gtcttaaact cctgacctca ggtgatccac cagcccgggg ctcccaatgt gctgggatta   30000
caggtgtgag ccaccgcacc cggccaatat tgttaattaa aacaaaaatc actgtctttt   30060
atttctgtat ctctatttgc atagtacagt ctgccatcag tcggggttca aaaaatattt   30120
gctcaatcta tcaataaatt acaagttctc tcttccacca gcctagcagt gggaactaac   30180
acaatgttaa aagtgggaaa ttggctgggc agtgtggctc actcctgtaa tcccaacact   30240 tgggaggcc gaggcaggat gactgcttga ggacaggagt tgagatcag cctgggcaac   30300 acagtgagac tccatctaca cacacacaca cacacacacc ccacaaatta gctaggggca   30360
tggttgttgg tgcctgtagt cccagctagt cgagaggctg aggtggggga tagtttgagc   30420
ccaggagtcc aaggttgcag tgaaccatga tcatgccact gcattccagc ttgggtgaga   30480
taaggtgaaa ccatttctcc aaaaataaaa aatataagtg tgttggctgg gcacagtgac   30540
tcacacctgt aatctcagca cttgggtgg ccgaggcagg cggatcacca ggtcaggaaa   30600
ttgagaccat cctagctaac agggtgaaac cccgtctcta ctaaaaatac aaaaaattag   30660
ctgggtgtag tggcgagtgc ctgtaatccc agctactcag gaggctgagg caggaaaatc   30720
gcttgaacct gggaggcgga ggtcgcagtg agcaaccact gcactctaac ctgggcgaca   30780
gagcgagact ccaactcact caaaaaaaaa aaaaaagtg tgaaattgtt ggtcagaagc   30840
ttccttaaat caatttttt ttccttacag ctcctgtgtt cctttgtctt gataagtata   30900
ctcaatagat aagtaaataa aatatgaaag gcttttgaag cttttggatt acatggacta   30960
aaacactttc taccttttat tttgctattt tgaacatatt ttcatttaaa aagtcactgt   31020
catgtagtta tcagttgaaa actttattt aacttatttt aaaaattgat tcaaaacttt   31080
ttatcttctt tattaggtat tctaccctta gatttaacac tcatttttcc cgagtatatt   31140
ttctcttcaa tatacaaagg aatatatttt catagagtgt gttgaatatt aggaaaatca   31200
agagttctgg ttctgtcagg tgcagtattt agagtgttat tttgataaaa tccagttgct   31260
ctgatatggc ttgaaaatac ttgctccttt ggagtataat tgcaggggaa aaactgtgga   31320
ataggtagaa attcaccata atgacttgaa ttggttttat acataatcat ttgaggtttt   31380
gatagtgagg tggctgtctg gagtgtcttt ggatccaaca tacatgaaaa cacaggattg   31440
```

```
ccagggttca cacaaggagg cagttgttca gatttcattt ctgtgtctga atttgaaggt    31500
gaagtacttt tcttatccta aaagataaac acataaaatc attctccatt ataaagttct    31560
gaaaaaaaaa aaatttaatt cagtcccacc cacttccctt tttcaggaat tctgttctct    31620
tgagggcatt gaatgtcagg cctctgagcc caagctaagc catcatatcc ctagtgacct    31680
gcacgtatac atccagatgg cctgaagcaa gtgaagaatc acaaaagaag tgaaaatggc    31740
cggttcctgc cttaactgat gacattacct tgtgaaattc cttctcctgg ctcagaacct    31800
cccccactga gcaccttgtg acccctgccc ctgcccgcca cagaataacc ccctttgact    31860
gtaattttcc attacctacc caaatcctat aaaacggccc caccccctatc tcccttcgct    31920 gactgtcttt tcggactcag cccgcctcca cccaggtgat taaaaagctt tattgctcac    31980
acaaagcctg tttggtggtc tcttctcttg acgttgaaga ctacccttaa aatcacatac    32040
acctgtacac agagcaaagt tgtcaaaaat atgctaagtt accttttaa acattctgta     32100 ctagaactat gagaatttat ttaaaaatct gtaaatcata gggaaaaatc tgtaaaagtc    32160
atagttagaa gaggaagtac agcttgattt tagagtgaga aaggaacaag ataaacatcc    32220
agggttagcc tgggtatgtg ggcagccatt aaataactaa ttacatagct aactgaataa    32280
ttacaattgt gataactgct atgaagaaaa aaaaatacaa gatattaatg aagacagaat    32340
gggggttctt atctagtgtt gggggttagg gaaagccatt ccactgaagt accattcaat    32400
ctaagattga ctataaggca aggaagtaaa agatagaagt ggggacaaag tatggcaaaa    32460
gtcaagtaaa ttagggtgaa aatatcatga gatcagaata gagagccagg ggttagatct    32520
cttagggttt tgttgactgt gtttaaaatc tgaatctta ttgtaaaagc aatgaaaaac     32580
tattgaaggg ttttaaggag aggagtgaca tgaggtaata taattctagt aaaattactt    32640
tggctgttgt tagggcctgt gtgaatgtgg tgaggagctg cagtagtcca tgtgagtaat    32700
gatgacaata tatagtaggt ggtagcatgg agatggagca aatttgtttg ttttgttttg    32760
ttttgtgtgt ttgttttttg agacagagtc tcgctctgtc atccaggctg gactgcaatg    32820
gtgcagtctc ggcttactgc aacctccgcc tcccgggttc aagcaattct cctgcctcag    32880
cctcccaact agctgggatt atgggagctc accacgacaa ccagctaatt ttttttttatt   32940 tttagtagag acagggtttc accatgttgg ccagactggt ctcgaactcc tgacctcagg    33000
tgatccacct accttggcct cacaaagtgt tgggattaca ggtgtgagcc accgcgccca    33060
gcctatggag caaatttgaa atatattttg gaagtagaat tcacaggatc tcatgattga    33120
ttggaggtgg gtggtgaggg aaaaggacag atctaggata acttccaggt ttctggacaa    33180
acacttgggc ggatggtggt gccatttact acaatgtact acaatgtaat atgtaaatta    33240
aatatatata tgtagtttta tatatagatg atacataatt ttggcactga aaagcacttt    33300
gcattgatga tggcttgata aattaatata acaagtttcg tccaggcgca atggctcaca    33360
cctgtaaatc ccagcacttt gggaggccaa ggtgggcgga tcacgaggtc aagagattga    33420
gaccatcctg gacaacatgg tgaaaccccg tctctactaa aaatacaaaa attagctggt    33480
tgtggtggga tgtgcctgta gtcccagcta ctcgggaggc tgaggcagga gaggatccct    33540
tggacccatg aggcagaggt tgcagtgagc caagatcacg ccactgcact ccagcctggt    33600
gacagagcaa aagactctat ctctctctct ctctatatat ataacaatgt ttaaaaaaac    33660
caacaaactg catgaaaaac tctaaaaaat gtcatgactg aatcctgaaa ttctgattgt    33720
gaattctatc ctaagaaact ttattgtaga aaaatttaat tcacagcatt acttacaaaa    33780
```

```
gaactgaaat gtgtactgat ttagatggaa gttaatttta attctaatgc taatgccaaa    33840
aatactaagg gagaagacca cccctcatat tgtcttatgc ccaatttctg cctccaaaga    33900
aagaagaggt aaaaactaaa aggcagaaat gaaatccaca ggcagacagc ccggcactac    33960
accctgggcc tggtagttaa agatcgaccc ctgacctaat cggttatgtt atctgtagaa    34020
tacagacatt ttatggaaaa gcattgtgaa aatccctgtc ctgttcggtt ccattctaat    34080
tactggtgca tgcagccccc agtcacgtac ccgctgcttg ctcaatcgat caggactctc    34140
tcacgcggac cccttagag ttgtaagccc ttaagaggga cgggaattgc tcactcaggg    34200
agctaggttg ttggagacgg gattcttgcc gaatggccga ataaagccct ccttcccctt    34260
ccctcttttt tttttttttt tttgagacga gtttcactc tcgtccccca ggctggagtg    34320
caatggcagg atctcagctc actgcaacct ccgccttcca ggttcaagcg attgtcctgc    34380
ctcagcctcc cgagtagatg ggattacagg cacctggcta ttttttgtat ttttagtgga    34440
gacagggttt caccatgttg gccaggctgg tctccaactc ctgaccttag gtgatccacc    34500
tgcctcggcc tcccaaagtg ccgggattac aggcgtgagc caccacgccc ggccaagccc    34560
ttccttcttt aactcggtgt ctgagggggtt ttgtctgcgg cttgtcctgc tacaatacta    34620
atagaagtac ttgaaaatag cttatttcct taaatagtta agtttcttct gcaaccttac    34680
attgatgtaa gataaacgtt cacccagccc tggtataatt atgtcagaat aattacaaac    34740
tgggtattct ctaaagtgct gttagtataa atagactttt tgtttaataa atttcacttt    34800
gagatggttc acctattaaa agttaataga tgaacaatca atgttttgtt tttcttttt    34860 ttgagatgga gtctcactct gttgcccagg ctggagtgta gtggcgccat ctcggctcac    34920
tgcaacctcc ccatcttggg ttcaagcaat tctcatgcct cagcctccca agcagctggg    34980
attacaggcg tgcgccacca tgcccagcta attttttgtat tttagtagag atggggtttc    35040
accatgttgg ccaggctggc ctcggacttc tgacctgagg tgatccaccc gcctcaacct    35100
ccaaaaatga tgggattaca ggcgtgagcc accatgccca gctggaaaat ctattaaaag    35160
ttaatgactt cacttactaa cttttttgga agacttacaa tgactaatcc tttataaatt    35220
taatttcatt tgcatttcta gttgggaaaa ttacaaatat aagaacattt ctaggccgag    35280
tgcggtggat cacctgaggt caggagtctg agatcagcct ggccaacatg gtgaaaccct    35340
gcctctacta aaaatacaaa aaattagcca agcgtggtgg cacacacctg taatcccagc    35400
tactcgggag gctgaggcag gggaattgct tcaacccggg aggccaaggt tgcagtgatc    35460
cgagattatg ccactcactg actccagccg ggcaacaag agtgaaactc tgtctcaaaa    35520
aaaaaaaaaa caaaaaaaaa ccaggcctgg cgcggtggct cacgcttgta atcccagcac    35580
tttgggaagc tgaggcgggc agatcacagg gtcaggagat ccagaccatc ctggctaacg    35640
cggtgaaacc ctgtctctac taaaaataca aagaattagc cgggcgtggt ggcgggcgcc    35700
tgtagtccca gctactcggg aggctgaggc aggagaatgg cgtgaacctg ggagatggag    35760
cttgccttga gccgagatcc tgccactgca ctccagcctg ggcgacagag cgagactccg    35820
tctcaaaaaa aaaaaagcat ttctctatgt aatatcttat atctactcat attttaaatg    35880
tacttagagc tgaaaaataa aaaaagtcct aatgagttga aatgaagctg atttaaaatg    35940 cttccccat aaaaacagtc tttttttttt ttttttttg aaacggagtt ttgctcttgt    36000
tgcccaggct ggagtgcaat ggcgcgatct tggctcactg caacctctgc ctcccaggtt    36060
caagcgattc tcctgcctca gcctcccgag tagctgggat tacaggcatg tgccacacca    36120
ggcccagcta attttttgtatt tttagtagag acagggtttc tccatgttgg tcaggctggt    36180
```

```
ctcaaactcc cgacctcaag tgatctgcct gccttggcct cccaaagtgc tgggattaca    36240
ggcgtgagac accacggccg gcccttaaaa acattcttaa agggcagctt ttaattaact    36300
gttttggtgt ggagaaggga gaaagttttt ctctgtcact caggctagag tgcagtagtg    36360
atcgtagttc actgcagcct caaactcctg gattccagtg accctcccaa gtagctagga    36420
ctacatgcac accaccatac ccagctaatt tttataattt ttttttttt ttgagacgga    36480
gtctcactct tttgcccagg ccggagtgca gtggcgcgat cttggctcac tgcaagctcc    36540
acctcctggg tttacgccat tctcctgcct cagcctcccg agtagctgga actacaggcg    36600
ccagccaccg tgcccggcta atttttttgta tttttagtag atgggggtt tcaccgtgtt    36660
agccaggatg gtctcgatct cctgacctcg tgatccgccc gccttggcct cccaaagtgc    36720
tgggattata ggtgcgcacc accgcgccca gccttaattt ttataatttt tttgtaggga    36780
tgaggtcttg ctatgttgcc caggctggtc ttgaactcct ggtctcaagc aatcctcctg    36840
ccttggcttc ccacagcact gggattacag gcataagcta ccatatcaat ccccagcttt    36900
taacttaaaa gtactataaa accatattca atctactctt catcaacttt ttcttttttt    36960
tgagacagag atctcacttt gttgcccagg ctggagtgca ctggctgttc acaaatggga    37020
taatagtgca ctgcaacctg gaactcctgg gctgaagtga tcctcaggcc ttggcttctc    37080
aaggtgggac ttcaggtaca tgccacagtg tccagctttc agtcaattat taatgttcta    37140
cctgaatagt gtccctacta agttttttga aagtattttt ccatgaataa ggggactgaa    37200
aatatgaatc aaatataaag caatttaaac ttggacaagt cacttagatt ctctgtgcct    37260
aaaatttgtt tgtaaaacag tggagcctgg attatttgac ctctcagatc tcttctacca    37320
actccacaga atttattaac cttataaact tgaggcagaa tcacagtgta gtatactatg    37380
ttttcatgtt ttgctttatt ttaatgagaa tcataagcga aagagggctg gatgtgatat    37440
attggaagag tagcacaagg cagcaactat gacctaggtt ctcatacttt atcatttcac    37500
cttatttgt atattatctg taaaactggt aaataaaaat ctgccatagt tcctatggtt    37560
gtggagatta aatgaaagaa aatttgatgt aaatggtgaa tcactatatg aatgggatca    37620
attttttttt tttttttttt tttttgtgg agacaaagtc tcactctgtt gcccagtctg    37680
gagtgcaatg gtgtgatctt ggctcactgc aacctctgcc tcctgggttc aagcaattct    37740
cctgccttag cctcccaaat cgctgggctt aaaggcgtgc gccaccacgc tcagctaaat    37800
ttatttattt ttttttgtga aaggagtttt tgctcttgtt gcccaggctg gagggcaatg    37860
gtgcaatctc agctcaccgc aacctccgcc ttctgggttc aagccattct cctgcctcag    37920
actcccgagt agctgtgatt acaggcatgc accaccatgc ctggctaatt gtgtattttt    37980
agtagagatg gggtttctcc atgttagtca ggttggtctc gaactcccaa cctcaggtga    38040
tccgcccgcc tcggcctccc aaagtgctgg aattacaagc gtgagccacc gtgcctagcc    38100
taattttgt attttagta gagatggggt ttcaccatga tggccaggct ggttttggac    38160
tcctgacctc aagtgatcca cctgcctcgg cttcccaaag tgttgggatt acaggtgtga    38220
gccactgcgc ctggccaaat ggaatcaatt tttatcacta ttttatttta tttttgaga    38280
tggagttttg ctctgtcacc taagctggag tgcagtggcg cagtcgcagc tcattgtaac    38340
ctctgcgtcc caggttcaag tgattcccct gcctcagctt ccagagtagc tgggactaca    38400
ggtgcctgcc aacacacctg gctaattttt gtgtttttag tagaaatggg gtttcaccat    38460
gttggccagg ctgttcccaa actcctgacc tctgatgatc cgcctacctc agcttccaa    38520
```

-continued

```
agtgctggga ctacagtcgt gagccaccat gcctcaccaa atttattat tttcttttt  38580
gcaggtttac ctcaatgtat gatcttccag aaacagttct gaaacctaca ggttaatgac  38640
cttgtattag cataatatgg tttgctaata ttcacttaat actcataagt ttgtagttgg  38700
caaagctgga aatagaactc aggttcactg agtgtcatca atgttattct catcagatct  38760
tgctgtttat tctttttgaa actgcttatt aatttgcttt aaatattaac aacacagata  38820

ctggataata gtaaatcata agaattttaa aattttgatg gtatctcaac tgatcagctt  38880
ttcttaaatt ttctaggttt cctcagcaca ggggaaagct ttataggtgg aaggtggagg  38940
ccctgtgact tgcgcagaaa agtaccactg taatttactt ttatgggcac ctaagcaggt  39000
tgcccagggc aacttgtaga ttttgttgtt gttgttgtta atactatctc cttcagtcac  39060
tgagaactct tttttatttt tttatttttt gagatggagt tttgctcttg ttgcctaggc  39120
tggagtgcag tggcgtgatc ttggctcact gcaacctccg cctcccggat tcaagcgatt  39180
ctcttgcctc agccacccga gtagctggga ttataggcat gcgtcaccac gcccggctaa  39240
ttttgtgttt ttagtagaga tagtgtttct ccatgttggt caggctggtc tcgaactctt  39300
gaactcaggc gattcgcctg cctcggcctc ccagagtact gggccttaaa tgctggaatt  39360
ataggcatga gccaccgcgc ccagctgaga actcttcttg ttatcaaatg accctcttta  39420
ctactggttc tagaatttcg ttcagctttg gctcaaaaca taatgcagaa aacgaaatct  39480
agtaaaaaca gaagacaaat tagctgataa actttgttgg cataattagt accataaaat  39540
ctggaaaagc taaatcttaa attaaaaatt ttttagattt ccaggataat tcacaaatgt  39600
ttatagattc agaaacaaaa ggtccattgc tttatacttt acatcataga caaccactgc  39660
agttttctaa tatgggtttc accttcttca aacctgatat tcttaaaatg tggagttcaa  39720
actgactata gttaagaacg aaacaaatag ccaatacaaa gaataataaa aggatgagtt  39780
caaattatct gccacatgtc atcaactttt attaaatgat aaaaaggtta attaaaattg  39840
taaatgattt ttcagaagaa attacatctt aaaattggcc tgtgaaagtg gcttgaaagg  39900
tataaaaatc taccagtagc tggtattagc tttcttagta atttaatttt cagttagaga  39960
aagccagacc actttgacct ttcgaagtcc tttggtatag atacatatac atttaaaaag  40020
ataaatgaaa acaagccatt gattaataat gcccatcgca gaagctgtaa ttataaaatt  40080
aagatttttt gatgtcactg ttgatgttga atatagttaa tagaaaagca aaaataaaaa  40140
ataaaaaagg tctaattttg aggcactctt ttgtctctgc tcaggtccac cgtcttcctt  40200
gctaatgttt acgtttatta ttaatttttc catttattta tttactttta ccacaattag  40260
gggacagaga atgaaaccta aactttttat tgcttctgta aagagtgaat ataaatgtaa  40320
gatttttttt ttttgagacg gagttttgct cttgttgccc aggctgcagt tcagtggcgc  40380
aatctcggct cactgcaacc tctgcctccc aggttcaagc aattctgctg tctcagcctc  40440
ccaagtagct gggattacag gcccgcgcca cctctcctgg ctaatttttt gtatttagta  40500
gagacggagt ttcaccatgt aggtcaggct ggtctcgaac tcctgacctc aggtgatcca  40560
cccgcttcgg cctcccaaat tgctgggatt acaggcgttg agccccggcg cccggccacc  40620
aaatcctttt tcaaaacaac tcccttcttt gacacagtgc aatttaaata agtatacaat  40680
taacaaagta cgtttttctt gttcaaaacc atcactgaac agtttgcaac agtagggtat  40740
gaatgcatac aatctcgatg gtctttacac cttcagaggc tattcggact taaggaaacg  40800
tgcatttaca agtgtaaatg taaaagctca gtagttgcct tgtaaagtgc ttttcggggt  40860
tgtggggttg gggtggtag gagtaggtgg tgcctcaaat tatactagcg aataccaaca  40920
```

```
ttcccaaaca tctagccctc tgcctaaact cacccggttg cggtctgtca ttttcgctct    40980
tctttgttaa ttttttcggc aaagtcagtt ttcatgcagc agatggcaag aaagccggtg    41040
aacgcctagg gacgtggcct tttaaccgca cccaattaaa gcagcaaaca gaagatgaat    41100
agctgggtgg atcagtatgt gtaaacctat ccgtttaatc cggggagctg ttttcccggg    41160
tgaaaccacg aattctttct ggaggttgca actcgtaacc atagcaactg gaagtggtcg    41220
ccggctcccg gatgttgtgg ggatctgcgg ccgcctggcc cagcttcccg cagccgcccg    41280
gcggcggcct gcgctccact tcgggagtgg tagttcttct cttcaccgct gccgggcagg    41340
aggcgcaggc gggactacgc gtcacggcat gcactgcggc gcccagccgg tcaccgcctg    41400
ccggctgcag acgcctgcga gcaggttgtt tttataagag gcgtcattgg cgcccgagct    41460
gtgaccgccg ccactggggc agccagcaca atcgggcgga ggtggcgctg ccccttcagg    41520
tactgtacta gcgggcttta gaccccggga gggggtttgt gccgactgtc tgagtccctg    41580
gccgacacgc tcggctcagt agaggagcag tggcggggtc cgcctcctag gctggggctg    41640
ctcgggcggg gacttgacgc ctggtgtcag cggccgcacg ggcgacctcc tcgggccgtg    41700
cgcgagtgca cagctccgga ggcccgagcc gaccctgggg cgtccggtcc ggtggtcttg    41760
cagcctccaa accccgagtg ctataccgaa ctgcgcgcca agggtgggag agctgacggc    41820
ctgggccacc cttcttcctt cactgggcag gctttgaggt gcttgtcggt ctggactgat    41880
gaaaatccat atggtaagat gttatgtgcg tcaccctgcc gggtttaatg ccagcctgtc    41940
ttttgatgac atttgagccc ccgtgatgtc aggaatagaa agattaaata ttaaataatg    42000
cccggagact tccgctagca cgccagcctg atgatgatca aatacctctc catatccttc    42060
tccagttcca gtggcctcct ttagcttttgg tctccctaat cgatttgtcc tcattagcag    42120
ctgtcccatg cagtgccttg tacgcgttgt ttatgtttag cactattggg agcgccaagt    42180
aaggtatttt attgagtggt gaagtttgca ctgttctgct ctactttat tgaaaaacac    42240
agttgggcat tcttgtagtt agaatagcta actatatagt actatgaatt ttagatttgt    42300
ctcctccaat ctacaggata gtgcttgaaa tatcgctatt actgcatcgt atcttttaag    42360
attagaatca tattgggtcc cacacgtctc agggatatt tatcacacac atccagtgtg    42420
aatggtttac ttttattttc tgagttcagg tcatatagca gaagatggag atggtgaggg    42480
tattatttta attcatattt tttttttttt tgagagaggg tttcgctctt gttgcccagg    42540
ctggagtgca gtggcgcgat ctcggctcac tgcaacctct gccttccagt ttcaaacgat    42600
tctcctgcct cagcctcccg agtatctggg attacaggcg cccgccacca cgcccagcta    42660
aattttgtat ttttagtaga gacggcgggg cgggggggg ggtctcaacg tgtcggccag    42720
gctggtcttg gactcctgac ctcgtgatcc gcccacttcg gcctcccaga gtgctgggat    42780
tacaggcgtg acccaccgcg cgggcgttaa ttcataattt ttaaccttt acgctgaggg    42840
cggaatttca gtcaaaaaag ctgattaaaa atcagcccaa atacaattta aaggtgtggg    42900
aaatactcct tcttagatga aaacagttta gaaaatagtg taattgcaat tttgtaaacc    42960
atggaacaaa aagtgaacat aacttctttt agaaatgact taaagggtcc agagcggtgg    43020
ctcaggcttg taatcccagc actttgggag gccatgcag gtggatcacc tgaggtcagg    43080
agttcgagac cagcctggcc gacacggtga accccgtct ctactaaaaa tacaaaaatt    43140
agcctgtaaa cccagctact tgggaggctg aagcaggaga attacttgaa cccgggaggc    43200
ggaggttgca gtgagccaca agatctggcc accgcactcc aacctgggtg acagagtgag    43260
```

```
attatctcaa aaaaacaaaa aaaaaaaaac aaaaaaaaaa aaagagaaaa agaaagaaaa    43320
gaaataaagg atattcacag ttataaaagt gtagatagtg aaactagaaa tgattttttct   43380 tgtactttcc tgtattttc  aagttttctg tagaaaaaac ttttaaaaaa ggatgcaagt    43440
attaacagca ctttgagagt ttctatatca ttttttttcac tttctagtgg aaagccccac   43500
ccttatgcaa aaaaaaaaaa aaagcagcaa ttccagttat ggactctatg aacattactt    43560 taaaagaaa  ataaaggcct agagcagtgg ctcatgcctg taatcccagg actttgggaa    43620
gccaaggcag gcggatcact tgaggtcagg acttcaaggc cagcctggcc aacgtggcaa    43680
aaccccgtct ctactaaaaa tacaaaaatt agctgggcat ggtggcggat gcctgttatc    43740
tcagctattc aggaggctga ggcaggagaa tcgcttgaac ccgggaggca gaagttgcag    43800
tgagccgaga tcatgccact gtactctagc ctgggtgaca gagtgagact gtctcaaaaa    43860
caccaaataa gcaacaacag taaaaaacac aggcaaagtc cctgttgctg catctgtaga    43920
ctatatgaat ttaagtgtaa attatttgga gagtagggac aataaatgaa atagttggac    43980
tcgaagaaaa taacagatcc gacaatttgt agcatttgta gatctcattt tattttttgg    44040
agatgatgtc ttgctctgtc acctagtctg gagtgcagtg gcctggacac gacttactgc    44100
agcctcctgg gctcaagtga tcccaacaca gcctcccaca tagctggggc tacaggcaca    44160
tgtcaccagg cctaggcctg gctattactt tttttgagac agagtcttgc tctattgtat    44220
ggtggttcag tctcggctca ctgcaacctc tgcttcctag tagctgggat tacagtgtga    44280
ttcaagctga gttcaagtgt gattctcctg cctcagcctc ccagtagctg tcacatgtca    44340
cagacatgtg acaccatgcc ccactaaatt ttttttttgag acggagtttc gctcttgttg    44400
cctagactgg agtgctatgg caagatctca gctcaccaca acctccgcct cctggtttca    44460
agtggttctc ccgcctcacc ctcccgagta gctgggatta caggcatgtg ccaccatgcc    44520
cggctaattt tgcattttt  agtagagaca gagtttttc  catgttggtc aggctggtct    44580
caaactcccg acctcaggtg gtccgcctgc ctcagccttc taaagtgctg ggattacaga    44640
cgtgacccac tgcccctgac ctaattttg  tattttagt agagactggg ttttgccatg    44700
ttagccgggc tggtcatgaa ctcctggcct caagtgatct gtccgccttg gcctcccaaa    44760
gtgctgggat tacaggcacg tagctgggat tacaggcaca caccaccatg cccggctaat    44820
ttttgtattt ttagtagaga tggggtttca ccataatggc caggatggtc tcgatctcct    44880
gaatgcgtga tccggttgcc tgggcctccc gaagtgctgg cattacaggc gtgagccacc    44940
gcacctggcc ctaattttaa aattttatgt agaggcaggg tctcgctatg tttcccaggc    45000
tggtctcttt gaactcctgg gttcaagcga ttttcctgcc ttagcctccc agagtgctgg    45060
atacaggcat gagagctcca tgtctggcct gtacatccca tcttttgatc tggtttctt    45120 tcactttgta cagttaaatc agaggtgaaa gtacttagct tttcttcact taagcctgga    45180
aaatcttaaa cttgtcaaca ttgaatcacg ttcagaacca tgttttatat gtctgatatt    45240
ttggcttatg tctattttg  tttttattt  ttgttatggt tatgttggat atggactggt    45300
aagtagtata atcaatcatt agcccacatt ttgctttctg ttgtaaaggg ctacattgtt    45360
cttccacagt aatatacagt acattttct  tttttttggc tactatcagc ccttaaaaat    45420
taagggggtt taccttaaca ccaagtgtcc attaacactg gataaaatat ctattctaaa    45480
gtgttttaca aaaaacactg gtaacacgtt gtttttcagg ttgtggtgtt catactttat    45540
tttcttaggt tgtcttcttt ggagcttgcc tactccaaat gtcaatttct ttcaatatt     45600 ttttacctta taattttgta tattctgtgt actgagttgg ctcaatatgt tattaggctt    45660
```

```
tgggtctatt cacagggcat aagaaaaatt cataattgat taacatgtct gatttactaa    45720
ctcattccac agtattattg tatgggttgt ataattatat tcttatgcaa gttaaagaaa    45780
gacttttaaa aattaggtgc atatgaactg ctaaaatcat ggaagtagta gttttttgaac   45840
atgttaagaa catgaacaca gcagcaaggc ctgttaagtc caaggtactt taaacaaaaa    45900
atgcagactc atctaacagt gcagaactgc tggaggctga attatgtttg tgtttctttg    45960
tggtgaagat gaggaagttg cagtattgta agtgataaag gattacattt tcacaaattt    46020
ccttcctgac agttccataa ttgtaactag actaaaacac ttggtttcaa aggtcatttg    46080
caatgtattg catcagataa acttggccat attttctctc aatttgagtt ctaagatgaa    46140
attcagccct atgatatggg aaggattgta attaagtgat aaataaaggg attttttccc    46200
ccaaagggta tttaatgtgt ggaaacctct ttaagggtct atagaattac ctgaggaagt    46260
attagaaaat aagaagtggg agttaagtat ttttttctgt catcacagga agcctgaaat    46320
cttttttttt ttttaagtac ttatccaaat cactattctt ttaaaatctt acaaaatctt    46380
acttctggtt catattgcca gcatgttgaa atgtaaaaag agcattaggt tggaaatcag    46440
aggattttta atgatgttga ggaagttatt atttataatt ttctgttcgt tttcatttgg    46500
aatttgtaaa taatagcaag ctgcctttat gggggtattt gtgaagatta aatcagatat    46560
gaaaatgaaa ttgctttgta agtggtggag ttatctactc atatgaagta ttattgtact    46620
aagtgcattt acataaagca cttatatgtt tgaagtgtga tgccttgatg tgataaatac    46680
tttttgactg ggaagtttga tgaagaaaaa aagtcaaatg ggttattcat ttgatttctt    46740
ggtagagatt ggtggctttt tccagactga aggaaacctg gctcctctcc tgactgtgac    46800
tttgcactct gttgcatcaa atgtcctgaa actgcagtgt acttctgtgg ttgagctttt    46860
aatttttggtt ttgatttgtt ttaatctcac ttctataagt gtaagaatgg tcatcagtct    46920
agtttgacaa taggaagtag ctattgtttt taatattctc aaatggatct ttaagttatt    46980
tcatgaacaa tgagactaca ttgaatgtga aatctcaggt cctctgagaa atacatttca    47040
tgtttaaagc attagtcttt gagccaaaga aataatggag tttagatttt tccttctggg    47100
gaagttatct ctggctatga gaggatctga cccttgagat taacttcaag ttaggttgat    47160
atatagaata tttacgataa agaaaaagta ttttagaaac aagtacatat tggctgggtg    47220
tggtggctca tgcctgtaat cccagcactt tggaaggtcg aggagagtgg atcacctgag    47280
gtcaggagtt tgagaccagt ctggcccaac atggtgaaac cccgtctcta ctaaaaatac    47340
aaaaattagc ctgacttggt ggtgtgtacc tgtagtccca attactcagg aggctgaggt    47400
gggaggatcg cttgagccaa ggagtttgag gttacagtga gctgtgatgg tgccactgta    47460
ctcccgcctg ggtgagtgac agagcgagat cctgtctcta aaataaagc tataataaag     47520
acattaacaa ataaaattgg agctatttat caaaactttg aacttaatac taattaataa    47580
agtagctcaa ggaaaaaagt aagtagtgta agctaccatt aggcaaatta tgctgagaag    47640
tatagtaagt gctatagatt caggggaaaa tgaaatctgt atgtcagaaa cagtgatcta    47700
ggaaaatttc atgggagaag acagctttaa atacagaaat cagaatgaag gaagaaaagc    47760
atttcaggaa gtgaagacat ggagttaggg ttgtccatt tgtgttcaga agacagcaat     47820
taaattactt cagccatatg acgaggaaag ctaatcagat tagttgcaaa ttaggtgaga    47880
accagatagt gggagttttt cagtgtcaca ctaaggagtg tgtctttatt gtacagaata    47940
cttactctta aagttgggca gactctgagt gggaagaaaa atattttagc actgggtata    48000
```

```
agtgtatgta acctgcagtc tctttcatct ttgcctctat gtttataggg tagtagtggt   48060
tttttttttt ttttgagacg gagtttcatt cttacgccca ggctggagtg aaatggcgtg   48120
gtctcggctc actgcaacct ccacctcctg gttcaagtga ttctcctgcc tcagcctccc   48180
gaatagctgg gattacaggc atgggccacc atgcctggct aattttttgta ttttttagtag  48240
agacggagtt tcgccatatt ggccaggcta gtcttgaact cctgacctca ggtgattcac   48300
ccgcctcggc ctcccaaaat gctgggatta taggcatgag ccactgcgcc cagcagtagt   48360
gtgtttttag ggagggacag ggaaggttga aaaatggcac tgtagaaagc catcagtacc   48420
atagcaatta aaccagcgtt gtagtggttc aggaatagaa aatagatcag tggaacagaa   48480
tagagaacac agaaatggat taataaatgt gtgggacttt atatgacaaa aggtggcatt   48540
tcaaattata gaaaaagtgt ggaatattca atatttggtt taatttccac ttcacaccaa   48600
aagaaaaaaa atccaaatgc atgaattaaa cagctaaatg taaaagccaa aaactgtgga   48660
agtattagta gaaaatacag gagaataatt ttatagtctt gggagcagga aaaactttct   48720
aaaacaagat acaaaatcta gatactataa aggacaccct gttttccagc ctctacattg   48780
actgtataaa atttgaaaca taataaagat actttaaaaa tgtttgaggc atgctagaac   48840
attaattcat gacccaactt ataaggaact acaaatcagt aatgacaatc taataggaaa   48900
gtgaacatat gaatatagat gcttcacaga aaaggagatg aggatagcca gtaaacacaa   48960
gatgcacagc cccactgaag tcttcctgga agtgcagatt aaggaattta ttattttgct   49020
catgagatga gcggaaatta aagatggttg ttactctgtt ggtgggattg tggagaaata   49080
ggtactttca tatgttgttg gcagcaactt tgtactacct ttgggagagc aatttagcaa   49140
tatctataat ttttttttgtt tgttttgttt tgttttttgtt tttttgagat ggagtttcac   49200
tggagtgtgc ctggcctttt taatttattt ttgagatgga gtctggctct gtaacccagg   49260
ccttagtgca gtggtgtgat ctcggctcac tgcaaccccc acctcctggg ctcaagcgat   49320
tcttctgcct cagcctccca gtagctggg attacaggca cgcaccatca tgcctggcta   49380
atttttctat tttagtacag gtgggtgttc accatgttga ccaggctggt ctcgaactca   49440
tgacctcgtg atccgcccac ttcggcctcc caaagtgctg ggattacagg tgtgactcac   49500
caccoctggc cttttttttt tttttttttt tttttgagg tagagtatct tgtccaggct   49560
ggagtgcagt ggtattatct cggctcagtg caacctccac ttcctgggtt caagcagcaa   49620
ttcttgtgcc tcagcctccc gagtagctgg gattaaaggc tcctgccact atgtgggcct   49680
agctaatttt tttgtatttt tagtagagat ggggttttgc cacgggccag gctggtctca   49740
agtgatcctc ccaaagtgct gggattatag gtgtgagcca ccacgcccta ctaatttgtt   49800
gtattttttag tagagatggg tcttcaccat gttgcccagg ctggtctcaa actcgtgagt   49860
tcaagcgatt tgcctgcctt ggcctcccaa agtattggaa ttacagacgt gagccaacgg   49920
gcccggcctg tggcttttcg tggagttctt agaacgtaag ttttctgtgc tgttgtgcct   49980
tctactttct ctacctttg                                                50000
```

<210> SEQ ID NO 9
<211> LENGTH: 50000
<212> TYPE: DNA
<213> ORGANISM: Homo sapiens
<220> FEATURE:
<223> OTHER INFORMATION: human DYXC1 chromosomal gene region,
      nucleotides 150001-200000

<400> SEQUENCE: 9

```
gaatgtcttc actttccagt cccttttacc tagataattt gaattactct ctgaaggctc      60
aacctacttt tcatgagtta cagatatttg cttcttaagg atcttttttt atcagtttca     120
ttttgatatt ttagatgtga attcaatttg gttgacagag tcttgctctg tcacccaggc     180
tggagtgcag tggcacaatc ttggctcact ttaatctctg cctcctggat tcaagccatt     240
cttctgcctc agcctcccaa gtagctggga ctacaggtgc ccaccaccat gcccggctag     300
tttttttttt tttttttttt ttgtattttt agtggagatg aggtttgcac catgttggcc     360
aggctaatct ggaactgtac ccgacctgac agttgatctt tttaatatttt agcttagctt     420 atctctaggt gtttcatcca tagaactaaa tctcagttgt gttcaggtac aaaaaagatg     480
gaaaactact cattcattct tcagaactgt tttcaggact tcaaggaggc cttccctaac     540
caccctattt aacattccag ttcttgcacc atccccaccc ctactctgcc ctcacttttt     600
tctccatggc actgggcacc agctggctaa ctctgtcttc aaaaagtact tttctttggg     660
ggaggttttt cttttgtttt tgttttcttt ctttcagtcc tgtatcttca gcacttagaa     720
gagttcatgg cacacagtag gtactcaata agcatatgtt gaaagaatga atgcagtttc     780
atgttccgga tgaggatagg ctcatttaaa atattttcat atgtttatta gacaaaaagt     840
agccttcaaa aaagttttca tgctgggcgc agtggctcac acctgtaatc ccagcacttt     900
gggaggccaa ggcaggcgga tcatgaggtc aagagatcga gaccatcctg gccaacatgg     960
tgaaaccgca tctctactaa aaatacaaaa attagctcgg catggtggtg cgcacctgta    1020
atcccagtta cttgggaggc tgaggcagga gaatctcttg aacccggaaa gcagaggttg    1080
cagtgagccg agatcgcgcc actgctctcc agcctggaga cagagtgaga ctctgtctca    1140
aaaaaaaaaa agttttcatt agttgggatc ttgtatcctc ttccctttct caagtgatgt    1200
gttttaaagc agacattttc atatcctttg gcggaggtga agacccaga cctttgaaa    1260 agtattttac aaatacgttc ttgaaagcac tccagactga ctcgcttatc tttggtcaca    1320
tgacagtaca gctgcacttt gaggcctttg cctatagcct attggttgcc ttacttcgga    1380
attgtagacg tgtgggagaa taatgctccc attcttctcc atcttatcta gttctagaag    1440
atataatggt aatggaaacc tcaccttttt catagtaaaa tgtagctacc caggaatgat    1500
gaggggcacc atcatatcag gtaatattca ttccagttat attttatgag gtaaaattga    1560
tactgttgtt gtgttgttct tacagatttt gacaggctcc accaaagtgt ttttaaatga    1620
cttatttagc ctctaactct ccctgaatt cagtctccag acgcctactt tatgtttcct    1680
cttggatgtg ataataacta tctcagattt aaaatgcccc aaaccaattt gctggtttcc    1740
ttttcttctt cttttttttt cttgagatgg agtcttgttc tgtctcccag gctggagtgc    1800
cgtggcatag tctcggctca ctgcaacctc cacctcccga gttcaggcga ttctcctgcc    1860
tcagcctccc gagtagctgg gactacaggc atccaccaga ccacctgcc aattttttgta    1920 tttttaatag agacagggtt tcaccatgtt ggtcaggctg tcatgaact ccttacgtca    1980 agtgatctgc ccacctcggc ctcccaaagt gctgggatta caggtgtgag ccaccatgcc    2040
cggcccaatt tactgatttt cttctcataa cctgctcttt ttgaagtctt tctgcctcag    2100
tagctattcc attctagtac tcggtgaggc caggagtcat cctttatacc ccatattcaa    2160
tacatcagga agtcctgttg gctgctgtac ctttgaaatc cgtgtataat ctgtccattt    2220
ctcactgtct tcactgccac cattctagtc caaaccacca tcatgtctca cctggattat    2280
catagtagcc atgcaaatga acttcttgct tctgcctttg ctcccccaca atgctgtccc    2340
agtaggtagc cagagtgatc ttttattcct tttctcaaaa cgcttctgtg acttttagtt    2400
```

```
ctcagagtgt aaagctaaaa cgcttttaa aaggagtctt aggatctgta agccctactc    2460
agtctgtccc cttgccacca ctctgtttat tatcttgtgg gttttttttt ttgtttgttt    2520
tttttttgaga cggagtctcg ctctgtcgcc caggctggag tgcagtggcg ccatctcggc    2580
tcactgcaag ctccgcctcc cgggttcacg ccattctact gcctcagcgt ccgaagtagc    2640
tggaactaca ggcgcccgct accacgcccg gctaatcgcc cggctaattt tttgtgtttt    2700
tttgtagaga cagagtttca ctgtgttagc caggatggtc tcgatctcct gacctcgtga    2760
tccgcccacc tcggcctgga gtgctgggat tacaggcgtg agccaccgcg cccggcttat    2820
cttgtgttta atcttttcct cctctctcct gctaggcgat ccacacaggc ctccttgctg    2880
tttctcagag gtagagctct gatctcagct ttatagctac tatttcttaa atgctcttcc    2940
tccagttaac tgtatataat ggtgcctcac tcattcaaat ctttgctcac atatacttca    3000
gcaatgaagc ttgccctgac catcgttttt agagttaagc ttctctatcc cagcataaat    3060
ctatcccaga ataaatctcc tcaaatattt tacagggttt gactgttttt gtcgacataa    3120
gtctaaggtt tttgacctga atgtgtggtg actcttgctt gtaatggctg tattgttttt    3180
ggctactgca attctgtgag ttagcagaaa taggagcagc aggaagatga tttcagtatt    3240
gtagctgttg tgtgttaaac acttgagaaa cctgcaaggg gacatcaaaa gcaattggaa    3300
atatatgact agagatcgag ttaaagaaac tactctgagg aataaaagga agcctgagcc    3360
taaacagagc ttcaagttta ttgtcttcac aaagtattct tctttttata accgtatgat    3420
ttcttagcct ttgtaactgt cctgtaaatt ctgcttattt ctaaattact attagtaaag    3480
ctcttaaaat ggggagggtt tatacattta ccaatggtca gattaatggg agaggaagct    3540
catggatttc tccagaattt tgagttcttt ttttttttt tttttggagg tggagtcttg    3600
ctctgttgcc caggctggag tgcagtggtg cgatcttggc tcactgcaac ctccacctcc    3660
tggtttcaag caattctcct gactcaggct cctgagtagc tgagactaca ggcgcacgcc    3720
agcatgcccg actaattttt gtattttag tagagatggg gtttcactat gttggccagg    3780
ttggtctttta actcctgacc tcctgatctg cctgccttgg cctcccaaag tgctgggatt    3840
acaggtgtga gccaccgcac ccagcctaat tttgagttct gtaaagaaca attaactgca    3900
ctatcaccca gacgtggtta ccttcttgt ttattgattg cttaatatgt atttagcatt    3960
cattcaatat gtgttgggaa tacattatag gctggtaaac aagcaattac agcacaatat    4020
tctatattaa gtgccagatg cagaaaataa taagagtctt agggatgggg tcaagggatg    4080
gttctcaaag gaaatgaacc gttagctgag acaagcagag gagtttcggt ggaggtaaag    4140
gggatgggca actgatcaga atatgtaaag ccctggagta aagacaaagc caagcatttt    4200
gaggggaact gagaaggttg ggcaaagcgg gaatgaatta aaagagatga gagctagaga    4260
taaaatactt gatattcaag gctttggggc attatcttga agaaaatctt aacattttaa    4320
aggaattaca taatgagatt atcatttgaa gatctctagc tataatgggg aggttcaaac    4380
tgccaggggg ctttcatatt cactgtgtct aggatagggc ttaaaaagtt acttttttt    4440
ttttcctttg attgtagtac acgcccaaca ttttgagaac agttgaatta ataggttct    4500
ttagtaagcc tgttagtttt gcttatccaa attgtcatgg tggtgttagg gccagcggga    4560
aatctttttc tcttttgggc tggatggtgt taccaaaaca ccaggggttt ggtctaggtc    4620
ctgctgcttg ccgcacagaa agccaatcac agagacgggt attgccaggg aagaaggctt    4680
taattgggtg ctgcagccaa ggacatggga gatcagtctc aaatccatct cagtctcaaa    4740
```

```
tccatctctg actgactaaa attagaggtc tatatagcag agaagaaatg taaccatgtg    4800
tgggcaaaca ggaattagag aggggtgagg aagagaagtt ggtcaacagg cagcaggtgg    4860
tcagttaagc aatcatgcag gctctggctt ctcattgtcc agttgcagtg atctgttaag    4920
taagtttcag cttcttaata ctatctagga ggcctgatgg tttgtttcct aagaaaggag    4980
cttagataac acaaatagaa ctttctcaag ttttaagact gtgaggatca atttctgtat    5040
ttattcagag aaaccataaa gatcagttct gtgggataat tggctggttt caatgttatc    5100
tttccttgaa ggaagtaaac aaagcattaa actgggcct gattaaagtg ggcttattga     5160
tttgagaaat tcaagtatgg taagttgtcc caagtcagta atgtatttta cttttttttg    5220
taatctgtta aagatgggaa gcaggcaaag ggaaggaggg aagctttcac acagtggaga    5280
aagaatgctt tttaggcttc agccagtttt tcttatcaca aagccctcac ctacttcttg    5340
tttcatatag aattcttcca gttacccagt cacttaaacc agaaacctgt gagctatcct    5400
acactttctc ccttatatag ttggttattc agtcctttaa taaaataatc tttaggctgt    5460
gtacagtggc tcacacctgt aatcccagca ctttgggagg ccgaggtggg tggatcactt    5520
gagcccagaa gtttgagacc agcctaccaa actagcaaga ccccgactct aaaaagaaa    5580 ttagctgggc agggtggcac atacctgtat agtcctagct acttgggagg ctgagatggg    5640
agcatctact tgaacctggg agtttgaggc tgtgttactg gtggagggtg tccaggttct    5700
tggcatcttg aacaaagaac tggacaaaac acacagacaa agcaaggaag ggatgaagtc    5760
agagatttat tgaaaatgaa agtacactcc acagtgtggt ggcgggccct agcgtagggg    5820
ctcaagggca ccgttataga atttgtgggg gtttcaatac cctctagagg cttccattgg    5880
ttacttggtg tatacctat gtgaatggag aggtgaagta aagttacaaa gtcatttact     5940
tggtgtatgc cctatggaga ggatatttcc tgtcatagct gaagtgtgaa tcggcctaat    6000
gttccctgcc tccagaccct attttcccat ctcagcaagc cgtgttcata ctactgtact    6060
ccagcctgag tgacagagtg agaccttgca tccaaataat gataaaaata ataaaataac    6120 cttcatgtc ttctcagatc tcttcaaaac ccttcccgct atcttctaaa ccctttccct     6180
catcaacact ggttaagttc agatgctcat attttttcatg gaatattatg ttgcttcctt    6240
gcatcccaca ggtctagggt tgttgagttg cttccctatc ttgaaaaaaa acatttttt     6300 gagacagggt cttgctctgt tacccaggct ggagtgcagt catgcagtca tagctcactg    6360
caactttgaa ctcctgagct caaatgatcc tcctgcctcg gcttcccaag tagctaggac    6420
aacaggtgtg ggccaccatg tcctgctgat taaaaattt tttttggtag agatggggag     6480
tctcactatg ttgcccagcc tggtcttgaa cgcctggcct caagtgatcc tcccacctca    6540
gcctccgaaa gtgctgttac aggtgcaagc cgccactctt ggccctgcca tcttaatata    6600
tgctatttaa tttaattaat taatttattt attttgagac ggagtttccc tcttgttgcc    6660
caggctggag tgcaatggcg ccatcttggc tcaccgcaac atccgcctcc tgggttcaag    6720
caattctcct gcctcagcct ctcgagtagc tgggattaca ggtgcttgcc accatgcccg    6780
gctaattttt tgtattttta gtagagacag ggtttcatca tctttgccag gctggtgttg    6840
aactcctgcc cttatgatct acccgccttg gcctcccaaa gtgctgggat tataggcgtg    6900
agccactgca cctggccaaa tctgaccaga taaccgct tatgcctgtc atcctagtac      6960
tttgagaggc caagaaaggt ggatcacttg agctcaggag tgtgaaacca acctgggcaa    7020
catggcaaaa ccctgtcttt acaaaaaata caaatattag gcatggtggc gcacacctgt    7080
agttccagct actcaggagg ctgaggtggg agggtagctt gagcctggga ggtcaaggct    7140
```

```
gcaatgaact gtgttcatgt cactgccctc cagcctgggt gacaaagcga atcctgtct    7200 caaaaattaa aaaaaaaatc atggccaggt gcggtggctt catgcttgta atcccagcac   7260
tttgggaggc tgagttgggt ggatcatgat gtcaggagat ggagaatctc ctggccttta   7320
gtagagatgg tgaaaccccg tctctactaa agtacaaaa attagctggg catggtggcg    7380
cgtgcctgta atcccgcta ctcgggaggc tgaggcagga gaatcgcttg aaccagggag    7440
tcagaggttg tggtgagccg agatgacgcc actgcactcc agcctggtga cagagtgaga   7500
ctccgtctca aaaaaaaaa aaaaaaaat caaatctgat cttttaaact atatttgtac     7560
tagattgtct tttttatttt ttatttttt aaagaactt catattcttt tacattttc      7620 tgcctttgtt tttcctgtgt gatgcttttt ccttttttcac tgggacatct ttccttgtca  7680
tcagatcttt tgattttttt tttttttttt taggaatcag aaatcgtttt gtttgttttt   7740
tgcaatgttg cccaggctga tcttgaactc ttggacttga gcggtccttc cgtcttggcc   7800
tctccgtgtt ggggttacag acgtgagcta ccacacctag ccccccccc cctttttttt   7860 tttttttaaa gagtcaaggt ttcactgtat tacccagtct ggagtgcaat ggcagttcac   7920
aggcatgatc attatggctc ttaacagcct tgaactcctg gcctcaaggg atcttccttc   7980
ctcagtctcc caggtagctg ggattaatag gcactctcca ctgcttccgg ctccagaaat   8040
cttcatttta atgtagtatc tcaatttta aattttgaca actgttaatt tactttaaaa    8100
aatgctatca aatttgcagc ctcatttata gagatttcct tgatcattct cctttccccc   8160
tgcaaattta attgctcagt cttttgtgtat ttctgtcatt gcataatttt caagctatta  8220
taaacatgat tctcatacaa atagacattg atacatatca taaacttttt tgaaagtcct   8280
gaaaaatagt ggaatgagaa attgggattt atatagtcag tttaggccag gtgcagtggc   8340
tcacgcctgt aatcccagcg ctttgggaag ctgaggaggg cggattgctt gaggccaggc   8400
cttccagacc agcctggcca acatggccaa acgttgtctc tacaaaaaat acaaaaaatt   8460
agctgggcat agtggcacat gcccatctac ttatggggct gaggcaggag gatcgattga   8520
gcttgggagg tcagggttgt ggtgagccat gattacgcca ttgcactcaa gcctgtatga   8580
cagaacggga ccctgtcaca ctcaaaataa agaaagaaa tatagtcagt ttaataaga    8640 atgctgaaat aaaattgcta agatataaac gtggttaata tcctacaggg tatttaaact   8700
gtagcttttt ggataaccte tactgactgg acagaaaaaa tttattttac cgtagtagtt   8760
ttctgtaagt ttacttttaa atttgtagag ttataaactg cctgggcctt aattgaaatt   8820
agaaataaaa caattagatg acctcaggtg agcctattac aaaatgctct tgtcataaca   8880
ttaaaagtca tacaattgat accttatttc aggttttgaa taattcattt gaaacatgtt   8940 aattttata ctattagcga ccaaccttt tgtatcctct ctttttgaaa tattaatgta     9000
caggagtttt cagaataatt aacagattat atagatctga cttgaggcta ggagtttgag   9060
accagcctgg ccaacattcg caacgagtga aacctcgtct ctactaaaaa taccaaaaaa   9120
caaaacaaaa cccccaaaaa cagattatat agatctgtat ttttgccctg ttctcatttg   9180
agcactagtt ccatattgtc ttcagtagag ttctattaga acttggatct aatgtgttca   9240
cagtatatgt ccaataacag aagcataaga cacatgtaga ataaatcagt aggagtacta   9300
tttgctttac taagttgggt tttgaagttt aaaggagttt cagatacaaa aagaaaaaac   9360
caggtggagt gaccattgta tgctggctta gggcttgagt ccaggttgtt gccagtgacc   9420
agatgtttgt aaccaacctc tggtgtcttc cccctgccc caactttaac acaactgaag   9480
```

-continued

```
tattgctgac acagttattt tcataaaaac agtttgattg ccgggcgcag tggttcacgc   9540
ctgtaatccc agcactttgg gaggctgagg caggcggatc acgaggtcag gagttcgcga   9600
ccagcctggc caacatagtg aaaccccgtc tctactaaaa atacaaaaat tagtggggcg   9660
tggtggcacg cgcctgtagt cccagctact cgggaggctg aggcaggaga atcacttgaa   9720
cccgggaggc ggaggttgca gcaagtcgag atcgtgccac cgcactccaa ccggtcgaca   9780
gctcgagact ccgtctcaaa acagtttcat catgtttctt ctatgtttga aaatgtaaat   9840
tacttcatgt tgccaacata cagacttcat tttcttggca taggagcttt tcagtttccc   9900
tgtgcttctc agtttctgca gtcatgtttt tcacaccttta ctgttcattg aaaatagagt   9960
cctttactgt tgctgcctgc tccccattca cgattatcct tttccttcac ctctgtctgg  10020
ccaaatgcta cattttcttt tagacataac tttctccttc attccaacaa tataactgtt  10080
gagactgttc tagtccagga gggtctcctt atcttagaag tttgcttcta tctgttcata  10140
caggtatgca gtcctgtcat gttctgtatg gtaaatctat gggtggcttg tctctgtttc  10200
acctggaaga cagtaaacca cttttcaaac ttagtgtcac atatagtgct tcctatagaa  10260
ttaaaaaaaa tgtgtctcat gagtcaatat gttttttgtat ttgtagacct gaaagatgtc  10320
tgaaaattcc agtgacagtg attcatcttg tggttggact gtcatcagtc atgaggtatg  10380
atatttaata cttttttataa ggtaatttgt aatattaatg ttaccagtga tgtaaactgt  10440
gttctttgaa gatcagtctt tttctacctt taagcaaaaa gttccaatgg acattttccc  10500
tctcatatta aacttcactg ctgaaaacgc ttcatgagcc agcatcttct acattattgt  10560
acatagcttt gagacattag gcaaatattt attgaaggtt tgttattgtt caggccctgt  10620
gctttacttt cattttcata taattttgtc ttttttttttt ttttttttttt tgagacagag  10680
tctcactctg ttgcccaggc tggagtgcag tggcgtgatc tcagctcact gcaacctccg  10740
ccccactgga ctgaaatgat tctcctgcct cagcctcctg agtagctgga attacaggtg  10800
cctgctacca tgcccagcta atttttgtat tttcagtaga gacgagtttc accatcttgg  10860
ccaggctgat cgtaaactcc tgacctcgtg atccatctgc ctcggcttcc caacatgctg  10920
ggcttacaga tgtgagccac tgtgcctggc caattttgtc ttttttttttt tttaaaggga  10980
caggatcttg ctctgttgcc caggctagag tgcagtggct gttcacatgt gcaatcatag  11040
taccatgtaa cctttaactc cttgggctca agtgatcctc ccaagtagct gggactatag  11100
gcatatgcca ccatccctg ttcttaaata attttgaata tttcactgtg atacatactg  11160
ttttcattct tattttatag ttgagaaaac taaagcttag agaggttaag taatttggtc  11220
aagattatgc agctagaaaa tagatcctgg atttgaacag atcagaaagg agaatggaga  11280
acatgtgttc catttacgtt atagcagaac ttcacaggga aaaggccaga accctatcac  11340
aaaatgaatt ttataataga agattgatat acatacaaca agtatacata acttgtacat  11400
tttgtttatt ttttcatacc agtaatatat gttcactgta gaaaaatggc agtatattga  11460
taaacagaaa tatacttact ccaggttta ctccaggttt taatggacat ctataatttt  11520
cccatttgtt tttagggtat tgtaagcctc acttgttttc ttttttttctt ttttgagatg  11580
gagttttgct cttgttgtcc aggctgtcgc tcttgttgtc ttgtacagtg acgcaatctc  11640
ggctcacagc aaccttcgcc tcctgggttc aagccattct cctgcctcag cctctggagt  11700
agctgggatt acaggcatgt gccaccacgc ccgactaatt ttgtattttt agtagagacg  11760
gggtttctcc atgttggtca ggctggtctc gaactcccga cgccaggtga tccgcccgcc  11820
tcggcctccc aaagtactgg gattacaggc gtgagccacc gtgcccggcc acttgttttt  11880
```

```
ttaataaaaa ttataggccg ggcgtggtgc tcacgcctgt aattccagca ctttgggagg   11940
ccgaggtcgg ggcagatcac tgaggtcggg agttcgacac cagcctgacc aacatggaag   12000
aaacccggtc tctactaaaa atacaaaatt agccaggcgt ggtcgcacat gcctgtaatc   12060
ccagctattt gggaggttga ggcaggacaa tcgcttgaac ctgggaggcg gaggttgcgg   12120
tgagcagagt tcgtgccatt gcactccagc ctgggcaaca agagtgaaac tgtctcaaaa   12180
aaagaaaaaa aaaattaaaa aattttttgtt ttttaaacta ttagttaagg ttcaggtagt   12240
tatgtttaga aaacattaac agaaaaaaac aagattgcct tttctgcatt aaaatttcaa   12300
aatttaaaag catctatcat ttgagattga gatgattctt ctttttaaaa tcttcagtga   12360
cttttctatt tttagcttgt tttcttcaaa ggattagatc aactcccata gcaacttctc   12420
cttcaaggat aattaacaat ataggagcaa ggcagctatg ggagtcttac ctgttagtct   12480
gcagggtgga gtatgacagc agacctctgt ctggcactca gtcaagtgtg tcattagggt   12540
gttctgtact ggatgttatg tcccagattg aatcatattt gtactttat ctctcttctt   12600 ctatatctgc tttccaggtt ctactctttc ttgctaattt ctcttacatg tgtccctt    12660 tcctctccca ttactgccat tctcatttgg gccagaattg gtttccccag caattcctaa   12720
tacataacct tgcttagcc tctaccattc tcctgccact atagacaacc tcggagtctt   12780
gcattccgaa ttctcattag ggctcaactt aaacgctact ttttttctta cttttttttt   12840
tttgagatgg agtcttgctc tgtcgcccag gctggagtgc agtggcagga tctctgctca   12900
ctgcaagctc cgccccatcg gttcacgcca ttctcctgcc tcagcctctg gagtagctgg   12960
gactacaggc gcccgccacc acgctcggct atttttttt tgtatttta gtagagatgg    13020 ggtttcaccg tgttagccag gatggtctcg atctcctgac ctcgtgatcc gcccgcctca   13080
ggctcccaag gtgctgggat tacaggcgtg agccactgcc ccggccctac tttttcatg    13140 aattctttta attttgctg tcttgagtta tgtatacgca agagaatgca gacctttcga    13200
ttccatgtgt cagcagacta tagtgggac atagggaaag acggaatcac cttagtggtt   13260
aactttgttt tacaattaag acacaaagaa aaattgtatg atccgctatt attaatgaaa   13320
agacagtctg acatcaaagt aggaaagata acctcagaat aaaaagatag tctaaaattg   13380
tgtgaggaga gtattcatta accctatagg tttatttaat ccatgtcatt aaagctttag   13440 ccattttag tttatagtgc cataataagt agttatttgc atatgggtgt ttctctgaat    13500
atgttgtaaa attgaatttt ggatttcatt tttttttt tttttgaga cggaattttg      13560 cttttttgt gatccaccgg cctcagcctc ccaaagtgct gggattacag gcgtgagcca   13620
ccgtgcccag ccagatttga atttttata tcccacagca tctagcgaag tgccttgtct    13680
agagtagttc cataaatgtt aagtagaaac aaattattat agaaataacc aaatttagac   13740
ccttattctc tggaattcaa atttattgct tgagctcata aaatagagca ttccacttttt   13800 gggctgacct gacttagaat ttaaacctga gactccattg tgccattttc ctgccatagg   13860
cctttgtgga ctaaattgaa caaaagcttg tctaattaga tactgttcct ttggagtatg   13920
gcagcatctg agacttttaa taatggaaga agcatttaca tgtagtcaaa tctagctttg   13980
aggagctaat aggcaaataa ctgaaagatt atcacttttc cttagggtc agatatagaa    14040 atgttgaatt ctgtgacccc cactgacagc tgtgagcccg cccagaatg ttcatcttta    14100 gagcaagagg agcttcaagc attgcagata gagcaaggag gtaagttgtt cacaaattct   14160
aatttttttt ttaatatgat atatgagtga tattatgagt cttgccttct ttccaggtgg   14220
```

```
gtggcctttc tggctaatct aagggggtcgt tggaggatta gaacttcagt gtaggttggg     14280
cacagtagct cacacctgta atcccagcat tctgggaggc tgaggtgggc ggatcatttg     14340
aggtcaggag ttcaagagca gtctggccaa catggtgaaa ccctgtctct actaaaaata     14400
caaaaaatta gccgggtgta ttggcaggtg cctgtaatcc cagctactca gaaggctgag     14460
gcaggagaat cgcttgaacc tgggaggcgg agtttgcagt gagccgagat tgtgccattg     14520
cactccagcc tgggcaacag agtgagactc catttaaaac aaacaaacaa agaaaaactt     14580
cagtgtggat ttggtgaagg cccacagaac ccagagtcat cagcctgccc caggggttta     14640
tttgcagctg tagtatattt tgggttttc agatacactt tgttgctaca gaggtaaacca    14700 gtgacaaaaa aagtgtttca tggtttaatc tgaatttgtt tggtagtttc tatttccttg     14760
tcatttgttt ggtagtttgt atttacttgt cattattaaa gttaagaaaa aaattattca     14820
ttgatcacaa gagatttact aacctgtttt ccagttatta tcatgttgat ggagttacag     14880
acatgcctct catttttattc tgctttgctt tattgtactt cgcagatact acatttttta    14940
caaattgaaa gtttgtggca accctgtgtt gagcaagtct attaatgcca ttttccgat     15000 agcatatgcc cacttcatgt ctctgtgtct cattttttata attataatat ttcatttatt    15060
tttattttat tttattgaat tgaattggcg gagtttcgct cttgtttccc atgctggagt     15120
gcaatggtat gatcttggct cactgcagcc tctgcctctt gggttcaagt tatcctcctg     15180
cctcagcctc tcagctggga ttacaggcat gcgccaccgt gcccagctaa ttttgtgttt     15240
ttaatagaga cggagtatca tcatgttggt tagcctggtc tcgaactcct gacctcaggt     15300
gatccacctg tgtcaacctc ccaaagtgct gggattacag gcgtgagcca ctgcgcctgg     15360
cctgtaattg tcatatttca aactttttca ttattattac atcagttatg gtgatctgtg     15420
atcagagatc tttgatttta ctattgtaat tcctttggga caccatgaac cgtgcctatg     15480
aaagacagtg aacttaataa atgtgtgtgt tctgactgct ctactgactt gccattcccc     15540
catctctctc cctctccttt ggcctccctg ttcctggaga caacaacaat attgaaatca     15600
ggccaattaa taaccctaca gtggcctcca ggtgttcagg tgaaaggaag agttgtgtgt     15660
ctctcacttc aaatcaaaag ctaaaaatga ttaagcttat ttgaggaagg catgtcaaaa     15720
gctaagtctc ttgggccaga tagttagcca agttgtgaat gcaaaggaaa agttcttgaa     15780
ggaaattaaa agtccttctt agtgaacaca tgaatgataa ggaagccata tagccttatt     15840
gctgacatgg agaaaatttt agtggtcttg gtagaagatt gaaccagcca caaaattccc     15900
ttaagccata gcctaatcca gaacaagtcc ttcctaactt gcttcaagtc tatgaaggct     15960
aagagtggtt aagaagctgt agaaagaaag gcggaagcta gctgaggttg gttcatgagg     16020
tttaaggaaa gaagctatgt ccgtaacata aaagtgcaag gtgaagtagc aagtgctgat     16080
gtagaaggcg caccaagtta tccaggagat ctaactgaga taatggatga aggtggctac     16140
cccaaccagc agattttcag tatagatgac acaactttct attggaagaa gatgccatct     16200
aggactttcc taactacaga gaagtcaata tctgcttcta ggcttcaaag aacaagctca     16260
ctttcttgtt agaggcaaat gtagctggtg actttaagtt gaagccagtg tttacttacc     16320
atgccttgag aaatcctagg acccttaaaa aatatgctac atctactctg cctgtgctct     16380
gtaaatggaa caacaaagcc taggtgacag ccatgtgttt acaacatggt ttactgaata     16440
ttttaagctc agtgttgaga cctgctgctc agaacaaaaa gattcctttc aaaatactag     16500
acattgtata gcaatacctg gtcaatcacc gaagggctct gatggagatg tacaaggaga     16560
ttcatgttac tttgtttcct gctaacacaa catccagtct gtagtccatg gatcaaagag     16620
```

```
tagttttgac tttcaggttg tattatttaa taaatacatt ttgtaaggct gtagctgcta    16680
tagatagtga ttgttctgat ggatctgggc aatgtgtgtg aattgaaaat cttcaggaaa    16740
ggattcacca ttctagatgc ctttaagaac aattgtgatt tgtgggaaaa ggtcaaaata    16800
tcaacattaa caggagtttg gaagaagttg atttcaacct tcatgacttt gagtggttca    16860
agactttaat ggaggaagga actgcagatg tggtagaagt agcaagagaa ttagaattag    16920
aagtggatcc tggtcgggtg cggtggctca tgcctataat cccagcactt tgggaggctg    16980
aggtgggcgg atcatgaggt caggagatcg agaccatcct ggctcacacg gtgaaatccc    17040
atctctacta aaaatacaaa caattagctg ggcgtggtgg caggcgcctg tagtcccagc    17100
tactcgggag gctgaggcag gagaatggcg tgaacctggg aggcggagct tgcagtgagc    17160
caagatcgcg ccactgcact ctagcctggg caacagagcg agactctgtc tcaaaaaaaa    17220 aaaaaaaga gtggatcct gaaaatgtga tccaattgtt gtaatctcat gataaacttg    17280
aacagataag gagttgcttc ttatggatga gcaaagaaag tagtttcttg agatgcaatc    17340
tactcttggt gaagatgctg tgaatattat tgaaatgaca acagaggatt tagaatatta    17400
cacaaactta gttaataaag cagtggcagg gttttgagaag attgactcca attttgaaag    17460
ttgttctact gtgggcaaag tgctatcaaa cagcattgca tgctacagag aaatcttttca    17520 tgaaaggaga gtcaatccat gtgggaaact tcagtgttgt catacttcaa gaaattgccc    17580
cagctactcc acccttcagc agctaccaca gtggtcagtc agcagccatc atctttgaag    17640
taagactctc caccagcaaa aatattacaa ttcactgaag gctcagatga tcactagcac    17700
tttttagcaa taatgtattt ttaaattaag atatgtacag ttttttagac atgatgttat    17760
tgcacactta atagattaca gcatagtgta aacctaactt ttacatggac agggaaacca    17820
aaaaattcat gtgacttgct ttattacatt ggtttggaac tgaacttgca gatatctgag    17880
atatgcctgt actctggttc caatctggta aaatggaatt tgactactgt attgcatctg    17940
tattatgtat acttcacatg ggatttgatg cacacattat ttatatagag aaataggact    18000
cctgaacaat tactgcatac acttatgttc gtatttaaat tacttcatta acttttaaa    18060 aaaattacag taaaatgcat acagaacatt tcccctcagg agaaaaagt ggatgtgtca    18120 aggccagaaa tagaagagat tatagctgtt aattttttta agcctacacg ttgattatta    18180
ctactctcat ttgaaaagtg attctcatct tttttgtgtc agagatcctt ttgagaatct    18240
gaaagctatg gacagtttct tccaagaaat gcatttactt gcatatgtta aagaaaattt    18300 tcttttttt ctttttcttt atgagacaga gtctcgcact gttgcccagg ctggagtgca    18360
gtggcacaat gatctcagct cactgtaacc tccgcctccc tggttcaagt ctcagcctcc    18420
tgtgtagctt ggattacagg tgcctgccac tatgcccagc tatttttttt ttattttta    18480 tttttagtag acgggggtt ttcaccatgt tggccactct ggtctcgaac tcctgacctc    18540
ctgatcagtc tgcctcggcc tcccaaagtg ctgtgattac aagcatgagc cactgtgccc    18600
ggcctaattt ttttgttttt tgagatggtg tcttgctctg ttgcccaggc tggagtgcag    18660
tggcgggatc tcggctcgct gcaagctccg cctcccgggt tcacgccatt ctcctgcctc    18720
agcctcccaa gtagctggga ctacaggtgc ccaccaccac gctcggctaa ttttttgtat    18780
ttttagtaga cgggggttt cactgtgtta gccaggatgg tcttgatctc ctgacctcgt    18840
ggtctgtccg ccttggcctc ccaaagtgct gagattacag gcgtgagccg ccgcgcccgg    18900
ccattttaat agcgacggga tttcactatg ttggtcaggc tggtcttgaa ctcctgacct    18960
```

```
cgtggtctgc ctgcctcagc cgctcaaagt gctgggatta caggcatgag tcaccgcgcc    19020
tggccccagc accccggccg agtactgtgg cggaatctca cctctaaatt aattaatttt    19080
ctgttagagg gtatataatg ctgaaaaata ttttttttc cctgttcttt gcaggactta     19140
aattacataa gaaatgcatg atcgaccggg cgcggtagct catgcctata atcccagcac    19200
tttgggtggc cgaggcgggc ggcttacggg gtcaggagat caagaccatc ctggctaaca    19260
cggtgaaacc ccgtctgtac taaaaataca aaaaattagc cgggcgtggt ggtgggcgcc    19320
tgtagtccca gctacttggg agcctgaggc aggaggatgg cgtgaacccg ggaggcggag    19380
cttgcagtga gccgagacgg cgccactgca ctccagcctg ggcgacagag ggggactccg    19440
tctcaaaaca aaacaaaaca aaaaaaaac aaaagaaat gcatgttcat gatagggaaa      19500
aaaaaatagt aagcaaaaga aatttaaaat ggtctataat tcttttatct agaataatt     19560 actgttgata tttggtgtac tttgctcata aatttatatg ttatattatt tttaactttt    19620
cttaatattt tatgctcttt tctttttttt tttttttaag acagagtttc actcttgttg    19680
cccaagctgt agtgcaatgg catgatctcg gctcactgca accttcgcct cctgggttca    19740
agcaattctc ctgcctcagc ctctggagta gctgggatta caggcgcgca ccaccacacc    19800
tggctaattt tttgtatttt tagtagaaac ggggtttcac cgtgttagcc aggctggtct    19860
caaactcctg acctcaggtg attcacctgc attggcctcc caaactgctg ggattacagg    19920
tttgagccac tgtgcccggc ctttatgctc ttttcatta aaatatatt gtgaagtcat      19980 cattctgttt gtacacattt tctttgagga ggttcttata aatatatct tctgtagtga     20040 catttagttt ttctgtgttt tgagttcttt cttttttaaa aaaaattatt ggtagaactg    20100
gtctcgctat gttgcctagg ctggttttga actcctggct ttaagtgatt ctcacacatt    20160
ggcctaccaa agtcctggga ttacaagcat gagccactgt gcctggactg ccctctctct    20220 gactttttt tgagacatag tcacactctc ttgtccaggc tggagtgcag tggcatgatc      20280
atggctcact gcagcctcaa ctcctaggct caagtaatcc tcctgcctca gctttctgag    20340
tagctagtac tataggcaca taccaccatg cccaaataat ttttaatttt tatttttgt     20400 agagacaggg tcttgctgtg ttgcccaggc tggtcttgaa cttgtagcgt caagcagtcc    20460
tccagccttg gcctcccaaa agtgctaggg tgacaggtat gagtcactgc accccgcctg    20520
agtccttgtt ttttatagtt tatgttttct tataaggcat ttagacacac acacacacac    20580
acacacacac acacacgtac atatacatac atactttcat aaatcatagt ttgaagccac    20640 ggttttatt cttacggtac caggcattga cagccattag aatggtcttt agaaacttcg     20700
aataaacttt taagaattca ggaaatgtat cactaggtat ctaatgatag attttttcat    20760
attaggtatt aatgaacata ctggatcaag taatttggta atgtaaggta gaggttttat    20820
ttacttagtc aaggtagctt tgagttctta ataaatcttg tggctgggca cgatggctca    20880
tacctgtaat cccagcactt tgggaggcca aggtgggcgg atcgcttgaa gtcaggagtt    20940
cgagaccagc ctgggcaaca tggtaaaacc ctatctctag tagaaataca aaaattagcc    21000
gtggcgtatg tctgtaatcc cagttgctta ggaggctgag gcaggagaat cacttgaacc    21060
caggaggcag aggttgcagc gagccaagat agtgccactg cactccagcc tgggcaacag    21120
agcaagactc catctccaaa aaaaaaaaa atcttaaatg attgcatttt cttatccaaa     21180
attatcacct gacagtttca aataaatgaa gttcattagc aacagtggag tgacttctat    21240
aattgtatgt gacatttcat taaatctatc ctaacatatt aggaagagat ttttatctac    21300
ccagattata tgttggctgc agaaagtcaa cagagagttt taaattaaga aataattata    21360
```

```
ttgatctttg ctttatatca gaaagcagcc aaaatggcac agtgcttatg gaagaaactg    21420
cttatccagc tttggaggaa accagctcaa caattgaggt aaacttgtat tttacactgt    21480
ggatatatgt taaatagtat ccttagaata ctatttaaag cctctaattc tatttatgca    21540
ttctattcct attttgaatt ataagcaatt ttgacttcta agttagatgt cttagaggac    21600
atctaagcaa agtattttat tggtattgtg ttaaagatct atcttttcac ctctaatata    21660
attcttttg gaagtagatt gcattcttga attatattga aaaattaaac tgttaggttt     21720
catgtctaaa atggtggttc attttaaaat ttggtaacaa cctgagactt atgctttggg    21780
gttttacttg acttctgtat aaaactagat agctagatga tcatttttaca tggtgtttta   21840
gtctgtttgt actgatctga caaaatacct gatactgggt gatttataac aaacagaaat    21900
ttatttctca cagttataga ggctgggaag tttaagatca aagtgtggac aagttcagtg    21960
tttgctgatg acatgctgtc ttgttttccaa atggcatttt gttgctacat ctttaagagg   22020
agatgggcaa aaaaaggctg gatgctgcat gaagcctgtt ttataaagac cttaatcata    22080
ttcctagggg aggatccctt ataactcagt cacctcctaa aggtcccact tcttagtact    22140
atcacattgg cgattacatt ccagcgtaga aattttggg gacaccttca gatacattca     22200
gtacaagata cagctgttga agtttattac gtacataacc taaaaagttc agtgagtctt    22260
ttttgggctt ccacactaca gagttgtgct cgaatagaac catggaactc gtgagagaag    22320
tgagctcttt tttctgtggt tattgagggg gcaaagatgg gcttctcagc ttctgcagcc    22380
cactaggaga atgcagtggt ttgatctaat tctgagagtt gtcaagggat ctgatggtgt    22440
tctcaagcta tatgatgagc ctgctattgc ataattcttt actaatagta ggaatcatat    22500
cttttatttt aactcagatg actataatac ttactactgt tgtattctaa gaaaatgtaa    22560
gacccttaaa tgattgttga acttaccatc tctaaaatta tgattcttca ggcagaggaa    22620
caaaagatac ccgaagacag tatctatatt ggaactgcca gtgatgattc tgatattgtt    22680
acccttgagc cacctaagtt agaagaaatt ggaaatcaag aagttgtcat tgttgaagaa    22740
gcacagagtt cagaagactt taacatgggc tcttcctcta gcagccagta tactttctgt    22800
cagccagaaa ctggtaagaa tacactgata agagacttaa agacatgtac gaccacattt    22860
tatataaagg cttgttttct acccctaata atttagtctc tagttttgaa tatgtttggg    22920
taaaactcaa gacaagacta ttttgtgtg tgaaatctat taatacctag tgtttcgcta     22980
gactgttctg gagcatagca atcttttact gtaacagtaa ccatcttttg ccattaaata    23040
gaagacaaaa ttgcttcagt gagatttgtt aaaatcacaa atgctccaaa attctttgg    23100
tgcttttag atcttgaaga gtgggagatt ggggatgtta atattttgc ttgcagtagt     23160
gtacattttg taatatagaa atagtgaaaa aaattgttat taaagtctct tcagatatat    23220
tcaattatta atcatgcaac aaacatttat tgagtaccta ccatatgtga aacagagttc    23280
aaggtgctat caatacagct agtcttccaa agctcgtgac cttcagatct tttgttttag    23340
attctgttat gaaaatgtca ctagtgtaag ccacatttt aatgcaatca atgcccgttg     23400
tacagacaga ctcattcaga gattaaagtg tgagttgctt gatttctttc tgctatgctt    23460
cagctcagtt ttagcagtat gtataacatc ttttaatgtg atgtaagtat gtaggtataa    23520
agttcctgga tatatcagtt attaacccac aattataact aagcgtgagt tatggcagag    23580
acaacttgaa acactgctag tgattctaaa aatttcctaa tttgacgaag aaacaggaaa    23640
caggtagtat ctatttaga taatttttttt agattttacc attctttaat atttacattt    23700
```

```
gccaaccaga atcagacaat agaatttctg tcattccagt ttaagctaat aaaatgtcaa   23760
gtagaggttc ttggctgggc atagtggctc atgccagtaa ttccagcact ttgtaaagct   23820
gaggcaggtg gattacctga acccaggatt tcgagaccag cctgggcaac atagcgagac   23880
ctcatctcta caaataataa aaagccaggc atgatggcgt gcgcatgtgg tcccagccac   23940
ttgggaggct gaggtgggag gattgcttga gcctgggagg ttgaggctgt agtgagctga   24000
gattgcgcca ctgcacccag attgccaacc tgggtgacag agcaggatcc tgtctcaaaa   24060
aaaaaaaaaa aaagtagaga ttcttggcta tctcatttaa tgagaagtta ttttcagtta   24120
gtatatcagt ggtttgccta taaacatgaa cgtgaaaaca cttttttccag ctatttgaat   24180 attcatgtga cattcttgat gttcagagga aaacttcagg ctttgttaga atagcattca   24240
tagtatcttt atttatggag gggtattgta attgatttta gaatccttgt tagtcatcaa   24300 atttatattat tattttttta aactccagga tttgtgttgt attcaggtag tttccccacc   24360
cccgcttcct ttcctgcctc tggtttaatt agagaatatt catggcccag aaaagtcaaa   24420
ttgaagccag agtattatag aatggtcaga tatataagaa actgacatag acgtaaaagg   24480
aactacatac tgttgctggg cgtggtggct cacgcctgta atcccagcac catctcaaaa   24540
aaagaaagaa attacatatt aactttttc aggaagttgt atagttctaa gaccattctt   24600
ctaatattta tcttctttct gaattctgac ttccttgagat ttttgtggac taagaggaat   24660
atttgattaa ctgtattttt acccattgtt attcctccta aagatattgt ttcaataaac   24720 caaatgtta aagacgaaat tttggactat actgaaaaca ctgcatataa accagttgcc   24780 aaaagtttt gttttggggc cgggcacttt ggctcatgcc tgtaatccct gcactttggg   24840
agactgaggc aggcagatta cctgaggtaa ggagtttgag accagcctga ccaacacggc   24900 aaaaacccctt ctctactgaa aatacaaaat ttagccaggt gcctgtaatc ccagctactt   24960
gggattagct gcctgtggta gcgcaggcct gtaatcccag ctactctgga ggctgaggca   25020
ggagaatctc ttgaacccag gaggcggagg ttgcagtgag ccaagattgc gccactgcac   25080
tccagcctgg gcaatagagg gagacccccgt ctcaaaaaaa taaaaaagat ggttttgtt   25140 tttccctttt agttttgttaa ttttgtgcta gccattgctt aattttgttt tttccttttcc   25200 ctttcttcat ccttaaggat ttcaacttca attttttctt ctcctgactt atattcttgt   25260
ggcagtgtac gttttgttgg gttaagaaca ctgcctgctt cctctttatg aactctcttc   25320
cctgacaaaa agcaaagttg gtagtgtaga gaagtttgta ttgtgtgttt ttaagaaggc   25380
atggttatta cgttttaatt ttgtacggat aacaatgtta agtgataatt aagtattttt   25440 aattctttt tttctttta gtctttataa tatagcttta tgcctcttttt tttcctgttt   25500 attcacaaaa gaaaggtggt gggagaagct gtggaagatt cctgagtgca tatggggatg   25560
ggatgatcag ctgaaacacc atgttcctag ccaactcgct ttccaaggtg gtgtgactaa   25620
atctgaccag cttctctaga gctgagtgtg cctagtcaca tttactattt accgagtgct   25680
ttaaagatac ctgttgtcat ccgcaatact ctaaacaggt gttcagaatc tcttgtaaag   25740
gagctggcca agcttattgc atgccttttgc attgcttgca tctatgggcc aaattaagct   25800
tttttaaaag aagttaaaaa tcaaatatatt tcagctatta tatgtatggg ttaaaaaagt   25860
tggaagcatt agataaggac atgaatatat taatgtgggt taggctgttt tgttagaata   25920
tataatgaag gtaatgttaa tgtagaattg aacaattatt taaataagtt ttacaaatgg   25980
tttgttttta catttaccta tcttaatttt atgtcagaaa gcctgactta aatactctaa   26040
ccatgatcat gaatgccttt gtattatgta atgctttgtt taagtcttcc tttctttctc   26100
```

```
tttgtccaag aaatataatc tcacacctga ggcgacggca tctttgaaaa actagtgatc  26160
aagaataacc agataaacat gatgggcata agggtcatga ccaaaaagat ctctcagtgg  26220
catctgtatc actaaatatt aggaatattc attcatttca gtagtgcctt ctgtctttgt  26280
gtttattgtt gtaagtgtga aagtgaactg aatactccat gatccatctc tgaaaaatat  26340
tgcctaacct aaatcaccag cttttcctgtg catggatat cctgtcttct gaagaactgt  26400
ttttgctttt ctggagcatg aatgtttgtt gttttagagc tctttgtatt cgagttcata  26460
ttttatcctt attttagtg cttttcctct aagtagcttg tggaaattat ttctgagtaa  26520
ttgaagcttc tgtgtcaaca taatagtttg ttgacataag aaacagtgtt aagaaattat  26580
gcatttggaa aaaactgaag gtgatttttt ccagggaatt tgtttcctgg acttgggatt  26640
tcttgtgcaa attttcccca ctagtttgtt tttctctact attattttca taaaggagca  26700
gcaccagaat agtccttaat atcggagata gctgttgtgt cacttcctca tgctgacata  26760
tttactagag ggtaaaatta ataaccttct agtaagagtg gcagtcgaag ggaagggctc  26820
atctgacttc tggaaaccta tgttaaaata cagtgctttg aaccttgatc atgggctaat  26880
taggttggaa atgaaactag agaccagata cacccaagga aacttttggt agttatttta  26940
ctttataagt cacaggaaat gcttgtgtac tttcctgtgt tccttaaata gttgcactta  27000
aattacctct ttgaaactga atgaagagac agagagtatt ttttttcttt ccagaaataa  27060
tacttgttta tacctgtaat agcaatgaaa ttttgtttct tttgagacag agttttgctc  27120
tgtctcccag tctggagtat agtggcagga tctcagctca ctgcaacctc cacctcccag  27180
gttcaagtga ttctcctgcc tcagcctccc aagtagctgg gactataggt gcactaccat  27240
gcccggctaa ttttttgtatt tttagtagag aaggggtttc gccatgttgg ccaggctgat  27300
ctcgaactcc tgacctcagg tgatctgccc gcctcggcct cccaaagtgc tgggattaca  27360
ggtgtgagcc actgctcctg gccagcaatg aaacttgagg ctatgcgaat gaaggattgt  27420
tctaagagtg taaactataa ggcgaggagg attaaataaa aaaacagaga taggctctca  27480
aagcaccaaa tagtatgatt aacagattct tgtgtatcac atttgaaatg ctttatgttt  27540
tggctttatg ttgatgagtt gaaaacccgt gttttgttt atgttgtttg gttttgttt  27600 ttggctatct tatgtagaaa ggcatgtaag ggatggcatt gattattcta ataattttt  27660 actgggaaag ctttcccaag atttttgaata gctaaatgtc aacttttttc ttaatagtat  27720
tttcatctca gcctagtgac gatgaatcaa gtagtgatga aaccagtaat cagcccagtc  27780
ctgcctttag acgacgccgt gctaggaaga agaccgtttc tgcttcagaa tctgaagacc  27840
ggctagttgc tgaacaagaa actgaacctt ctaaggagtt gagtaaacgt cagttcagta  27900
gtggtctcaa taagtgtgtt atacttgctt tggtgattgc aatcagcatg ggatttggcc  27960
atttctatgg taagtactca aaaatgtgtt atacataacc tgatgggata gtgtagagga  28020
acttaagagt gaggactctt gggatctgtt ttcagtgcca ttattaaatg tgtggccttg  28080
aaaacttgaa gcctgtttga gcctcagttt tctcattcgg gaagtgggtg ctgcctatct  28140
cacaaagctt tttattaaaa taaggtagta gttattaaga aatgtaagga taataaccat  28200
atatgtttgt gactctttta aagttaaaag attggaagat taaaaatctg aaatgctcac  28260
catgaggcaa atcatttaca tttagaatca cacttaaact aagttgaagt gtgacttat  28320 taggaagatt atttaaatcc cagttgaaat agttacattt gaaatgtgta aataataagt  28380
gttcattatt tctactttga ggtttcatgt aagtatcata ctttgtaact ttcattgttg  28440
```

```
cttctgtgat tcacatgaat tgagagtttg tcatctttgt tcttatactt tgctctttat    28500
tatgattgat actgtttata tatgttgatt atcttatcaa ttcaaagctt ttaaatgcct    28560
tttgggtgag aagaggaagg tattctattg gtgttacttt acttttcat ttaggagcct     28620 cacccattga ctctctcctt tgttttttgg agacggagtc ccactctgtc gcccaggctg    28680
gagtgcagtg gcacaatctc agctcaatgc aaactccacc cccagggttc tagcaattct    28740
cctacctcag cctccggagt aactgggata acaggcgccc gccaccatgc ctggctaatt    28800
tttttatatt tgtagtagag acggggtttt gccatgttgg ccaggctggt ctcgaagtct    28860
tttttttttt ttttcttttt ttttgagacg gagtctcact ctgtcgccca ggctggagtc    28920
cagtggtgcg acctcggctc aatgcagcct ctgcctctgg gttcaagtga ttctcctgcc    28980
tcagcctcct gagtagctgg gactacaggc gcctgccacc acgcccagct aattttttg    29040 tattttagt agagacgggg tttcaccatc ttggccaggc tggtctcaat ctcctgacct     29100
tgtgatccac ccgcctcggc ctcccaaagt gttgggatta caggcgtgag ccaccgcacc    29160
cagccagtct gaactcttg acctaaggtg atccacccca ctcagcctcc cagagtgctg     29220
ggattatagg catgagccac cgtgcctggc ctgagtctct tatttaaggt atgtgtttgt    29280
acaatgactg gagtatttga aacctgaact ttgactctct ttgctatatt ggaatttggg    29340
gtagagacac tttaaaagga aatgtcttag atcttgtcaa cttcccaaat tttagcttgc    29400
tttacattaa ctactttag atttttttgc ctgcataatc cacagtctta acttttcgtt     29460
ttgctagttc attcgaaaaa tgtatttctt atgcaaagat tgaagaatta catgtaccct    29520
atgtggattt gtggaaaagg tatattattc aacatagcgt aatgttagaa taaacttaat    29580
gaagacaata cctgtttaaa gtcagagctt gcaagatgtt tcttgtattt atattaataa    29640
aaatatgtat ttagatttct gatggatacc tgcttgaatt taatactgag atactattat    29700
ttgtatcctt tcttgaaatt tgttgtaata agatttgatt tgaaatatat atttaccttt    29760
atagactatc tagctgaaac aatcaataag tatttgagta tgattttccc tccacaagta    29820
aacatgaggg taacaatgga gaagatctta tcttaatctt ttttttcttac ttcaaaaaaa   29880 attggatagt gatttaaagt gttaatccaa attgcattaa aacttcacca tttacatgac    29940
ctttgaatat tttgtagaaa ataattttta cagaagtgct ttcaaaatga gaagttactt    30000
ctctgttatg taggattttg gttattagta aaatttaccct taatagttaa ttaataaaac   30060
attgtccttt acttgatatt agccttttca ggctatgaaa agcctggata acatattatg    30120
aagtaggcct acatagtaat gagattagtt gaattaacat acaagacctg acctaaatga    30180
cttttccaag tcactactta aaagacatca ctttttttt tttttgagaca gagttttgct    30240 cttgttgccc aggctggagt gcagtgcgtg atctcggctc accgcaacct tcgcctcccg    30300
ggttcaagca attctcctgc ctcagcctcc cgagtatcta ggattacagg catgcaccac    30360
catgtccagc taattttgta ttttttagtag agatggggtt tctccatgtt ggtcaggctg    30420
gtctcgaact cctgacctca ggtgatctgt ccacctcggc ctcccaaagt gctgggatta    30480
caggcgtgag ccaccgcacc tggcaagaca tcacattttt taatttcagc actgatctca    30540
acattctttg gagttgattt cagagccgtt ttgaattttc tattcaccgt aaagtcggtc    30600
attgcatccc atagtcattc attcacttta taatttatt tttttttgag acagagtctt     30660
gctctgttcc ccaggctgga gtgcagtggt atgatcttgg ctcactgcca cctccgtctc    30720
ccaggttcaa gcgatccttc tgtctcaccc tcctgagtag ctaggattac aggcatccgc    30780
cagcacgcct ggctactttt tgtatttta gaagagatga ggtttcgccc tgttggccag     30840
```

-continued

```
gttggtctcg aactcctgac cttaagtgat ccgcctgcct cggcctccca aagtgctggg    30900
attataggcg tgagccaccg tgcctggccc gctttataat aatttaacaa taccatatta    30960
ctaattgaat cattctgcgt ttgccagccc tggtgccata cagatttgaa ttggcagatc    31020
tatactgcag ggaagagaaa gctagcatga ctaaggatag tgaggcagtg tactccaggt    31080
atttggttct gaaaatgctt ccagaagttt tattaaaaag tttcatgaga aagcagtctt    31140
tcttattctt acatttgctt gtgactatca acattccaaa tcatcaatgg agttcaattg    31200
atttggtttt ctcctcgagt tgctttaagt attgatagac tacccggctc ttcggcagac    31260
tattatataa caagatatct agatgctaag ttatagagca cagaatgaat tacagctcaa    31320
agggtacact tactgaatta tcctggaggt ggtaagattt aagttgtgtc taatcatagt    31380
aagtttatga tagactcaag ggaaggtgga acattccagc gacagagaat ctgataacct    31440
gaggaagacg taatcttggg tttgggagca gtgaaaagac tgcttggact acagcagagt    31500
gtaggtattt agaaataatg gaataggtgg ggtgctatta tagtcatccc ttgatataca    31560
tgagggatgg gttccaggat gcacccccat accaaaatcc atacgtacta aagtcccttg    31620
actgcggacc tcacatatat gaaaagtcac ctctccatat acctggatttt tgcatcctgc    31680
catgtagttc aaactcatgt tgctcaaggg tcaactgtgt attgtaaaac gtcttggaat    31740
ctagatagga aagtttgatt tattgagtaa cctgctatca ggttagagaa aaaagtgccg    31800
gaactttttg ctggtgtgga aaaggtggta tggaaaaatg tagaatagtc agtcagttaa    31860
gagttctgta atctggatat ttggtgagga ggaccttgac aattggaata acagtgggaa    31920
tggaataagg gacattgaag gaataatgga aaataatggc aatttattaa attgtagaaa    31980
atgtgctagc tgcttcactt ttggagttgg ggttactggg gaagttttgc cagatgataa    32040
atagatggta agcacagttt ggtttggttt tacccaaatt tgttctagac aaatttggtt    32100
tggggcaggt gttgaggttt gattttttttt tttttccac cctacaaaca ggcccccctac    32160
acagctggat gtgttggcta gaagctctga tgagaagtta ggacaagatc tgtagcttgg    32220
aattcttaat aggagtgata gcaaaatctg acagcgctgc aacatggtaa ataggcagc    32280
atttgtagac atgactaggc caaagattgt atcttgagga taagacttta ggtagctgaa    32340
ggtgcaggaa aaaccccccaa gtgattagtc agtaatattg taaaaggcca cattaagaca    32400
gtaatcaagc atatgctata ttatactatc ttgaattcag acctcaacac agttttagat    32460
tattttccag tgggcaaagg aattaatctc agcagtttga aatagaaatt gcagaagttt    32520
tctgttactc tgggaactat agataaattt caacatttga aaaaaatctg ggattctgct    32580
gagtaatttt gaaacaagct tgccgtgctt ctataaattg agaaatctaa agagaggaaa    32640
tgaattctaa cacagaatat catagctaga ctatgtaaca gttacctgta aattggcaaa    32700
agttgttttc ggtgtttttc aagatgtatt gaagacattt aaaataattt ttatagcagt    32760
aagggaagaa atagtgatca ctgcatcctt tctttgtaaa attctatagt atctatactc    32820
agtagatgta atgttaaggt tgctaactgc attttgcctt attttttgatt tcgtggtttt    32880
ttccccccat acatgacgca tgtgaatagc atgtctgagt aaagtaacat tttgatttt    32940
aggatgaaaa tatgaagaat cctagttggt ttaagattct tttttgaga cggagtttcg    33000
ctcttgttgc ccaggctgga gtgcagtggc gcgatcttgg ctcaccacaa cctccacctc    33060
ccgggtttaa gcgattctcc tgccgcagcc tcccgagtag ctgggattac aggcacatgc    33120
caccactccc tggctaatat tgtattttta gtagagacag ggtttctcca tgttggtcag    33180
```

```
gctggtctcg aactcctgac ctcaggtgat ccatctgctt tggcctccca aagtgctggg    33240
attacaggcg tgagctactg tgcctgtcca attcttttat cactgttggg ataaggacag    33300
tgctactcca gtacagattt aaccattgca gaattcttaa caaatttggc cttgagaatg    33360
gtgcacaatc accattagcc aattattttc tgtgctgtac ttttttgggct ttgttgtatc    33420 cttaaggcaa aatagtaaaa aaaaaaaaaa ttttcatttt tccttattga cttacgacct    33480
gtgaaaaaat accagggttt gttcatttct ctgtataagg gaggctgaaa cacttttttgt    33540 acttaaaaga taaccccaaa acaacaaagc tgagtgcctt caatatagta agataagaac    33600
attacataaa ttgttctctt ggttagagcc atatgggctg gcctgtgtgt tttaatacaa    33660
aagatagtga actgcttaaa tgttcctggg tgtatgtaaa taaatgtttt taagaactag    33720
cctacttggc cttacttata ttacgttaac gttcaccacc atttgatgaa tgattgatca    33780
tgggctttca tttactttttc tttttttatt ttattttatt tttattttta gtagagacag    33840
ggtttcacca tgttggccag gctggtcttg aactcctgac ctcaaatgat ctacctgcct    33900
tggcctccca atgtgctggg attacaggcg tgagccactg tgcccagcct cagttactta    33960
ttctctattt atgtaatcag aattttttaaa gaacggtgaa atgctgatac tctgaatgaa    34020
atgattgtca agattacata ggttatggcc aggcacagtg gctcacacat gtaatcccag    34080
cactctgaga agccaaggtg ggtggatcac ttgaggccgg gagtttgaga ccagcctggc    34140
caacatggca aaaccctgtc tctataaaaa attagttggg cctggtggcg cttccctgta    34200
gtcccagaca ctcgggaagc tgagtcacga gaattgcttg aaccagggag gcagaggttg    34260
cagtgagctg agatcatacc agcctgggca atggagcaag actcttctca aaaaacaaaa    34320
aaaaaacaaa aaaagacta catagcttat atgcagatta ccaatattaa aaaatacata    34380
aaacatttaa tgataatatt tttgttacat acctttaata aaaatattta ttttaggcac    34440
aattcagatt cagaagcgtc aacagttagt cagaaagata catgaagatg aattgaatga    34500
tatgaaggat tatcttttccc agtgtcaaca ggaacaagaa tcttttatag attataaggt    34560
atgtaccact aacagtattt aaaataattg ttagtaatta ttttgcttat tagttagagc    34620
ttattgtgct tattagtgca gattagtaaa tcagtaataa tgctgatcat tgttgaattg    34680
agtacgggta tttagtgtgt cctagtcatt gtcatgagtg taccatatag agtatttctc    34740
ttattctcac aatatgtgaa ttaagcaatt actaactttt ataggtggaa aagaggttta    34800
gaaaagttaa gtgactttct caaggtagca actggcagag ctagtttgtt tttgtttgtt    34860
tgtttattta tttgagatgg agtctcgctc tgttgcccag gctggagtgc agtggtgcaa    34920
cctcaggttg ctgcaacttc cacctcctgg gttcaagcga ttcttgtgcc tcagcctccc    34980
aagtagctgg gattacaggt gtgcacctct atgcccggca aatttttttg tatttttagt    35040
agagacgggg tttcactatg ttggccacgc tggtcttgaa ctcctgacct ccgtctaccc    35100
acctcagtct cctaaagtgc tgggattaca ggtgtcagcc accatgctcg gccatggcct    35160
ttttttgttt tgttttgttt tgtttgggag agctaattaa ttgattctaa ggatttgact    35220
taagaactct tatccctagc tgctattttta tagttaacat cttttataag tgacatttta    35280
tatgtgtata tagacatttt tattaacatt attttcacag agcgaagcaa acattttcag    35340
ttggcaggag ggaaagagga gagttttggt tttatagcct ctctaagatc ttctcttgat    35400
caggggacat agctattcct ttccattgtt tttttttatt ctgatggaag ggagagcatg    35460 ttatctttt ctgcctataa ctcacctaga tctcgtctca caggactgta ctgtccattc    35520
tgtcattacc taacacctct gtgggtttat gaggatcagc aaaatagctg gtctcttatc    35580
```

```
tagttttttc ctaagaaggt tgtagagaga aatgcagggt agaaaaataa gctatgtctg   35640
ggtgtggtgg caacctctca aattcccaaa gttggtaacc ttgggaagcc aaggtaggtg   35700
gattgcttga gcccaggagt tcaagaccag cctggccaat atggtgaaac cttgtctcta   35760
ctaaaaatac aaaaatcagc cgggtgtggt ggcacatacc tgtaatccca gcttttggg    35820 aggcttaggc acaagaattg cttcaatcta ggaggcagag gttatagtaa gctgagatca   35880
cactattgca ctccggcctg gccacagag  gaagactgtc tcaaaaaaaa aaaaaaaaa    35940 aaaaaaaaa ggaaaaggaa agaaaagtaa gctattgttt tttccttcat ttttccaccc    36000
ccaattctca cacttaattt atgtatgctt cccttacagg ttatatttct tgaaaagaca   36060
aaaatactac tttgtaacta aattgtatct ttcagggagg tacttctccc atccaagtac   36120
taaccaggcc agaccctgcc tagcttctgc catcagagga gactggcggc atttagggtg   36180
ttatggctgt agacacaggg aggtacttct gaagttaatt ataaatagtt cagttttcc    36240 tacctgtatt agaagatgcc attttcttct tcaccacagt gttttctggt tccataggat   36300
aacattggct tttggaaaac tcaccacgca ttaacctcta gagagagttt gtagtttggt   36360
ttgggtttgg gttttttttt tgttttgttt gttttttttc tgagatggag cctcgctctg   36420
ttgcccaggc tggagtgcag tggcatgatc tcagctcact ggaacctctg cctcctgggt   36480
tcaagtgatt ctcctgcctc agtctcccaa gtagctggga ttacaggctc cctccaccat   36540
gcccggttca ttttttgcat ttcagtaga  gatggggttt cactatgttg gccagggtgg   36600
tcttgaactc ctgacctcag gtaatctgcc tgcctcggcc tcccaaagtg ctgggattac   36660
aggcgtgagt cactgcgcct ggcctgtttt ttttgttttt gttttttaag acagggtt     36720 tcattcttat tgcccaggct ggagtgcagt ggtgtgatca tggctcactg ctgccttaac   36780
ttctgggctc aagcaatcct cctggcttag cctctcaagt agctgcgacc acaagcacac   36840
gccaccatgt ccaacttggt ttttaaattt ttcatagaga tggggtctca ctatgttgcc   36900
caggctattc tggaacttct gggttcaagt gatcctccca ccttggcctc aaaatactgg   36960
gattaaagga ttgagccact gtgcccagct agagagtcag ttttacaga  tctcttattt   37020 ctggctgtta agtgtggatc agatagattt tgaagctctt tggaagacct ggtcaggatc   37080
tgcttatcaa tcacttatgt caacatcata tttactgcac gaggaatgct gtactcttct   37140
ttcatcctgt ggcttcctgg gcttgtgcat ttcaagatta tgccacacca gtgcatcagt   37200
ctcttctact ccacagtcca ctgctgttgg gtagaagaaa tttctttttct ctcatacagg   37260 tagagcagat gaaatgactg tgattaaatt ttaaatcttt atttgttctc tgaagattaa   37320
tgagccagaa cgtgaagcag tcatttcaga tagttatttt tcaagtgtat attagtgtca   37380
ttctcttaaa ggacttgtat ttttttttcc tttttttttt ttcttatttc tgaatccagg   37440
taattgactg ctctgactca aatgggggtaa ccataacgtt tgtgataaat taagccaaat   37500
ttaagtatca ttttgcagat ttatacatag gatattttta actcgatgta taatgcttta   37560
agaacctgtt gaaccatatt gtttaagttt tgactgtttt tggttagatt ttgttactaa   37620
tgcatatgtg taaagaaaa  ttcaaatcag tcaaggatac ccttattgaa gcagtaaaat   37680
tctataagcc gaattgacca tgatttctac cacgggtgct gactttcagt tatagtaatc   37740
tatagattaa tcttcagagt tatattaatc tgtacagatt acagaacttc aaaaatttac   37800
cataaaattg gataagttag ttataaatgt tcaagattca gtctgtcttc taacatggtt   37860
atagaattta tggcttatct gtacttactt agaaatgtta attgcatagg actaaaatgt   37920
```

```
ttcaaatagg actaagattg ttagaatttc atcctttgaa gggtacactg agtacaaaca   37980 attttttgaag ccgtaagtca gctctcgatg taattttact tttatttttt atttgttttt   38040
tttttgagac agagtctcgc tctgtcgcca ggctggagtg cagtggtgcg atctcggctc   38100
actgcaacat tcgcctcccg ggttcaagcg attcccctgc ctcatcctcc caagtagctg   38160
ggactacagg tgcatgccac catgcccagc taattttttgt attttttagta gagatggggt   38220 ttcaccacgt aggccaggat ggtcttgatc tcttgatctc gtgatccacc cacctcagcc   38280
tcccaaagtg ctgggattac aggcatgagc caccgcgccc agctaataat tttacctttt   38340
ataaaaggta atctcttttc ctgattcaga aaagccttta gtcctgcaag ctctagctaa   38400
ctttctgtct tttaaattct tccagccagg cgcggtggtt catgcctata atgccagcac   38460
tttgggaggc tggagagtcg cttgaactca agaggcagag gttatagtga ccgagattg   38520 cgccactgca ctctagtctg acgacagag tgagactcca tctcaaaaaa aaaaaaattc   38580
ttacaccatg ctgtagttct caatttgatg tagctctctg ctctgcgttt tcttgcatat   38640
gaaccttgta tttcccaatg tttatactat tgaaaatact acccgggggg ttgtatctgt   38700
agaagtaaag acacaaaagc ttatggggta ttatatcttg aagatttaaa ttcagctttt   38760
aaagcatttg acattttatt tcttctcttt caaaaaaaat gtagtcattg aaagaaaatc   38820
ttgcaaggtg ttggacactt actgaagcag agaagatgtc ctttgaaact cagaaaacga   38880
accttgctac agaaaatcag tatttaagag tatccctgga aaggaagaa aaagccttat   38940 cctcattaca ggaagagtta aacaaactaa gagaacagat tagaatattg gaagataaag   39000
ggacaagtac tgaattagtt aaagaaaatc agaaacttaa gcagcatttg aagaggaaa   39060 agcagaaaaa acacagcttt cttagtcaaa gggagactct gttgacagaa gcaaagatgc   39120
taaagagaga actggagaga gaacgactag taactacggc tttaaggggg gaactccagc   39180
agttaagtgg tagtcagtta catggcaagt cagattctcc caatgtatat actgaaaaaa   39240
aggaaatagc aatcttacgg gaaagactca ctgagctgga acggaagcta accttcgaac   39300
agcagcgttc tgatttgtgg gaaagattgt atgttgaggc aaaagatcaa aatgaaaac   39360 aaggaacaga tggaaaaaag aaagggggca gaggaagcca cagggctaaa aataagtcaa   39420
aggaaacatt tttgggttca gttaaggaaa catttgatgc catgaagaat tctaccaagg   39480
agtttgtaag gcatcataaa gagaaaatta agcaggctaa agaagctgtg aaggaaaatc   39540
tgaaaaaatt ctcagattca gttaaatcca ctttcagaca ctttaaagat accaccaaga   39600
atatctttga tgaaaagggt aataaaagat ttggtgctac aaaagaagca gctgaaaaac   39660
caagaacagt ttttagtgac tatttacatc cacagtataa ggcacctaca gaaaaccatc   39720
ataatagagg ccctactatg caaaatgatg gaaggaaaga aaagccagtt cacttttaaag   39780 aattcagaaa aaatacaaat tcaaagaaat gcagtcctgg gcatgattgt agagaaaatt   39840
ctcattcttt cagaaaggct tgttctggtg tatttgattg tgctcaacaa gagtccatga   39900 gccttttttaa cacagtggtg aatcctataa ggatggatga atttagacag ataattcaaa   39960
ggtacatgtt aaaagaactg gatacttttt gtcactggaa cgaacttgat cagttcatca   40020
ataagttttt cctaaacggt gtctttatac atgatcagaa gctcttcact gactttgtta   40080
atgatgttaa agattatctt agaaacatga aggaatatga agtagataat gatgcagtat   40140
ttgagaagtt ggatgaatat atatatagac acttctttgg tcacacttttt tcccctccat   40200 atggacccag gtcggtttac ataaaaccgt gtcattacag tagtttgtaa catttgtaga   40260
ttggatagca ttttttatgat ttgatgagtt tcttgtaagg ttaccgtttc taagagttgt   40320
```

```
gctttatggc cactgagaga attcagaata aattgaaaga tggagtctaa aaattattag    40380
ctgttacaaa tggaacattt cattataacg tgatcacttt gacttgagca aatggtttaa    40440
tttttatctt aaaaatcagt taagaatata taaaatccta ctttggccaa gtttgtttct    40500
tttcattata gtttatatga aaagatcacc ttaagtgaaa ttattttcct ttaatctttt    40560
atgtatttat tcactttggg aagctaggaa tgagcaacac aaattttact ctgaagtcag    40620
aagagctcat atataataat tctaatgtcc cacctatttt cacttgtcca ttccatgtac    40680
cagcttagtt atgatactta gtcacataat tatctttgat aaaggtagag cacaaagag    40740 gcaaactaag caagtcaaat tctaatgtgt gtacttcata ataattttttt atccattttc    40800 atctttatat tctgtaacat gaaacttacc taatcttcaa atgttagctt catttttttac    40860 ctttgaaata cttaatcttt ctgaataaat ataatgtgtc tataaaataa tgagactgat    40920
tctggtgtct ttagtcatta agctggtatc tagtcctata atgaacaaag gtgaagctgc    40980
cttgaggaga caagtgaaaa attttttgctt caaaggagct cacaagctaa gtaaataaat    41040
gaaattaagg tatggggcat ggtggcctca ggctgtctgg aggtgtttgg aaaggcttct    41100
tgagtgaggt ggccttttgaa ctgaacttag ttttttaaagt agcttttgga agagaaatga    41160
ggatttgcta tgcagacagg gaagggaatt tcacttaaaa ggaaggtcat ttggagatgt    41220
gaagatacac tgctttaagg aagcagggta gagctggagg ataagagatg cagaccatga    41280
agggccccat tttatgctaa aggttttgtc ctgtaggaca tggagaactt ctgaagaatt    41340
ttcaaggcgg gtgggataag attatattgt attttagatt acagtagtcc ccccttatct    41400
tcaggatata tgttccaaga ccccccagtgg atgctggaaa ccagggatag aacataattc    41460
tatatatact atgcatgaat ttcttttttcc ttctttacaa tctcacacat aggtttgttc    41520
ttactataga tcttaccaat ctcagcatac ttttatttct cttgagaacc ttcacccttt    41580
cacttaaagg aggcgcttta tagcttctct ttggcatatc caaatgccag catcactgtt    41640 gtatttggg gtcattatta agttacttaa tcatccttaa tccttatctt agggatactt    41700
gaacacaaac actgtggtag gataacagta tatctgatta acagactgct actaggtgat    41760
taatgggtgg gtagtgtaaa tacacaagaa aaggatgatt cacatcccat gtgggatgga    41820
gcagaactgc attatttcat tacattactc agaacaggca tataattgaa aacttatgaa    41880 ttttttttttt taattatttg agatggaatc ttgctttgtc agccaggctg gagtgcagtg    41940
acacgatctc agctcactgc aacctctgtc tcctgggttc aggtgattct cctcccctagt    42000 ctcccaagta gctgggacta taggcacgtg ccaccacacc cggctaattt tcatattttt    42060
agtagagatg gggtttcacc atgttggcca ggctgttctt gaaatcctga cctcaagtga    42120
tccacacatg tctacctccc aaagtgctgg gattacagtc gtgagccact gtaccccgcc    42180
taaaactgat gaattattttc tgaaattttc tatttaacat tttcagacca cagttgacca    42240
caggtaacgg aaacctcaat cacagaaagt aaagccgtgg atacggtggg actaatgtat    42300
tggtagcagc ctagaggatt gatgggaaag gtatgaagct agaaggtggt caatataata    42360
cagacatgag ctgatgaaca tctaaactgg gactatacta gtaggagagg aaaggaaaaa    42420
acatttggaa aatagtaaca ttgatatttc ttgtgaagga gaagtagaaa gtaacagtga    42480
cttctagatt tctgggttgg gtcatctgtt gttggatagt agtaccactg agatagggaa    42540
ttcaaggttt ggggcaaggg taattggaga tgagaattgt gtttggaggt aactactgac    42600
attcaagtgg agagggttag ttggcagtta gttctatggt catctctttt gccgagactg    42660
```

```
tatatttatc agactcctgg gagaacacca acatccatgg ggttgtaggg aaggctaagg    42720
acaagagtgg ggagtggtac cttgaaaatc caaaagccat ctcaagtaaa aggaataaat    42780
gtgtcatgct ttttaaaaag ttgatgtgcg gaaaatgttt tcttggcttg gaaactgggc    42840
ggccagggga tgacagtatg gacttccagt gaagtagtga cggaagcctg atcatagaca    42900
ttaaggaaag cggtgtaggt gttgtgagct tttgctgtaa gaaaaagttg agacttttgt    42960
tttgctttgt ttgtgagaga tgtgtatgta tttctgctga gtgataaagc cagcggggag    43020
ggactgattt ttataggaaa ggaggaaaaa taatggaaac acatctcatt attttattgt    43080
cacatttctt ttctttgtta tcttttgagt gtttcccttt tttgccagta gagttattgt    43140
ctattttttc tttctatagg acaaaaaaac taatacagac tcctttattt ttatatggat    43200
atactaggat tgtaattcag atatttaata tcttttatca gtgttcagat catagattaa    43260
tggagaaaac atttaaaatt gttttaaatt taaatacatt gaactctaac atagatgaaa    43320
aatgtgttta ctgctttcag tcgacctgat aaaaagcaac gtatggtaaa tattgaaaac    43380
tccaggcatc gaaaacaaga gcagaagcac cttcagccac agccttataa aagggaaggt    43440
aaatggcata aatatggtcg cactaatgga agacaaatgg caaatcttga aatagaattg    43500
gggcaattac cttttgatcc tcaatactga ttcacaattg agttaaatta gacaactgta    43560
agagaaaaat ttatgctttg tataatgttt ggtattgaaa ctaatgaaat taccaagatg    43620
acaatgtctt ttcttttgtt tctaagtatc agtttgataa ctttatatta ttcctcagaa    43680
gcattagtta aaagtctact aacctgcatt tccctgtagt ttagcttcgt tgaatttttt    43740
ttgacactgg aaatgttcaa ctgtagtttt attaaggaag ccaggcatgc aacagatttt    43800
gtgcatgaaa tgagacttcc tttcagtgta agagcttaaa gcaagctcag tcatacatga    43860
caaagtgtaa ttaacactga tgtttgtgtt aaatttgcag cagagcttga gaaaagtaca    43920
ttgttctgga atttcatcat taacatttta taatcttaca ctcacttctt gtcttttgt    43980 gggttcaaga gccctctgac ttgtgaagaa tttgctgccc tcttaagagc ttgctgactt    44040
gttttcttgt gaaatttttt gcacatctga atatcgtgga agaaacaata aaactacacc    44100
atgaggaaaa ctaaaggtct ttatttaaaa tctggcattg tattaacatg taattttata    44160
ctatgtggta ttttatacat ttcctcagta gtgatatttg gtaaagcagt tcatacagct    44220
tttttctaag ttccatgaat cttacccagt gtttaccgaa gtatttaagc agcatctgaa    44280
tatttccacc cagcaatgtt aatttatcta ggaaagttca gaatttcatc gtcatgttga    44340
atttcccttt taacttccgt tcatagacat atatgtgact tccaattcga ccctctggca    44400
agtgagtgtg gaagaaaaca gcagttcttt tataattgct tgaaattagg aaagcgctta    44460
tttcctagaa gcaaataaat gtttgagtaa ataaaggcta cattttgctg agtactgttt    44520
cagtcaattt tagaattgcc tattctaatt gctgtctaca acttttttgct taataaaaga    44580 attaacttat aggaagtaaa atactttgat agttacagaa ctggggctaa ttttgactgg    44640
agaaaagact aattatgaaa tgtgggttga aacagaccat aaaaaggtta tattatctat    44700
ttacctgagg gtttcctaaa cctggggtaa aattaaaata ctgagttttc ctctttttca    44760
tgtttactta cctcttccaa aatgccgaag gtgatcaagt gagtaggcaa tgatgcatca    44820
tcatgaaact ctctatgtaa ccagtttaag ggatttaggt aaaatacatc tgcttcatca    44880
agataatgac ttttccagt caggtctggc gggcactgga gaaatctcat gggaagtggg    44940
cagtgaacat ggctatgaaa agaaaagtta ccataataaa tacaagtaaa acatgaaagt    45000
tttcattagt cttaagatat gtcatttata cttagcaaaa tgtgaaatct gaatctgtaa    45060
```

-continued

```
actgtgttgc agttaagtga agaagcaagc ctttaactca ttttctcaaa gataaaaaaa    45120
acatgattct tataccatgt acctatgcag cagcagcagt ataacctata agcccaaact    45180
agtgcataga agtccatttc aaggagggaa gtaggtcagt aggggactc aacattctgt     45240 agcattggta ttctgttccg gaaacataaa tggtcctcag gaccaggtaa gttaacttgt    45300
taataggaga gtaattctcc ataggtgtat ttgataaagt aggaaactgt gatcataatc    45360
agaaaggatt cttctctct tcccttctg ctctgatagg ggatggatca catacttata      45420
tggcaagttt ttttttttg aagacaagag tttcgctctc gtcacccagg ctggagtgca     45480
atggcgcaat ctcagctcac tgcaacctcc acctcccagc aattctcctg tctcagcctc    45540
ccaagtagct gggattacag gcgcccgcca accacgcctg gctgattttt gtatttttt     45600 agtagagatg gggtttcacc atgttggcca ggctggtcct gaactcctaa cctcaggtga    45660
tccacccgcc tcagccttcc aaagtgctgg gattacaggt gtgagccacc acgcccagcc    45720
acatggcaag tttgaagtgt tttttttttt tatttaagat gattgagaag tagagagcaa    45780
catatgtcca ctgattaaca tccaaataag taatggtttt attgtggcat agaaagacta    45840
gagtaggccg ggtgcagtgg cttatgcctg taatcccaga actttgggag gccaaggcat    45900
gtggatcact ggaggtcagg agttcaagac cagcctggcc aacatggtga aaccctgtat    45960
ctactaaaag tacaaaaatt agccgggcat ggtggtatgt gcctgtagtt ccagctactc    46020
aagaggctga ggcaggacaa tttcttgaac ccagaagacg gaggttgcag tgagctgaga    46080
tcatatgcca ctgcactcca gcctgggcga cagagcaaga gtctgtctca aaacaaaaaa    46140
aagattagag tataaaaaag atggattcat ttctaatacc agttatgaca atttaagcca    46200
gttacttagg tcatgcaaaa agccatgttt ataattgcct taggaaaaat taaacctcac    46260
tgatacaaac atttaaaatt tccagttaga aatggagtta gtaattatgc aggaggttta    46320
tttatgaaat gcataaaaat taaatgtaca caagacctaa tagtgattta tttattggaa    46380
atgaaggtct tctttcaaag ggaagcagaa attcctcaga aaaagctgcc ggcctactct    46440
agtctttcta tgccacagta aagccattac ttatttggat gttaatcaag ggacagatgt    46500
tgctctctac ttccaagtct gatgcaaaat aggcatcaga cttcctctc ttgtgtgctt      46560 tgaaaaggtg tggagaactt ggtgaactat tcaaagccta agacatcaac tgactacagt    46620
taagtataaa gaacatcttg gtacatctag gattcctgtt ctcctcagta ttatccctaa    46680
tgtgagcatg gagagtgaat gtccctttt cagccacata tacatatagt agggaatcct     46740
caagttgaaa ggatacttga tgtcttcctt ttagcctgtg gttttgcta ggatctccat      46800 ttttctaaac tgtatattaa ttactggcat taatgattag ttaaatagga gtattccaag    46860
tgttaaattc ccctaaaatg ataaccactg taattaaatt aattgaacgt gcataggaga    46920
cattaactcc agattgttta aagccagact gagttaaata gttatagatt ttatgtattt    46980
atttatttat ttttaggttg agtctcgctc tgtcgcccag gttggagtgc aatggtatga    47040
cctcagctca ctgcaacctc cgcctcccga gtagctagga ctacaggcat gcgccacaac    47100
acctggccaa ttttttttgt attttagtag agtcaggggt tcaccatgtg gcccaggcta    47160
gtctcaaact cctgagctca ggcagtctgc ccgcctcggc ctcacaaagt gctaggatta    47220
caggcgtgag ccacaacgcc cagcctggta tataattttc tgtaggaaat ctggctcctt    47280 tgccccctata ccattactgg gtaattagta actaatacag cttcctgaaa taaagcacag    47340
gaacaaatgg atgtcttttt aaaggccata catagttgag gcaatttag tatatttccc     47400
```

```
agaaacactt aattcaagca ttagaatatc atctagtcgc attccctaat ttttacagg    47460 tgagacaact gatgtccaaa gagattaaaa atctagttta aggccgggtg cggtggctca    47520
cgcctgtaat cccagcgctt tggggaggct gaggtgggcg gatcacctga ggtcgggagt    47580
tcgagatcag cctgaccaac atggagaaac cctgtctcca ataaaaatac aaaattagcc    47640
gggcatggtg gcacattcct gtaatcttag ctactcagga ggctgaggca ggagaatcgc    47700
ttgaacccgg gaggcagagg ttgtagtgag ccaagatcac gccattgcac tccagcctgg    47760
gcaacaagag caaaactcca tctaaaaaaa aaaaaaaaga agtctagttt aagatgaggg    47820
caataatcca gtagtaaatc tggactaaaa tccatgtttt ttttttttt tttttttgga    47880 gacagagtct tgctctgttg cccaggctgg agtgcagtgg tgcaatctcg gctcactgca    47940
aactccgcct cctgggttca tgccattctc ctgcctcagc ctcccgagta gctgaactta    48000
caggcacctg ccaccacgcc cggctaattt tttgtatttt tagtagagac ggggtttcac    48060
ccagcttagc caggatggtc tcgatcttct gaccttgtga tccacccgcc tcggcctccc    48120
aaagtactgg gattacaggc gtgagccacg cgcccggcc taaaatccat gttttaagat    48180
taattcaaat tgtgtaaaga tgtatcacag agatttgtag taaggtaagt aatacatgag    48240
tttctttact aagaagacta tcagatacct acaaattgtt ttatactgat ttaaatcaga    48300
attaggtgta agtaaattgt ttttaaagaa taataaagtt tacggccgag cacggtggct    48360
cacacctgta atccccgcac tttgggaggc caggcaggc agatcacgag gtcaggagat    48420
cgagactacc ctggctaaca cggtgaaacc ccatctctac taaaaataga aaaaattagc    48480
cgggcatggt ggcaggcacc tgtggtccca gctactcggg aggctgaggc aggagaatgg    48540
cgtgaacctg ggaggcggag cttgcagtga gccgagatcg cgccactgca ctccagcctg    48600
ggcaatagaa cagactccgt ctcaaaaaaa aaaaaaaag aaaaaagtt tatttaaaac    48660 attttctttg acacagttca agtggttttt aaaatccatc agtgaataaa tatgtgggag    48720
tttaaaattt atcatttgat cagtgaccaa ttaattcaaa tccaggaatc tgaaagggaa    48780
ttttaaagta gtcagtttca gtttcttaac agcatatagt ggaacatctt ttattacctg    48840
taataaggag tagagtggca aggcatcatt ataaatattg aagctgaaga tttattggga    48900
ttgttgtaac aaacttttg aatatgactc atgacatcaa gagtacctcg ttgatgaact    48960
aaaccagtat aaagggcgag gaacaaattt gataaaaaca ggaaacttag agctggtttc    49020
ttccatgttt tcaggtgggt taatgagtat cctatatgaa gatagacata ttgaacctta    49080
acactgacaa tcttttgtta tgttaactgc aaatacatct gtaattttta atggaaatag    49140
caaaaactgt aatactgtta tagacaaata agaaataagc aataagtcat atctctgacc    49200 attccaccatt cactactgtc atctaggtct tgactttttc tagtaaaagg tattgaggta    49260
tagtggaaag atgatggtta tggagtccaa caggtccaga tttgaattcc agttctagca    49320
caagtcgttt tactttgctg gtcattggga taatagtacc ttattcaagt gttagaaaaa    49380
atgtccagtg actgccctgg tacatagtag ttgctaaata aataggactt ttaattattc    49440
catttaccta cctctttaat ctcccaagca ctaataattg gtatttagt gtgtaatacg    49500 agtttcaata atgtgtccct ttaggaaaat aagccattgg gcacctggga gattttccgt    49560
aagtatatga gtggaagaaa aggtgctatg tcttacattt tttttcccac aacagtggga    49620
aattttgttt tcccactaca gtcaggcaat ttggagatgc tgaacaattt ttctttttg    49680 atttatgaaa gggattattc tgtggggcaa aacaaaacaa aaaaccaaag gaaaaaacca    49740
agtagaatga atagacgggt ataaaaggat aagtaaaagt ctctctcccc tctgatagtc    49800
```

```
ctttcttca gcaacagcca ctattaatgg acatattagg atctactgag aatacaaaga    49860
acaggccttt ccactggaaa agattaagct tattagtaag catgacattt tgttcataat    49920
ttacatacac tcttttttata gaactagata atagttcttt ttgaacttgg gtattcttca   49980
tccaaacctt ggtttgccca                                                50000
```

<210> SEQ ID NO 10
<211> LENGTH: 17386
<212> TYPE: DNA
<213> ORGANISM: Homo sapiens
<220> FEATURE:
<223> OTHER INFORMATION: human DYXC1 chromosomal gene region,
       nucleotides 200001-217386

<400> SEQUENCE: 10

```
aaatgttagt acaatactga atgggaccaa ggcagtgttt tttattttgt tcctcctatg      60
aatatgttaa tatcatccac agttcatacc tcatgagttg gaatatcaca tgtccatgtc     120
acctagtatt ttttaatcta cttgaaatag ttctgattaa agaataatct gaaaagtggt     180
gtggtgaaaa atgtagcaag attaagaaaa ctaagcctat cacttaaatc tacatttata     240
agatgtttga atggtaaaa tgaggaacct actaaaagga atgataatta gaactagctt      300
tatttgaaat aaaatagctg agatgagagg attgcttgag gccaggagtt caagaccagc     360
ctgggcaaca tagtgagact ccatttaaaa taaaaaaaaa ttagccaggc gtgatagtgc     420
gcacctgtag atccagctac tgggaaggct gaggcaggag gttcacctgt gctcatgagt     480
ttgaggggac agtgagctat gaccacgcca ctgcactcca gcctgggtga caccctgtct    540
ctacgaaaat aaaaatgaat aaaataggc caggtgcggt agctcacacc tgtaatccca      600
gtactttggg aggacaaggc aggcggatca cttgaggtca ggagttcaag accagcctgg    660
ccaacagagt gaaaccccca tctctactaa aatataaaaa ttagccgggc gtggtgtcag    720
aggttgcagt gagccgagat cacgccactg cactccagcc tgggcaacag agtgaaactg    780
tctcaaaata aattaaaaaa taggattcta aaagttcaac catctgtaat aacccccaatc   840 acagacacag cagatcccca aatataagtt gaagcactta acttaggttg gtaggctaaa    900
acaacatcta ctttagtagg ctcaaataca aaaagctaca ttaaagccct gtctttgttt   960
gtactgctat actggaatac ctgagactgg ctaatttata tttacttggc tcatggtcct   1020
gcaggttgta caagaagcat ccactggtga gggcttcagg ctgcttccac tcatggcaga    1080
aggtgaaggg gagtcagttt gtgcagagat cacatggtga gagagcagaa gcaagaaagt    1140
ggaaggtgcc aggctctttt gtacagccag cactcggggg aactctcatg gaacctaata    1200
taaggagaac tcacttacta ctccaggatg gtgccaagcc attcatgaag gctccacccc    1260
catgatcgaa gcatctccca ttaggcccca cctccaacag tggggatcaa atttcaacta    1320
aggtttaggg gacaaacgtc caaactacag caagcccatc ctacagcaag gcccgagaag    1380
atacagtttg ttctcaatta tttgaagata cttacaaggt gagcatgtgt aaagtgattc    1440
acttattaat aatttgttca ttcaaggccg ggggctgtgg ctcacgcctg taatcccagg    1500
actttgggag gccaaggcgg gcagatcgcg aggtgaagag atcgagacca tcctggccaa    1560
catcgtgaaa acccatctct actaaaaata caaaaattag ctaggtgtgg aggcgcatgc    1620
ctgtagtccc agctgaggca ggctgaggca ggagaatcac ttgaacccgg caggcatagg    1680
ttgcagtgag ctgagatcgt gccactgcac tccagcctgg tgacagagcg agatgtcgtc    1740
tcaaaaaaaa aaaaagaaa ctatggcact aggaatacaa tagtataggt gggtgacaca    1800
```

```
aaatgggaat acttggtgat caagactgtg aaaatagcac tctgggtaga atgctggaag    1860
ataacatgct tgtgtttcca gcatcttcag tactggtgag acagagcgtc tcttaagtta    1920
ggtaatgctt gccttacatg atggtgattt taactctctg agcttagctc attttaggat    1980
ggatcatttt agtgagaact gaatctccat attacttaga gaagtaatat aaagaaaatg    2040
ctgggaagag aaggaacagc tgaacaatgc cagggagagt caggtgatag cttagttttc    2100
ttggggacag tggatactga aacagttgcc attcaaaatt gtcttcaaca gtattatgga    2160
tccgatgagc ttttgtgtaa tattctggga gccttactac atgtcacagt attatttcta    2220
agaaaaaaat atttcaggtt ccaacttaaa aatgaagttt ggggataaaa ccttatttaa    2280
aatagaactg tctttatgat tattattttt ttgagatgga ctctcgctct ttcgcccagg    2340
cgggagtgca agtggcatga taccggctca ctgcaacctc cacctcctgg gttacaagcg    2400
attctcctgc cttagcctcc tgggtagctg ggattacagg tgcctgccgc catgcccggc    2460 taattttttgt attttaagta gagatggggt ttcaccatgt tggccaggct ggtctcaaac    2520
tcaggtgatc tgcccgccac agcctcccaa agtgctggga ttacaggcgt gagccacagc    2580
gcccagccag aactgccttt atttacatgt ttagcatcct ataagcatta ctatgcattt    2640
gacatataaa gaaatatct ttataatttc agttatcatc aaatgacttg tgcacatgtt    2700 agaaagaac ccaactttag agtataagtc aagagtcctg aatttaaggc ctctgagggg    2760
tttttaaacc ttctggcact gaaagcttcc aaagggatt tcagaaatga gttgctaaag    2820
gaagggttgg aaagattttc cagttccaat gctagactga gtgaaccaca agagaagcct    2880
aaggtccatg gttttcttat agaccagtag tattgtttca tcaatattta aaacaaatga    2940
acaagattcc agtaggtgac atccagtaag tctacttaat ggcacgcaca aatttgggaga    3000 tggagttctc actgaaataa tccaccctca aatgacctag cttcagaaag tgatcatccc    3060
caccacgtaa atgatgtgta tcccaatcac tgaagattta agactgtgtg tgtaccccag    3120
tgactaaagt ataggttcct tccttttaca tagtaacaac ccattgctaa ctggatgcta    3180
aacatcaccc ctaaatactt aatttgctcc tgttatctgg gcctacaaaa agatacttga    3240
aagtcggtat acagaaaatt tctggaagaa ctgcttaaga aagtgataac aatagttacc    3300
tctggggaat gggactagat gacttgagga tgacacacta ttttttgtacc atcggcattt    3360 attttttataa taaaaaaata cactgggctc ctatcagatc atgttcatca gactactgtt    3420
acagaaatgt ttaaaatcca ttacatctca gttgactact cttcaggata aaatctaaaa    3480
acctgagcat ataagaagat acttcatgag gtggttcctt tataaagcca tatctcttaa    3540
tcatcatgta ttatttagct tgatatacac actttaaaaa ttttggatat ctagcgtggc    3600
attctgtatt ttccagcaat cactaatacg ttccttctta ccaaggtaag gttcacggta    3660
atagagagga tgggagtatc tgagactgta cattgctgat tccatcctgg ttttgacaag    3720
aattatcagg aaacctaatg ttaagaaaaa aaatccctac cacatttac caattagaga    3780 gatatctgag ttactgtttc tattttttaaa tactctttga gaaagcttag tttcagtgtt    3840
tagataagaa caacaaaagg tggttcaatt ctggaatggg acatacagta gaatggggct    3900
gggaaagaga gactttgaac tactaaccat aatgagggta ctgggcacag atgaaggtat    3960
caagaagaat ttttttttttt tagacagaat ctcgctctgt cacccaggct ggagtgcagt    4020
ggtgccgatc tcggctcaat gcaacctcca cctccaggt tcaagtgatt ctcctgtctc    4080
agcctcccaa gtagctggca ttacaggtgc gtgccaccac acccagctaa ttttttgtatt    4140
```

```
tttagtagag acagggtttc accctgttgg ccaggctggt cttgaactcc tgacctcagg   4200
tgatccaccc acctcagcct cccaaagtgc taggattaca ggcgtcagcc actggcagct   4260
ggccaggaag aattttatgt tgctattttg ttaaggaagt aaagccatct ttccatcttc   4320
gatagaattc aacagttaat gcctaaaaca aagacctttg agtggcatta taaatgtttt   4380
agagatatcg agataaatac caaaataacc agctgaaaga atgcttaagt gattgttttt   4440
ggggagagga aatagggaga gcaggggaac aattttttt tttaattcct tgtggaatgt    4500
cttctgaaat aatgtacata tgcaattttg ataaaaagat tagaatatgg gccagctgt    4560 ggtgcctcat gccgtaatcc cagcactttg ggaggccaag gcaggtggat catctgaggt   4620
caggagttcg acaccagcct ggtcaacatg gtcaagcccc aactaaaaat acaaaaatta   4680
gctggctgtg gtggcatggg cctgtaattc cagctactct ggaggctgag gcaggagaat   4740
ctcttgaacc caggaggcgg aggttgtggt gagctgagat tgcgccactg cactccagca   4800
tgggcgacag agagagactc tgtctcaaaa aaaaaaaaa aaaaaaaaag ataagaatat    4860
ggaaaaacaa agtggcccag taagagagaa gtctatatta gccactgtgg taaaaacaga   4920
taagcagaca ctcaactcag aatcagtagt gggtgctgaa ctctgtcagc acaaatgaga   4980
gattcaaact aagaatttaa ttagtgttgc taaaatatca ccttttcttt acagataagg   5040
aaaatgaggc acattgttga acaattcact aaagatcaga gccagtcaca aaatatattt   5100
tctagagttg agtcctattt tataggacta agggaaattc aaattaggca agagaagtta   5160
ccgtagactg aaaaaactgc tgcaattatt tttcttcctg tgtcccatcc cactatgagg   5220
ttggcattta tttccccacc tcttgaatct ggcctggccc agtgacttgc tttcatgaaa   5280
agaatgtggt ggaagtgaca gtatgcaaat tccaagccct tgtctcaaag gccttgcat    5340 atttgctccc tctcttggaa cccggcctat gccaagtgaa caagccctag ctggcctgtt   5400
ggaggaagag aaaactcaga agagctgaga agacttggcc tacagctagt tgaaccccag   5460
acatgagagc ccagcctagg tcaatagagc tatccaccca atctgcagct gtgtaagtga   5520
gctcagtgga gatgagaact gcccagttga aatgtagacc tgtaaattat aataaatgga   5580
gttttaagcc actacagttt tgaggtggcc ttttacacag caatggctga cagagttgtc   5640
atgtttacat aaaaataggt taaaacaagt cacacaaagc agaataaggc tgaaatttgt   5700
ggtataactc aagatttcaa gtagttagga aagattcaaa ctgggtcact aaaacatcaa   5760
gagctccaaa gagaactgtt ctaaatgtcc agagatttct gtctaggtga catcactaga   5820
cagaactgat cctactgttg gaacctcttg gcattaaaca gccctgactg ttagtggaag   5880
tacaaatctc ctaggaatta gagttttttg acccactcta gaaccttagg tagggtgtgg   5940
aggaaaagaa tgcatcctgt gaggagatca aggggttttc taggttgctg tcttttaggg   6000
atccttctaa gtagacagag gatggaagaa ggggtgattc ttacctatta gaaggggctc   6060 tctttaccc tcatcagcat tttatctcaa taaactgtga ataggccctg ttacaggga    6120 tcttgccact taaagattca atctttaga ctggcaatga ggattcagac aactcaatct    6180
ttgtgtaaat acttggtaaa gcaacaggac acagaagagg aatgctggaa aaatctggtt   6240
tatgaaaaca gaaatcaaac caagttacta accaacctcc ccgtcccctc caggcacaca   6300
aaaacatttg cctttgtact ctgccaatgc ttgatttaat tataatacac actcaagtgg   6360
ctgtaaaaaa acccaacaga acagaaacca tttaacatct gaatagtgat ttatgaacag   6420
atttcctctg acaaatgggg ccagctattc ttaaggcttg ccaaatagct gttagatgtc   6480 taaattttg tatgtgcctg cgtttgtatg tggttacact gtaaagtaat gacagactga   6540
```

```
ggctttgatt tcagaacttc agatgtatca aaaatacaga ttttaatat ttgattttat   6600 atttgtatgt ttatcttctt aaattgaaga gattatacat ctcagatctg taggagttga   6660
tgtatacttg gtcaaacatt gcctaactca atgttttct ttttttttaa gtaaaaaata   6720
agtttgaaaa ctgtaactcc ctaggttttt tccagcctcc agttccagtt ggctagtcat   6780
ttcttctctc tcaacgctgt gattttttt aaggtcttaa tatttgaagg aagtcaacag   6840
tcatttattc cgaattaaac ttgaagttaa taaagtttca attcgtaatt tttccaaacc   6900
aaccaatgta aaaacccaga ttttcctgaa ttgagtcatg taaggatttt tgtaagtgac   6960
aaaaaaatac atgttaagac tgtggaaaaa tggagaaaag gcctgaataa aatcaggagt   7020
taattactta aaaaatggca tatgccaggc tgggcgcggt ggctcacgcc tgcaatccca   7080
gcacttttgg gaggctgagg cgggtggatc atctgaggtc aggagttcga gaccagcctg   7140
gccaacacgg tgaaaccctg tctctactta aaatacaaaa attagccggg tatggtggcg   7200
gatgcctgta atcccagcta ctcgggaggc tgaggcagga gaattgcttg aacacaggga   7260
ggtggaggtt gcagtgagcc aagatcgtgc cactgcactc cagcctgggc agcagagtga   7320
gactctgtct aaaaagataa taataataat tgcatatgcc ttagagtgag tttttaaaagt   7380 gtaaatgttt tgtgtgtaaa agcattaaaa actagtttca acagcagtaa atacatttt   7440 cctttgtgaa aatgaagacc cttacagttt aaccataaac ttaaaatagc taatctaaaa   7500
acagacatgt tacttacctt tttagtgaga aacaccacca ccaaatagaa acaccaccac   7560
caaaaactgc tttgggtatt ggatatttat gtgggttttt tgtttgtctg ttttttgaga   7620
gaaggacttg ccatatggta ggctggtctc aaactcctgg gctcaggtga tcctcctgcc   7680
tcaggcttct gagtagctgg gattaaaagt gcacaccact gcactgggct aggatcttta   7740 tgttttatc tcactttaga ggatatagga aaaagatat ttggactaca aaaagggaat   7800
attgcagtaa tataattaat ctgtaattaa gtaattcctt attaacctag ttgaaaatag   7860
acatagttta atgaggatgt gttgtcttta gactatttct atataattta ttttctataa   7920
caaacaaaag cacttaccac agaacaccat acagaatggt aaaactggat aaataaacct   7980
gaattctttg tggctcaaca tgctgtaata aaaacaaata ttattaaaaa atattaatta   8040
tcatgttata tgatagattg agaaagtaat atatttaata taaatatat ttaacttgat   8100 ctatttattt tctaagtatt cagactgaat ttcttgcttc agaaattcat cttattttt   8160 agttataagg tgattacgat atggtaaaac taatcataaa atatgatgtc aatttgaaat   8220
tacaaagtac agttacattc taaaaacggg atttctattt caatccaagt aagtgaaatt   8280
agtcaaattt ggaataagga tacatacatt tttattttag aatgtatttc tgtggtcctt   8340
caatttaaaa ttttggtagt attgattgac tgattgactg agacagggtc ttgttttgtc   8400
acccagactg gagtgcagta gcacaatcat agctcactgc aaccttaaat tcctgggctc   8460
aagcagtcct tctgcctcag cttccccaat agctaggact acaggcacat gccatcatgc   8520
cctggtaatt ttaaattttt tttcagagag agggtcttgc tatgttgctc aggctggtca   8580
tgaactcctt gcttcaagca atcctcccac cttggccttc aaagtattga aattacaggc   8640
atgagcaact gtgcctggtc tgttttttt tttttaaag caaataaaat tagtccaagt   8700
tcttaaaaat tgagtgtaat ccttattaag caaactacat atctaaagta ttcactctag   8760
tgcctccata attactacta cttgtatctt ctaagataat tcccactaac aaaagttaat   8820
ggcacctcca aaacataaag tttacttttt gaagaattta atttgatttc ttggtaacat   8880
```

```
aaaaaatttt agccttttga acaaataaaa tcttacctat aaacaagcag tgtccacagc   8940
acagtcacca aaagtatccg gtatctcttt ggtgctagat agcagccatg aataaagaag   9000
ggtaagtgag tacccaagat aactggaaat ccttgactga agtaccagtg ccatggatga   9060
gaaccataaa atgttcccaa gttctgcagc acgttaaatt tcaaaaaatt aaattgaacc   9120
agagtccact ggcaccgttg aaggaaaaat aaatagaaat gtgttagtgc caagtagtaa   9180
tctttggcat taggggattg atacaatttt gacattaaat cagaattgaa gtctaaaaac   9240
caggcaatag tttacattaa taattttttt tttttttttt ttttttttaag atggagtctt   9300
gctctgtcgc ccaggctgga gtgcagtggc gcgatctcgg ctcactgcaa gctccgcctc   9360
gcgggttcac gccattctcc tgcctcagcc tcccgagtag ctgggactac aggcgcccgc   9420
caccacgccc ggctaatttt ttctattttt agtagaacg gggtttcacc atgttagcca   9480
ggatggtctc aatctcctga cctcgtgatc tgcctgcctc ggcctcccaa agtgctgcga   9540
ttataggtgt gagccaccat gcctggccta ataattttaa ttaatgactg tatgaaatcc   9600
ttcttaactg ttattttttc ttctttaagt attaatgtgt tccttgttaa tttgtaaaac   9660
tagatttttg agattcaaag tgagaatcaa acttatattt tggcagtcta agtttgtgtt   9720
tttatttcaa gttttttgggg tacagatggc ttctggttac atgaataagt tctttagagg   9780
tgatttctag gattttggtc cacccatcac ccaagcaatg tacactgtac ccatatgta    9840
ctcgaaataa gaatttctca cccctctctc acccttcccc accctgagtc accagagtcc   9900
attatatcat tcttatgtct ttgcatccca tagcttagct cccacttata agtaagaaca   9960
tatgatattt ggctttccat tcctgagtta tttcacttag aataatggcc tccagctcca  10020
tccaagtttt atatccagtt aagagataaa gaggatagta gacatatttt tcggactgtg  10080
tggtacttta caatgtgaca tattacctgt gaagataaag ctttgaaaac attacaattt  10140
gaattacagc gtaaagctga caataatgac agaaacagca acaggtaaca ttcagtgctc  10200
acttaataat tccctgcctt aaaatgtact ctcctgaata ttagctagga gtactaattc  10260
ttttatgtag aaagcacaac aaattgaacc aaaggcttat taggatatgc ctagaagtct  10320
tttgtaatgt atcccatatc atttaaaaaa tcatttgcct ctgttctaaa gtattaatgg  10380
attaaaaata aaaatagctg ttagcttaat atacttttac ttacttggcc aaaaaaaata  10440
cgatcaatca tcagagacaa actcaaagta acaaagctga aaaacaaaaa tagcatagtg  10500
attcacattt ggagcttgct gaaaatccac tattagcata tggctttgta cgtgccttgc  10560
atcaaaagcc actataaaaa tgctttacag tttcaccaac tgaatataga tttacacatt  10620
ttgaaaggta tctactgaaa aagatcagta gataagatta tataatcgat taatattgta  10680
aaaaatatat taataaaaag attattgaaa gactactgct gtataacaaa ttaccccaaa  10740
acttgttaac ttaaactatg aatatttacc atttcatagt tcctgtggat caagaaccta  10800
ggtgttgctt agctgggtgc ctctggctcg aggtcgctca tgaattgtag tcaagctctt  10860
agcaggggct acagtttcat ctgaaggttc aattacaggt ggagagatca gcttccaaat  10920
ttgctcacat ggttgctggt ggggctaagt tcctcaacat atggccgttt ccttaaagct  10980
gcctcatgac ataattaact ggcttaaccc agggtaagtc agccaagagt gagtgagaca  11040
ggcacccaag atgaagccaa taatctttt atttatgtat tcttttcttt tttttagaga  11100
cagggtcttg ctctgtcacc caggctggag tgcagtagtg tgtgatcatg gctcactgca  11160
gccttgacct cctgggctca agtgatcctc ccacctcagc cttccaagta actaggacta  11220
caggtgtgtg ccgccatgac tggataattt ttggattttc tgtagagatg ggtctcact   11280
```

-continued

```
atattaccca actggtctca aactccgggc ctcaagcagt acttccccat tggcctccca    11340
aaatgctggg attacagata taagccactg tgcctggcca ccatagtctt ttcataaccc    11400
agtcttgtaa gtgatatccc atcccttctg ctgtattcta ctcattagaa ttgagtcgac    11460
aaatctagcc catgttcaag ggggagggga ttatacaaag acataaatag caggaggatg    11520
ggatcactgg aggccatctc agagactgcc tccaacaaac acatatacag aaaaatacgc    11580
tatgaaggta aagctctatg aatcatcact acatgaacac aactgtgtac gtgccataca    11640
gagcaggata aagagtatta gcagcaccac cttgtccctc aatcagtca gtccctacct     11700
cctccccaaa agtaacccaa aggtaaccct tcctcttccc aaaggtaacc actatcctaa    11760
tttctgataa catagatgag ttttatcttt ttttgaattt tataagaata ggatcatacc    11820
atatgtgctc atgtctaaat tcctttagtc attgtgcttg tgagattgaa ccaagttttt    11880
ttgcgtgctg tagttcattc ctttacaata ctgtgtattg taactatgta taccacactg    11940
tatgtattcc ttctattgat ggacactgtg cttccatttc cagctattgt gaatagtgct    12000
gcaatgaaca ttcttttaca catcttttgg tatccatata tgtgcatttc tgttagacat    12060
atacctagga ttggaattgg tgggccctaa ggtagcggtc cctaaccttt ttggcaccag    12120
ggtctggttt cttgaaagac agttttccca caaacaggtt gcgggggtgg gagtggggca    12180
tggtttctgg atgaaactgt tccacctcag atcactggac attagatgct catacggagc    12240
acaacctaga tcccttgcat gtgcagttca cagtagggtt cacacttctg taagaatgtg    12300
acaggaggtg gagctcaggc agtaatgctt gcttgcttgc tcacctcctg ctgtgcagcc    12360
cagttcctaa gaggccatgg actggggcca gtccacagcc ttgggactgg tgacccctgc    12420
cctaagttgt aagtgcaact atgtatttat ttagcttttg taagtactta aaagttttcc    12480
aaaatagtgt attagtttgc agtcccacag gaatatataa gttccacatc attttagcca    12540
tttgggtgga tgtatagtat agtagtattt catggtggct ttactttgtt tttccttgat    12600
aacaaatgaa atgagtctct ttatatttat tggccatttt aatattttt gaagtacctg      12660
atgaaacctt ttcaataatt tttctatgag ttatctttt cttatagatt tttaaaagtt       12720
ttatatataa tctggatgta aggttttatt tttgagatgg agcctcactc tgttgcccag    12780
gctggagtgc agtggtgcaa tttcagttca ttgcaacgtc tacctctggg gttcaatcgt    12840
ttctcctgcc tcagcctccc aagtagctgg gattataggc atgtgccaca atgcccagct    12900
aatttttttg tatttttagc agagacaggg tttcatcata ttggccaggc tggtcttgaa    12960
ctcctgacct caggtgatct gcctgcctca gcctcccaaa gtgctgggat tataggcgtg    13020
agccatcgtg cccaaccact agaacacttt aaatcactgg gtaagaatta caatccctaa    13080
ctgatgatga ttcaacctac gattttttcaa ctttaaaatg gtacccatac agccattctg    13140
tttttcactt tcagtacagt attcaatgaa ttacatgaga tattcaaata ttttattatg    13200
aaataggctt tgtgttagat gattttgctc aactgtaggc taatgtaagc gttctgagca    13260
cgtttatggt aggctaagct gtgatgttca gtacgttaga tgtgttaagt gcattttga     13320
cgtagaatat tttctttgtt atttatttg tttagagaca ggttatcact ctgtttccca       13380
ggctggagtg cagtggaatg atcatagctc actgcaacct tgaactcctg ggttgaaggg    13440
atcctcctgc ctcatcctcc caagtagcta ggaccacagg cgtgcctagt gccacctata    13500
cttggccaat tttaaatttt ttttgttgag atgggtctc attatgttgc tcaggttgtt      13560
cttgaactcc tggtctccca gggcactggg attacaggtg tgagccactg tgccttgcct    13620
```

```
gacttatgat attttcaacc tgcaatgagt ttatcaagat gtaaccctga gtcaaggagc   13680
atctgtattg ttatatcttt ttcccccaca gactttgact ttgagagcag acactgtatc   13740
ttactcactt ctgaattatc aaatgctgga tacaaagtag gttaaatgct tattaaatga   13800
ataagttatt atcatgctgc tgatgagatt aaaaaggctt tctatctccc tcagtggtaa   13860
agccgatagg aactgagccc ctgctatctc tctgacctca ttattacatt ctcccaaact   13920
cactctcttt tagccacatc agtctccttg ctgttccttg aacatgccca gcatacttag   13980
tacttggctg gcccctttgc ctggaatact ctctcatcaa gtaactacat ggttcactct   14040
ctcaactcct ttaagttttg gctccagtgt caccttatca tggtgatctt tcccaactac   14100
cctatttaaa aataacagct cccccattac cccaagcact ggcattctat ccttcttatc   14160
ccacaattat ttttccctgt attaccatca cttgacaaat atatatttac tcttatcttt   14220
ttagctgtct gtctctccct actagaatgt aaacttcatg aaggcaggta cttttttttgg  14280 ttaaactgat gcatctccta catctggaac actgcctggc acatagtagg attaaataat   14340
tcctgaatga atgaatacat ttaatgcaat gttattaata catctgagaa acgacaacag   14400
tagcaactga gatgcaagat aatttagtcc ttttcagatt gctacccgaa aaatacttgt   14460
gactagtgaa tactagtaca gtcatgcatt gcttaacaat ggggatacat tctgagaact   14520
gcatcattag gcagtttcat cattgtgcaa acatcataga gtgcacttac acaagcctag   14580
atggtacagc ttacagacat ctaggctata tggtatagcc tactgctcct aggctacaaa   14640
cctatacagc atgatagtat gctgaatatt gtaagcaatt gcaacacaat gctatgtatc   14700
tgtgtatcta actatagcta aacaggctgg gcatggtggc ccatgcctgt atttccagca   14760
ctttgggagg ccaaggtggg tggatcacct gaggtcagga gtttgagact agctggccaa   14820
catggtgaaa ccccaactcg actaaaaata aaaaaattag ccaggcgtgg tggcaggcgc   14880
ctgtaatccc agctgtttgg gaggctgagg caggagaatc acttgaacct gggaggcgga   14940
ggctgcagtg aagtgagaat gcaccactgc actccagcct aggtgacaga gtgagactcc   15000
gtctcaaata aaaaaatata tatagccaaa cagagaaact aaagtacact aaaatacggt   15060
aatataatct tatgggacca ctgtcataaa tgcagtccag tgctaaccaa aatgtcatta   15120
tgcggtgcat gattgtatat taaaaagatt actgttgtaa gagtcagaat gcagtcatcc   15180
cttcagtaaa taattattcg gggtagtcta ctagatactt gggatacaac tcatcctagg   15240
agctcatagt gtagttagaa gatgtgggtt tcaataccag tatagcaacc agcccaatga   15300
ctttgactaa tacattttaa atttctgcga gcctcctgtt ttctctacta caaaataaaa   15360
acatatattg cctagactga agtattatga aaattatgag gtaatatgtg aaaacacatt   15420
atgaattata aagccttata caaatgtaaa agaatcaagt atctctaaaa tatatgtgag   15480
aaatatttag gaaataaagc attggaaaac actaagttag aaataattac aaaagcactc   15540
agttaagcaa attaaaatag ttataatcag gatcataaat aaaaaatata agttttgcat   15600 tattctatt ccttggacta agagttctca ctgacattag aagataaaat aattaactga    15660
aagatgtaaa atcttgttcg taatctgtga tttgtaggct actaaaataa atggatggat   15720
tattgccaca cttaccctac aggtaaaaaa tgatgtagaa taagatcaag ctttcttggt   15780
tcttgacaga aatgtctgaa gagcaaaggt gtccacagaa tgcagctgt gggacgaatt    15840 atgaaggcaa gtgccaccag ggatgagtat ttgacactat aagaggaaaa tgtgtgataa   15900
gacaagtggg aaattaactt gaagttatct atcatttaca ctgtgatttg acattttcct   15960
tttggtataa atagctatat gaacttttttt ttgttttgtt ttgtttttttt tgagacagag  16020
```

```
tctcactctg tcacccaggc tggagtgcag tggcatgatc ttggctcacg gcaacttctg    16080
cctcccaggt gcaagtgatt ctcctgcctc agcatcccga gtagctggga ttacaggtgt    16140
gtaccaccat gcccgactaa ttttttgtat tttcagtaga gatggggttt caccttgttg    16200
gccaggctgg cctcaaactc ctgacgtcag gtgatctgcc cacctcagcc tcctaaagtg    16260
ctgggattac aggctaatcc ccatgccagg ctaattttt gtattttag tgggagacag     16320 ggttttacca tgttggccag gctggtctca aactcctgac ctcaggcgat ccgccagcct    16380
cagcctccta aagtgctggg attacaggca ggagccacag tgcctggcct aaatagctat    16440
attaactttt gcaggttact tacgctttct gggtcttagt ttttcttatc ttttaaaaaa    16500
ggtaatatct aaagccgttt tcagtgctca tcttctaatt ctagtatttt caaataagaa    16560
gttatcatat gtcttaatgc cagtcttgtg tgctaaaaag catgctttt acctcataac     16620 tttgccaatt actttcttga ttgaaaaaaa aatgatcaag tttctcctaa ggagctataa    16680
gaaagtcata aagagaggct ttctctaaga aaaagcatga gcatttaaag aaacaggatt    16740
atttaggcag tgatgggctc agagtattta gaattttgtt ttgaaagtta attttagcca    16800
agtgaaatat atatgcatac aactgataaa aggcctactg tataaactgt atgatcatgg    16860
atagaaatac agattttat taacaggact tctctaaact aatggttgaa agagacaatt      16920
tgataattta atcatgagga ctatggatag tatattatta tgtggaaaaa tacttagtcc    16980
tgtaaaaaat taaagaaag caaaataaga caacctatat taccattata tacctattaa     17040
ctaataaaaa taactataaa gaaatctgta ggccaggtgt ggtggctcag gcctgcaatc    17100
ccagcacttt gggaggccga ggtgggtgga tcacctgaag tcaggagttc aagaccagtc    17160
tggccaaaat ggtgaaaccc tgtctctact aagatagaa aaaaattagc tgggtgtggt     17220
ggcaggtgcc tgtaatccca gctacttggg aggctgaggc aggagaatca cttgaacctg    17280
ggaagtggag gttgcaatga gctgagatca tgccattgca ctctagcctg ggcaacaaga    17340
atgaaactcc atctcaaaaa aagaaaaaa aaaaagaat gaattc                      17386
```

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: RT-PCR
      primer

<400> SEQUENCE: 11
gttgacagaa tgctgttcca cgtcg                                            25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: RT-PCR
      primer

<400> SEQUENCE: 12
caagctgagg cacgaagagc aatga                                            25

<210> SEQ ID NO 13
<211> LENGTH: 1263
<212> TYPE: DNA
<213> ORGANISM: Pan troglodytes
<220> FEATURE:

-continued

```
<221> NAME/KEY: CDS
<222> LOCATION: (1)..(1260)

<400> SEQUENCE: 13
```

| | | | | | | | | | | | | | | | | |
|---|---|---|---|---|---|---|---|---|---|---|---|---|---|---|---|---|
| atg | ccc | ctt | cag | gtt | agc | gat | tac | agc | tgg | cag | cag | acg | aag | act | gcc | 48 |
| Met | Pro | Leu | Gln | Val | Ser | Asp | Tyr | Ser | Trp | Gln | Gln | Thr | Lys | Thr | Ala | |
| 1 | | | | 5 | | | | | 10 | | | | | 15 | | |
| gtc | ttt | ctg | tct | ctg | ccc | ctc | aaa | ggc | gtg | tgc | gtc | aga | gac | acg | gac | 96 |
| Val | Phe | Leu | Ser | Leu | Pro | Leu | Lys | Gly | Val | Cys | Val | Arg | Asp | Thr | Asp | |
| | | | 20 | | | | | 25 | | | | | 30 | | | |
| gtg | ttc | tgc | atg | gaa | aac | tat | ctg | aag | gtc | aac | ttt | cct | cca | ttt | tta | 144 |
| Val | Phe | Cys | Met | Glu | Asn | Tyr | Leu | Lys | Val | Asn | Phe | Pro | Pro | Phe | Leu | |
| | | 35 | | | | | 40 | | | | | 45 | | | | |
| ttt | gag | gca | ttt | ctt | tat | gct | ccc | ata | gac | gat | gag | agc | agc | aaa | gca | 192 |
| Phe | Glu | Ala | Phe | Leu | Tyr | Ala | Pro | Ile | Asp | Asp | Glu | Ser | Ser | Lys | Ala | |
| | 50 | | | | | 55 | | | | | 60 | | | | | |
| aag | att | ggg | aat | gac | acc | att | gtc | ttc | acc | ttg | tat | aaa | aaa | gaa | gcg | 240 |
| Lys | Ile | Gly | Asn | Asp | Thr | Ile | Val | Phe | Thr | Leu | Tyr | Lys | Lys | Glu | Ala | |
| 65 | | | | | 70 | | | | | 75 | | | | | 80 | |
| gcc | atg | tgg | gag | acc | ctt | tct | gtg | acg | ggt | gtt | gac | aaa | gag | atg | atg | 288 |
| Ala | Met | Trp | Glu | Thr | Leu | Ser | Val | Thr | Gly | Val | Asp | Lys | Glu | Met | Met | |
| | | | | 85 | | | | | 90 | | | | | 95 | | |
| caa | aga | att | aga | gaa | aaa | tct | att | tta | caa | gca | caa | gag | aga | gca | aaa | 336 |
| Gln | Arg | Ile | Arg | Glu | Lys | Ser | Ile | Leu | Gln | Ala | Gln | Glu | Arg | Ala | Lys | |
| | | | 100 | | | | | 105 | | | | | 110 | | | |
| gaa | gct | aca | gaa | gca | aaa | gct | gca | gca | aag | cgg | gaa | gat | caa | aaa | tat | 384 |
| Glu | Ala | Thr | Glu | Ala | Lys | Ala | Ala | Ala | Lys | Arg | Glu | Asp | Gln | Lys | Tyr | |
| | | 115 | | | | | 120 | | | | | 125 | | | | |
| gca | cta | agt | gtc | atg | atg | aag | att | gaa | gaa | gaa | gag | agg | aaa | aaa | ata | 432 |
| Ala | Leu | Ser | Val | Met | Met | Lys | Ile | Glu | Glu | Glu | Glu | Arg | Lys | Lys | Ile | |
| | 130 | | | | | 135 | | | | | 140 | | | | | |
| gaa | gat | atg | aaa | gaa | aat | gaa | cgg | ata | aaa | gcc | act | aaa | gaa | ttg | gaa | 480 |
| Glu | Asp | Met | Lys | Glu | Asn | Glu | Arg | Ile | Lys | Ala | Thr | Lys | Glu | Leu | Glu | |
| 145 | | | | | 150 | | | | | 155 | | | | | 160 | |
| gcc | tgg | aaa | gaa | tat | caa | aga | aaa | gct | gag | gag | caa | aaa | aaa | att | cag | 528 |
| Ala | Trp | Lys | Glu | Tyr | Gln | Arg | Lys | Ala | Glu | Glu | Gln | Lys | Lys | Ile | Gln | |
| | | | | 165 | | | | | 170 | | | | | 175 | | |
| aga | gaa | gag | aaa | tta | tgt | caa | aaa | gaa | aag | caa | att | aaa | gaa | gaa | aga | 576 |
| Arg | Glu | Glu | Lys | Leu | Cys | Gln | Lys | Glu | Lys | Gln | Ile | Lys | Glu | Glu | Arg | |
| | | | 180 | | | | | 185 | | | | | 190 | | | |
| aaa | aaa | ata | aaa | tat | aag | agt | ctt | act | aga | aat | ttg | gca | tct | aga | aat | 624 |
| Lys | Lys | Ile | Lys | Tyr | Lys | Ser | Leu | Thr | Arg | Asn | Leu | Ala | Ser | Arg | Asn | |
| | | 195 | | | | | 200 | | | | | 205 | | | | |
| ctt | gct | cca | aaa | ggg | aga | aat | tca | gaa | aat | ata | ttt | act | gag | aag | tta | 672 |
| Leu | Ala | Pro | Lys | Gly | Arg | Asn | Ser | Glu | Asn | Ile | Phe | Thr | Glu | Lys | Leu | |
| | 210 | | | | | 215 | | | | | 220 | | | | | |
| aag | gaa | gac | agt | att | cct | gct | cct | cgc | tct | gtt | ggc | agt | att | aaa | atc | 720 |
| Lys | Glu | Asp | Ser | Ile | Pro | Ala | Pro | Arg | Ser | Val | Gly | Ser | Ile | Lys | Ile | |
| 225 | | | | | 230 | | | | | 235 | | | | | 240 | |
| aac | ttt | acc | cct | cga | gta | ttc | cca | aca | gct | ctt | cgt | gaa | tca | caa | gta | 768 |
| Asn | Phe | Thr | Pro | Arg | Val | Phe | Pro | Thr | Ala | Leu | Arg | Glu | Ser | Gln | Val | |
| | | | | 245 | | | | | 250 | | | | | 255 | | |
| gca | gaa | gag | gag | gag | tgg | cta | cac | aaa | caa | gct | gag | gca | cga | aga | gca | 816 |
| Ala | Glu | Glu | Glu | Glu | Trp | Leu | His | Lys | Gln | Ala | Glu | Ala | Arg | Arg | Ala | |
| | | | | 260 | | | | | 265 | | | | | 270 | | |
| atg | aat | act | gac | ata | gct | gaa | ctt | tgc | gat | tta | aaa | gaa | gaa | gaa | aag | 864 |
| Met | Asn | Thr | Asp | Ile | Ala | Glu | Leu | Cys | Asp | Leu | Lys | Glu | Glu | Glu | Lys | |
| | | 275 | | | | | 280 | | | | | 285 | | | | |
| aac | cca | gaa | tgg | ttg | aag | gat | aaa | gga | aac | aaa | ttg | ttt | gca | aca | gaa | 912 |
| Asn | Pro | Glu | Trp | Leu | Lys | Asp | Lys | Gly | Asn | Lys | Leu | Phe | Ala | Thr | Glu | |

```
                290              295              300
aac tat ttg gca gct atc aat gca tat aat tta gcc ata aga cta aat    960
Asn Tyr Leu Ala Ala Ile Asn Ala Tyr Asn Leu Ala Ile Arg Leu Asn
305             310              315              320 aat aag atg cca cta ttg tat ttg aac cgg gct gct tgc cac cta aaa   1008
Asn Lys Met Pro Leu Leu Tyr Leu Asn Arg Ala Ala Cys His Leu Lys
                325              330              335 cta aaa aac tta cac aag gct att gaa gat tct tct aag gca ctg gaa   1056
Leu Lys Asn Leu His Lys Ala Ile Glu Asp Ser Ser Lys Ala Leu Glu
            340              345              350 tta ttg atg cca cct gtt aca gac aat gct aat gca aga atg aag gca   1104
Leu Leu Met Pro Pro Val Thr Asp Asn Ala Asn Ala Arg Met Lys Ala
        355              360              365 cat gta cga cgt gga aca gca ttc tgt caa cta gaa ttg tat gta gaa   1152
His Val Arg Arg Gly Thr Ala Phe Cys Gln Leu Glu Leu Tyr Val Glu
    370              375              380 ggc cta cag gat tat gaa gcg gca ctt aag att gat cca tcc aac aaa   1200
Gly Leu Gln Asp Tyr Glu Ala Ala Leu Lys Ile Asp Pro Ser Asn Lys
385              390              395              400 att gta caa att gat gct gag aag att cgg aat gta att caa gga aca   1248
Ile Val Gln Ile Asp Ala Glu Lys Ile Arg Asn Val Ile Gln Gly Thr
                405              410              415 gaa cta aaa tct taa                                                1263
Glu Leu Lys Ser
            420

<210> SEQ ID NO 14
<211> LENGTH: 420
<212> TYPE: PRT
<213> ORGANISM: Pan troglodytes

<400> SEQUENCE: 14

Met Pro Leu Gln Val Ser Asp Tyr Ser Trp Gln Gln Thr Lys Thr Ala
1               5                   10                  15

Val Phe Leu Ser Leu Pro Leu Lys Gly Val Cys Val Arg Asp Thr Asp
            20                  25                  30

Val Phe Cys Met Glu Asn Tyr Leu Lys Val Asn Phe Pro Pro Phe Leu
        35                  40                  45

Phe Glu Ala Phe Leu Tyr Ala Pro Ile Asp Asp Glu Ser Ser Lys Ala
    50                  55                  60

Lys Ile Gly Asn Asp Thr Ile Val Phe Thr Leu Tyr Lys Lys Glu Ala
65                  70                  75                  80

Ala Met Trp Glu Thr Leu Ser Val Thr Gly Val Asp Lys Glu Met Met
                85                  90                  95

Gln Arg Ile Arg Glu Lys Ser Ile Leu Gln Ala Gln Glu Arg Ala Lys
            100                 105                 110

Glu Ala Thr Glu Ala Lys Ala Ala Ala Lys Arg Glu Asp Gln Lys Tyr
        115                 120                 125

Ala Leu Ser Val Met Met Lys Ile Glu Glu Glu Arg Lys Lys Ile
    130                 135                 140

Glu Asp Met Lys Glu Asn Glu Arg Ile Lys Ala Thr Lys Glu Leu Glu
145                 150                 155                 160

Ala Trp Lys Glu Tyr Gln Arg Lys Ala Glu Gln Lys Lys Ile Gln
                165                 170                 175

Arg Glu Glu Lys Leu Cys Gln Lys Glu Lys Gln Ile Lys Glu Glu Arg
            180                 185                 190

Lys Lys Ile Lys Tyr Lys Ser Leu Thr Arg Asn Leu Ala Ser Arg Asn
```

-continued

```
             195                 200                 205
Leu Ala Pro Lys Gly Arg Asn Ser Glu Asn Ile Phe Thr Glu Lys Leu
    210                 215                 220

Lys Glu Asp Ser Ile Pro Ala Pro Arg Ser Val Gly Ser Ile Lys Ile
225                 230                 235                 240

Asn Phe Thr Pro Arg Val Phe Pro Thr Ala Leu Arg Glu Ser Gln Val
                245                 250                 255

Ala Glu Glu Glu Trp Leu His Lys Gln Ala Glu Ala Arg Arg Ala
            260                 265                 270

Met Asn Thr Asp Ile Ala Glu Leu Cys Asp Leu Lys Glu Glu Lys
            275                 280                 285

Asn Pro Glu Trp Leu Lys Asp Lys Gly Asn Lys Leu Phe Ala Thr Glu
    290                 295                 300

Asn Tyr Leu Ala Ala Ile Asn Ala Tyr Asn Leu Ala Ile Arg Leu Asn
305                 310                 315                 320

Asn Lys Met Pro Leu Leu Tyr Leu Asn Arg Ala Ala Cys His Leu Lys
                325                 330                 335

Leu Lys Asn Leu His Lys Ala Ile Glu Asp Ser Ser Lys Ala Leu Glu
            340                 345                 350

Leu Leu Met Pro Pro Val Thr Asp Asn Ala Asn Ala Arg Met Lys Ala
            355                 360                 365

His Val Arg Arg Gly Thr Ala Phe Cys Gln Leu Glu Leu Tyr Val Glu
    370                 375                 380

Gly Leu Gln Asp Tyr Glu Ala Ala Leu Lys Ile Asp Pro Ser Asn Lys
385                 390                 395                 400

Ile Val Gln Ile Asp Ala Glu Lys Ile Arg Asn Val Ile Gln Gly Thr
                405                 410                 415

Glu Leu Lys Ser
            420

<210> SEQ ID NO 15
<211> LENGTH: 1263
<212> TYPE: DNA
<213> ORGANISM: Gorilla gorilla
<220> FEATURE:
<221> NAME/KEY: CDS
<222> LOCATION: (1)..(1260)

<400> SEQUENCE: 15 atg ccc ctt cag gtt agc gat tac agc tgg cag cag acg aag act gtg      48
Met Pro Leu Gln Val Ser Asp Tyr Ser Trp Gln Gln Thr Lys Thr Val
 1               5                  10                  15 gtc ttt ctg tct ctg ccc ctc aaa ggc gtg tgc gtc aga gac acg gac      96
Val Phe Leu Ser Leu Pro Leu Lys Gly Val Cys Val Arg Asp Thr Asp
            20                  25                  30 gtg ttc tgc acg gaa aac tat ctg aag gtc aac ttt cct cca ttt tta     144
Val Phe Cys Thr Glu Asn Tyr Leu Lys Val Asn Phe Pro Pro Phe Leu
        35                  40                  45 ttt gag gca ttt ctt tat gct ccc ata gac gat gag agc agc aaa gca     192
Phe Glu Ala Phe Leu Tyr Ala Pro Ile Asp Asp Glu Ser Ser Lys Ala
    50                  55                  60 aag att ggg aat gac acc att gtc ttc acc ttg tat aaa aaa gaa gcg     240
Lys Ile Gly Asn Asp Thr Ile Val Phe Thr Leu Tyr Lys Lys Glu Ala
 65                  70                  75                  80 gcc atg tgg gag acc ctt tct gtg acg ggt gtt gac aaa gag atg atg     288
Ala Met Trp Glu Thr Leu Ser Val Thr Gly Val Asp Lys Glu Met Met
                85                  90                  95
```

-continued

| | |
|---|---|
| caa aga att aga gaa aaa tct att tta caa gca caa gag aga gca aaa<br>Gln Arg Ile Arg Glu Lys Ser Ile Leu Gln Ala Gln Glu Arg Ala Lys<br>100                         105                        110 | 336 |
| gaa gct aca gaa gca aaa gct gca gca aag cgg gaa gat caa aaa tat<br>Glu Ala Thr Glu Ala Lys Ala Ala Ala Lys Arg Glu Asp Gln Lys Tyr<br>115                         120                        125 | 384 |
| gca cta agt gtc atg atg aag att gaa gaa gaa gag agg aaa aaa ata<br>Ala Leu Ser Val Met Met Lys Ile Glu Glu Glu Arg Lys Lys Ile<br>130                         135                        140 | 432 |
| gaa gat atg aaa gaa aat gaa cgg ata aaa gcc act aaa gaa ttg gaa<br>Glu Asp Met Lys Glu Asn Glu Arg Ile Lys Ala Thr Lys Glu Leu Glu<br>145                         150                        155                        160 | 480 |
| gcc tgg aaa gaa tat caa aga aaa gct gag gag caa aaa gaa att cag<br>Ala Trp Lys Glu Tyr Gln Arg Lys Ala Glu Glu Gln Lys Glu Ile Gln<br>                         165                        170                        175 | 528 |
| aga gaa gag aag tta tgt caa aaa gaa aag caa att aaa gaa gaa aga<br>Arg Glu Glu Lys Leu Cys Gln Lys Glu Lys Gln Ile Lys Glu Glu Arg<br>180                         185                        190 | 576 |
| aaa aaa tta aaa tat aag agt ctt act aga aat ttg gca tct aga aat<br>Lys Lys Leu Lys Tyr Lys Ser Leu Thr Arg Asn Leu Ala Ser Arg Asn<br>                         195                        200                        205 | 624 |
| ctt gct cca aaa ggg aga aat tca gaa aat ata ttt act gag aag tta<br>Leu Ala Pro Lys Gly Arg Asn Ser Glu Asn Ile Phe Thr Glu Lys Leu<br>210                         215                        220 | 672 |
| aag gaa gac agt att cct gct cct cgc tct gtt ggc agt att aaa atc<br>Lys Glu Asp Ser Ile Pro Ala Pro Arg Ser Val Gly Ser Ile Lys Ile<br>225                         230                        235                        240 | 720 |
| aac ttt acc cct cga gta ttc cca aca gct ctt cgt gaa tca caa gta<br>Asn Phe Thr Pro Arg Val Phe Pro Thr Ala Leu Arg Glu Ser Gln Val<br>                         245                        250                        255 | 768 |
| gca gaa gag gag gag tgg cta cac aaa caa gct gag gca cga aga gca<br>Ala Glu Glu Glu Glu Trp Leu His Lys Gln Ala Glu Ala Arg Arg Ala<br>                         260                        265                        270 | 816 |
| atg aat act gac ata gct gaa ctt tgc gat tta aaa gaa gaa gaa aag<br>Met Asn Thr Asp Ile Ala Glu Leu Cys Asp Leu Lys Glu Glu Glu Lys<br>                         275                        280                        285 | 864 |
| aac cca gaa tgg ttg aag gat aaa gga aac aaa ttg ttt gca aca gaa<br>Asn Pro Glu Trp Leu Lys Asp Lys Gly Asn Lys Leu Phe Ala Thr Glu<br>290                         295                        300 | 912 |
| aac tat ttg gca gct atc aat gca tat aat tta gcc ata aga cta aat<br>Asn Tyr Leu Ala Ala Ile Asn Ala Tyr Asn Leu Ala Ile Arg Leu Asn<br>305                         310                        315                        320 | 960 |
| aat aag atg cca cta ttg tat ttg aac cgg gct gct tgc cac cta aaa<br>Asn Lys Met Pro Leu Leu Tyr Leu Asn Arg Ala Ala Cys His Leu Lys<br>                         325                        330                        335 | 1008 |
| cta aaa aac tta cac aag gct att gaa gat tct tct aag gca ctg gaa<br>Leu Lys Asn Leu His Lys Ala Ile Glu Asp Ser Ser Lys Ala Leu Glu<br>                         340                        345                        350 | 1056 |
| tta ttg atg cca cct gtt aca gac aat gct aat gca aga atg aag gca<br>Leu Leu Met Pro Pro Val Thr Asp Asn Ala Asn Ala Arg Met Lys Ala<br>                         355                        360                        365 | 1104 |
| cat gta cga cgt gga aca gca ttc tgt caa cta gaa ttg tat gta gaa<br>His Val Arg Arg Gly Thr Ala Phe Cys Gln Leu Glu Leu Tyr Val Glu<br>370                         375                        380 | 1152 |
| ggc cta cag gat tat gaa gcg gca ctt aag att gat cca tcc aac aaa<br>Gly Leu Gln Asp Tyr Glu Ala Ala Leu Lys Ile Asp Pro Ser Asn Lys<br>385                         390                        395                        400 | 1200 |
| att gta caa att gat gct gag aag att cgg aat gta att caa gga aca<br>Ile Val Gln Ile Asp Ala Glu Lys Ile Arg Asn Val Ile Gln Gly Thr<br>                         405                        410                        415 | 1248 |

```
gaa cta aaa tct taa                                                     1263
Glu Leu Lys Ser
        420

<210> SEQ ID NO 16
<211> LENGTH: 420
<212> TYPE: PRT
<213> ORGANISM: Gorilla gorilla

<400> SEQUENCE: 16

Met Pro Leu Gln Val Ser Asp Tyr Ser Trp Gln Gln Thr Lys Thr Val
 1               5                  10                  15

Val Phe Leu Ser Leu Pro Leu Lys Gly Val Cys Val Arg Asp Thr Asp
                20                  25                  30

Val Phe Cys Thr Glu Asn Tyr Leu Lys Val Asn Phe Pro Phe Leu
            35                  40                  45

Phe Glu Ala Phe Leu Tyr Ala Pro Ile Asp Asp Glu Ser Ser Lys Ala
        50                  55                  60

Lys Ile Gly Asn Asp Thr Ile Val Phe Thr Leu Tyr Lys Lys Glu Ala
 65                  70                  75                  80

Ala Met Trp Glu Thr Leu Ser Val Thr Gly Val Asp Lys Glu Met Met
                85                  90                  95

Gln Arg Ile Arg Glu Lys Ser Ile Leu Gln Ala Gln Glu Arg Ala Lys
            100                 105                 110

Glu Ala Thr Glu Ala Lys Ala Ala Lys Arg Glu Asp Gln Lys Tyr
        115                 120                 125

Ala Leu Ser Val Met Met Lys Ile Glu Glu Glu Arg Lys Lys Ile
        130                 135                 140

Glu Asp Met Lys Glu Asn Glu Arg Ile Lys Ala Thr Lys Glu Leu Glu
145                 150                 155                 160

Ala Trp Lys Glu Tyr Gln Arg Lys Ala Glu Glu Gln Lys Glu Ile Gln
                165                 170                 175

Arg Glu Glu Lys Leu Cys Gln Lys Glu Lys Gln Ile Lys Glu Arg
            180                 185                 190

Lys Lys Leu Lys Tyr Lys Ser Leu Thr Arg Asn Leu Ala Ser Arg Asn
            195                 200                 205

Leu Ala Pro Lys Gly Arg Asn Ser Glu Asn Ile Phe Thr Glu Lys Leu
        210                 215                 220

Lys Glu Asp Ser Ile Pro Ala Pro Arg Ser Val Gly Ser Ile Lys Ile
225                 230                 235                 240

Asn Phe Thr Pro Arg Val Phe Pro Thr Ala Leu Arg Glu Ser Gln Val
                245                 250                 255

Ala Glu Glu Glu Glu Trp Leu His Lys Gln Ala Glu Ala Arg Arg Ala
            260                 265                 270

Met Asn Thr Asp Ile Ala Glu Leu Cys Asp Leu Lys Glu Glu Lys
            275                 280                 285

Asn Pro Glu Trp Leu Lys Asp Lys Gly Asn Lys Leu Phe Ala Thr Glu
        290                 295                 300

Asn Tyr Leu Ala Ala Ile Asn Ala Tyr Asn Leu Ala Ile Arg Leu Asn
305                 310                 315                 320

Asn Lys Met Pro Leu Leu Tyr Leu Asn Arg Ala Ala Cys His Leu Lys
                325                 330                 335

Leu Lys Asn Leu His Lys Ala Ile Glu Asp Ser Ser Lys Ala Leu Glu
            340                 345                 350
```

```
Leu Leu Met Pro Pro Val Thr Asp Asn Ala Asn Ala Arg Met Lys Ala
        355                 360                 365

His Val Arg Arg Gly Thr Ala Phe Cys Gln Leu Glu Leu Tyr Val Glu
    370                 375                 380

Gly Leu Gln Asp Tyr Glu Ala Ala Leu Lys Ile Asp Pro Ser Asn Lys
385                 390                 395                 400

Ile Val Gln Ile Asp Ala Glu Lys Ile Arg Asn Val Ile Gln Gly Thr
                405                 410                 415

Glu Leu Lys Ser
            420
```

```
<210> SEQ ID NO 17
<211> LENGTH: 1263
<212> TYPE: DNA
<213> ORGANISM: Pongo pygmaeus
<220> FEATURE:
<221> NAME/KEY: CDS
<222> LOCATION: (1)..(1260)

<400> SEQUENCE: 17
```

| | | | | | | | | | | | | | | | | |
|---|---|---|---|---|---|---|---|---|---|---|---|---|---|---|---|---|
| atg | ccc | ctt | cag | gtt | agc | gat | tac | agc | tgg | cag | cag | acg | aag | act | gcg | 48 |
| Met | Pro | Leu | Gln | Val | Ser | Asp | Tyr | Ser | Trp | Gln | Gln | Thr | Lys | Thr | Ala | |
| 1 | | | | 5 | | | | | 10 | | | | | 15 | | |

```
gtc ttt ctg tct ctg ccc ctc aaa ggc gtg tgc gtc aga gac acg gac    96
Val Phe Leu Ser Leu Pro Leu Lys Gly Val Cys Val Arg Asp Thr Asp
             20                  25                  30 gtg ttc tgc acg gaa aac tat ctg aag gtc aac ttt cct cca ttt tta   144
Val Phe Cys Thr Glu Asn Tyr Leu Lys Val Asn Phe Pro Pro Phe Leu
         35                  40                  45 ttt gag gca ttt ctt tat gct ccc ata gac gat gag agc agc aaa gca   192
Phe Glu Ala Phe Leu Tyr Ala Pro Ile Asp Asp Glu Ser Ser Lys Ala
 50                  55                  60 aag att ggg aat gac acc att gtc ttc acc ttg tat aaa aaa gaa gcg   240
Lys Ile Gly Asn Asp Thr Ile Val Phe Thr Leu Tyr Lys Lys Glu Ala
 65                  70                  75                  80 gcc atg tgg gag acc ctt tct gtg acg ggt gtt gac aaa gag acg atg   288
Ala Met Trp Glu Thr Leu Ser Val Thr Gly Val Asp Lys Glu Thr Met
                 85                  90                  95 caa aga att aga gaa aaa tct att tta caa gca caa gag aga gca aaa   336
Gln Arg Ile Arg Glu Lys Ser Ile Leu Gln Ala Gln Glu Arg Ala Lys
            100                 105                 110 gaa gct aca gaa gca aaa gct gca gca aag cgg gaa gat caa aaa tat   384
Glu Ala Thr Glu Ala Lys Ala Ala Ala Lys Arg Glu Asp Gln Lys Tyr
        115                 120                 125 gca cta agt gtc atg atg aag att gaa gaa gaa gag agg aaa aaa ata   432
Ala Leu Ser Val Met Met Lys Ile Glu Glu Glu Glu Arg Lys Lys Ile
    130                 135                 140 gaa gat atg aaa gaa aat gaa cgg ata aaa gcc act aaa gaa ttg gaa   480
Glu Asp Met Lys Glu Asn Glu Arg Ile Lys Ala Thr Lys Glu Leu Glu
145                 150                 155                 160 gcc tgg aaa gaa tat caa aga aaa gct gag gag cac aaa aag att cag   528
Ala Trp Lys Glu Tyr Gln Arg Lys Ala Glu Glu His Lys Lys Ile Gln
                165                 170                 175 aga gaa gag aaa tta tgt caa aaa gaa aag caa att aaa gaa gaa aga   576
Arg Glu Glu Lys Leu Cys Gln Lys Glu Lys Gln Ile Lys Glu Glu Arg
            180                 185                 190 aaa aaa tta aaa tac aag agt ctt act aga aat tcg gca tct aga aac   624
Lys Lys Leu Lys Tyr Lys Ser Leu Thr Arg Asn Ser Ala Ser Arg Asn
        195                 200                 205 ctt gct cca aaa gga aga aat tca gaa aat ata ttt act gag aag tta   672
```

```
Leu Ala Pro Lys Gly Arg Asn Ser Glu Asn Ile Phe Thr Glu Lys Leu
        210                 215                 220 aag gaa gac agt att cct gct cct cgc tct gtt ggc agt att aaa atc    720
Lys Glu Asp Ser Ile Pro Ala Pro Arg Ser Val Gly Ser Ile Lys Ile
225                 230                 235                 240 aac ttt acc cct cga gta ttc cca aca gct ctt cgt gaa tca caa gta    768
Asn Phe Thr Pro Arg Val Phe Pro Thr Ala Leu Arg Glu Ser Gln Val
                245                 250                 255 gca gaa gag gag gag tgg cta cac aaa caa gct gag gca cga aga gca    816
Ala Glu Glu Glu Glu Trp Leu His Lys Gln Ala Glu Ala Arg Arg Ala
            260                 265                 270 atg aat act gac ata gct gaa ctt tgc gat tta aaa gaa gaa gaa aag    864
Met Asn Thr Asp Ile Ala Glu Leu Cys Asp Leu Lys Glu Glu Glu Lys
        275                 280                 285 aac cca gaa tgg ttg aag gat aaa gga aac aaa ttg ttt gca aca gaa    912
Asn Pro Glu Trp Leu Lys Asp Lys Gly Asn Lys Leu Phe Ala Thr Glu
    290                 295                 300 aac tat ttg gca gct atc aat gca tat aat tta gcc ata aga cta aat    960
Asn Tyr Leu Ala Ala Ile Asn Ala Tyr Asn Leu Ala Ile Arg Leu Asn
305                 310                 315                 320 aat aag atg cca cta ttg tat ttg aac cgg gct gct tgc cac cta aaa    1008
Asn Lys Met Pro Leu Leu Tyr Leu Asn Arg Ala Ala Cys His Leu Lys
                325                 330                 335 cta aaa aac tta cac aag gct att gaa gat tct tct aag gca ctg gaa    1056
Leu Lys Asn Leu His Lys Ala Ile Glu Asp Ser Ser Lys Ala Leu Glu
            340                 345                 350 tta ttg atg cca cct gtt aca gac aat gct aat gca aga atg aag gca    1104
Leu Leu Met Pro Pro Val Thr Asp Asn Ala Asn Ala Arg Met Lys Ala
        355                 360                 365 cat gta cga cgt gga aca gca ttc tgt caa cta gaa ttg tat gta gaa    1152
His Val Arg Arg Gly Thr Ala Phe Cys Gln Leu Glu Leu Tyr Val Glu
    370                 375                 380 ggc cta cag gat tat gaa gcg gca ctt aag att gat cca tcc aac aaa    1200
Gly Leu Gln Asp Tyr Glu Ala Ala Leu Lys Ile Asp Pro Ser Asn Lys
385                 390                 395                 400 att gta caa att gat gct gag aag att cgg aat gta att caa gga aca    1248
Ile Val Gln Ile Asp Ala Glu Lys Ile Arg Asn Val Ile Gln Gly Thr
                405                 410                 415 gaa cta aaa tct taa                                                1263
Glu Leu Lys Ser
        420

<210> SEQ ID NO 18
<211> LENGTH: 420
<212> TYPE: PRT
<213> ORGANISM: Pongo pygmaeus

<400> SEQUENCE: 18

Met Pro Leu Gln Val Ser Asp Tyr Ser Trp Gln Gln Thr Lys Thr Ala
1               5                   10                  15

Val Phe Leu Ser Leu Pro Leu Lys Gly Val Cys Val Arg Asp Thr Asp
            20                  25                  30

Val Phe Cys Thr Glu Asn Tyr Leu Lys Val Asn Phe Pro Pro Phe Leu
        35                  40                  45

Phe Glu Ala Phe Leu Tyr Ala Pro Ile Asp Asp Glu Ser Ser Lys Ala
    50                  55                  60

Lys Ile Gly Asn Asp Thr Ile Val Phe Thr Leu Tyr Lys Lys Glu Ala
65                  70                  75                  80

Ala Met Trp Glu Thr Leu Ser Val Thr Gly Val Asp Lys Glu Thr Met
```

85                  90                  95
Gln Arg Ile Arg Glu Lys Ser Ile Leu Gln Ala Gln Glu Arg Ala Lys
                100                 105                 110
Glu Ala Thr Glu Ala Lys Ala Ala Lys Arg Glu Asp Gln Lys Tyr
            115                 120                 125
Ala Leu Ser Val Met Met Lys Ile Glu Glu Glu Arg Lys Lys Ile
        130                 135                 140
Glu Asp Met Lys Glu Asn Glu Arg Ile Lys Ala Thr Lys Glu Leu Glu
145                 150                 155                 160
Ala Trp Lys Glu Tyr Gln Arg Lys Ala Glu His Lys Lys Ile Gln
                165                 170                 175
Arg Glu Glu Lys Leu Cys Gln Lys Glu Lys Gln Ile Lys Glu Arg
                180                 185                 190
Lys Lys Leu Lys Tyr Lys Ser Leu Thr Arg Asn Ser Ala Ser Arg Asn
            195                 200                 205
Leu Ala Pro Lys Gly Arg Asn Ser Glu Asn Ile Phe Thr Glu Lys Leu
        210                 215                 220
Lys Glu Asp Ser Ile Pro Ala Pro Arg Ser Val Gly Ser Ile Lys Ile
225                 230                 235                 240
Asn Phe Thr Pro Arg Val Phe Pro Thr Ala Leu Arg Glu Ser Gln Val
                245                 250                 255
Ala Glu Glu Glu Glu Trp Leu His Lys Gln Ala Glu Ala Arg Arg Ala
            260                 265                 270
Met Asn Thr Asp Ile Ala Glu Leu Cys Asp Leu Lys Glu Glu Glu Lys
        275                 280                 285
Asn Pro Glu Trp Leu Lys Asp Lys Gly Asn Lys Leu Phe Ala Thr Glu
    290                 295                 300
Asn Tyr Leu Ala Ala Ile Asn Ala Tyr Asn Leu Ala Ile Arg Leu Asn
305                 310                 315                 320
Asn Lys Met Pro Leu Leu Tyr Leu Asn Arg Ala Ala Cys His Leu Lys
                325                 330                 335
Leu Lys Asn Leu His Lys Ala Ile Glu Asp Ser Ser Lys Ala Leu Glu
            340                 345                 350
Leu Leu Met Pro Pro Val Thr Asp Asn Ala Asn Ala Arg Met Lys Ala
        355                 360                 365
His Val Arg Arg Gly Thr Ala Phe Cys Gln Leu Glu Leu Tyr Val Glu
    370                 375                 380
Gly Leu Gln Asp Tyr Glu Ala Ala Leu Lys Ile Asp Pro Ser Asn Lys
385                 390                 395                 400
Ile Val Gln Ile Asp Ala Glu Lys Ile Arg Asn Val Ile Gln Gly Thr
                405                 410                 415
Glu Leu Lys Ser
            420

<210> SEQ ID NO 19
<211> LENGTH: 1263
<212> TYPE: DNA
<213> ORGANISM: Pan paniscus
<220> FEATURE:
<221> NAME/KEY: CDS
<222> LOCATION: (1)..(1260)

<400> SEQUENCE: 19 atg ccc ctt cag gtt agc gat tac agc tgg cag cag acg aag act gcg     48
Met Pro Leu Gln Val Ser Asp Tyr Ser Trp Gln Gln Thr Lys Thr Ala
  1               5                  10                  15

```
gtc ttt ctg tct ctg ccc ctc aaa ggc gtg tgc gtc aga gac acg gac      96
Val Phe Leu Ser Leu Pro Leu Lys Gly Val Cys Val Arg Asp Thr Asp
             20                  25                  30 gtg ttc tgc acg gaa aac tat ctg aag gtc aac ttt cct cca ttt tta     144
Val Phe Cys Thr Glu Asn Tyr Leu Lys Val Asn Phe Pro Pro Phe Leu
         35                  40                  45 ttt gag gca ttt ctt tat gct ccc ata gac gat gag agc agc aaa gca     192
Phe Glu Ala Phe Leu Tyr Ala Pro Ile Asp Asp Glu Ser Ser Lys Ala
 50                  55                  60 aag att ggg aat gac acc att gtc ttc acc ttg tat aaa aaa gaa gcg     240
Lys Ile Gly Asn Asp Thr Ile Val Phe Thr Leu Tyr Lys Lys Glu Ala
 65                  70                  75                  80 gcc atg tgg gag acc ctt tct gtg acg ggt gtt gac aaa gag atg atg     288
Ala Met Trp Glu Thr Leu Ser Val Thr Gly Val Asp Lys Glu Met Met
             85                  90                  95 caa aga att aga gaa aaa tct att tta caa gca caa gag aga gca aaa     336
Gln Arg Ile Arg Glu Lys Ser Ile Leu Gln Ala Gln Glu Arg Ala Lys
            100                 105                 110 gaa gct aca gaa gca aaa gct gca gca aag cgg gaa gat caa aaa tat     384
Glu Ala Thr Glu Ala Lys Ala Ala Ala Lys Arg Glu Asp Gln Lys Tyr
        115                 120                 125 gca cta agt gtc atg atg aag att gaa gaa gaa gag agg aaa aaa ata     432
Ala Leu Ser Val Met Met Lys Ile Glu Glu Glu Glu Arg Lys Lys Ile
130                 135                 140 gaa gat atg aaa gaa aat gaa cgg ata aaa gcc act aaa gaa ttg gaa     480
Glu Asp Met Lys Glu Asn Glu Arg Ile Lys Ala Thr Lys Glu Leu Glu
145                 150                 155                 160 gcc tgg aaa gaa tat caa aga aaa gct gag gag caa aaa aaa att cag     528
Ala Trp Lys Glu Tyr Gln Arg Lys Ala Glu Glu Gln Lys Lys Ile Gln
                165                 170                 175 aga gaa gag aaa tta tgt caa aaa gaa aag caa att aaa gaa gaa aga     576
Arg Glu Glu Lys Leu Cys Gln Lys Glu Lys Gln Ile Lys Glu Glu Arg
            180                 185                 190 aaa aaa ata aaa tat aag agt ctt act aga aat ttg gca tct aga aat     624
Lys Lys Ile Lys Tyr Lys Ser Leu Thr Arg Asn Leu Ala Ser Arg Asn
        195                 200                 205 ctt gct cca aaa ggg aga aat tca gaa aat ata ttt act gag aag tta     672
Leu Ala Pro Lys Gly Arg Asn Ser Glu Asn Ile Phe Thr Glu Lys Leu
210                 215                 220 aag gaa gac agt att cct gct cct cgc tct gtt ggc agt att aaa atc     720
Lys Glu Asp Ser Ile Pro Ala Pro Arg Ser Val Gly Ser Ile Lys Ile
225                 230                 235                 240 aac ttt acc cct cga gta ttc cca aca gct ctt cgt gaa tca caa gta     768
Asn Phe Thr Pro Arg Val Phe Pro Thr Ala Leu Arg Glu Ser Gln Val
                245                 250                 255 gca gag gag gag gag tgg ctg cac aaa caa gct gag gca cga aga gca     816
Ala Glu Glu Glu Glu Trp Leu His Lys Gln Ala Glu Ala Arg Arg Ala
            260                 265                 270 atg aat act gac ata gct gaa ctt tgc gat tta aaa gaa gaa gaa aag     864
Met Asn Thr Asp Ile Ala Glu Leu Cys Asp Leu Lys Glu Glu Glu Lys
        275                 280                 285 aac cca gaa tgg ttg aag gat aaa gga aac aaa ttg ttt gca aca gaa     912
Asn Pro Glu Trp Leu Lys Asp Lys Gly Asn Lys Leu Phe Ala Thr Glu
290                 295                 300 aac tat ttg gca gct atc aat gca tat aat tta gcc ata aga cta aat     960
Asn Tyr Leu Ala Ala Ile Asn Ala Tyr Asn Leu Ala Ile Arg Leu Asn
305                 310                 315                 320 aat aag atg cca cta ttg tat ttg aac cgg gct gct tgc cac cta aaa    1008
Asn Lys Met Pro Leu Leu Tyr Leu Asn Arg Ala Ala Cys His Leu Lys
```

```
                    325                 330                 335
cta aaa aac tta cac aag gct att gaa gat tct tct aag gca ctg gaa    1056
Leu Lys Asn Leu His Lys Ala Ile Glu Asp Ser Ser Lys Ala Leu Glu
            340                 345                 350 tta ttg atg cca cct gtt aca gac aat gct aat gca aga atg aag gca    1104
Leu Leu Met Pro Pro Val Thr Asp Asn Ala Asn Ala Arg Met Lys Ala
        355                 360                 365 cat gta cga cgt gga aca gca ttc tgt caa cta gaa ttg tat gta gaa    1152
His Val Arg Arg Gly Thr Ala Phe Cys Gln Leu Glu Leu Tyr Val Glu
    370                 375                 380 ggc cta cag gat tat gaa gcg gca ctt aag att gat cca tcc aac aaa    1200
Gly Leu Gln Asp Tyr Glu Ala Ala Leu Lys Ile Asp Pro Ser Asn Lys
385                 390                 395                 400 att gta caa att gat gct gag aag att cgg aat gta att caa gga aca    1248
Ile Val Gln Ile Asp Ala Glu Lys Ile Arg Asn Val Ile Gln Gly Thr
                405                 410                 415 gaa cta aaa tct taa                                                1263
Glu Leu Lys Ser
            420

<210> SEQ ID NO 20
<211> LENGTH: 420
<212> TYPE: PRT
<213> ORGANISM: Pan paniscus

<400> SEQUENCE: 20

Met Pro Leu Gln Val Ser Asp Tyr Ser Trp Gln Gln Thr Lys Thr Ala
1               5                   10                  15

Val Phe Leu Ser Leu Pro Leu Lys Gly Val Cys Val Arg Asp Thr Asp
            20                  25                  30

Val Phe Cys Thr Glu Asn Tyr Leu Lys Val Asn Phe Pro Pro Phe Leu
        35                  40                  45

Phe Glu Ala Phe Leu Tyr Ala Pro Ile Asp Asp Glu Ser Ser Lys Ala
    50                  55                  60

Lys Ile Gly Asn Asp Thr Ile Val Phe Thr Leu Tyr Lys Lys Glu Ala
65                  70                  75                  80

Ala Met Trp Glu Thr Leu Ser Val Thr Gly Val Asp Lys Glu Met Met
                85                  90                  95

Gln Arg Ile Arg Glu Lys Ser Ile Leu Gln Ala Gln Glu Arg Ala Lys
            100                 105                 110

Glu Ala Thr Glu Ala Lys Ala Ala Lys Arg Glu Asp Gln Lys Tyr
        115                 120                 125

Ala Leu Ser Val Met Met Lys Ile Glu Glu Glu Arg Lys Lys Ile
    130                 135                 140

Glu Asp Met Lys Glu Asn Glu Arg Ile Lys Ala Thr Lys Glu Leu Glu
145                 150                 155                 160

Ala Trp Lys Glu Tyr Gln Arg Lys Ala Glu Gln Lys Lys Ile Gln
                165                 170                 175

Arg Glu Glu Lys Leu Cys Gln Lys Glu Lys Gln Ile Lys Glu Arg
            180                 185                 190

Lys Lys Ile Lys Tyr Lys Ser Leu Thr Arg Asn Leu Ala Ser Arg Asn
        195                 200                 205

Leu Ala Pro Lys Gly Arg Asn Ser Glu Asn Ile Phe Thr Glu Lys Leu
    210                 215                 220

Lys Glu Asp Ser Ile Pro Ala Pro Arg Ser Val Gly Ser Ile Lys Ile
225                 230                 235                 240
```

-continued

```
Asn Phe Thr Pro Arg Val Phe Pro Thr Ala Leu Arg Glu Ser Gln Val
            245                 250                 255

Ala Glu Glu Glu Trp Leu His Lys Gln Ala Glu Ala Arg Arg Ala
        260                 265                 270

Met Asn Thr Asp Ile Ala Glu Leu Cys Asp Leu Lys Glu Glu Lys
            275                 280                 285

Asn Pro Glu Trp Leu Lys Asp Lys Gly Asn Lys Leu Phe Ala Thr Glu
        290                 295                 300

Asn Tyr Leu Ala Ala Ile Asn Ala Tyr Asn Leu Ala Ile Arg Leu Asn
305                 310                 315                 320

Asn Lys Met Pro Leu Leu Tyr Leu Asn Arg Ala Ala Cys His Leu Lys
            325                 330                 335

Leu Lys Asn Leu His Lys Ala Ile Glu Asp Ser Ser Lys Ala Leu Glu
            340                 345                 350

Leu Leu Met Pro Pro Val Thr Asp Asn Ala Asn Ala Arg Met Lys Ala
            355                 360                 365

His Val Arg Arg Gly Thr Ala Phe Cys Gln Leu Glu Leu Tyr Val Glu
            370                 375                 380

Gly Leu Gln Asp Tyr Glu Ala Ala Leu Lys Ile Asp Pro Ser Asn Lys
385                 390                 395                 400

Ile Val Gln Ile Asp Ala Glu Lys Ile Arg Asn Val Ile Gln Gly Thr
                405                 410                 415

Glu Leu Lys Ser
            420

<210> SEQ ID NO 21
<211> LENGTH: 15
<212> TYPE: PRT
<213> ORGANISM: Homo sapiens

<400> SEQUENCE: 21

Cys Ala Thr Glu Ala Lys Ala Ala Ala Lys Arg Glu Asp Gln Lys
  1               5                  10                  15

<210> SEQ ID NO 22
<211> LENGTH: 20
<212> TYPE: DNA
<213> ORGANISM: Artificial Sequence
<220> FEATURE:
<223> OTHER INFORMATION: PCR PRIMER EKN1-1F

<400> SEQUENCE: 22
aacagactgc ctggtgctct                                            20

<210> SEQ ID NO 23
<211> LENGTH: 23
<212> TYPE: DNA
<213> ORGANISM: Artificial Sequence
<220> FEATURE:
<223> OTHER INFORMATION: PCR PRIMER EKN1-1R

<400> SEQUENCE: 23
cacaccaaag tttgagaacc act                                        23

<210> SEQ ID NO 24
<211> LENGTH: 20
<212> TYPE: DNA
<213> ORGANISM: Artificial Sequence
<220> FEATURE:
<223> OTHER INFORMATION: PCR PRIMER EKN1-2.1R
```

-continued

```
<400> SEQUENCE: 24
aagatgagcc tgttgctcgt                                                20

<210> SEQ ID NO 25
<211> LENGTH: 22
<212> TYPE: DNA
<213> ORGANISM: Artificial Sequence
<220> FEATURE:
<223> OTHER INFORMATION: PCR PRIMER EKN1-2.1F

<400> SEQUENCE: 25
caagcagagg gtatgggtct ac                                             22

<210> SEQ ID NO 26
<211> LENGTH: 19
<212> TYPE: DNA
<213> ORGANISM: Artificial Sequence
<220> FEATURE:
<223> OTHER INFORMATION: PCR PRIMER EKN1-2R

<400> SEQUENCE: 26
agaagcttcg gaccacacc                                                 19

<210> SEQ ID NO 27
<211> LENGTH: 20
<212> TYPE: DNA
<213> ORGANISM: Artificial Sequence
<220> FEATURE:
<223> OTHER INFORMATION: PCR PRIMER EKN1-3F

<400> SEQUENCE: 27
cgcgtgctta atttgtgtaa                                                20

<210> SEQ ID NO 28
<211> LENGTH: 23
<212> TYPE: DNA
<213> ORGANISM: Artificial Sequence
<220> FEATURE:
<223> OTHER INFORMATION: PCR PRIMER EKN1-3R

<400> SEQUENCE: 28
tcccctacac aatataggtg ctt                                            23

<210> SEQ ID NO 29
<211> LENGTH: 22
<212> TYPE: DNA
<213> ORGANISM: Artificial Sequence
<220> FEATURE:
<223> OTHER INFORMATION: PCR PRIMER EKN1-4F

<400> SEQUENCE: 29
aaagaaatct catcctgggt ca                                             22

<210> SEQ ID NO 30
<211> LENGTH: 21
<212> TYPE: DNA
<213> ORGANISM: Artificial Sequence
<220> FEATURE:
<223> OTHER INFORMATION: PCR PRIMER EKN1-4R

<400> SEQUENCE: 30
gaaaatgctg aggaagtcca g                                              21

<210> SEQ ID NO 31
<211> LENGTH: 24
```

```
<212> TYPE: DNA
<213> ORGANISM: Artificial Sequence
<220> FEATURE:
<223> OTHER INFORMATION: PCR PRIMER EKN1-5F

<400> SEQUENCE: 31
caatggcaag agtttagagg tatg                                    24

<210> SEQ ID NO 32
<211> LENGTH: 22
<212> TYPE: DNA
<213> ORGANISM: Artificial Sequence
<220> FEATURE:
<223> OTHER INFORMATION: PCR PRIMER EKN1-5R

<400> SEQUENCE: 32
tcaatgtgcc aaaacagtaa cc                                      22

<210> SEQ ID NO 33
<211> LENGTH: 20
<212> TYPE: DNA
<213> ORGANISM: Artificial Sequence
<220> FEATURE:
<223> OTHER INFORMATION: PCR PRIMER EKN1-6F

<400> SEQUENCE: 33
tgtttaggat ttgggggtga                                         20

<210> SEQ ID NO 34
<211> LENGTH: 26
<212> TYPE: DNA
<213> ORGANISM: Artificial Sequence
<220> FEATURE:
<223> OTHER INFORMATION: PCR PRIMER EKN1-6R

<400> SEQUENCE: 34
ggaaattcta aaacatattc atgacg                                  26

<210> SEQ ID NO 35
<211> LENGTH: 20
<212> TYPE: DNA
<213> ORGANISM: Artificial Sequence
<220> FEATURE:
<223> OTHER INFORMATION: PCR PRIMER EKN1-7F

<400> SEQUENCE: 35
ccactggagg aagatggaaa                                         20

<210> SEQ ID NO 36
<211> LENGTH: 25
<212> TYPE: DNA
<213> ORGANISM: Artificial Sequence
<220> FEATURE:
<223> OTHER INFORMATION: PCR PRIMER EKN1-7R

<400> SEQUENCE: 36
tgtcttcata catgataaag ctcat                                   25

<210> SEQ ID NO 37
<211> LENGTH: 21
<212> TYPE: DNA
<213> ORGANISM: Artificial Sequence
<220> FEATURE:
<223> OTHER INFORMATION: PCR PRIMER EKN1-8F

<400> SEQUENCE: 37
```

```
ggtaagccat cctctttgtc a                                                  21

<210> SEQ ID NO 38
<211> LENGTH: 25
<212> TYPE: DNA
<213> ORGANISM: Artificial Sequence
<220> FEATURE:
<223> OTHER INFORMATION: PCR PRIMER EKN1-8R

<400> SEQUENCE: 38
tcaactgaac agaaaaagat catca                                              25

<210> SEQ ID NO 39
<211> LENGTH: 20
<212> TYPE: DNA
<213> ORGANISM: Artificial Sequence
<220> FEATURE:
<223> OTHER INFORMATION: PCR PRIMER EKN1-9F

<400> SEQUENCE: 39
ctccccaagt gttgggatta                                                    20

<210> SEQ ID NO 40
<211> LENGTH: 21
<212> TYPE: DNA
<213> ORGANISM: Artificial Sequence
<220> FEATURE:
<223> OTHER INFORMATION: PCR PRIMER EKN1-9R

<400> SEQUENCE: 40
tggagtcctt aaaagtcacg a                                                  21

<210> SEQ ID NO 41
<211> LENGTH: 26
<212> TYPE: DNA
<213> ORGANISM: Artificial Sequence
<220> FEATURE:
<223> OTHER INFORMATION: PCR PRIMER EKN1-10F

<400> SEQUENCE: 41
ggtacttgtt ctgaaccatg ctacta                                             26

<210> SEQ ID NO 42
<211> LENGTH: 27
<212> TYPE: DNA
<213> ORGANISM: Artificial Sequence
<220> FEATURE:
<223> OTHER INFORMATION: PCR Primer 126403-F

<400> SEQUENCE: 42
caagggcaag cttaattcag taacaca                                            27
```